(12) United States Patent
Harper et al.

(10) Patent No.: US 8,198,059 B2
(45) Date of Patent: Jun. 12, 2012

(54) ACTIVATION AND TRANSFER CASCADE FOR UBIQUITIN

(75) Inventors: Jeffrey Wade Harper, Wellesley, MA (US); Jianping Jin, Pearland, TX (US)

(73) Assignee: President and Fellows of Harvard College, Cambridge, MA (US)

( * ) Notice: Subject to any disclaimer, the term of this patent is extended or adjusted under 35 U.S.C. 154(b) by 113 days.

(21) Appl. No.: 12/498,436

(22) Filed: Jul. 7, 2009

(65) Prior Publication Data

US 2010/0047255 A1  Feb. 25, 2010

Related U.S. Application Data

(63) Continuation of application No. PCT/US2008/051312, filed on Jan. 17, 2008.

(60) Provisional application No. 60/946,757, filed on Jun. 28, 2007, provisional application No. 60/885,431, filed on Jan. 18, 2007.

(51) Int. Cl.
 *C12N 9/00* (2006.01)
(52) U.S. Cl. ........................ 435/183; 435/193
(58) Field of Classification Search ............ 514/44; 435/183, 193
See application file for complete search history.

(56) References Cited

U.S. PATENT DOCUMENTS

2004/0043386 A1  3/2004  Pray et al.
2006/0189636 A1  8/2006  Critchley et al.

FOREIGN PATENT DOCUMENTS

WO  0206485 A2  1/2002

OTHER PUBLICATIONS

Accession No. AAU76631 and SEQ ID No. 5 (sequence alignment).*
Pitha-Rowe Ian et al "Involvement of UBE1L in ISG15 conjugation during retinoid-induced differentiation of acute promyelocyctic leukemia", The Journal of Biological Chemistry Apr. 30, 2004, pp. 18178-18187, XP002593703.
Tsukamoto S et al "Himeic acid A: a new ubiquitin-activating enzyme inhibitor isolated from a marine-derived fungus, *Aspergillus* sp", Bioorganic & Medicinal Chemistry Letters, Pergamon, Elsevier Science, GB LNKD-DOI:10.1016/J.BMCL.2004.10.012, vol. 15, No. 1, Jan. 3, 2005, pp. 191-194 XP025313436.
Matsuzawa Masayoshi et al: "Enantio- and diastereoselective total synthesis of (+) -panepophenanthrin, a ubiquitin-activating enzyme inhibitor, and biological properties of its new derivatives." Chemistry, An Asian Journal Dec. 18, 2006 LNKD-PUBMED:17441127, vol. 1, No. 6, Dec. 18, 2006, pp. 845-851, XP002593704.
Groettrup M et al: "Activating the ubiquitin family: UBA6 challenges the field" Trends in Biochemical Sciences, Elsevier, Haywards, GB LNKD-DOI:1016/j. TIBS.2008.01.005, vol. 33, No. 5, May 1, 2008, pp. 230-237, XP022679146.
Supplementary European Search Report, EP 08 72 7833, Jul. 26, 2010, 2 pages.
International Preliminary Report on Patentability and Written Opinion of the International Searching Authority corresponding to PCT/US2008/051312, (2008).
Pelzer, et al. UBE1L2, a Novel E1 Enzyme Specific for Ubiquitin. J. Biol. Chem., v.282(32):23010-4, (2007).
International Search Report and the Written Opinion of the International Searching Authority, or Declaration corresponding to PCT/US08/51312, (2008).
Pelzer, et al. UBE1L2, a Novel E1 Enzyme Specific for Ubiquitin. J.Bact. Chem., v.282(32):23010-4, (2007).
Jin, et al. Dual E1 Activation Systems for Ubiquitin Differentially Regulate E2 Enzyme Charging. Jun. 2007. Nature, v.447(7148):1135-8.
Chiu, et al. E1-L2 Activates Both Ubiquitin and FAT10. Sep. 2007. Mol. Cell, v.27(6):1014-23.
Gen Bank No. NM_018227 *Homo sapiens* ubiquitin-like modifier activating enzyme 6 (UBA6), mRNA, (2008).
Gen Bank No. NP_060697 ubiquitin-activating enzyme E1-like 2 [*Homo sapiens*], (2008).
Gen Bank No. NM_172712.2 Mus Musculus ubiquitin-like modifier activating enzyme 6 (Uba6), mRNA, (2007).
Gen Bank No. NP_766300.1 ubiquitin-like modifier activating enzyme 6 [Mus musculus], (2007).
Gen Bank No. NM_023079.2 [this record has been replaced by NM_023079.3] *Homo sapiens* ubiquitin-conjugating enzyme E2Z (putative) (UBE2Z), mRNA, (2007).
Gen Bank No. NP_075567.1 [this record has been replaced by NP_075567.2] ubiquitin-conjugating enzyme E2Z (putative) (*Homo sapiens*), (2007).

* cited by examiner

*Primary Examiner* — Tekchand Saidha
(74) *Attorney, Agent, or Firm* — Banner & Witcoff, Ltd.

(57) ABSTRACT

A novel activating enzyme for ubiquitin, Uba6, is provided. Compositions and methods for inhibiting ubiquitin via the Uba6 pathway are provided. Methods of identifying novel inhibitors of ubiquitination are also provided. Novel RNAi molecules are also provided.

6 Claims, 63 Drawing Sheets

|  | Charging by | | |  | Charging by | |
|---|---|---|---|---|---|---|
|  | Uba1 | Uba6 |  |  | Uba1 | Uba6 |
| E2A/Rad6A | + | +/- | E2J2 |  | + | - |
| E2B/Rad6B | + | +/- | E2K/HIP2 |  | + | - |
| E2C/UbcH10 | + | +/- | E2L3 |  | + | + |
| E2D1/Ubc4 | + | + | E2L6 |  | - | - |
| E2D2 | + | + | E2M/Ubc12 |  | - | - |
| E2D3 | + | + | E2M2 |  | - | - |
| E2D4 | + | + | E2Q2 |  | + | - |
| E2E1/Ubc5 | + | +/- | E2R1/Cdc34A |  | + | - |
| E2E2 | + | +/- | E2R2/Cdc34B |  | + | - |
| E2E3 | + | + | E2S |  | + | + |
| E2G1/Ubc7 | + | +/- | E2T |  | + | + |
| E2G2 | + | + | E2U |  | + | - |
| E2H | + | - | E2W |  | - | - |
| E2I/Ubc9 | - | - | E2Z |  | + | - |
| E2J1 | + | - |  |  | - | + |
FIG. 3B
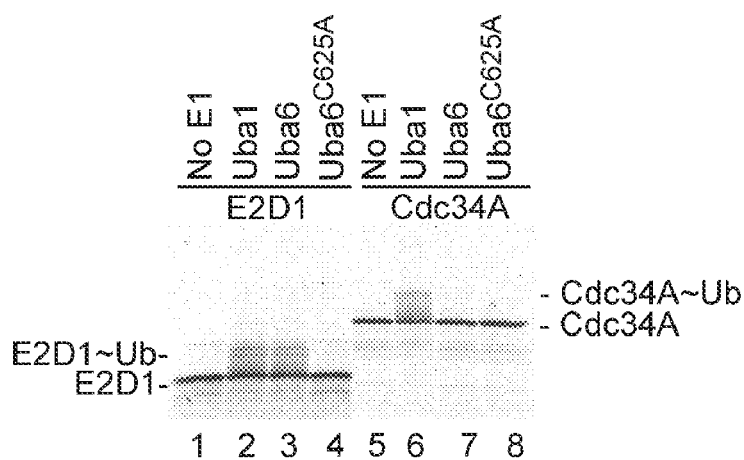
FIG. 3C
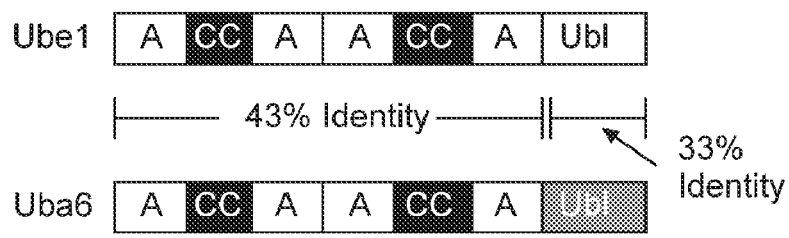
FIG. 4A

```
gcggcggtgt ctcaggcggc aatggaagga tccgagcctg tgccgccca tcaggggaa
aaggcgtcct gttcttcctg gggactggc agcacaaata aaatttgcc cattatgtca
acagcatctg tggaatcga tgatgcattg tatagtcgac agagtacgt tcttggagac
acagcaatgc agaagatggc caagtcccat gttcttaa gtgggatggg tggtcttggt
ttggaaattg caaagaatct tgttcttgca gggattaagg cagttacaat tcatgataca
gaaaaatgcc aagcatggga tctaggaacc aacttctttc tcagtgaaga tgatgttgtt
aataagagaa acaggctga agctgtactt aaacatattg cagaactaaa tccatacgtt
catgtcacat catcttctgc tcctttcaat gagaccacag atctctcctt tttagataaa
taccagtgtg tagtattgac tgagatgaaa cttccattgc agaagaagat caatgactt
tgccgtttcc agtgccctcc aattaagttt atcagtgcag atgtacatgg aatttggtca
agttatttt gtgatttcgg tgatgaattt gaagtttag ataacacagg agaagaacca
aagaaatttt tcatttcaaa cataacgcaa acaaatcctg gcattgttac ttgccttgaa
aatcatcctc acaaactgga gacagacaa ttcctaacat ttcgagaaat taatgaatg
acaggtttaa atggatctat acaacaaata acggtgatat cgccatttc tttagtatt
ggtgacacca cagaactgga accatattta catggaggca aacatccaaa gtgccttatt
cctaaaacat ttttttga atcactggag aggcagttca gagattcaca cagcatgct tgccttggac
gtggatttta gcaaccctga ggcaccttta ggcacctgga aatgttggat gccaacaaga ttcagaagaa
cagtttcagg agaaatacag tcgcaagcca tataagtgaa acttggat agagcctga tgtaaatgct
ctgttgaaac tagcaacatc ttggactgcc caaggctttt tatctccact tgctgcagca
gacattgtgc attgctctc agtactgcc caggcttttt tatctccact tctgcagca
gtaggaggtg ttgccagcca agaagtattg aaagctgtaa caggaaaatt ttctccttg
```

```
tgccagtggt tatatcttga agcagcagat attgttgaat cactagcaa acctgaatgt
gaagaattc tcccacgagg agatagatat gatgccttaa gagcttgcat tggagacact
ttgtgtcaga aactgcaaaa tttaaacatc ttcttagtag ggtgtggagc cataggctgt
gaaatgttga aaaattttgc tttacttggt gttggcacaa gcaaagagaa aggaatgatt
acagttacag atcctgactt gatagagaaa tccaacttaa atagacagtt cctattcgt
cctcatcaca tacagaaacc taaaagttac actgctgctg atgctactct gaaaataaat
tctcaaataa agatagatgc acacctgaac aaagtatgtc caaccactga gaccatttac
aatgatgagt tctatactaa acaagatgta attattacag cattagataa tgtggaagcc
aggagatacg tagacagtcg ttgcttagca aatctaaggc ctcttttaga ttctgaaca
atgggcacta agggacacac tgaagttatt gtaccgcatt tttgtactc ttacaatagt
catcggatc cccagaaga ggaaatacca tgactgagtc taaaatcctt tccagctgct
attgaacaca ccatacagtg ggcaagagat aagtttgaaa gttccttc ccacaaacct
cagagtggac acagtttg gcaaacctat caagtgtttt aagaagtctt acagaagata
agaaattggt cccagtgtgt agaattagca agattaaagt agttacttag cagaagacct
aaggctcttc agcttcttca ctgtttccct cttgacatac ttgaaaaata tttaaccat
tttggcagt caccaaagag gccaccctct ccaataaaat ttgatttaaa tggcagttta
cacctcagtt tccttcagaa tgctgcaaaa ctatatgcta cagtatattg tgagcctttg
gcagaagagg acttatcagc agatgccctc ttgaatattc tttcagaagt tattccattt
gaattcaagc cttccaataa gttgttcaa acagatgaaa ctgcaagaa aagattcag
gttcctatta gcagtgaaga gtgagggaat gcaatttcc aactagaaaa accagaccat
tctaatgaag ccaccaaaag tgaccttcag atggcagtgc tttcatttga ggctatta
gatcataatg gacataga tttcatcaca atcctcgtgc caaatgtac
```

FIG. 5 (Continued)

```
agcattgaac cagctgaccg tttcaaaaca aagcgcatag ctggtaaaat tatacctgct
atagcaacaa ccactgctac agtttctggc ttggttgcct tggagatgat caaagtaact
ggtggctatc cattgaagc ttacaaaat tgttttctta acttagccat tccaattgta
gtattacag agacaactga agtaaggaaa actaaaatca gaaatggaat atcattaca
atttgggatc gatggaccgt acatggagcca gaagattcca ccctccttga tttcataaat
gcagtcaaag agaagtatgg aattgagcca acaatggtgg tacaggagt caaaatgctt
tatgttcctg taatgcctgg tcatgcaaaa agattgaagt taacaatgca taaacttgta
aaacctacta ctgaaaagaa atatgtggat cttactgtgt cattgctcc agacattgat
ggagatgaag atttgcgggg acctccagta agatactact tcagtcatga cactgattaa
tacaagttgt cttaacgtta acctcaggac acttgattct ggaaagagtg cacttaattc
agaagctaaa gaaaatcagt tcatatact atggatttct cttcattaa gccttaattt
taaggaaac atcagtaaga aactgcactg aagaattata aaacatttg gggcatagca
tacacttgtc taacgttca cacggtgcta tgatcacaag caacttgaa ctgaatgct
attacaaaa gttttgtgta ttaatctc tctggataaa aagaaggaaa
aaatatgtat gaccagaaca gatatggatg aagcaatag tgcagatgag tgcaactatt
caaaaagttt aatttatga atttctttt tgtttagtct gctcttagag ttttctatgc
aaatagtgtt tggcatcctg cacctctgat atgattggc tttgagaatt taataccact
gggaagaagt atggtagtgg tggatgaagg gtggatattt gtggatattt gtggatatt agttacagtt
tactgtccta ttacctctgc tcgtttaacc agtttgttat atcactgtgt cccaaaatc
aggatttttg ttgatagcat cagtgttgta ggagcaatag gtcagatgag acatattaac
ttagactaaa cgtgaacagt ttcatatgga ctctcacaac gtctcttaga aatcgctgaa
tgtgaacaga caaatgtggc taaccatttg attcttcagt atgccttcta atgtggctat
tttattatg tgagactcta acctgattg tcctaatata taaaactaaa agatttgta
```

FIG. 5 (Continued)

```
aaggagtgt cttagaaat agatgaaatg tagaatgtta aaaattattg ctagggtagt
cttttttcc agaaacctaa ttagggtatt aaatttgtg tttttttttt tttttttt
ttaaacagaa gcatgttatt tcattcccat tcccagaaag ggagttaatg aagataaaaa
tttatttttt aaggtcttta ttgagagaaa ctttgttttc tgatatgaac tattgcagat
gttttataa atactttcat taaaatgatg taaacagtag taccaacac tgtaaactca
gtgaaatag taaatgattc tttattact aagactgtta tgcattctga agcagttggc
tttttttaa ccataggaag tcattccct ctagctcct cccttctact ctcctgctca
gaccattagt aggtactttg ttaaataaaa aactagatta acatcaatat tactccaatt
tggtatcttt tacactatgt attataccta ctttctttt atttcattta caaatagttt
aaattactt atcaaccagc tgtattgttt cccctcttgta aaagtaccat caagtgggga
aaatgtatgt ggagtggag agtgaatttg tatgactaaa ggataatctg tacatggga
agtggcaaa agtagatagg atgaattaa agaaaatgac taccttttgga aaaaagaaat
taaatttgt tcacatatcc taccctttcc cattgtgcat atcccaagtg tcatatttaa
aactaaggtt acttaaaaca gaatccagga atatcaaggc tctgtggctt cactttgttt
aggataggac taataaaagg actttgcaa agaaggcttt tttccacgtt ttcagcagtc
tgtgtctttt gaaagtaact gatactttc gggtagttaa tctcgacagc tcttcagaag
atccagtaag ttgcttatat tttattgaag tagtgttta gcagataaaa caaaatcaac
acgatgctgt cagtcatat ttataga ttccattact tttttctat
aaaaattaag ttcattttgt gattaaacct gcaaccattt tccattact tttttctat
agttaatggt tattgccatg atttcttctg tttggttcta ctaagctaga aagccaggt
gaagttaatg ataattccca ttatttatt tctgtaccat gagattgctg ttgatgactg
aaataccagg tgcaaaatt aatgatttga tttttgtaca gtttcaatga gtatttta
cttattaaaa ataattaag aatgcaaaa aaaaaaaaa aaaaaa
```

Figure 6:
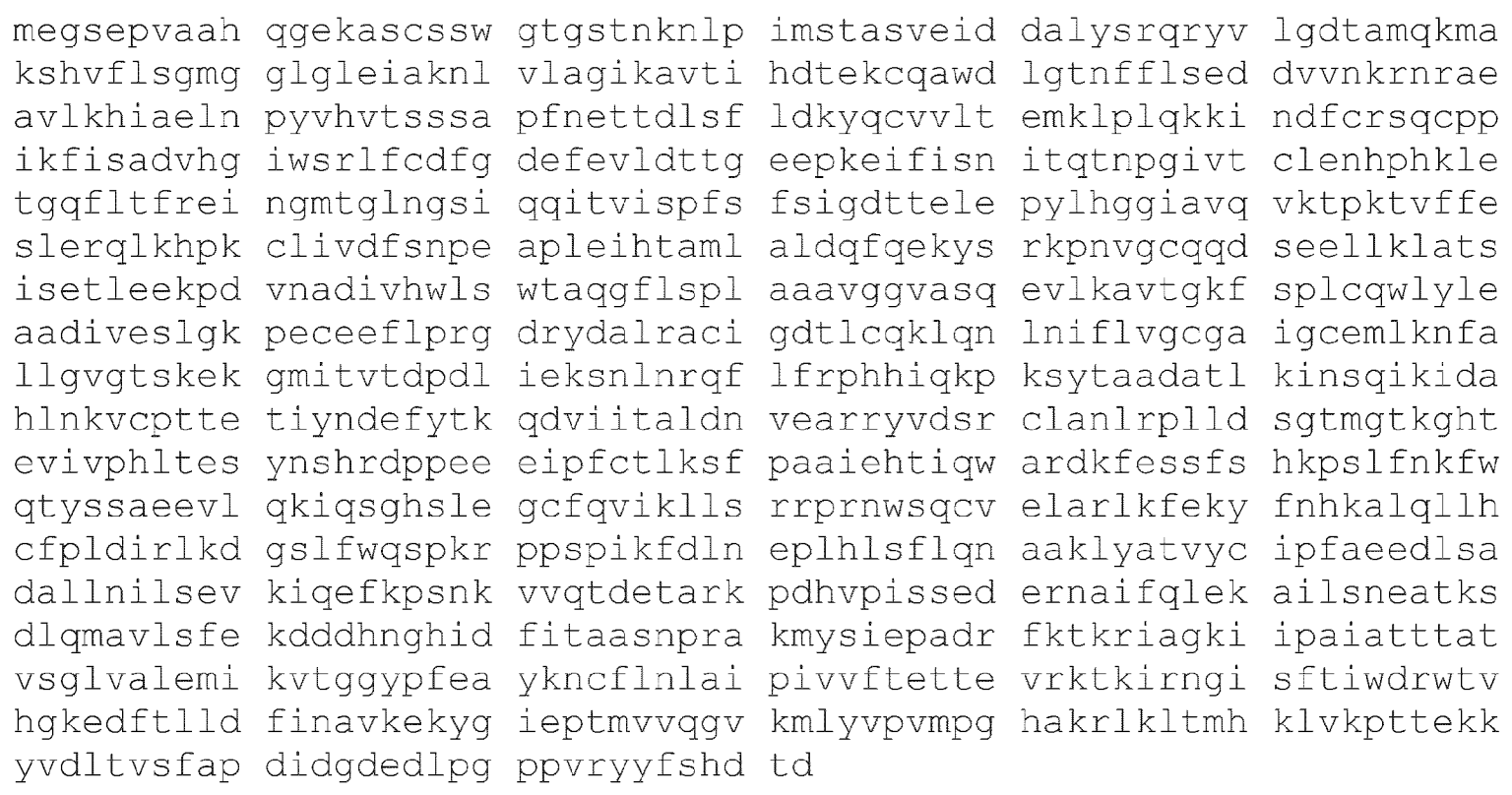

```
megsepvaah qgekascssw gtgstnknlp imstasveid dalysrqryv lgdtamqkma
kshvflsgmg glgleiaknl vlagikavti hdtekcqawd lgtnffised dvvnkrnrae
avlkhiaeln pyvhvtsssa pfnettdlsf ldkyqcvvlt emklpl

```
aggcgatgga gcggtccgag ccgttggctg tgcttttcctg tgaagaggcg tcctgctcct
cctgggagc ctgcggtgca agtaaaaatt tacctaccat gacaacagaa tctttggaaa
tcgatgatgg attatacagt cgccagagat atgttcttgg tgacacagca atgcagaaga
tggccaagtc ctgtgtcttc ttaagtggta tgggtggtct tggagtggaa attgcaaaga
atcttgttct tgcaggatt aaggccctaa caattcatga tacaaaaaaa tgccaagcat
gggatctagg gaccaatttc ttcctgtgtg aagatgatgt tgttaatgag agaacaggg
ctgagctgt acttcatcgt attgcagaac tgttcaggtc tcatcatcct
ctgcccctct tgatgaaacc acagacctct ctttcttaga tgtgtagtat
tgactgaaat aaaactgaca ttacaaaaga agatcaacaa tttttgccat tctcattgcc
ctccaattaa gttcattagt gcagatgtac atggaatttg gtccaggttg tttttgtgatt
tttggtgatga attgaagtt tcagatacaa caggagaaga accaaaagaa attttcattt
caaacataac gcaagctaat ccaggtattg tcacttgcct tgaaagtcat cctcacaagc
ttgacacagg acagttccta acattccta aaattcgag aatgacaggc ttaaatggat
ctgtacaaca dataactgtc atatccacat tttccttcag cattgtgat actacaaaac
tggaccata tttacatgga ggcatagccg tgcaggtgaa gactcctaaa acattctgct
ttgaaccct ggagacaccag ataaaacatc caaggtgcct tattgcagat tttagcaaac
ctgaggcacc tttagagatt catctcgcta tgcttgcctt ggaccagttt caggagaact
```

FIG. 7

```
ataaccgtaa gccaaatatc agatgtcagc aggattcaga tgaactattg aagctaacag
tatctataaa tgaaaccttg gaagagaagc ctgaagtgaa tgctgacatt gtgcactggc
tttcgtggac tgcccaaggc ttttaccac cactcgctgc tgcagttgga ggtgttgcta
gccagagaag cttaaaagct gtgacgggga agttctcgcc cttgtgtcaa tggtttgtacc
ttgaagcagc agatactgtg gaatcctag gcaatcctgg gcatgaagag tttctcccac
gaggagatag atatgatgcc atacgtgcct gcattggaaa tacattgtgt cagaagctac
aaaatttgaa tatcttctta gtaggatgtg gtgccatagg ctgtgaaatg ttaaaaaatt
ttgcattact gggtgttggt acaggcagag agaaaggaat ggtaacagtt acagatcctg
acttgataga aaaatccaat ttaaacagac agttcctgtt tcgtcctcat cacatacaga
aacctaaaag ctatactgct gctgaagcaa agttcctgaa aaatcctcaa atacagatag
atgcacacct gaacaagtt tgtccagcca ctgagagtat atacagtgat gaatttaca
ctaagcaaga tatcattatt acagcactag ataatgtgga agccaggaga tatgtagaca
gtcgctgttt agcaaatcta cggctcctct tagattctgg aacaatgggc accaaggac
atactgaaat tatcgtacct caattaactg aatcttataa tagtcatcga gacccccccg
aagaggaaat accatttgc actctaaagt cctttccaca acttcactg catactatcc
agtgggcaag agacaagttt gaaagttcct tcttacagaa gatacaaat tttaacaagt
tttggcaagc atatccctct gcagaagatg ttagagctac ccataaggct tggtcccagt
taagaggctg ttttcaagtt attaagctac aatactttaa aatactttaa ctgcagcttc
gtgtagagtt agcagacta aagtttgaaa aagtttgaa caatcaccaa
ttcactgttt tcctcttgag acaagactaa aaatttgatt taaatgaacc tttgcacctc agttttcttc
aaaggccgcc ttctcaata ttctccaata aaatttgatt taaatgaacc tttgcacctc agttttcttc
agatgctgc cagtgaatag ctacagtat attgtattcc gttttcagaa aggacttat
cagtgaatag cctcatggac attctttcag aagttaaaat tgaggaattc aagccttcca
```

FIG. 7 (Continued)

```
acaaggttgt tcaaacagac gaaactgcaa ggaagcccga ccatgttcct gtctccagtg
aagatgaaag gaatgctgtt ttccaactag aagaggctct ttcctctaac aaagctacca
aaagtgacct tcagatgaca gtgctttcat ttgaaaaaga tgatgaccgt aatggacaca
tagatttcat cacagctgct tccaaccttc gagccaaaat gtatagcatt gaaccagctg
accgttttaa aactaaacgc atagctggta aaattatacc tgctatagca acatctactg
ctgcagtttc tggcttggtt gctttggaga tgatcaaggt agctggtggc tatcccttcg
acgcttacaa aaactgtttc cttaatttag ccattccaat aatagtgttt acagagacat
ctgaagtaag aaaaactgaa atcagaaatg gaatatcatt tacaatttgg gacagatgga
ctgtacatgg aaaagaaaga ttcaccctct cagatttcat aaatgctgtc aaagaaaact
atggaattga gccgacaatg gtggtgcagg gagtcaaaat gctttatgc cctgtaatgc
caggtcatgc aaaaaggcta aagttaacaa tgcacaaact cccagacgc tccactgaga
agaaatatgt ggatcttact gtgtcatttg tactccagtc atgacactaa tgatggagat gaagatttgc
ccggcccctcc agtgagatac tactacttat tttggaaagt gtacttaatt cagaagactca gctcataata
atactccagc actactttat ctttttgcct taatgtaagg gaaccatcag ttgctcccct gcggttatga
ctgtgatttt cttggatttg agcatagtac acatccattt acattgtct gttgctccct gtggatgaaa
agaattacaa accattttga aatacactgg aatacctatt tctaatactt attaagccct attaagaaat
tcacagcacc tttgaactgg agcaaaata atcatatgacc agaagaaata aagatgaaga tttattggt
gaaggaacaa gaaatcattt tactattcag aagttaacg ccttcttcca cgttttcttt tgctgcttac atgattaggc
agtgaattg tactattcag aagttaag atataaatag tgtggcactg tgctgcactg aggtgatgag tagagatta
atttgaaacc cattatttca atataaatag taggagagg ggtggcagat agtgtgatat attactccct
tttgaaaatt ccatagctga taggagctgag gtggcagat ctgtgctaac agtgtgatac attactccct
aaactgtagt tacagttagt gtcctgttgt gctgctac ctgtgctaac ctgatgaagg attactccct
tccctaagtc aggattgtcc ctgatctgat cagtttgat aacagtgagg taacatgaca
```

FIG. 7 (Continued)

```
tgttaacttg gactaaatgt taacagtatt acatgcactc tgatagagaa tccataaatg
tgagcagata aatatggtta atcattttgat tgttaatata cctttatttt atttatctgg
aagtctaaac tagtcatagt atttaagacc ttaattggt aaaaattttt tataaaggaa atattcttag
aatagatga agttacaca ttaattggt tgtctttt tcctttcca gcaatgtaat
ggagaaaaa aaaaaatata tatatatagt attttttt aaggaggca tgttatttca
ctcttcattc ccaaattggg gattgactga aatagaaaaa attatatttt tttagatttt
tctttactga aagaaatact ccattgcctg atgtgaacag ttgctactta tgatataatt
gggtccatta aatatatata acaatacttg actgtaaaat cactgaaaac agccagtaag
tcttttac aagggttatc acgcattcta aacaagtgct tacagcctct ggaagttact
tgcctggagt tcctattctt aagaccatta ctaaatactt tgatgaatta aaatttagat
tgcatcagta ttaactccaa tggtatctct ttatactcta tactttcttt ccattacaa
acaatttatg atctctgtgg taaccagctt ttttgtttcct cctttacga agtgtccagt
tgggaaatgg ggtgagtttg tacaataaaa tgatctgttc attcagaggt ggagaaaagt
ggacagggtt tgttttaaag aactggctac ctttaaaata aactatagtt tttatcatat
cctaccttc ccaagttca taaattgaat ccatgaatat caaaggctct gtggcttaga
acttaatgac aaaaagaagt cctattttcc agtttcact ttgttttctc ttctttggta
gtaacgtatt ctgtaggtaa tcattcagga atcctcaaac agtaaatgag agccatgctt agcttggctc
tgtttactta agtctacacg tatctttgaa agtaaatgag agccatgctt tgtagagtgc
tttagtaaat aaaatcaacc aggtttggtt tgtttctaat taaatccaca accattttgt
cattgggttt tgtttttgtt tttctgtagg tagtgattat tactgtccta ctaaattata
ctgaactgga aagccataat gaagttaatg acttttttt tttgttcatt ttgtactta
agattcttgg tactaaaata tagctattga atactgagtg caaaaaaaaa aaaaaaaaa
a
```

FIG. 7 (Continued)

```
merseplavl sceeaascssw gacgasknlp tmttesleid dglysrqryv lgdtamqkma
kscvflsgmg glgveiaknl vlagikalti hdtkkcqawd lgtnfflced dvvnernrae
avlhriae GCGATGGCGGAGAGTCCGACTGAGGAGGCGGCAACGGCGGCGGCCCGGCGCGGGCCGAGCA
GCGTTGCTGCTGTGTTGGCGCGTTAGCGGCCAGCGGCGGCCGGGCCGGTTCCTGCCGATGTGTG
GGCGGCGGCCGGGGCCAGCGGGGGCCGGGCCCCGGGAGCGGCCGCCCTGGCTCCGGCTCCCG
CCCTCAGCCGCCGCTGCCGCCACGGCGGCCGCCTGCTTAGCCACGCTGGGACTGGGACTCCGACTGGGACG
GCGAGCGGCACCGCCGCCAGTGTCTACTCCGGATCAAGCGGATATCATGTCCATTTATAAGGAGCCTCC
TCCAGGAATGTTCGTTGTACCTGATACTGTTGACATGACTAAGATTCATGATCACAGGCCCATTT
GACACTCCTTATGAAGGGGTTTCTTCCTGTTCGTGTTTCGGTGTTCCGACTATCCCATCCACCCAC
CTCGGGTCAAACTGATGACAACGGGCAATAACACAGTGAGGTTTAACCCAACTTCTACCGCAATGGGAA
AGTCTGCTTGAGTATTCTAGGTACACATGGACCTGCCTGGAGCCCCAGAGCATCTCCTCAGTG
CTCATCTCTATCCAGTCCCTGATGACTGAGAACCCTATCACAATGAGCCCGGCTTTGAACAGGAGAGAC
ATCCAGAGAGCAGCAAAAACTATAATGAATCAGAGACCATCAGAGTTGCAGTCTGTGACAT
GATGGAAGGAAAGTGTCCCTGCCTGAACCCTACGAGGGGTGATGGAGAAGTCCTTTCTGGAGTATTAC
GACTTCTATGAGGTGCCTGCAAAGATCGCCTGCACCTTCAAGGCCGCCTTGATGCCTCAGAAAAGTGCTGGA
AGAAGCGGGCCACTTTGACTACCCAGTCCCTCTTGATACTCTGATAGCCAGTTCATCTGGGACAGAGACAGACCTTCAT
GAGGCTCCATAATGAGAATGCAGAGAATGACTTCATCTCCCCCACTCAAGAGTCCCAGCAGAATCCCTT
GGGAGCCTGAGGGTTTAGACCCTTCCCCTTCCCCACTGTATCTCCCCAGAGTCGAAGTCATCCTGCAAGATGGCA
CCCCCACCCAGGATGGGAGGCACTGGGTCCCAGGGCCTGTCCCGGTCTGACCTCCTTGGCACT
AGAACCAAGCAAGCTCCGATCCGTTCATTCATCCGTATCCAGGGCCAAGTACCTTTACAGGAGCACCTA
GGAGCATCTGGGGCTTCGGCAAAAACAAACAACCACACCTCTCCACAGGCCAGCTCCCACAGGCCAGTCCTTAGGATAAG
TGGAAGATGGAAATTGCAATTCCAAGAGGGGAGTGTGCCCAAATGATTTATGGGATACCTGGAAGGGAGC

FIG. 9

TTGGGGTGGGGCTGTCTGTGACACTTAAGCAGTCTGGGTGGTGTCTATTTGTCTGTCTTCAGTCTTGA
AGCAGGGCTTCCCAATGCCCTTTCCTCCCTGCCTCCTTCCCACAGCCAGCATAAT
TTTGTTTTCCTAATTTATAGTCACTGTTCTAGACAGAAGACCAAAGAGAAGGAACAGTGGTGGAGTCTAGGC
TGCTGATCAGTAAGCTTTACCTAGCACCTGAGCACCTTTCTCCCCTCTTCTCACCCTTTCTA
GATGTAAGACAGAAGGTAAATGTGTTCCCGCAATCACTGATTTGAAAAGTTCCCAACACAGGCAGCTGCTGTGT
GAAGCTGAAAATACTGTTTGTCCCGCAATCACTGATTTGAAAAGTTCAACACAGGCAGCTGCTGTGT
ATATGGGATTAGAGCCACTACACATAGAATAGTCTTACAGATTTCATAAATACTAGTCACAATAAGGGT
ATTTTCTTGGGGTGGAGTAAGGGGAGACTGATGCTAGTCCTCAACCCCAGGATTTGTGTATTTTGTTGGGCTGTCCTTG
TGTATTTCACCCCAGCCTGTAGTCCTGTAGTCCTCAACCCCAGGATTTGTGGGAGCAAGGGTAGCCA
ATGGCAGAGGGGGTTGGGGCTGGGACTCTGGAGGCTCCTCCTCTGCCTTTCCTCTGCCTCCCCG
TGCCCCCAGCTCTGATCCTTTAGCTGGTGGGCTCAGAAAAAATGTCTTTAAGGTGCCCTGTAATCCTG
TAGCTGCAGTGATCCTTTAGCTGGTGGGCTCAGAAAAAATGTCTTTAAGGTGCCCTGTAATCCTG
GGCATCAAGGGAATCCATCCTCCCCTTTGATATGTTCTCCCGTACTTCCAGATTTATTGTTATGC
TCCCAGTGGTATTGGCCCTGCCCCTCTTGTGAAGGCCTCAGTCAGTCGCCTTGTGCCTATTTGGAGACTCCCCCTTGGAG
ATAGTGTGTACCCTGCCCCTCTGGGCACAAGGAGAATGTCCTATTTGGATACCCTTGAAGAGGCTGGTCTCTTCAC
GATCTGTGCAAAGGGGCTTGGGCTGGGAACGGAAGTTTATCTTCCCCTTCTCCTGAGCTACTCCAGGCTTAGAA
GAATGCTCTTGGTCTGTGGGTCCCAGTGTTGTCTGTCATCCATTTAAGTGTTCCCACTTTCAAGTGACAAT
CCTCCTTGGCCTGCCATAGGGCAGAGCATGTCTGGCATAGCCCTGACTTTTATGCCCTAATCTTG
AGTTGAGGAAATATATGCACAGGAGTCAAAGATGTCTTTATATCTGACTGTATAAATGAAGTTTTT
TTGTTTTTTTGTTTCCTTTTGTTTTGGCAATAAAGTTTGTTTTGGCAGAAAAAAAAAAAAAAAAAA
AAAAAAAAAAAAAAAAAAAAAAAAAAAAAAAx

FIG. 9 (Continued)

MAESPTEEAATAGAGAAGPGASSVAGVGVSGSGGGFGPPFLPDVWAAAAAGGAGGPGSGL
APLPGLPPSAAAHGAALLSHWDPTLSSDWDGERTAPQCLLRIKRDIMSIYKEPPPGMFVVPD
TVDMTKIHALITGPFDTPYEGGFLFVERCPPDYPIHPPRVKLMTTGNNTVRFNPNFYRNGK
VCLSILGTWTGPAWSPAQSISSVLISIQSLMTENPYHNEPGFEQERHPGDSKNYNECIRHET
IRVAVCDMMEGKCPCPEPLRGVMEKSFLEYYDFYEVACKDRLHLQGQTMQDPFGEKRGHFDY
QSLLMRLGLIRQKVLERLHNENAEMDSDSSSSGTETDLHGSLRV

FIG. 10

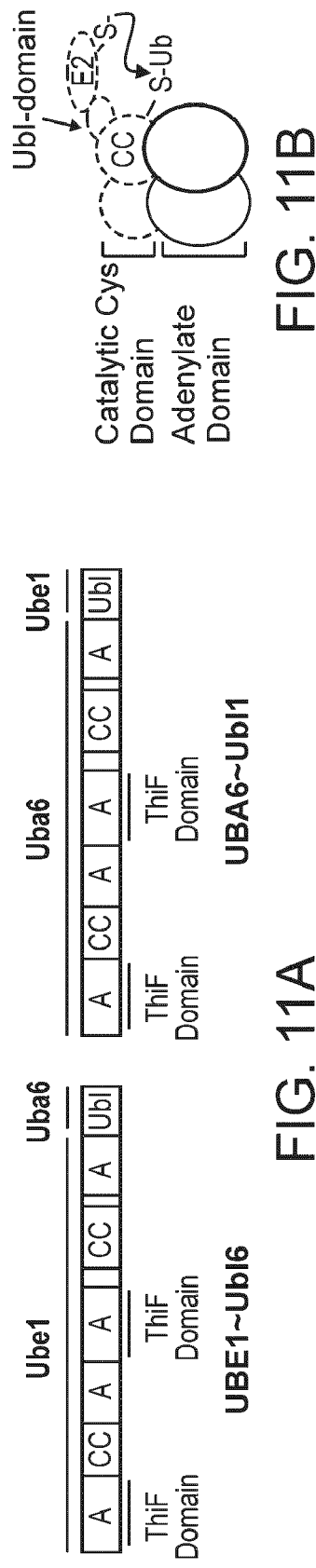

| Position | Charge | m/z | Ubiquitin Peptide | Uba6C625S~Ub | | Uba6~Ub | |
|---|---|---|---|---|---|---|---|
| | | | | XCorr | dCn | XCorr | dCn |
| 64-72 | +2 | 534.3 | ESTLHLVLR | 2.790 | 0.25 | 2.2093 | 0.17 |
| 55-63 | +2 | 541.5 | TLSDYNIQK | 2.544 | 0.22 | --- | --- |
| 30-42 | +2 | 762.6 | IQDKEGIPPDQQR | 3.841 | 0.41 | 3.8893 | 0.38 |
| 12-27 | +2 | 894.6 | TITLEVEPSDTIENVK | 4.663 | 0.44 | 3.4795 | 0.43 |

|  | Charging by | |
|---|---|---|
|  | Ube1 | Uba6 |
| E2H | + | − |
| E2I/Ubc9 | − | − |
| E2A/Rad6a | + | +/− |
| E2B/Rad6b | + | +/− |
| E2G2 | + | + |
| E2G1 | + | +/− |
| E2R2/Cdc34A | + | − |
| E2R1/Cdc34B | + | − |
| E2C/UbcH10 | + | +/− |
| E2U | − | − |
| E2S | + | + |
| E2D2/UbcH5B | + | + |
| E2D3/UbcH5C | + | + |
| E2D1/UbcH5A | + | + |
| E2D4/UbcH5D | + | + |
| E2E1 | + | +/− |
| E2E3 | + | + |
| E2E2 | + | +/− |
| E2K | + | − |
| E2T | + | + |
| E2N/Ubc13 | nd | nd |
| E2N-like | nd | nd |
| E2M/Ubc12 | − | − |
| E2F | − | − |
| E2L3 | + | + |
| E2L6 | − | − |
| UFC1 | nd | nd |
| E2J2 | + | − |
| E2J1 | + | − |
| Use1 | − | + |
| E2Q2 | + | − |
| E2W | + | − |
FIG. 14A
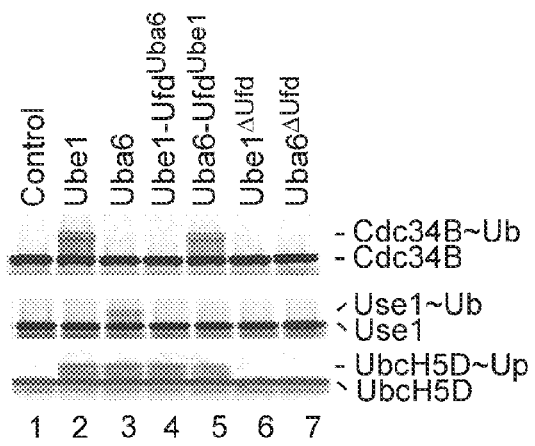
FIG. 14D
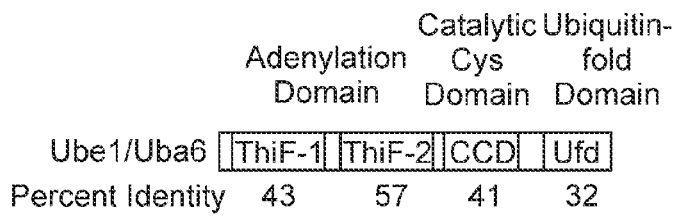
FIG. 14C

| | % Identity/%Similarity | | |
|---|---|---|---|
| | Uba6 Adenylate | Uba6 Cat Cys | Uba6 Ufd |
| Ube1 | 44/64 | 42/57 | 32/51 |
| Ube1L | 40/56 | 36/54 | 24/52 |

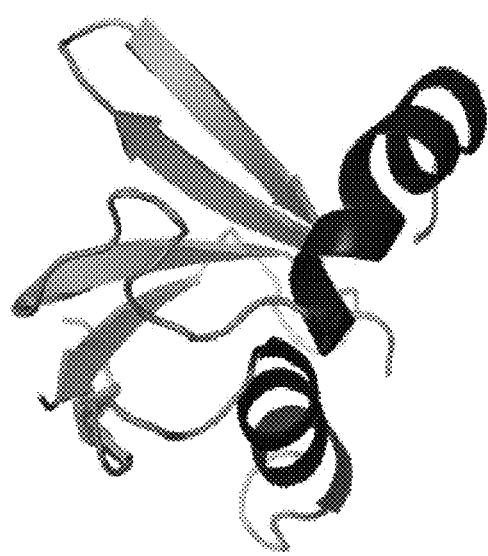
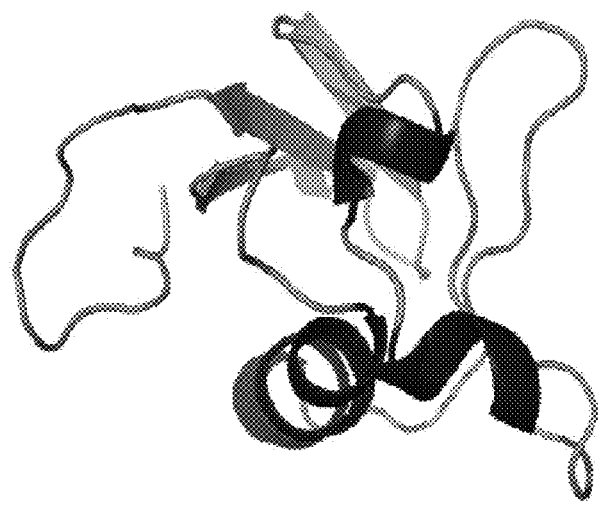
FIG. 16B

| UBL Protein | C-terminal Peptide | Protease Used | XCorr | dCn | charge |
|---|---|---|---|---|---|
| Ub | S.DYNIQKESTLHLVLRLRGG | Asp-N | 3.090 | 0.552 | 2 |
| Nedd8 | A.DYKILGGSVLHLVLALRGG | Asp-N | 6.210 | 0.708 | 2 |
| SUMO | K.ELGMEEEDVIEVYQEQTGG | Trypsin | 5.142 | 0.787 | 2 |
| Fub1 | R.M*LGG | Trypsin | 0.760 | 0.3447 | 1 |
| Urm1 | Q.DSVLFISTLHGG | Asp-N | 4.422 | 0.588 | 2 |
| ISG15 | F.MNLRLRGG | Chymotrypsin | 2.309 | 0.6312 | 1 |
| Fat10 | K.GNLLFLASYCIGG | Trypsin | 4.461 | 0.722 | 2 |

FIG. 18F

```
Human     1 ------MAESPTEEAAT---------AGAGAAGPGASSVA------GVVGVSGGGFGP
Mouse     1 ------MAESPTEEAATAT-------AGAGAAGPGSSSVA------GVVGVSGGGFGP
Rat       1 ------MAESPTEEAATAT-------AGAGAAGPGSSSVA------GVVGVSGGGFGP
Xenopus   1 ------MAESP--EAIIL---------------PCAAAGG------GVV----------
Danio     1 ------MASVTEEANGSVGAAQCHGAQLS-SINSIPGHSASPPPADTGAVEPGMAHTIT
Spur      1 METMEFPDEHIEAT-----------------------------------------------
consensus 1       maespte eaatat           agagaagpg  sgva        gvvgvsgggfgp
```

FIG. 20B

```
Human      40  PFLPDVWAAAAAGGAGGPGSGLAPLPGLPPSAAAHGAALL--------SHWDPTLSSDWDGE
Mouse      42  PFLPDVWAAAAAGGAGGPGSGLAPLPGLPPSAAAHGAALL--------SHWDPTLSSDWDGE
Rat        42  PFLPDVWAAAAAGGAGGPGSGLAPLPGLPPSAAAHGAALL--------SHWDPTLSSDWDGE
Xenopus    23  PHLS-------------GLQTPGISLLTTS------------------SVWDPSASADWDNE
Danio      59  PAVESGLGVLTHAVSSTVPVAVIPSIPGIGSGVPAGALSQIHAISWDPTLSDWDNE
Spur       16  --------------------ATLMSQLVQAQ---------LSPWDPIKCKDWENQ   e
consensus  61  pflpdvwaaaaaggaggpgsglaplpglppsaaahgaall        shwDPtlssDwd e Human      95  RTAPQCLLRIKRDIMSIYKEPPPGMEVVPDTVDMTKIHALITGPEDTPYEGGFELFVERC
Mouse      97  RTAPQCLLRIKRDIMSIYKEPPPGMEVVPDTVDMTKIHALITGPEDTPYEGGFELFVERC
Rat        97  RTAPQCLLRIKRDIMSIYKEPPPGMEVVPDTVDMTKIHALITGPEDTPYEGGFELFVERC
Xenopus    54  RASTQCLLRIKRDIMSIYKEPPPGMEVVPDPHDMTKIHALITGPEDTPYEGGFELFERC
Danio     119  KASQQCLLRIKRDIMSIYKEPPPGMEVVPDPHDMTKIHALITGPEDTPYEGGFELFERC
Spur       43  NPSQLLLRIKRDIMNLTPPLGMCIVE--EDTIHALITGPEDTPYEGGFHFVKF
consensus 121  rt pqCllLRIKrDIMsIYkePPpGMfvVPdtvDmTkiHALITGPFDTPYEGGFFlFvfrc
```

FIG. 20B (Continued)

| | | |
|---|---|---|
| Human | 155 | PPDYPIHPPRVKLMTGNNTVRFNPNFYRNGKVCLSILGTWTGPAWSPAQSISSVLISIQ |
| Mouse | 157 | PPDYPIHPPRVKLMTGNNTVRFNPNFYRNGKVCLSILGTWTGPAWSPAQSISSVLISIQ |
| Rat | 157 | PPDYPIHPPRVKLMTGNNTVRFNPNFYRNGKVCLSILGTWTGPAWSPAQSISSVLISIQ |
| Xenopus | 114 | PPDYPIHPPRVKLMTGNNTVRFNPNFYRNGKVCLSILGTWTGPAWSPAQSSVLISIQ |
| Danio | 179 | PPDYPIHPPRVKLTGHNTVRFNPNFYRNGKVCLSILGTWTGPAWSPAQSISSVLISIQ |
| Spur | 102 | PPDYPIRPPRKLMTTGDGVRFNPNLYRSGKVCLSILGTWRGPAWSPAQSSVLISIQ |
| consensus | 181 | PPDYPIhPPRvKLmTTGnntVRFNPnfYRngKVCLSILGTWtGPAWSPAQSiSSVLiSIQ |

| | | |
|---|---|---|
| Human | 215 | SLMTENPYHNEPGFEQERHPGDSKNYNECIRHETIRVAVCDMEGKCPCPEPLRGVMEKS |
| Mouse | 215 | SLMTENPYHNEPGFEQERHPGDSKNYNECIRHETIRVAVCDMEGKCPCPEPLRGVMEKS |
| Rat | 217 | SLMTENPYHNEPGFEQERHPGDSKNYNECIRHETIRVAVCDMEGKCPCPEPLRGVMEKS |
| Xenopus | 174 | SLMTENPYHNEPGFEQERHSGDSKNYNECIRHETIRVAVCMEGKCQCPALRSVMEKS |
| Danio | 239 | SLMTENPYHNEPGFEQERHPGDSKNYNECIRHETIRVAVCDMEGKVSCPEALWSVMEKS |
| Spur | 162 | SLMNEKPYHNEPGFEQ-------------------------------------------- |
| consensus | 241 | SLMtEnPYHNEPGFEQerhpgdsknynecirhetirvavcdnnegkcpcpeplrgvmeks |

FIG. 20B (Continued)

```
Human      275 FLEYYDFYEVACKDRLHLQGQTMQDPFGEKRGHFDYQSLLMRLGLTRQKVLERLHNEN---
Mouse      277 FLEYYDFYEVACKDRLHLQGQTMQDPFGEKRGHFDYQSLLMRLGLTRQKVLERLHNEN---
Rat        277 FLEYYDFYEVACKDRLHLQGQTMQDPFGEKRGHFDYQSLLMRLGLTRQKVLERLHNEN---
Xenopus    234 FLEYYDFYEAVCKDRFHLQGQNMQDPFGEKRGHFDYQSLISRLQTHQLVREKHRPET---
Danio      299 FLEYYDFYEGVCKERLHLQGQNMQDPFGEKRGRFDYGLLTRLRATQRRTFEKCPPEDND
Spur       178 -----------------------------DFGEKRGKEDYALLKTLKALKVLIDEASQMEV---
consensus  301 fleyydfyevackdrlhlqgqtmqDPFGEKRGhFDYqsLLmrLglirqkvLErlhnEn Human      333 AEMDSDSSS-SGTETDLHGSLRV-
Mouse      335 AEMDSDSSS-SGTETDLHGSLRV-
Rat        335 AEMDSDSSS-SGTETDLHGSLRV-
Xenopus    292 VDIDSDSSS-SETETDTQGSSNP-
Danio      359 GDSDSDISS-SGIIPDSQGSSQP-
Spur       212 -SSDSISSGGSDLLKKISGPDTSS
consensus  361 aemDSdsSs SgtetdlhGslrv
```

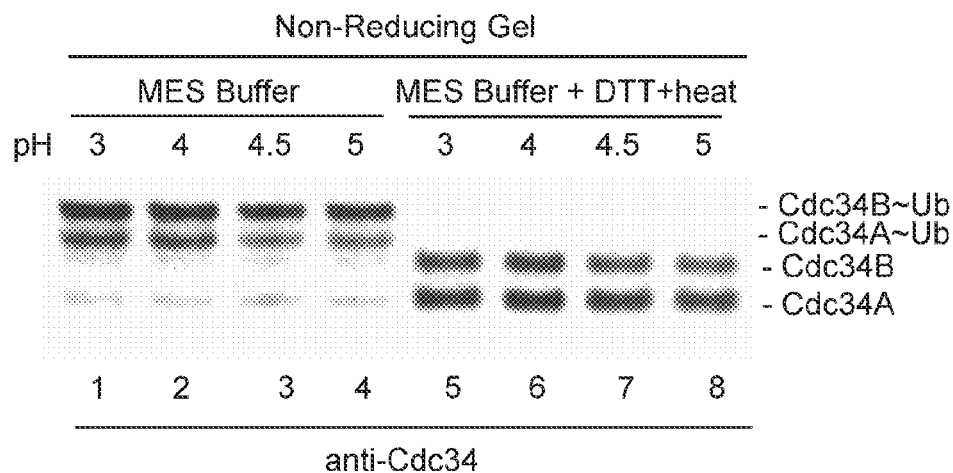
FIG. 20F
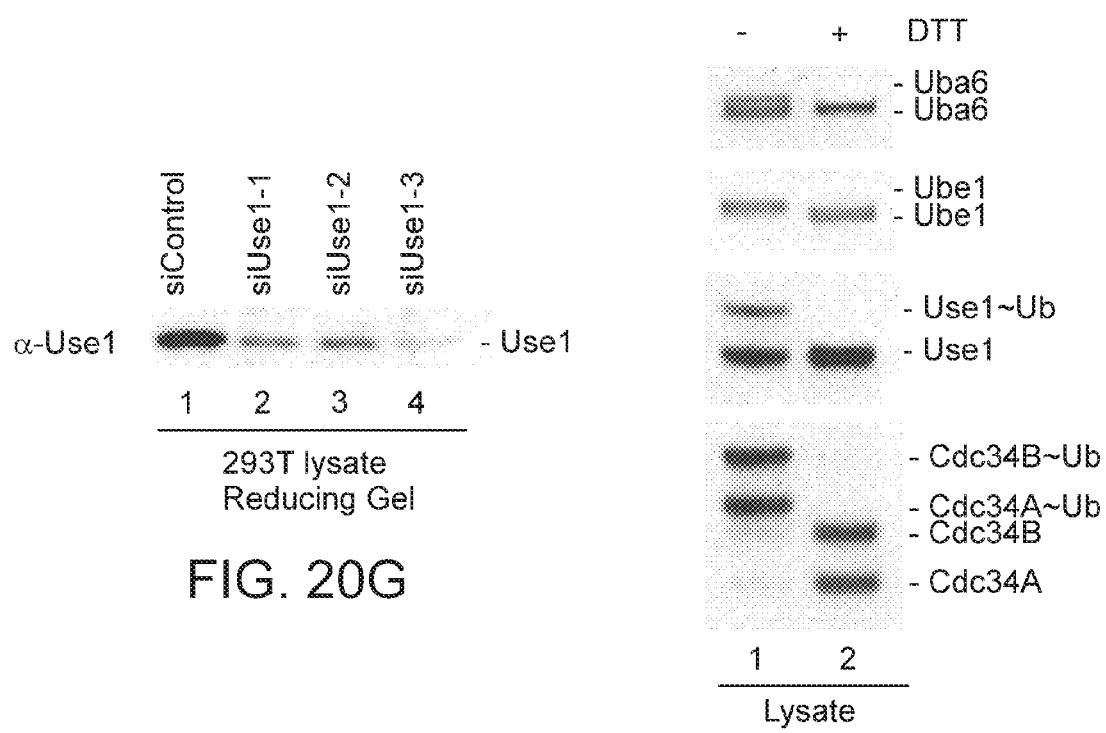
FIG. 20G
FIG. 20H

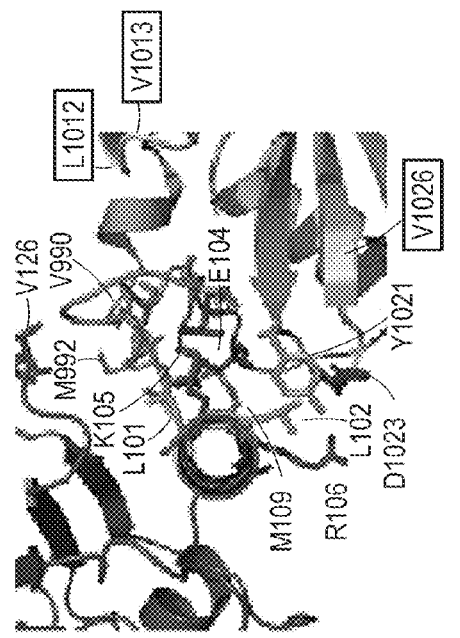
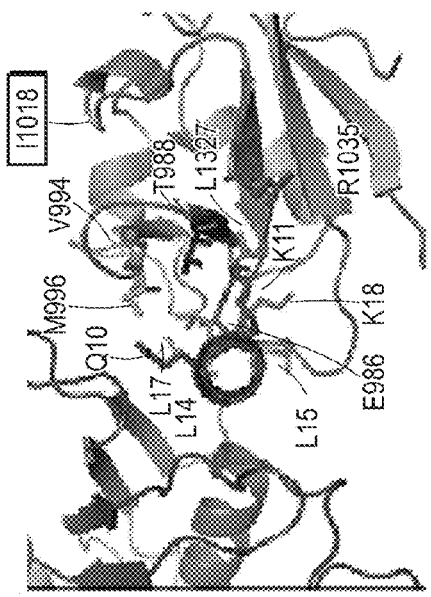
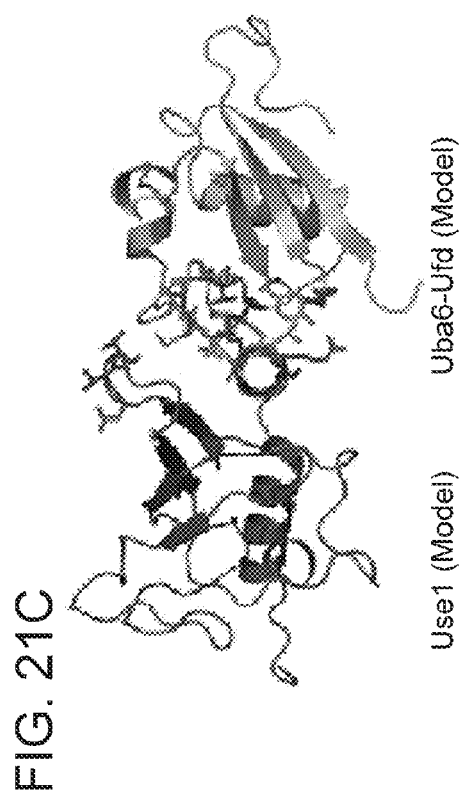
FIG. 21C
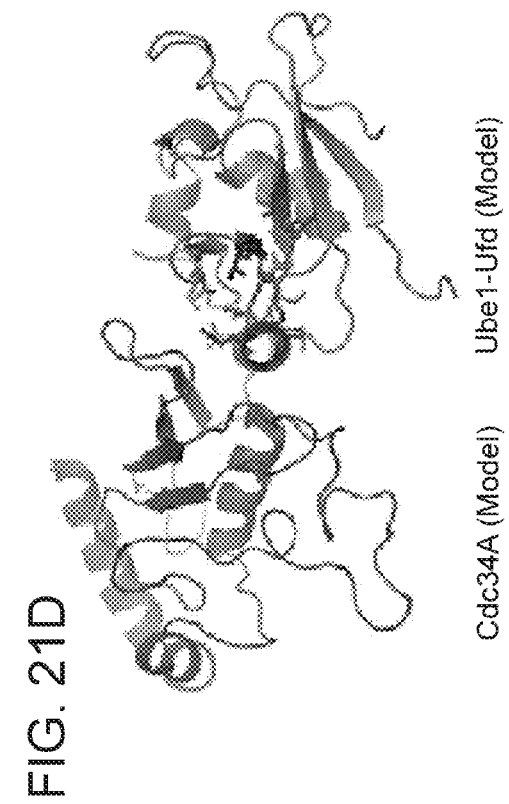
FIG. 21D

| | | | | |
|---|---|---|---|---|
| UbcH5b | E2D2 | NM_003339 | 7322 | 16.74 |
| UbcH5c | E2D3 | NM_181893 | 7323 | 16.9 |
| UbcH5d | E2D4 | NM_015983 | 51619 | 16.65 |
| | E2E1 | NM_003341 | 7324 | 21.41 |
| | E2E2 | NM_152653 | 7325 | 22.26 |
| | E2E3 | NM_182678 | 10477 | 22.92 |
| | E2G1 | NM_003342 | 7326 | 19.51 |
| | E2G2 | NM_003343 | 7327 | 18.57 |
| | E2H | NM_003344 | 7328 | 20.66 |
| Ubc9 | E2I | NM_194261 | 7329 | 18.01 |
| | E2J1 | NM_016021 | 51465 | 35.21 |
| | E2J2 | NM_194315 | 118424 | 30.98 |
| | E2L3 | NM_003347 | 7332 | 17.86 |
| | E2L6 | NM_004223 | 9246 | 17.77 |
| Ubc12 | E2M | NM_003969 | 9040 | 20.9 |
| NCE2 | E2F | NM_080678 | 140739 | 21.08 |
| | E2Q2 | NM_173469 | 92912 | 42.83 |
| HIP2 | E2K | NM_005339 | 3093 | 22.41 |
| Cdc34A | E2R1 | NM_004359 | 997 | 26.74 |
| Cdc34B | E2R2 | NM_017811 | 54926 | 27.17 |
| | E2S | NM_014501 | 27338 | 23.85 |
| | E2T | NM_014176 | 29089 | 22.53 |
| | E2W | NM_001001481 | 55284 | 18.66 |
| | E2U | NM_152489 | 148581 | 26.69 |

FIG. 22 (Continued)

SEQUENCE LISTING

```
<160> NUMBER OF SEQ ID NOS: 61

<210> SEQ ID NO 1
<211> LENGTH: 25
<212> TYPE: RNA
<213> ORGANISM: Artificial Sequence
<220> FEATURE:
<223> OTHER INFORMATION: siRNA

<400> SEQUENCE: 1
ccuuggaaga gaagccugau guaaa                                           25

<210> SEQ ID NO 2
<211> LENGTH: 25
<212> TYPE: RNA
<213> ORGANISM: Artificial Sequence
<220> FEATURE:
<223> OTHER INFORMATION: siRNA

<400> SEQUENCE: 2
acacugaagu uauuguaccg cauuu                                           25

<210> SEQ ID NO 3
<211> LENGTH: 25
<212> TYPE: RNA
<213> ORGANISM: Artificial Sequence
<220> FEATURE:
<223> OTHER INFORMATION: siRNA

<400> SEQUENCE: 3
gggaucgaug gaccguacau ggaaa                                           25

<210> SEQ ID NO 4
<211> LENGTH: 5386
<212> TYPE: DNA
<213> ORGANISM: Homo sapiens

<400> SEQUENCE: 4
gcggcggtgt ctcaggcggc aatggaagga tccgagcctg tggccgccca tcaggggaa       60 aaggcgtcct gttcttcctg ggggactggc agcacaaata aaaatttgcc cattatgtca    120
acagcatctg tggaaatcga tgatgcattg tatagtcgac agaggtacgt tcttggagac    180
acagcaatgc agaagatggc caagtcccat gttttcttaa gtgggatggg tggtcttggt    240
ttggaaattg caaagaatct tgttcttgca gggattaagg cagttacaat tcatgataca    300
gaaaaatgcc aagcatggga tctaggaacc aacttctttc tcagtgaaga tgatgttgtt    360
aataagagaa acagggctga agctgtactt aaacatattg cagaactaaa tccatacgtt    420
catgtcacat catcttctgc tcctttcaat gagaccacag atctctcctt tttagataaa    480
```

```
taccagtgtg tagtattgac tgagatgaaa cttccattgc agaagaagat caatgactt      540 tgccgttctc agtgccctcc aattaagttt atcagtgcag atgtacatgg aatttggtca     600
aggttatttt gtgatttcgg tgatgaattt gaagttttag atacaacagg agaagaacca    660
aaagaaattt tcatttcaaa cataacgcaa acaaatcctg gcattgttac ttgccttgaa    720
aatcatcctc acaaactgga gacaggacaa ttcctaacat ttcgagaaat taatggaatg    780
acaggtttaa atggatctat acaacaaata acggtgatat cgccattttc ttttagtatt    840
ggtgacacca cagaactgga accatatttta catggaggca tagctgtcca agttaagact   900
cctaaaacag tttttttga atcactggag aggcagttaa acatccaaa gtgccttatt     960 gtggatttta gcaaccctga ggcacccttta gagattcaca cagctatgct tgccttggac  1020
cagtttcagg agaaatacag tcgcaagcca atgttggat gccaacaaga ttcagaagaa    1080
ctgttgaaac tagcaacatc tataagtgaa accttggaag agaagcctga tgtaaatgct   1140
gacattgtgc attggctctc ttggactgcc caaggctttt tatctccact tgctgcagca    1200
gtaggaggtg ttgccagcca agaagtattg aaagctgtaa caggaaaaatt ttctcctttg  1260 tgccagtggt tatatcttga agcagcgat attgttgaat cactaggcaa acctgaatgt    1320
gaagaatttc tcccacgagg agatagatat gatgccttaa gagcttgcat tggagacact   1380
ttgtgtcaga aactgcaaaa tttaaacatc ttcttagtag ggtgtggagc cataggctgt   1440
gaaatgttga aaattttgc tttacttggt gttggcacaa gcaaagagaa aggaatgatt    1500
acagttacag atcctgactt gatagagaaa tccaacttaa atagacagtt cctatttcgt   1560
cctcatcaca tacagaaacc taaaagttac actgctgctg atgctactct gaaaataaat   1620
tctcaaataa agatagatgc acacctgaac aaagtatgtc caaccactga gaccatttac   1680
aatgatgagt tctatactaa acaagatgta attattacag cattagataa tgtggaagcc   1740
aggagatacg tagacagtcg ttgcttagca aatctaaggc ctcttttaga ttctggaaca   1800
atgggcacta agggacacac tgaagttatt gtaccgcatt tgactgagtc ttacaatagt   1860
catcgggatc ccccagaaga ggaaatacca ttttgtactc taaaatcctt tccagctgct   1920
attgaacaca ccatacagtg ggcaagagat aagtttgaaa gttccttttc ccacaaacct   1980
tcattgttta caaattttg gcaaacctat tcatctgcag aagaagtctt acagaagata    2040
cagagtggac acagtttaga aggctgtttt caagttataa agttacttag cagaagacct  2100
agaaattggt cccagtgtgt agaattagca agattaaagt ttgaaaaata ttttaaccat   2160
aaggctcttc agcttcttca ctgtttccct cttgacatac gattaaaaga tggcagttta   2220
ttttggcagt caccaaagag gccaccctct ccaataaaat ttgatttaaa tgagcctttg  2280
cacctcagtt tccttcagaa tgctgcaaaa ctatatgcta cagtatattg tattccattt   2340
gcagaagagg acttatcagc agatgccctc ttgaatattc tttcagaagt aaagattcag  2400
gaattcaagc cttccaataa ggttgttcaa acagatgaaa ctgcaaggaa accagaccat  2460
gttcctatta gcagtgaaga tgagaggaat gcaattttcc aactagaaaa ggctatttta   2520
tctaatgaag ccaccaaaag tgaccttcag atggcagtgc tttcatttga aaagatgat    2580 gatcataatg gacacataga tttcatcaca gctgcatcaa atcctcgtgc caaaatgtac   2640
agcattgaac cagctgaccg tttcaaaaca aagcgcatag ctggtaaaat tatacctgct   2700
atagcaacaa ccactgctac agtttctggc ttggttgcct tggagatgat caaagtaact  2760
ggtggctatc catttgaagc ttacaaaaat tgttttctta acttagccat tccaattgta   2820
gtatttacag agacaactga agtaaggaaa actaaaatca gaaatggaat atcatttaca   2880
```

```
atttgggatc gatggaccgt acatggaaaa gaagatttca ccctcttgga tttcataaat    2940
gcagtcaaag agaagtatgg aattgagcca acaatggtgg tacagggagt caaaatgctt    3000
tatgttcctg taatgcctgg tcatgcaaaa agattgaagt taacaatgca taaacttgta    3060
aaacctacta ctgaaaagaa atatgtggat cttactgtgt catttgctcc agacattgat    3120
ggagatgaag atttgccggg acctccagta agatactact tcagtcatga cactgattaa    3180
tacaagttgt cttaacgtta ctccaggacc acttgatttt ggaaagagtg cacttaattc    3240
agaagctaaa gaaaatcagt tcataatact atggatttct ctttcattaa gccttaattt    3300
taagggaaac atcagtaaga aactgcactg aagaattata aaacattttg ggcatagcca    3360
tacacttgtc taacggttca cacgtggcta tgatcacaag caactttgaa ctggaatgct    3420 attttacaaaa gttttgtgta ttaatctgtg tattaatctc tctggataaa aagaaggaaa    3480
aaatatgtat gaccagaaca gatatggatg aagaaattga aagcaacgaa tgcaactatt    3540
caaaaagttt aattttatga atttcttttt tgtttagtct tgaagactga ttttctatgc    3600
aaatagtgtt tggcatcctg cacctctgat atgatttggc tttgagaatt taataccact    3660
gggaagaagt atggtagtgg tggatgaagg gtggatattt taaattgtgc agttacagtt    3720
tactgtccta ttacctctgc tcgtttaacc agtttgttat atcactgtgt ccccaaaatc    3780
aggatttttg ttgatagcat cagtgttgta ggagcaatag gtcagatgag acatattaac    3840
ttagactaaa cgtgaacagt attatatgga ctctcacaac gctcttagag aatccgtgaa    3900
tgtgaacaga caaatgtggc taaccatttg attcttcagt atgccttcta atgtggctat    3960
tttatttatg tgagactcta aacctgattg tcctaatata taaaactaaa agattttgta    4020
aagggagtgt ctttagaaat agatgaaatg tagaatgtta aaaattattg ctagggtagt    4080 cttttttttcc agaaacctaa ttagggtatt aaattttgtg tttttttttt tttttttttt    4140
ttaaacagaa gcatgttatt tcattcccat tcccagaaag ggagttaatg aagataaaaa    4200
tttatttttt aaggtcttta ttgagagaaa ctttgttttc tgatatgaac tattgcagat    4260
gtttttataa atactttcat taaaatgatg taaacagtag tacccaacac tgtaaactca    4320
gtgaaaatag taaatgattc ttttattact aagactgtta tgcattctga agcagttggc    4380
ttttttttaa ccataggaag tcatttccct ctagctcctt cccttctact ctcctgctca    4440
gaccattagt aggtactttg ttaaataaaa aactagatta acatcaatat tactccaatt    4500
tggtatcttt tacactatgt attataccta ctttcttttt atttcattta caaatagttt    4560
aaattacttt atcaaccagc tgtattgttt ccctcttgta aaagtaccat caagtgggga    4620
aaatgtatgt ggaagtggag agtgaatttg tatgactaaa ggataatctg tacatgggga    4680
agtgggcaaa agtgaatagg atgaatttaa agaaaatgac tacctttgga aaaagaaat    4740 taaattttgt tcacatatcc taccctttcc cattgtgcat atcccaagtg tcatatttaa    4800
aactaaggtt acttaaaaca gaatccagga atatcaaggc tctgtggctt ggaattttag    4860
aggataggac taataaaagg acttttgcaa agaaggcttt tttccacgtt cactttgttt    4920
tgtgttcttt gaaagtaact gatacttttc gggtagttaa ttcagcagtc cataaatatg    4980
atccagtaac ttgcttatat tttattgaag tctcgacagc tcttcagaag taaatttaga    5040
acgatgctgt cagttcatat ttatagatat tagtgtttta gcagataaaa caaaatcaac    5100
aaaaattaag ttcattttgt gattaaacct gcaaccattt ttccattact ttttttctat    5160
agttaatggt tattgccatg atttcttctg tttggttcta ctaagctaga aagccagggt    5220
gaagttaatg ataattccca ttattttatt tctgtaccat gagattgctg ttgatgactg    5280
```

-continued

```
aaataccagg tgcaaaaatt aatgatttga tttttgtaca gtttcaatga gtatttttta    5340
cttattaaaa ataaattaag aaatgcaaaa aaaaaaaaaa aaaaaa                   5386
```

<210> SEQ ID NO 5
<211> LENGTH: 1052
<212> TYPE: PRT
<213> ORGANISM: Homo sapiens

<400> SEQUENCE: 5

```
Met Glu Gly Ser Glu Pro Val Ala Ala His Gln Gly Glu Lys Ala Ser
1               5                   10                  15

Cys Ser Ser Trp Gly Thr Gly Ser Thr Asn Lys Asn Leu Pro Ile Met
            20                  25                  30

Ser Thr Ala Ser Val Glu Ile Asp Asp Ala Leu Tyr Ser Arg Gln Arg
        35                  40                  45

Tyr Val Leu Gly Asp Thr Ala Met Gln Lys Met Ala Lys Ser His Val
    50                  55                  60

Phe Leu Ser Gly Met Gly Gly Leu Gly Leu Glu Ile Ala Lys Asn Leu
65                  70                  75                  80

Val Leu Ala Gly Ile Lys Ala Val Thr Ile His Asp Thr Glu Lys Cys
                85                  90                  95

Gln Ala Trp Asp Leu Gly Thr Asn Phe Phe Leu Ser Glu Asp Asp Val
            100                 105                 110

Val Asn Lys Arg Asn Arg Ala Glu Ala Val Leu Lys His Ile Ala Glu
        115                 120                 125

Leu Asn Pro Tyr Val His Val Thr Ser Ser Ser Ala Pro Phe Asn Glu
    130                 135                 140

Thr Thr Asp Leu Ser Phe Leu Asp Lys Tyr Gln Cys Val Val Leu Thr
145                 150                 155                 160

Glu Met Lys Leu Pro Leu Gln Lys Lys Ile Asn Asp Phe Cys Arg Ser
                165                 170                 175

Gln Cys Pro Pro Ile Lys Phe Ile Ser Ala Asp Val His Gly Ile Trp
            180                 185                 190

Ser Arg Leu Phe Cys Asp Phe Gly Asp Glu Phe Glu Val Leu Asp Thr
        195                 200                 205

Thr Gly Glu Glu Pro Lys Glu Ile Phe Ile Ser Asn Ile Thr Gln Thr
    210                 215                 220

Asn Pro Gly Ile Val Thr Cys Leu Glu Asn His Pro His Lys Leu Glu
225                 230                 235                 240

Thr Gly Gln Phe Leu Thr Phe Arg Glu Ile Asn Gly Met Thr Gly Leu
                245                 250                 255

Asn Gly Ser Ile Gln Gln Ile Thr Val Ile Ser Pro Phe Ser Phe Ser
            260                 265                 270

Ile Gly Asp Thr Thr Glu Leu Glu Pro Tyr Leu His Gly Gly Ile Ala
        275                 280                 285

Val Gln Val Lys Thr Pro Lys Thr Val Phe Phe Glu Ser Leu Glu Arg
    290                 295                 300

Gln Leu Lys His Pro Lys Cys Leu Ile Val Asp Phe Ser Asn Pro Glu
305                 310                 315                 320

Ala Pro Leu Glu Ile His Thr Ala Met Leu Ala Leu Asp Gln Phe Gln
                325                 330                 335

Glu Lys Tyr Ser Arg Lys Pro Asn Val Gly Cys Gln Gln Asp Ser Glu
            340                 345                 350

Glu Leu Leu Lys Leu Ala Thr Ser Ile Ser Glu Thr Leu Glu Glu Lys
        355                 360                 365
```

```
Pro Asp Val Asn Ala Asp Ile Val His Trp Leu Ser Trp Thr Ala Gln
    370                 375                 380

Gly Phe Leu Ser Pro Leu Ala Ala Val Gly Val Ala Ser Gln
385                 390                 395                 400

Glu Val Leu Lys Ala Val Thr Gly Lys Phe Ser Pro Leu Cys Gln Trp
                405                 410                 415

Leu Tyr Leu Glu Ala Ala Asp Ile Val Glu Ser Leu Gly Lys Pro Glu
            420                 425                 430

Cys Glu Glu Phe Leu Pro Arg Gly Asp Arg Tyr Asp Ala Leu Arg Ala
        435                 440                 445

Cys Ile Gly Asp Thr Leu Cys Gln Lys Leu Gln Asn Leu Asn Ile Phe
    450                 455                 460

Leu Val Gly Cys Gly Ala Ile Gly Cys Glu Met Leu Lys Asn Phe Ala
465                 470                 475                 480

Leu Leu Gly Val Gly Thr Ser Lys Glu Lys Gly Met Ile Thr Val Thr
                485                 490                 495

Asp Pro Asp Leu Ile Glu Lys Ser Asn Leu Asn Arg Gln Phe Leu Phe
            500                 505                 510

Arg Pro His His Ile Gln Lys Pro Lys Ser Tyr Thr Ala Ala Asp Ala
        515                 520                 525

Thr Leu Lys Ile Asn Ser Gln Ile Lys Ile Asp Ala His Leu Asn Lys
    530                 535                 540

Val Cys Pro Thr Thr Glu Thr Ile Tyr Asn Asp Glu Phe Tyr Thr Lys
545                 550                 555                 560

Gln Asp Val Ile Ile Thr Ala Leu Asp Asn Val Glu Ala Arg Arg Tyr
                565                 570                 575

Val Asp Ser Arg Cys Leu Ala Asn Leu Arg Pro Leu Leu Asp Ser Gly
            580                 585                 590

Thr Met Gly Thr Lys Gly His Thr Glu Val Ile Val Pro His Leu Thr
        595                 600                 605

Glu Ser Tyr Asn Ser His Arg Asp Pro Pro Glu Glu Ile Pro Phe
    610                 615                 620

Cys Thr Leu Lys Ser Phe Pro Ala Ala Ile Glu His Thr Ile Gln Trp
625                 630                 635                 640

Ala Arg Asp Lys Phe Glu Ser Ser Phe Ser His Lys Pro Ser Leu Phe
                645                 650                 655

Asn Lys Phe Trp Gln Thr Tyr Ser Ser Ala Glu Glu Val Leu Gln Lys
            660                 665                 670

Ile Gln Ser Gly His Ser Leu Glu Gly Cys Phe Gln Val Ile Lys Leu
        675                 680                 685

Leu Ser Arg Arg Pro Arg Asn Trp Ser Gln Cys Val Glu Leu Ala Arg
    690                 695                 700

Leu Lys Phe Glu Lys Tyr Phe Asn His Lys Ala Leu Gln Leu Leu His
705                 710                 715                 720

Cys Phe Pro Leu Asp Ile Arg Leu Lys Asp Gly Ser Leu Phe Trp Gln
                725                 730                 735

Ser Pro Lys Arg Pro Pro Ser Pro Ile Lys Phe Asp Leu Asn Glu Pro
            740                 745                 750

Leu His Leu Ser Phe Leu Gln Asn Ala Ala Lys Leu Tyr Ala Thr Val
        755                 760                 765

Tyr Cys Ile Pro Phe Ala Glu Glu Asp Leu Ser Ala Asp Ala Leu Leu
    770                 775                 780

Asn Ile Leu Ser Glu Val Lys Ile Gln Glu Phe Lys Pro Ser Asn Lys
```

|  |  |  | 785 |  |  |  | 790 |  |  |  | 795 |  |  |  | 800 |
|---|---|---|---|---|---|---|---|---|---|---|---|---|---|---|---|
| Val | Val | Gln | Thr | Asp | Glu | Thr | Ala | Arg | Lys | Pro | Asp | His | Val | Pro | Ile |
|  |  |  |  | 805 |  |  |  |  | 810 |  |  |  |  | 815 |  |
| Ser | Ser | Glu | Asp | Glu | Arg | Asn | Ala | Ile | Phe | Gln | Leu | Glu | Lys | Ala | Ile |
|  |  |  |  | 820 |  |  |  |  | 825 |  |  |  |  | 830 |  |
| Leu | Ser | Asn | Glu | Ala | Thr | Lys | Ser | Asp | Leu | Gln | Met | Ala | Val | Leu | Ser |
|  |  |  |  | 835 |  |  |  |  | 840 |  |  |  |  | 845 |  |
| Phe | Glu | Lys | Asp | Asp | His | Asn | Gly | His | Ile | Asp | Phe | Ile | Thr | Ala |  |
|  | 850 |  |  |  |  | 855 |  |  |  |  | 860 |  |  |  |  |
| Ala | Ser | Asn | Pro | Arg | Ala | Lys | Met | Tyr | Ser | Ile | Glu | Pro | Ala | Asp | Arg |
| 865 |  |  |  |  | 870 |  |  |  |  | 875 |  |  |  |  | 880 |
| Phe | Lys | Thr | Lys | Arg | Ile | Ala | Gly | Lys | Ile | Ile | Pro | Ala | Ile | Ala | Thr |
|  |  |  |  | 885 |  |  |  |  | 890 |  |  |  |  | 895 |  |
| Thr | Thr | Ala | Thr | Val | Ser | Gly | Leu | Val | Ala | Leu | Glu | Met | Ile | Lys | Val |
|  |  |  |  | 900 |  |  |  |  | 905 |  |  |  |  | 910 |  |
| Thr | Gly | Gly | Tyr | Pro | Phe | Glu | Ala | Tyr | Lys | Asn | Cys | Phe | Leu | Asn | Leu |
|  |  |  |  | 915 |  |  |  |  | 920 |  |  |  |  | 925 |  |
| Ala | Ile | Pro | Ile | Val | Val | Phe | Thr | Glu | Thr | Thr | Glu | Val | Arg | Lys | Thr |
|  | 930 |  |  |  |  | 935 |  |  |  |  | 940 |  |  |  |  |
| Lys | Ile | Arg | Asn | Gly | Ile | Ser | Phe | Thr | Ile | Trp | Asp | Arg | Trp | Thr | Val |
| 945 |  |  |  |  | 950 |  |  |  |  | 955 |  |  |  |  | 960 |
| His | Gly | Lys | Glu | Asp | Phe | Thr | Leu | Leu | Asp | Phe | Ile | Asn | Ala | Val | Lys |
|  |  |  |  | 965 |  |  |  |  | 970 |  |  |  |  | 975 |  |
| Glu | Lys | Tyr | Gly | Ile | Glu | Pro | Thr | Met | Val | Val | Gln | Gly | Val | Lys | Met |
|  |  |  |  | 980 |  |  |  |  | 985 |  |  |  |  | 990 |  |
| Leu | Tyr | Val | Pro | Val | Met | Pro | Gly | His | Ala | Lys | Arg | Leu | Lys | Leu | Thr |
|  |  |  |  | 995 |  |  |  |  | 1000 |  |  |  |  | 1005 |  |
| Met | His | Lys | Leu | Val | Lys | Pro | Thr | Thr | Glu | Lys | Lys | Tyr | Val | Asp |  |
| 1010 |  |  |  |  | 1015 |  |  |  |  | 1020 |  |  |  |  |  |
| Leu | Thr | Val | Ser | Phe | Ala | Pro | Asp | Ile | Asp | Gly | Asp | Glu | Asp | Leu |  |
|  | 1025 |  |  |  |  | 1030 |  |  |  |  | 1035 |  |  |  |  |
| Pro | Gly | Pro | Pro | Val | Arg | Tyr | Tyr | Phe | Ser | His | Asp | Thr | Asp |  |  |
|  | 1040 |  |  |  |  | 1045 |  |  |  |  | 1050 |  |  |  |  |

<210> SEQ ID NO 6
<211> LENGTH: 5101
<212> TYPE: DNA
<213> ORGANISM: Mus musculus

<400> SEQUENCE: 6

```
aggcgatgga gcggtccgag ccgttggctg tgctttcctg tgaagaggcg tcctgctcct    60
cctggggagc ctgcggtgca agtaaaaatt tacctaccat gacaacagaa tctttggaaa   120
tcgatgatgg attatacagt cgccagagat atgttcttgg tgacacagca atgcagaaga   180
tggccaagtc ctgtgtcttc ttaagtggta tgggtggtct tggagtggaa attgcaaaga   240
atcttgttct tgcagggatt aaggccctaa caattcatga tacaaaaaaa tgccaagcat   300
gggatctagg gaccaatttc ttcctgtgtg aagatgatgt tgttaatgag agaaacaggg   360
ctgaagctgt acttcatcgt attgcagaac taaatccata tgttcaggtc tcatcatcct   420
ctgcccctct tgatgaaacc acagacctct ctttcttaga aaatatcag tgtgtagtat   480
tgactgaaat aaaactgaca ttacaaaaga agatcaacaa ttttttgccat tctcattgcc   540
ctccaattaa gttcattagt gcagatgtac atggaatttg gtccaggttg ttttgtgatt   600
ttggtgatga atttgaagtt tcagatacaa caggagaaga accaaaagaa attttcattt   660
```

```
caaacataac gcaagctaat ccaggtattg tcacttgcct tgaaagtcat cctcacaagc    720
ttgagacagg acagttccta acatttcgag aaattcatgg aatgacaggc ttaaatggat    780
ctgtacaaca gataactgtc atatcaccat tttccttcag cattggtgat actacaaaac    840
tggacccata tttacatgga ggcatagccg tgcaggtgaa gactcctaaa acattctgct    900
ttgaacccct ggagagccag ataaaacatc caaggtgcct tattgcagat tttagcaaac    960
ctgaggcacc tttagagatt catctcgcta tgcttgcctt ggaccagttt caggagaact   1020
ataaccgtaa gccaaatatc agatgtcagc aggattcaga tgaactattg aagctaacag   1080
tatctataaa tgaaaccttg gaagagaagc ctgaagtgaa tgctgacatt gtgcactggc   1140
tttcgtggac tgcccaaggc tttttaccac cactcgctgc tgcagttgga ggtgttgcta   1200
gccaagaagt cttaaaagct gtgacgggga agttctcgcc cttgtgtcaa tggttgtacc   1260
ttgaagcagc agatactgtg gaatccctag gcaatcctgg gcatgaagag tttctcccac   1320
gaggagatag atatgatgcc atacgtgcct gcattggaaa tacattgtgt cagaagctac   1380
aaaatttgaa tatcttctta gtaggatgtg gtgccatagg ctgtgaaatg ttaaaaaatt   1440
ttgcattact gggtgttggt acaggcagag agaaaggaat ggtaacagtt acagatcctg   1500
acttgataga aaaatccaat ttaaacagac agttcctgtt tcgtcctcat cacatacaga   1560
aacctaaaag ctatactgct gctgaagcaa ctctgaaaat aaatcctcaa ttaaaaatag   1620
atgcacacct gaacaaagtt tgtccagcca ctgagagtat atacagtgat gaattttaca   1680
ctaagcaaga tatcattatt acagcactag ataatgtgga agccaggaga tatgtagaca   1740
gtcgctgttt agcaaatcta cggcctctct tagattctgg aacaatgggc accaagggac   1800
atactgaaat tatcgtacct caattaactg aatcttataa tagtcatcga ccccccccg   1860 aagaggaaat accattttgc actctaaagt cctttccagc agctatcgaa catactatcc   1920
agtgggcaag agacaagttt gaaagttcct tctcccacaa accttcactg tttaacaagt   1980
tttggcaagc atatccctct gcagaagatg tcttacagaa gatacaaaat ggacaaagtt   2040
tagaaggctg ttttcaagtt attaagctac ttagcagaag acctagaatt tggtcccagt   2100
gtgtagagtt agcaagacta aagtttgaaa aatactttaa ccataaggct ctgcagcttc   2160
ttcactgttt tcctcttgag acaagactaa aagatggcag tttgttttgg caatcaccaa   2220
aaaggccgcc ttctccaata aaatttgatt taaatgaacc tttgcacctc agttttcttc   2280
agagtgctgc aaaactatat gctacagtat attgtattcc gttttcagaa aaggacttat   2340
cagtgaatag cctcatggac attctttcag aagttaaaat tgaggaattc aagccttcca   2400
acaaggttgt tcaaacagac gaaactgcaa ggaagcccga ccatgttcct gtctccagtg   2460
aagatgaaag gaatgctgtt ttccaactag aagaggctct ttcctctaac aaagctacca   2520
aaagtgacct tcagatgaca gtgctttcat ttgaaaaaga tgatgaccgt aatggacaca   2580
tagatttcat cacagctgct tccaaccttc gagccaaaat gtatagcatt gaaccagctg   2640
accgttttaa aactaaacgc atagctggta aaattatacc tgctatagca acatctactg   2700
ctgcagtttc tggcttggtt gcttggagat gatcaaggt agctggtggc tatcccttcg   2760
acgcttacaa aaactgtttc cttaatttag ccattccaat aatagtgttt acagagacat   2820
ctgaagtaag aaaaactgaa atcagaaatg gaatatcatt tacaaatttgg gacagatgga   2880 ctgtacatgg aaaagaagat ttcaccctct cagatttcat aaatgctgtc aaagaaaact   2940
atggaattga gccgacaatg gtggtgcagg gagtcaaaat gctttatgtc cctgtaatgc   3000
caggtcatgc aaaaaggcta aagttaacaa tgcacaaact tgtgaagcct tccactgaga   3060
```

| | | |
|---|---|---|
| agaaatatgt ggatcttact gtgtcatttg ccccagacgc tgatggagat gaagatttgc | 3120 | |
| ccggccctcc agtgagatac tacttcagtc atgacactaa tgagtagcat tgttaccgag | 3180 | |
| atactccagc actactttat tttggaaagt gtacttaatt cagaagctca gctcataata | 3240 | |
| ctgtggattt cttttgcct taatgtaagg gaaccatcag tagggaactt actagagtgg | 3300 | |
| agaattacaa accatttga agcatagtac acatttgtct gttgctccct gcggttatga | 3360 | |
| tcacagcacc tttgaactgg aataccattt tctaatactt attaagccct gtggatgaaa | 3420 | |
| gaaggaacaa gaaatcattt atctatgacc agaagaaata aagatgaaga aattgaaaat | 3480 | |
| agtgaatttg tactattcag aaagttaaat ccttcttcaa cgtttctttt tttatttggt | 3540 | |
| atttgagacc cattatttca atataaatag tgtggcactg tgctgcttac atgattaggc | 3600 | |
| tttgaaaatt ccatagctga taggaagagg ggtggcagat aggtgatgag tagagattta | 3660 | |
| aaactgtagt tacagttagt gtcctgctac ctgtgctaac agtgtgatat attactccct | 3720 | |
| tccctaagtc aggattgtcc ctgatctgat cagtgttgta aacagtgagg taacatgaca | 3780 | |
| tgttaacttg gactaaatgt taacagtatt acatgcactc tgatagagaa tccataaatg | 3840 | |
| tgagcagata aatatggtta atcatttgat tgttaatata ccttattt atttatctgg | 3900 | |
| aagtctaaac tagtcatagt atttaagacc aaaaatttt tataaaggga atattcttag | 3960 | |
| aaatagatga aagttacaaa ttaatttggt tgtcttttt tcccttcca gcaatgtaat | 4020 | |
| ggagaaaaaa aaaaaatata tatatatagt atttttttt aaaggaggca tgttatttca | 4080 | |
| ctcttcattc ccaaatttggg gattgactga aatagaaaaa attatatttt tttagatttt | 4140 | |
| tcttactga agaaatact ccattgcctg atgtgaacag ttgctactta tgatataatt | 4200 | |
| gggtccatta aaatatataa acaatacttg actgtaaaat cactgaaaac agccagtaag | 4260 | |
| tcttttttac aagggttatc acgcattcta acaagtgct tacagcctct ggaagttact | 4320 | |
| tgcctggagt tcctattctt aagaccatta ctaaatactt tgatgaatta aaatttagat | 4380 | |
| tgcatcagta ttaactccaa tggtatctct ttatactcta tactttcttt ccatttacaa | 4440 | |
| acaatttatg atctctgtgg taaccagctt tttgttcct cctttacga agtgtccagt | 4500 | |
| tgggaaatgg ggtgagtttg tacaataaaa tgatctgttc attcagaggt ggagaaaagt | 4560 | |
| ggacagggtt tgttttaaag aactggctac ctttaaaata aactatagtt tttatcatat | 4620 | |
| cctacctttc ccattgttca taaattgaat ccatgaaat caaaggctct gtggcttaga | 4680 | |
| acttaatgac aaaaagaagt cctatttcc agttttcact ttgttttctc ttctttggta | 4740 | |
| gtaacgtatt ctgtaggtaa tcattcagga atcctcaaac atgaagcaat agcttggctc | 4800 | |
| tgtttactta agtctacacg tatctttgaa agtaaatgag agccatgctt tgtagagtgc | 4860 | |
| tttagtaaat aaaatcaacc aggtttggtt tgtttctaat taaatccaca accatttgt | 4920 | |
| cattgggttt tgttttgtt tttctgtagg tagtgattat tactgtccta ctaaattata | 4980 | |
| ctgaactgga aagccataat gaagttaatg acttttttt tttgttcatt ttgtacttta | 5040 | |
| agattcttgg tactaaaata tagctattga atactgagtg caaaaaaaaa aaaaaaaaa | 5100 | |
| a | 5101 | |

<210> SEQ ID NO 7
<211> LENGTH: 1053
<212> TYPE: PRT
<213> ORGANISM: Mus musculus

<400> SEQUENCE: 7

Met Glu Arg Ser Glu Pro Leu Ala Val Leu Ser Cys Glu Glu Ala Ser
1               5                   10                  15

-continued

```
Cys Ser Ser Trp Gly Ala Cys Gly Ala Ser Lys Asn Leu Pro Thr Met
         20                  25                  30
Thr Thr Glu Ser Leu Glu Ile Asp Asp Gly Leu Tyr Ser Arg Gln Arg
         35                  40                  45
Tyr Val Leu Gly Asp Thr Ala Met Gln Lys Met Ala Lys Ser Cys Val
         50                  55                  60
Phe Leu Ser Gly Met Gly Leu Gly Val Glu Ile Ala Lys Asn Leu
65                   70                  75                  80
Val Leu Ala Gly Ile Lys Ala Leu Thr Ile His Asp Thr Lys Lys Cys
                 85                  90                  95
Gln Ala Trp Asp Leu Gly Thr Asn Phe Phe Leu Cys Glu Asp Val
             100                 105                 110
Val Asn Glu Arg Asn Arg Ala Glu Ala Val Leu His Arg Ile Ala Glu
         115                 120                 125
Leu Asn Pro Tyr Val Gln Val Ser Ser Ser Ala Pro Leu Asp Glu
         130                 135                 140
Thr Thr Asp Leu Ser Phe Leu Glu Lys Tyr Gln Cys Val Val Leu Thr
145                 150                 155                 160
Glu Ile Lys Leu Thr Leu Gln Lys Lys Ile Asn Asn Phe Cys His Ser
                 165                 170                 175
His Cys Pro Pro Ile Lys Phe Ile Ser Ala Asp Val His Gly Ile Trp
             180                 185                 190
Ser Arg Leu Phe Cys Asp Phe Gly Asp Glu Phe Glu Val Ser Asp Thr
             195                 200                 205
Thr Gly Glu Glu Pro Lys Glu Ile Phe Ile Ser Asn Ile Thr Gln Ala
             210                 215                 220
Asn Pro Gly Ile Val Thr Cys Leu Glu Ser His Pro His Lys Leu Glu
225                 230                 235                 240
Thr Gly Gln Phe Leu Thr Phe Arg Glu Ile His Gly Met Thr Gly Leu
             245                 250                 255
Asn Gly Ser Val Gln Gln Ile Thr Val Ile Ser Pro Phe Ser Phe Ser
             260                 265                 270
Ile Gly Asp Thr Thr Lys Leu Asp Pro Tyr Leu His Gly Gly Ile Ala
             275                 280                 285
Val Gln Val Lys Thr Pro Lys Thr Phe Cys Phe Glu Pro Leu Glu Ser
             290                 295                 300
Gln Ile Lys His Pro Arg Cys Leu Ile Ala Asp Phe Ser Lys Pro Glu
305                 310                 315                 320
Ala Pro Leu Glu Ile His Leu Ala Met Leu Ala Leu Asp Gln Phe Gln
             325                 330                 335
Glu Asn Tyr Asn Arg Lys Pro Asn Ile Arg Cys Gln Gln Asp Ser Asp
             340                 345                 350
Glu Leu Leu Lys Leu Thr Val Ser Ile Asn Glu Thr Leu Glu Glu Lys
             355                 360                 365
Pro Glu Val Asn Ala Asp Ile Val His Trp Leu Ser Trp Thr Ala Gln
             370                 375                 380
Gly Phe Leu Pro Pro Leu Ala Ala Ala Val Gly Gly Val Ala Ser Gln
385                 390                 395                 400
Glu Val Leu Lys Ala Val Thr Gly Lys Phe Ser Pro Leu Cys Gln Trp
                 405                 410                 415
Leu Tyr Leu Glu Ala Ala Asp Thr Val Glu Ser Leu Gly Asn Pro Gly
             420                 425                 430
His Glu Glu Phe Leu Pro Arg Gly Asp Arg Tyr Asp Ala Ile Arg Ala
```

-continued

```
                435                 440                 445
Cys Ile Gly Asn Thr Leu Cys Gln Lys Leu Gln Asn Leu Asn Ile Phe
    450                 455                 460
Leu Val Gly Cys Gly Ala Ile Gly Cys Glu Met Leu Lys Asn Phe Ala
465                 470                 475                 480
Leu Leu Gly Val Gly Thr Gly Arg Glu Lys Gly Met Val Thr Val Thr
                485                 490                 495
Asp Pro Asp Leu Ile Glu Lys Ser Asn Leu Asn Arg Gln Phe Leu Phe
            500                 505                 510
Arg Pro His His Ile Gln Lys Pro Lys Ser Tyr Thr Ala Ala Glu Ala
            515                 520                 525
Thr Leu Lys Ile Asn Pro Gln Leu Lys Ile Asp Ala His Leu Asn Lys
        530                 535                 540
Val Cys Pro Ala Thr Glu Ser Ile Tyr Ser Asp Glu Phe Tyr Thr Lys
545                 550                 555                 560
Gln Asp Ile Ile Ile Thr Ala Leu Asp Asn Val Glu Ala Arg Arg Tyr
                565                 570                 575
Val Asp Ser Arg Cys Leu Ala Asn Leu Arg Pro Leu Leu Asp Ser Gly
            580                 585                 590
Thr Met Gly Thr Lys Gly His Thr Glu Ile Ile Val Pro Gln Leu Thr
            595                 600                 605
Glu Ser Tyr Asn Ser His Arg Asp Pro Pro Glu Glu Ile Pro Phe
        610                 615                 620
Cys Thr Leu Lys Ser Phe Pro Ala Ala Ile Glu His Thr Ile Gln Trp
625                 630                 635                 640
Ala Arg Asp Lys Phe Glu Ser Ser Phe Ser His Lys Pro Ser Leu Phe
                645                 650                 655
Asn Lys Phe Trp Gln Ala Tyr Pro Ser Ala Glu Asp Val Leu Gln Lys
            660                 665                 670
Ile Gln Asn Gly Gln Ser Leu Glu Gly Cys Phe Gln Val Ile Lys Leu
        675                 680                 685
Leu Ser Arg Arg Pro Arg Ile Trp Ser Gln Cys Val Glu Leu Ala Arg
690                 695                 700
Leu Lys Phe Glu Lys Tyr Phe Asn His Lys Ala Leu Gln Leu Leu His
705                 710                 715                 720
Cys Phe Pro Leu Glu Thr Arg Leu Lys Asp Gly Ser Leu Phe Trp Gln
                725                 730                 735
Ser Pro Lys Arg Pro Ser Pro Ile Lys Phe Asp Leu Asn Glu Pro
            740                 745                 750
Leu His Leu Ser Phe Leu Gln Ser Ala Ala Lys Leu Tyr Ala Thr Val
        755                 760                 765
Tyr Cys Ile Pro Phe Ser Glu Lys Asp Leu Ser Val Asn Ser Leu Met
    770                 775                 780
Asp Ile Leu Ser Glu Val Lys Ile Glu Glu Phe Lys Pro Ser Asn Lys
785                 790                 795                 800
Val Val Gln Thr Asp Glu Thr Ala Arg Lys Pro Asp His Val Pro Val
                805                 810                 815
Ser Ser Glu Asp Glu Arg Asn Ala Val Phe Gln Leu Glu Glu Ala Leu
            820                 825                 830
Ser Ser Asn Lys Ala Thr Lys Ser Asp Leu Gln Met Thr Val Leu Ser
        835                 840                 845
Phe Glu Lys Asp Asp Asp Arg Asn Gly His Ile Asp Phe Ile Thr Ala
    850                 855                 860
```

Ala Ser Asn Leu Arg Ala Lys Met Tyr Ser Ile Glu Pro Ala Asp Arg
865                 870                 875                 880

Phe Lys Thr Lys Arg Ile Ala Gly Lys Ile Pro Ala Ile Ala Thr
            885                 890                 895

Ser Thr Ala Ala Val Ser Gly Leu Val Ala Leu Glu Met Ile Lys Val
        900                 905                 910

Ala Gly Gly Tyr Pro Phe Asp Ala Tyr Lys Asn Cys Phe Leu Asn Leu
        915                 920                 925

Ala Ile Pro Ile Ile Val Phe Thr Glu Thr Ser Glu Val Arg Lys Thr
930                 935                 940

Glu Ile Arg Asn Gly Ile Ser Phe Thr Ile Trp Asp Arg Trp Thr Val
945                 950                 955                 960

His Gly Lys Glu Asp Phe Thr Leu Ser Asp Phe Ile Asn Ala Val Lys
                965                 970                 975

Glu Asn Tyr Gly Ile Glu Pro Thr Met Val Val Gln Gly Val Lys Met
                980                 985                 990

Leu Tyr Val Pro Val Met Pro Gly His Ala Lys Arg Leu Lys Leu Thr
        995                 1000                1005

Met His Lys Leu Val Lys Pro  Ser Thr Glu Lys Lys  Tyr Val Asp
1010                1015                     1020

Leu Thr Val Ser Phe Ala Pro  Asp Ala Asp Gly Asp  Glu Asp Leu
1025                1030                     1035

Pro Gly Pro Pro Val Arg Tyr  Tyr Phe Ser His Asp  Thr Asn Glu
1040                1045                     1050

<210> SEQ ID NO 8
<211> LENGTH: 3054
<212> TYPE: DNA
<213> ORGANISM: Homo sapiens
<220> FEATURE:
<221> NAME/KEY: misc_feature
<222> LOCATION: (3054)..(3054)
<223> OTHER INFORMATION: n is g, a, t or c

<400> SEQUENCE: 8
gcgatggcgg agagtccgac tgaggaggcg gcaacggcgg gcgccggggc ggcgggcccc    60
ggggcgagca gcgttgctgg tgttgttggc gttagcggca gcggcggcgg gttcgggccg   120
cctttcctgc cggatgtgtg ggcggcggcg gcggcagcgg gcggggccgg gggcccgggg   180
agcggcctgg ctccgctgcc cgggctcccg ccctcagccg ctgcccacgg ggccgcgctg   240
cttagccact gggaccccac gctcagctcc gactgggacg gcgagcgcac cgcgccgcag   300
tgtctactcc ggatcaagcg ggatatcatg tccatttata aggagcctcc tccaggaatg   360
ttcgttgtac ctgatactgt tgacatgact aagattcatg cattgatcac aggcccattt   420
gacactcctt atgaagggg tttcttcctg ttcgtgtttc ggtgtccgcc cgactatccc   480
atccacccac ctcgggtcaa actgatgaca acggcaata acacagtgag gtttaacccc   540
aacttctacc gcaatgggaa agtctgcttg agtattctag gtacatggac tggacctgcc   600
tggagcccag cccagagcat ctcctcagtg ctcatctcta ccagtccct gatgactgag   660 aaccctatc acaatgagcc cggctttgaa caggagagac atccaggaga cagcaaaaac   720
tataatgaat gtatccggca cgagaccatc agagttgcag tctgtgacat gatgaagga   780 aagtgtccct gtcctgaacc cctacgaggg gtgatggaga gtcctttct ggagtattac   840 gacttctatg aggtggcctg caaagatcgc ctgcaccttc aaggccaaac tatgcaggac   900
ccttttggag agaagcgggg ccactttgac taccagtccc tcttgatgcg cctgggactg   960

```
atacgtcaga aagtgctgga gaggctccat aatgagaatg cagaaatgga ctctgatagc    1020
agttcatctg ggacagagac agaccttcat gggagcctga gggtttagac cctgctccca    1080
tctccccttc ccccactcaa gagtcccagc agaatcccctt ccccccaccc cagggatgga    1140
gaggcactgt gtatctccct ccagactcga agtcatcctg caagatggca agaaccaagc    1200
aagctccgat cccagggtgt gggagtgggg gcctgttccc ggtctgacct ccttggcact    1260
ggagcatctg ggcttcgtt catccattca tcccgtatca ggggccaagg tacctttaca    1320
ggagcaccta gagcgagggc ctttggcaaa acaaaacaa ccaacacacc tctccacagg    1380
gccagctcct tagggataag tggaagatgg aaattgcaat tccaagaggg agtgtgccca    1440
aatgatttat ggggatacct ggaagggagc ttggggtggg ggctgtctgt gacacttaag    1500
cagtctgggt ggttgtctat ttgtctgtct tcagtcttga agcagggctt cccaatgccc    1560
ttttcctccc tgccttcctt cccccattat ttcccacagg ccagcataat tttgtttttc    1620
ctaatttata gtcactgttc tagacagacc aaagagaagg aacagtggtg gagtctaggc    1680
tgctgatcag taagctttac ctagcacctg agcacctttc tcccctcccc tctttcctca    1740
cccttttcta gatgtaagac agaaggtaaa tgtgactggg acttaaccaa ggtcttggta    1800
aagcctgcat ggcaccgtaa gaagctgaaa atactgtttg ttcccgcaat cactgatttg    1860
aaaagttccc aacacaggca gctgctgtgt atatgggatt agagccacta catagaatag    1920
tctcttacag attttcataa atactagtca caataagggg attttcttg ggggtggagt    1980 aagggggaga ctgatgctag tccttgttgt attttgttgg gctgtccttg tgtattttca    2040
ccccagcctg tagtcctcct cacttcaacc ccagggattt gtggggagca agggtagcca    2100
atggcagagg gggttgggggc tgggactctg gaggctcctc cccttctttc tcttccttct    2160 gcctccccg tgcccccagc tgctcttgtc actgtctctg atgggtattt gcctggcttt    2220
gttgcttctc tatctgtatt tagctgcagt gatcctttag ctggttggct cagaaaaaaa    2280
aaaatgtgct ttaggtgccc tgtaatcctg ggcatcaagg gaatccatcc ttcccctttt    2340
tgatatgttc tccccgtact tccagattta ttgttatggc tcccagtggg tattggcgat    2400
tcttgtgatg cagggcctca gtcagtgtcc agccatgcat aagggagagg atagtgtgta    2460
cctgccctgc cctctgctat gaaggtctct gccttgtgga tcatgggact ccccttggag    2520
gatctgtgca aagggggggct gggcacaaag gagaatgtcc tatttgggag gcaggaagc    2580 aaaggaactg gacagggatt ggtgggcttg gggaacggaa gtttatcttg gatacccttg    2640
aagaggctgg gtctcttcac atgaagatcg aaaagggacc ctgcttccaa tttccctctt    2700
ccattcctcg agctactcca gggcttagaa gaatgctctt ggtctgtggg tccagtgttg    2760
tctgtcatcc atttaagtgt tcccactttc aagtgacaat cctctccttg gccctgccat    2820
agggcagagc atgtctggca tagcagcctg acttttatgc cctaatcttg agttgaggaa    2880
atatatgcac aggagtcaaa gagatgtctt tatatctgac tgtatataaa tgaagttttt    2940 ttgtttttt tgttttcctt tttggtgcaa taaagtttgt tttggcagaa aaaaaaaaa    3000 aaaaaaaaa aaaaaaaaa aaaaaaaaa aaaaaaaaa aaaaaaaaa aaan            3054
```

<210> SEQ ID NO 9
<211> LENGTH: 354
<212> TYPE: PRT
<213> ORGANISM: Homo sapiens

<400> SEQUENCE: 9

```
Met Ala Glu Ser Pro Thr Glu Glu Ala Ala Thr Ala Gly Ala Gly Ala
1               5                   10                  15
```

```
Ala Gly Pro Gly Ala Ser Ser Val Ala Gly Val Gly Val Ser Gly
            20                  25                  30

Ser Gly Gly Gly Phe Gly Pro Pro Phe Leu Pro Asp Val Trp Ala Ala
        35                  40                  45

Ala Ala Ala Gly Gly Ala Gly Gly Pro Gly Ser Gly Leu Ala Pro
 50              55                  60

Leu Pro Gly Leu Pro Pro Ser Ala Ala His Gly Ala Ala Leu Leu
 65          70                  75                  80

Ser His Trp Asp Pro Thr Leu Ser Ser Asp Trp Gly Glu Arg Thr
                85                  90                  95

Ala Pro Gln Cys Leu Leu Arg Ile Lys Arg Asp Ile Met Ser Ile Tyr
            100                 105                 110

Lys Glu Pro Pro Pro Gly Met Phe Val Val Pro Asp Thr Val Asp Met
            115                 120                 125

Thr Lys Ile His Ala Leu Ile Thr Gly Pro Phe Asp Thr Pro Tyr Glu
130                 135                 140

Gly Gly Phe Phe Leu Phe Val Phe Arg Cys Pro Pro Asp Tyr Pro Ile
145                 150                 155                 160

His Pro Pro Arg Val Lys Leu Met Thr Thr Gly Asn Asn Thr Val Arg
                165                 170                 175

Phe Asn Pro Asn Phe Tyr Arg Asn Gly Lys Val Cys Leu Ser Ile Leu
            180                 185                 190

Gly Thr Trp Thr Gly Pro Ala Trp Ser Pro Ala Gln Ser Ile Ser Ser
            195                 200                 205

Val Leu Ile Ser Ile Gln Ser Leu Met Thr Glu Asn Pro Tyr His Asn
210                 215                 220

Glu Pro Gly Phe Glu Gln Glu Arg His Pro Gly Asp Ser Lys Asn Tyr
225                 230                 235                 240

Asn Glu Cys Ile Arg His Glu Thr Ile Arg Val Ala Val Cys Asp Met
                245                 250                 255

Met Glu Gly Lys Cys Pro Cys Pro Glu Pro Leu Arg Gly Val Met Glu
            260                 265                 270

Lys Ser Phe Leu Glu Tyr Tyr Asp Phe Tyr Glu Val Ala Cys Lys Asp
            275                 280                 285

Arg Leu His Leu Gln Gly Gln Thr Met Gln Asp Pro Phe Gly Glu Lys
            290                 295                 300

Arg Gly His Phe Asp Tyr Gln Ser Leu Leu Met Arg Leu Gly Leu Ile
305                 310                 315                 320

Arg Gln Lys Val Leu Glu Arg Leu His Asn Glu Asn Ala Glu Met Asp
                325                 330                 335

Ser Asp Ser Ser Ser Gly Thr Glu Thr Asp Leu His Gly Ser Leu
            340                 345                 350

Arg Val

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide sequence used for RNA
      interference

<400> SEQUENCE: 10
ccttggaaga gaagcctgat gtaaa                                          25
```

```
<210> SEQ ID NO 11
<211> LENGTH: 25
<212> TYPE: DNA
<213> ORGANISM: Artificial sequence
<220> FEATURE:
<223> OTHER INFORMATION: Oligonucleotide sequence used for RNA
      interference

<400> SEQUENCE: 11
acactgaagt tattgtaccg cattt                                         25

<210> SEQ ID NO 12
<211> LENGTH: 25
<212> TYPE: DNA
<213> ORGANISM: Artificial sequence
<220> FEATURE:
<223> OTHER INFORMATION: Oligonucleotide sequence used for RNA
      interference

<400> SEQUENCE: 12
gggatcgatg gaccgtacat ggaaa                                         25

<210> SEQ ID NO 13
<211> LENGTH: 25
<212> TYPE: DNA
<213> ORGANISM: Artificial sequence
<220> FEATURE:
<223> OTHER INFORMATION: Oligonucleotide sequence used for RNA
      interference

<400> SEQUENCE: 13
gagaagctgg gcaagcagaa gtatt                                         25

<210> SEQ ID NO 14
<211> LENGTH: 25
<212> TYPE: DNA
<213> ORGANISM: Artificial sequence
<220> FEATURE:
<223> OTHER INFORMATION: Oligonucleotide sequence used for RNA
      interference

<400> SEQUENCE: 14
ccgacagctt gactcctaca agaat                                         25

<210> SEQ ID NO 15
<211> LENGTH: 25
<212> TYPE: DNA
<213> ORGANISM: Artificial sequence
<220> FEATURE:
<223> OTHER INFORMATION: Oligonucleotide sequence used for RNA
      interference

<400> SEQUENCE: 15
tcctcaactt ggccctgcct ttctt                                         25

<210> SEQ ID NO 16
<211> LENGTH: 1058
<212> TYPE: PRT
<213> ORGANISM: Homo sapiens

<400> SEQUENCE: 16

Met Ser Ser Ser Pro Leu Ser Lys Lys Arg Arg Val Ser Gly Pro Asp
1               5                   10                  15

Pro Lys Pro Gly Ser Asn Cys Ser Pro Ala Gln Ser Val Leu Ser Glu
            20                  25                  30

Val Pro Ser Val Pro Thr Asn Gly Met Ala Lys Asn Gly Ser Glu Ala
        35                  40                  45
```

```
Asp Ile Asp Glu Gly Leu Tyr Ser Arg Gln Leu Tyr Val Leu Gly His
    50                  55                  60
Glu Ala Met Lys Arg Leu Gln Thr Ser Ser Val Leu Val Ser Gly Leu
65                  70                  75                  80
Arg Gly Leu Gly Val Glu Ile Ala Lys Asn Ile Ile Leu Gly Gly Val
                85                  90                  95
Lys Ala Val Thr Leu His Asp Gln Gly Thr Ala Gln Trp Ala Asp Leu
            100                 105                 110
Ser Ser Gln Phe Tyr Leu Arg Glu Glu Asp Ile Gly Lys Asn Arg Ala
        115                 120                 125
Glu Val Ser Gln Pro Arg Leu Ala Glu Leu Asn Ser Tyr Val Pro Val
    130                 135                 140
Thr Ala Tyr Thr Gly Pro Leu Val Glu Asp Phe Leu Ser Gly Phe Gln
145                 150                 155                 160
Val Val Val Leu Thr Asn Thr Pro Leu Glu Asp Gln Leu Arg Val Gly
                165                 170                 175
Glu Phe Cys His Asn Arg Gly Ile Lys Leu Val Val Ala Asp Thr Arg
            180                 185                 190
Gly Leu Phe Gly Gln Leu Phe Cys Asp Phe Gly Glu Glu Met Ile Leu
        195                 200                 205
Thr Asp Ser Asn Gly Glu Gln Pro Leu Ser Ala Met Val Ser Met Val
    210                 215                 220
Thr Lys Asp Asn Pro Gly Val Val Thr Cys Leu Asp Glu Ala Arg His
225                 230                 235                 240
Gly Phe Glu Ser Gly Asp Phe Val Ser Phe Ser Glu Val Gln Gly Met
                245                 250                 255
Val Glu Leu Asn Gly Asn Gln Pro Met Glu Ile Lys Val Leu Gly Pro
            260                 265                 270
Tyr Thr Phe Ser Ile Cys Asp Thr Ser Asn Phe Ser Asp Tyr Ile Arg
        275                 280                 285
Gly Gly Ile Val Ser Gln Val Lys Val Pro Lys Lys Ile Ser Phe Lys
    290                 295                 300
Ser Leu Val Ala Ser Leu Ala Glu Pro Asp Phe Val Val Thr Asp Phe
305                 310                 315                 320
Ala Lys Phe Ser Arg Pro Ala Gln Leu His Ile Gly Phe Gln Ala Leu
                325                 330                 335
His Gln Phe Cys Ala Gln His Gly Arg Pro Pro Arg Pro Arg Asn Glu
            340                 345                 350
Glu Asp Ala Ala Glu Leu Val Ala Leu Ala Gln Ala Val Asn Ala Arg
        355                 360                 365
Ala Leu Pro Ala Val Gln Gln Asn Asn Leu Asp Glu Asp Leu Ile Arg
    370                 375                 380
Lys Leu Ala Tyr Val Ala Ala Gly Asp Leu Ala Pro Ile Asn Ala Phe
385                 390                 395                 400
Ile Gly Gly Leu Ala Ala Gln Glu Val Met Lys Ala Cys Ser Gly Lys
                405                 410                 415
Phe Met Pro Ile Met Gln Trp Leu Tyr Phe Asp Ala Leu Glu Cys Leu
            420                 425                 430
Pro Glu Asp Lys Glu Val Leu Thr Glu Asp Lys Cys Leu Gln Arg Gln
        435                 440                 445
Asn Arg Tyr Asp Gly Gln Val Ala Val Phe Gly Ser Asp Leu Gln Glu
    450                 455                 460
Lys Leu Gly Lys Gln Lys Tyr Phe Leu Val Gly Ala Gly Ala Ile Gly
```

```
                465                 470                 475                 480
Cys Glu Leu Leu Lys Asn Phe Ala Met Ile Gly Leu Gly Cys Gly Glu
                    485                 490                 495

Gly Gly Glu Ile Ile Val Thr Asp Met Asp Thr Ile Glu Lys Ser Asn
                500                 505                 510

Leu Asn Arg Gln Phe Leu Phe Arg Pro Trp Asp Val Thr Lys Leu Lys
            515                 520                 525

Ser Asp Thr Ala Ala Ala Val Arg Gln Met Asn Pro His Ile Arg
        530                 535                 540

Val Thr Ser His Gln Asn Arg Val Gly Pro Asp Thr Glu Arg Ile Tyr
545                 550                 555                 560

Asp Asp Asp Phe Phe Gln Asn Leu Asp Gly Val Ala Asn Ala Leu Asp
                565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
        595                 600                 605

Val Val Ile Pro Phe Leu Thr Glu Ser Tyr Ser Ser Ser Gln Asp Pro
    610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
                645                 650                 655

Lys Gln Pro Ala Glu Asn Val Asn Gln Tyr Leu Thr Asp Pro Lys Phe
            660                 665                 670

Val Glu Arg Thr Leu Arg Leu Ala Gly Thr Gln Pro Leu Glu Val Leu
        675                 680                 685

Glu Ala Val Gln Arg Ser Leu Val Leu Gln Arg Pro Gln Thr Trp Ala
    690                 695                 700

Asp Cys Val Thr Trp Ala Cys His His Trp His Thr Gln Tyr Ser Asn
705                 710                 715                 720

Asn Ile Arg Gln Leu Leu His Asn Phe Pro Pro Asp Gln Leu Thr Ser
                725                 730                 735

Ser Gly Ala Pro Phe Trp Ser Gly Pro Lys Arg Cys Pro His Pro Leu
            740                 745                 750

Thr Phe Asp Val Asn Asn Pro Leu His Leu Asp Tyr Val Met Ala Ala
        755                 760                 765

Ala Asn Leu Phe Ala Gln Thr Tyr Gly Leu Thr Gly Ser Gln Asp Arg
    770                 775                 780

Ala Ala Val Ala Thr Phe Leu Gln Ser Val Gln Val Pro Glu Phe Thr
785                 790                 795                 800

Pro Lys Ser Gly Val Lys Ile His Val Ser Asp Gln Glu Leu Gln Ser
                805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
        835                 840                 845

Phe Glu Lys Asp Asp Asp Ser Asn Phe His Met Asp Phe Ile Val Ala
    850                 855                 860

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Ile Pro Ala Ile Ala Thr
                885                 890                 895
```

```
Thr Thr Ala Ala Val Val Gly Leu Val Cys Leu Glu Leu Tyr Lys Val
            900                 905                 910

Val Gln Gly His Arg Gln Leu Asp Ser Tyr Lys Asn Gly Phe Leu Asn
            915                 920                 925

Leu Ala Leu Pro Phe Phe Gly Phe Ser Glu Pro Leu Ala Ala Pro Arg
            930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
            965                 970                 975

Asp Tyr Phe Lys Thr Glu His Lys Leu Glu Ile Thr Met Leu Ser Gln
            980                 985                 990

Gly Val Ser Met Leu Tyr Ser Phe Phe Met Pro Ala Ala Lys Leu Lys
            995                 1000                1005

Glu Arg Leu Asp Gln Pro Met Thr Glu Ile Val Ser Arg Val Ser
            1010                1015                1020

Lys Arg Lys Leu Gly Arg His Val Arg Ala Leu Val Leu Glu Leu
            1025                1030                1035

Cys Cys Asn Asp Glu Ser Gly Glu Asp Val Glu Val Pro Tyr Val
            1040                1045                1050

Arg Tyr Thr Ile Arg
            1055

<210> SEQ ID NO 17
<211> LENGTH: 1058
<212> TYPE: PRT
<213> ORGANISM: Mus musculus

<400> SEQUENCE: 17

Met Ser Ser Ser Pro Leu Ser Lys Lys Arg Arg Val Ser Gly Pro Asp
1               5                   10                  15

Pro Lys Pro Gly Ser Asn Cys Ser Pro Ala Gln Ser Ala Leu Ser Glu
            20                  25                  30

Val Ser Ser Val Pro Thr Asn Gly Met Ala Lys Asn Gly Ser Glu Ala
            35                  40                  45

Asp Ile Asp Glu Ser Leu Tyr Ser Arg Gln Leu Tyr Val Leu Gly His
50                  55                  60

Glu Ala Met Lys Met Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
            85                  90                  95

Lys Ala Val Thr Leu His Asp Gln Gly Thr Thr Gln Trp Ala Asp Leu
            100                 105                 110

Ser Ser Gln Phe Tyr Leu Arg Glu Glu Asp Ile Gly Lys Asn Arg Ala
            115                 120                 125

Glu Val Ser Gln Pro Arg Leu Ala Glu Leu Asn Ser Tyr Val Pro Val
            130                 135                 140

Thr Ala Tyr Thr Gly Pro Leu Val Glu Asp Phe Leu Ser Ser Phe Gln
145                 150                 155                 160

Val Val Val Leu Thr Asn Ser Pro Leu Glu Ala Gln Leu Arg Val Gly
            165                 170                 175

Glu Phe Cys His Ser Arg Gly Ile Lys Leu Val Val Ala Asp Thr Arg
            180                 185                 190

Gly Leu Phe Gly Gln Leu Phe Cys Asp Phe Gly Glu Glu Met Val Leu
            195                 200                 205
```

```
Thr Asp Ser Asn Gly Glu Gln Pro Leu Ser Ala Met Val Ser Met Val
    210                 215                 220
Thr Lys Asp Asn Pro Gly Val Val Thr Cys Leu Asp Glu Ala Arg His
225                 230                 235                 240
Gly Phe Glu Thr Gly Asp Phe Val Ser Phe Ser Glu Val Gln Gly Met
                245                 250                 255
Ile Gln Leu Asn Gly Cys Gln Pro Met Glu Ile Lys Val Leu Gly Pro
                260                 265                 270
Tyr Thr Phe Ser Ile Cys Asp Thr Ser Asn Phe Ser Asp Tyr Ile Arg
            275                 280                 285
Gly Gly Ile Val Ser Gln Val Lys Val Pro Lys Ile Ser Phe Lys
290                 295                 300
Ser Leu Pro Ala Ser Leu Val Glu Pro Asp Phe Val Met Thr Asp Phe
305                 310                 315                 320
Ala Lys Tyr Ser Arg Pro Ala Gln Leu His Ile Gly Phe Gln Ala Leu
                325                 330                 335
His Gln Phe Cys Ala Leu His Asn Gln Pro Arg Pro Arg Asn Glu
                340                 345                 350
Glu Asp Ala Thr Glu Leu Val Gly Leu Ala Gln Ala Val Asn Ala Arg
                355                 360                 365
Ser Pro Pro Ser Val Lys Gln Asn Ser Leu Asp Glu Asp Leu Ile Arg
370                 375                 380
Lys Leu Ala Tyr Val Ala Ala Gly Asp Leu Ala Pro Ile Asn Ala Phe
385                 390                 395                 400
Ile Gly Gly Leu Ala Ala Gln Glu Val Met Lys Ala Cys Ser Gly Lys
                405                 410                 415
Phe Met Pro Ile Met Gln Trp Leu Tyr Phe Asp Ala Leu Glu Cys Leu
                420                 425                 430
Pro Glu Asp Lys Glu Ala Leu Thr Glu Glu Lys Cys Leu Pro Arg Gln
                435                 440                 445
Asn Arg Tyr Asp Gly Gln Val Ala Val Phe Gly Ser Asp Phe Gln Glu
            450                 455                 460
Lys Leu Ser Lys Gln Lys Tyr Phe Leu Val Gly Ala Gly Ala Ile Gly
465                 470                 475                 480
Cys Glu Leu Leu Lys Asn Phe Ala Met Ile Gly Leu Gly Cys Gly Glu
                485                 490                 495
Gly Gly Glu Val Val Val Thr Asp Met Asp Thr Ile Glu Lys Ser Asn
                500                 505                 510
Leu Asn Arg Gln Phe Leu Phe Arg Pro Trp Asp Val Thr Lys Leu Lys
                515                 520                 525
Ser Asp Thr Ala Ala Ala Val Arg Gln Met Asn Pro Tyr Ile Gln
530                 535                 540
Val Thr Ser His Gln Asn Arg Val Gly Pro Asp Thr Glu Arg Ile Tyr
545                 550                 555                 560
Asp Asp Asp Phe Phe Gln Asn Leu Asp Gly Val Ala Asn Ala Leu Asp
                565                 570                 575
Asn Ile Asp Ala Arg Met Tyr Met Asp Arg Arg Cys Val Tyr Tyr Arg
                580                 585                 590
Lys Pro Leu Leu Glu Ser Gly Thr Leu Gly Thr Lys Gly Asn Val Gln
            595                 600                 605
Val Val Ile Pro Phe Leu Thr Glu Ser Tyr Ser Ser Ser Gln Asp Pro
            610                 615                 620
Pro Glu Lys Ser Ile Pro Ile Cys Thr Leu Lys Asn Phe Pro Asn Ala
625                 630                 635                 640
```

```
Ile Glu His Thr Leu Gln Trp Ala Arg Asp Glu Phe Glu Gly Leu Phe
            645                 650                 655

Lys Gln Pro Ala Glu Asn Val Asn Gln Tyr Leu Thr Asp Ser Lys Phe
            660                 665                 670

Val Glu Arg Thr Leu Arg Leu Ala Gly Thr Gln Pro Leu Glu Val Leu
            675                 680                 685

Glu Ala Val Gln Arg Ser Leu Val Leu Gln Arg Pro Gln Thr Trp Gly
690                 695                 700

Asp Cys Val Thr Trp Ala Cys His His Trp His Thr Gln Tyr Cys Asn
705                 710                 715                 720

Asn Ile Arg Gln Leu Leu His Asn Phe Pro Pro Asp Gln Leu Thr Ser
                725                 730                 735

Ser Gly Ala Pro Phe Trp Ser Gly Pro Lys Arg Cys Pro His Pro Leu
            740                 745                 750

Thr Phe Asp Val Asn Asn Thr Leu His Leu Asp Tyr Val Met Ala Ala
            755                 760                 765

Ala Asn Leu Phe Ala Gln Thr Tyr Gly Leu Thr Gly Ser Gln Asp Arg
770                 775                 780

Ala Ala Val Ala Ser Leu Leu Gln Ser Val Gln Val Pro Glu Phe Thr
785                 790                 795                 800

Pro Lys Ser Gly Val Lys Ile His Val Ser Asp Gln Glu Leu Gln Ser
            805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
            835                 840                 845

Phe Glu Lys Asp Asp Ser Asn Phe His Met Asp Phe Ile Val Ala
            850                 855                 860

Ala Ser Asn Leu Arg Ala Glu Asn Tyr Asp Ile Ser Pro Ala Asp Arg
865                 870                 875                 880

His Lys Ser Lys Leu Ile Ala Gly Lys Ile Ile Pro Ala Ile Ala Thr
            885                 890                 895

Thr Thr Ala Ala Val Val Gly Leu Val Cys Leu Glu Leu Tyr Lys Val
            900                 905                 910

Val Gln Gly His Gln Leu Asp Ser Tyr Lys Asn Gly Phe Leu Asn
            915                 920                 925

Leu Ala Leu Pro Phe Phe Gly Phe Ser Glu Pro Leu Ala Ala Pro Arg
930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
            965                 970                 975

Asp Tyr Phe Lys Thr Glu His Lys Leu Glu Ile Thr Met Leu Ser Gln
            980                 985                 990

Gly Val Ser Met Leu Tyr Ser Phe Phe Met Pro Ala Ala Lys Leu Lys
            995                 1000                1005

Glu Arg Leu Asp Gln Pro Met Thr Glu Ile Val Ser Arg Val Ser
            1010                1015                1020

Lys Arg Lys Leu Gly Arg His Val Arg Ala Leu Val Leu Glu Leu
            1025                1030                1035

Cys Cys Asn Asp Glu Ser Gly Glu Asp Val Glu Val Pro Tyr Val
            1040                1045                1050

Arg Tyr Thr Ile Arg
```

-continued

```
                           1055

<210> SEQ ID NO 18
<211> LENGTH: 1058
<212> TYPE: PRT
<213> ORGANISM: Mus musculus

<400> SEQUENCE: 18
```

Met Ser Ser Val Leu Ser Lys Lys Arg Lys Val Ser Gly Pro Asp
1               5                   10                  15

Ser Ser Leu Asp Ser Ser Trp Ser Pro Thr Tyr Ser Val Met Phe Gly
                20                  25                  30

Val Pro Pro Gly Pro Thr Asn Glu Met Ser Lys Asn Lys Glu Met Asp
            35                  40                  45

Ile Asp Glu Ser Leu Tyr Ser Arg Gln Leu Tyr Val Leu Gly His Glu
50                  55                  60

Ala Met Lys His Leu Gln Ala Ser Ser Val Leu Ile Ser Gly Leu Gln
65                  70                  75                  80

Gly Leu Gly Val Glu Ile Ala Lys Asn Ile Ile Leu Gly Gly Val Lys
                85                  90                  95

Ala Val Thr Leu His Asp Gln Gly Ile Ala Gln Trp Ala Asp Leu Ser
            100                 105                 110

Ser Gln Phe Cys Leu Arg Glu Glu Asp Ile Gly Lys Asn Arg Ala Glu
        115                 120                 125

Ile Ser Gln Pro Arg Leu Ala Glu Leu Asn Ser Tyr Val Pro Val Phe
130                 135                 140

Ala Tyr Thr Gly Pro Leu Ile Glu Glu Phe Leu Ser Gly Phe Gln Val
145                 150                 155                 160

Val Val Leu Thr Asn Thr Pro Leu Glu Tyr Gln Leu Gln Val Gly Glu
                165                 170                 175

Phe Cys His Ser His Gly Ile Lys Leu Val Val Ala Asp Thr Arg Gly
            180                 185                 190

Leu Val Gly Gln Leu Phe Cys Asp Phe Gly Glu Glu Met Ile Leu Thr
        195                 200                 205

Asp Ser Asn Gly Glu Gln Pro Leu Ser Ala Met Val Ser Met Ile Thr
210                 215                 220

Lys Glu Asn Pro Gly Ile Val Thr Cys Leu Glu Asp Ser Arg His Gly
225                 230                 235                 240

Phe Glu Ser Gly Asp Phe Ile Ser Phe Thr Glu Val Gln Gly Met Ser
                245                 250                 255

Glu Leu Asn Gly Ile Gly Pro Ile Glu Ile Lys Val Leu Gly Pro Tyr
            260                 265                 270

Thr Phe Ser Ile Cys Asp Thr Ser Ser Phe Ser Glu Tyr Ile Arg Gly
        275                 280                 285

Gly Ile Val Ser Gln Val Lys Val Pro Arg Lys Ile Asn Phe Lys Pro
290                 295                 300

Leu Leu Ala Ser Leu Ala Glu Pro Glu Phe Val Val Thr Asp Phe Ala
305                 310                 315                 320

Lys Cys Cys His Pro Ala Gln Leu His Ile Gly Phe Gln Ala Leu His
                325                 330                 335

Gln Phe Cys Thr Gln His Ser Arg Pro Pro Arg Pro Asn Glu Glu
            340                 345                 350

Asp Ala Glu Glu Leu Val Thr Leu Ala Gln Ser Val Asn Ala Gln Ala
        355                 360                 365

Leu Pro Ala Val Gln Gln Asp Cys Leu Asp Ile Asp Leu Ile Arg Lys

```
            370             375             380
Leu Ala Tyr Val Ala Ala Gly Asp Leu Ala Pro Met Asn Ala Phe Phe
385                 390                 395                 400

Gly Gly Leu Ala Ala Gln Glu Val Met Lys Ala Cys Ser Gly Lys Phe
                405                 410                 415

Met Pro Ile Arg Gln Trp Leu Tyr Phe Asp Ala Leu Glu Cys Leu Pro
            420                 425                 430

Glu His Arg Val Ala Phe Met Glu Asp Lys Cys Leu Pro His Gln Asn
                435                 440                 445

Arg Tyr Asp Gly Gln Val Ala Val Phe Gly Ser Asp Leu Gln Glu Lys
450                 455                 460

Leu Gly Lys Gln Lys Tyr Phe Leu Val Gly Ala Gly Ala Ile Gly Cys
465                 470                 475                 480

Glu Leu Leu Lys Asn Phe Ala Met Ile Gly Leu Gly Cys Gly Glu Asp
                485                 490                 495

Gly Glu Ile Thr Val Thr Asp Met Asp Thr Ile Glu Lys Ser Asn Leu
                500                 505                 510

Asn Arg Gln Phe Leu Phe Arg Pro Trp Asp Ile Thr Lys Leu Lys Ser
            515                 520                 525

Glu Thr Ala Ala Ala Val Arg Asp Ile Asn Pro His Ile Arg Ile
530                 535                 540

Phe Ser His Gln Asn Arg Val Gly Pro Glu Thr Glu His Val Tyr Asp
545                 550                 555                 560

Asp Asp Phe Phe Gln Lys Leu Asp Gly Val Ala Asn Ala Leu Asp Asn
                565                 570                 575

Val Asp Ala Arg Leu Tyr Val Asp Arg Arg Cys Val Tyr Tyr Arg Lys
            580                 585                 590

Pro Leu Leu Glu Ser Gly Thr Leu Gly Thr Lys Gly Asn Val Gln Val
            595                 600                 605

Val Val Pro Phe Leu Thr Glu Ser Tyr Ser Ser Gln Asp Pro Pro
            610                 615                 620

Glu Lys Ser Ile Pro Ile Cys Thr Leu Lys Asn Phe Pro Asn Ala Ile
625                 630                 635                 640

Glu His Thr Val Gln Trp Ala Arg Asp Glu Phe Glu Gly Leu Phe Lys
                645                 650                 655

Gln Ser Ala Glu Asn Val Asn Gln Tyr Leu Thr Asp Pro Lys Phe Met
                660                 665                 670

Glu Arg Thr Leu Gln Leu Ala Gly Thr Gln Pro Leu Glu Val Leu Glu
            675                 680                 685

Ala Ile His Cys Ser Leu Val Leu Gln Arg Pro Gln Thr Trp Ala Asp
            690                 695                 700

Cys Val Thr Trp Ala Tyr Gln His Trp His Thr Gln Tyr Ser His Asn
705                 710                 715                 720

Ile Gln Gln Leu Leu His Asn Phe Pro Pro Ala Gln Leu Thr Ser Ser
                725                 730                 735

Gly Ala Leu Phe Trp Ser Gly Pro Lys Arg Cys Pro His Pro Leu Thr
            740                 745                 750

Phe Asp Ile Asn Asn Pro Leu His Leu Asp Tyr Val Met Ala Ala Ala
            755                 760                 765

Asn Leu Phe Ala Gln Thr Tyr Gly Leu Gly Gly Ser Gln Asp Cys Ala
            770                 775                 780

Val Val Ala Lys Leu Leu Gln Ser Leu Pro Val Pro Lys Phe Ala Pro
785                 790                 795                 800
```

-continued

```
Lys Ser Gly Ile Arg Ile His Val Ser Glu Gln Leu Gln Ser Thr
            805                 810                 815

Ser Ala Thr Thr Ile Asp Asp Ser His Leu Glu Leu Lys Thr Ala
            820                 825                 830

Leu Pro Thr Pro Asp Lys Leu Leu Gly Phe Lys Met Tyr Pro Ile Asp
            835                 840                 845

Phe Glu Lys Asp Asp Asp Ser Asn Phe His Met Asp Phe Ile Val Ala
            850                 855                 860

Ala Ser Asn Leu Arg Ala Glu Asn Tyr Gly Ile Ser Pro Ala Asp Arg
865                 870                 875                 880

His Lys Ser Lys Leu Ile Ala Gly Lys Ile Ile Pro Ala Ile Ala Thr
            885                 890                 895

Thr Thr Ser Ala Ile Val Gly Leu Val Cys Leu Glu Leu Tyr Lys Val
            900                 905                 910

Val Gln Gly His Gln Gln Leu Glu Ser Tyr Lys Asn Ser Phe Ile Asn
            915                 920                 925

Leu Ala Leu Pro Leu Phe Ser Phe Ser Ala Pro Leu Ala Pro Glu Cys
            930                 935                 940

His Gln Tyr Tyr Asp Gln Glu Trp Thr Leu Trp Asp Arg Phe Asp Val
945                 950                 955                 960

Gln Gly Leu Gln Pro Ser Gly Glu Glu Met Thr Leu Lys Gln Phe Leu
            965                 970                 975

Asp Tyr Phe Lys Thr Glu His Lys Leu Glu Val Ile Met Leu Ser Gln
            980                 985                 990

Gly Val Ser Met Leu Tyr Ser Val Phe Met Pro Ala Ser Lys Leu Lys
            995                 1000                1005

Glu Arg Leu Asp Gln Pro Met Thr Glu Ile Val Ser Cys Val Ser
            1010                1015                1020

Lys Gln Lys Leu Gly His His Val Lys Ser Leu Val Phe Glu Leu
            1025                1030                1035

Cys Cys Asn Ser Asp Ser Gly Asp Asp Ile Glu Val Pro Tyr Val
            1040                1045                1050

Arg Tyr Ile Ile Arg
            1055
```

<210> SEQ ID NO 19
<211> LENGTH: 1058
<212> TYPE: PRT
<213> ORGANISM: Danio rerio

<400> SEQUENCE: 19

```
Met Ser Ser Ser Pro Leu Ser Lys Lys Arg Arg Val Ser Gly Ser Glu
1               5                   10                  15

Thr Lys Thr Gly Ser His Cys Ser Ser Asn Ser Val Arg Thr Glu
            20                  25                  30

Leu Ser His Thr Pro Ala Asn Gly Met Ala Lys Asn Gly Asn Asp Ala
            35                  40                  45

Glu Ile Asp Glu Gly Leu Tyr Ser Arg Gln Leu Tyr Val Leu Gly His
            50                  55                  60

Asp Ala Met Lys Arg Met Gln Ser Ser Asn Val Leu Ile Ser Gly Leu
65                  70                  75                  80

Arg Gly Leu Gly Val Glu Ile Ala Lys Asn Val Ile Leu Gly Gly Val
            85                  90                  95

Lys Ser Val Thr Leu His Asp Gln Gly Val Ala Glu Trp Lys Asp Leu
            100                 105                 110
```

```
Ser Ser Gln Phe Tyr Leu Arg Glu Glu Asp Leu Gly Lys Asn Arg Ala
    115                 120                 125
Asp Val Ser Gln Pro Arg Leu Ala Glu Leu Asn Ser Tyr Val Pro Val
130                 135                 140
Thr Ser Tyr Thr Gly Thr Leu Thr Asn Glu Tyr Leu Thr Lys Phe Gln
145                 150                 155                 160
Val Val Val Leu Thr Asn Ser Ser Leu Asp Glu Gln Thr Arg Ile Gly
                165                 170                 175
Glu Phe Cys His Ser Asn Gly Ile Lys Leu Ile Val Ala Asp Thr Arg
            180                 185                 190
Gly Leu Phe Gly Gln Leu Phe Cys Asp Phe Gly Glu Val Met Ile Val
        195                 200                 205
Phe Asp Thr Asn Gly Glu Gln Pro Leu Ser Ala Met Ile Ser Met Ile
210                 215                 220
Thr Lys Asp Ser Ala Gly Val Val Thr Cys Leu Asp Glu Ala Arg His
225                 230                 235                 240
Gly Phe Glu Ser Gly Asp Tyr Val Thr Phe Thr Glu Val Gln Gly Met
                245                 250                 255
Thr Glu Leu Asn Gly Cys Asp Pro Val Glu Ile Lys Thr Leu Gly Pro
            260                 265                 270
Tyr Thr Phe Ser Ile Cys Asp Thr Ser Ser Phe Ser Asp Tyr Val Arg
        275                 280                 285
Gly Gly Ile Val Thr Gln Val Lys Met Pro Lys Lys Ile Ala Phe Lys
        290                 295                 300
Ser Leu Ser Ser Ser Met Ala Glu Pro Glu Phe Leu Leu Thr Asp Phe
305                 310                 315                 320
Ala Lys Phe Asp Arg Pro Gly Gln Leu His Val Gly Phe Gln Ala Leu
                325                 330                 335
His Ala Phe Glu Lys Lys His Ser Arg Leu Pro Lys Pro Trp Asn Gln
            340                 345                 350
Ala Asp Ala Asp Glu Leu Met Thr Leu Ala Glu Glu Val Asn Ala Ala
        355                 360                 365
Gln Thr Gly Ser Ala Lys Gln Glu Glu Leu Asp Gln Ala Val Ile Lys
    370                 375                 380
Lys Leu Ala Cys Val Ala Ala Gly Asp Leu Ala Pro Val Asn Ala Phe
385                 390                 395                 400
Ile Gly Gly Leu Ala Ala Gln Glu Val Met Lys Ala Cys Thr Gly Lys
                405                 410                 415
Phe Met Pro Ile Met Gln Trp Leu Tyr Phe Asp Ala Leu Glu Cys Leu
            420                 425                 430
Pro Glu Pro Glu Glu Val Ile Leu Thr Glu Glu Cys Ala Pro Arg
        435                 440                 445
Asn Cys Arg Tyr Asp Gly Gln Ile Ala Val Phe Gly Ser Lys Leu Gln
    450                 455                 460
Glu Leu Leu Ala Lys Gln Arg Tyr Phe Leu Val Gly Ala Gly Ala Ile
465                 470                 475                 480
Gly Cys Glu Leu Leu Lys Asn Phe Ala Met Met Gly Leu Ala Ser Gly
                485                 490                 495
Glu Gly Glu Val Ile Val Thr Asp Met Asp Thr Ile Glu Lys Ser Asn
            500                 505                 510
Leu Asn Arg Gln Phe Leu Phe Arg Pro Trp Asp Val Thr Lys Met Lys
        515                 520                 525
Ser Glu Thr Ala Ala Ala Ala Val Lys Gln Met Asn Pro Ser Val Arg
    530                 535                 540
```

Ile Thr Gly His Gln Asn Arg Val Gly Pro Asp Thr Glu Lys Val Tyr
545                 550                 555                 560

Asp Asp Asp Phe Phe Glu Cys Leu Asp Gly Val Ala Asn Ala Leu Asp
                565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
        595                 600                 605

Val Val Ile Pro Phe Ile Thr Glu Ser Tyr Ser Ser Gln Asp Pro
    610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
                645                 650                 655

Lys Gln Pro Ala Glu Asn Ala Leu Gln Tyr Leu Thr Asp Ser Lys Phe
            660                 665                 670

Met Glu Arg Thr Leu Lys Leu Pro Gly Ala Gln Pro Leu Glu Val Val
        675                 680                 685

Glu Ser Val Tyr Lys Ser Leu Val Thr Asp Arg Pro Arg Asn Trp Asp
690                 695                 700

Asp Cys Val Thr Trp Ala Arg Asn His Trp Gln Cys Gln Tyr Asn Asn
705                 710                 715                 720

Asn Ile Arg Gln Leu Leu His Asn Phe Pro Pro Asp Gln Leu Thr Ser
                725                 730                 735

Ser Gly Ala Pro Phe Trp Ser Gly Pro Lys Arg Cys Pro His Pro Leu
            740                 745                 750

Glu Phe Ser Thr Asn Asn Asp Leu His Met Asp Tyr Ile Leu Ala Ala
        755                 760                 765

Ala Asn Leu Tyr Ala Leu Ser Tyr Gly Leu Pro Ser Cys Asn Asp Arg
        770                 775                 780

Ser Ala Leu Thr Lys Leu Leu Gln Asp Ile Lys Val Pro Glu Phe Thr
785                 790                 795                 800

Pro Lys Ser Gly Val Lys Ile His Val Ser Asp Gln Glu Leu Gln Ser
                805                 810                 815

Ala Asn Ala Ser Val Asp Asp Ser Arg Leu Glu Glu Leu Lys Thr Leu
            820                 825                 830

Leu Pro Ser Leu Glu Ala Ser Ser Gln Phe Lys Leu Cys Pro Ile Glu
        835                 840                 845

Phe Glu Lys Asp Asp Asp Thr Asn Phe His Met Asp Phe Ile Val Ala
850                 855                 860

Ala Ser Asn Leu Arg Ala Glu Asn Tyr Asp Ile Pro Pro Ala Asp Arg
865                 870                 875                 880

His Lys Ser Lys Leu Ile Ala Gly Lys Ile Pro Ala Ile Ala Thr
                885                 890                 895

Thr Thr Ala Ala Val Val Gly Leu Val Cys Leu Glu Leu Leu Lys Ile
            900                 905                 910

Val Gln Gly His Lys Lys Leu Glu Ser Tyr Lys Asn Gly Phe Met Asn
        915                 920                 925

Leu Ala Leu Pro Phe Phe Ala Phe Ser Glu Pro Ile Ala Ala Pro Lys
        930                 935                 940

His Lys Tyr Tyr Glu Ile Asp Trp Thr Leu Trp Asp Arg Phe Lys Val
945                 950                 955                 960

Lys Gly Ile Gln Pro Asn Gly Glu Glu Met Thr Leu Arg Gln Phe Leu

```
                   965                 970                 975
Asp Tyr Phe Lys Asn Glu His Lys Leu Glu Ile Thr Met Leu Ser Gln
                980                 985                 990

Gly Val Ser Met Leu Tyr Ser Phe Phe Met Pro Ala Ala Lys Leu Lys
                995                1000                1005

Glu Arg Leu Glu Leu Pro Met Thr Glu Ile Val Thr Lys Val Ser
       1010                1015                1020

Lys Lys Lys Leu Gly Lys His Val Lys Ala Leu Val Phe Glu Leu
       1025                1030                1035

Cys Cys Asn Asp Asp Thr Glu Glu Asp Val Glu Val Pro Tyr Val
       1040                1045                1050

Arg Tyr Thr Ile Arg
       1055

<210> SEQ ID NO 20
<211> LENGTH: 1024
<212> TYPE: PRT
<213> ORGANISM: Saccharomyces cerevisiae

<400> SEQUENCE: 20

Met Ser Ser Asn Asn Ser Gly Leu Ser Ala Ala Gly Glu Ile Asp Glu
1               5                   10                  15

Ser Leu Tyr Ser Arg Gln Leu Tyr Val Leu Gly Lys Glu Ala Met Leu
            20                  25                  30

Lys Met Gln Thr Ser Asn Val Leu Ile Leu Gly Leu Lys Gly Leu Gly
        35                  40                  45

Val Glu Ile Ala Lys Asn Val Val Leu Ala Gly Val Lys Ser Met Thr
50                  55                  60

Val Phe Asp Pro Glu Pro Val Gln Leu Ala Asp Leu Ser Thr Gln Phe
65                  70                  75                  80

Phe Leu Thr Glu Lys Asp Ile Gly Gln Lys Arg Gly Asp Val Thr Arg
                85                  90                  95

Ala Lys Leu Ala Glu Leu Asn Ala Tyr Val Pro Val Asn Val Leu Asp
            100                 105                 110

Ser Leu Asp Asp Val Thr Gln Leu Ser Gln Phe Gln Val Val Val Ala
        115                 120                 125

Thr Asp Thr Val Ser Leu Glu Asp Lys Val Lys Ile Asn Glu Phe Cys
130                 135                 140

His Ser Ser Gly Ile Arg Phe Ile Ser Ser Glu Thr Arg Gly Leu Phe
145                 150                 155                 160

Gly Asn Thr Phe Val Asp Leu Gly Asp Glu Phe Thr Val Leu Asp Pro
                165                 170                 175

Thr Gly Glu Glu Pro Arg Thr Gly Met Val Ser Asp Ile Glu Pro Asp
            180                 185                 190

Gly Thr Val Thr Met Leu Asp Asp Asn Arg His Gly Leu Glu Asp Gly
        195                 200                 205

Asn Phe Val Arg Phe Ser Glu Val Glu Gly Leu Asp Lys Leu Asn Asp
210                 215                 220

Gly Thr Leu Phe Lys Val Glu Val Leu Gly Pro Phe Ala Phe Arg Ile
225                 230                 235                 240

Gly Ser Val Lys Glu Tyr Gly Glu Tyr Lys Lys Gly Gly Ile Phe Thr
                245                 250                 255

Glu Val Lys Val Pro Arg Lys Ile Ser Phe Lys Ser Leu Lys Gln Gln
            260                 265                 270

Leu Ser Asn Pro Glu Phe Val Phe Ser Asp Phe Ala Lys Phe Asp Arg
```

-continued

```
                    275                 280                 285
Ala Ala Gln Leu His Leu Gly Phe Gln Ala Leu His Gln Phe Ala Val
290                 295                 300
Arg His Asn Gly Glu Leu Pro Arg Thr Met Asn Asp Glu Asp Ala Asn
305                 310                 315                 320
Glu Leu Ile Lys Leu Val Thr Asp Leu Ser Val Gln Gln Pro Glu Val
                    325                 330                 335
Leu Gly Glu Gly Val Asp Val Asn Glu Asp Leu Ile Lys Glu Leu Ser
                340                 345                 350
Tyr Gln Ala Arg Gly Asp Ile Pro Gly Val Val Ala Phe Phe Gly Gly
                355                 360                 365
Leu Val Ala Gln Glu Val Leu Lys Ala Cys Ser Gly Lys Phe Thr Pro
370                 375                 380
Leu Lys Gln Phe Met Tyr Phe Asp Ser Leu Glu Ser Leu Pro Asp Pro
385                 390                 395                 400
Lys Asn Phe Pro Arg Asn Glu Lys Thr Thr Gln Pro Val Asn Ser Arg
                    405                 410                 415
Tyr Asp Asn Gln Ile Ala Val Phe Gly Leu Asp Phe Gln Lys Lys Ile
                420                 425                 430
Ala Asn Ser Lys Val Phe Leu Val Gly Ser Gly Ala Ile Gly Cys Glu
                435                 440                 445
Met Leu Lys Asn Trp Ala Leu Leu Gly Leu Gly Ser Gly Ser Asp Gly
450                 455                 460
Tyr Ile Val Val Thr Asp Asn Asp Ser Ile Glu Lys Ser Asn Leu Asn
465                 470                 475                 480
Arg Gln Phe Leu Phe Arg Pro Lys Asp Val Gly Lys Asn Lys Ser Glu
                    485                 490                 495
Val Ala Ala Glu Ala Val Cys Ala Met Asn Pro Asp Leu Lys Gly Lys
                500                 505                 510
Ile Asn Ala Lys Ile Asp Lys Val Gly Pro Glu Thr Glu Glu Ile Phe
                515                 520                 525
Asn Asp Ser Phe Trp Glu Ser Leu Asp Phe Val Thr Asn Ala Leu Asp
530                 535                 540
Asn Val Asp Ala Arg Thr Tyr Val Asp Arg Arg Cys Val Phe Tyr Arg
545                 550                 555                 560
Lys Pro Leu Leu Glu Ser Gly Thr Leu Gly Thr Lys Gly Asn Thr Gln
                    565                 570                 575
Val Ile Ile Pro Arg Leu Thr Glu Ser Tyr Ser Ser Ser Arg Asp Pro
                580                 585                 590
Pro Glu Lys Ser Ile Pro Leu Cys Thr Leu Arg Ser Phe Pro Asn Lys
                595                 600                 605
Ile Asp His Thr Ile Ala Trp Ala Lys Ser Leu Phe Gln Gly Tyr Phe
610                 615                 620
Thr Asp Ser Ala Glu Asn Val Asn Met Tyr Leu Thr Gln Pro Asn Phe
625                 630                 635                 640
Val Glu Gln Thr Leu Lys Gln Ser Gly Asp Val Lys Gly Val Leu Glu
                    645                 650                 655
Ser Ile Ser Asp Ser Leu Ser Ser Lys Pro His Asn Phe Glu Asp Cys
                660                 665                 670
Ile Lys Trp Ala Arg Leu Glu Phe Glu Lys Lys Phe Asn His Asp Ile
                675                 680                 685
Lys Gln Leu Leu Phe Asn Phe Pro Lys Asp Ala Lys Thr Ser Asn Gly
690                 695                 700
```

-continued

```
Glu Pro Phe Trp Ser Gly Ala Lys Arg Ala Pro Thr Pro Leu Glu Phe
705                 710                 715                 720

Asp Ile Tyr Asn Asn Asp His Phe His Phe Val Val Ala Gly Ala Ser
            725                 730                 735

Leu Arg Ala Tyr Asn Tyr Gly Ile Lys Ser Asp Asp Ser Asn Ser Lys
        740                 745                 750

Pro Asn Val Asp Glu Tyr Lys Ser Val Ile Asp His Met Ile Ile Pro
    755                 760                 765

Glu Phe Thr Pro Asn Ala Asn Leu Lys Ile Gln Val Asn Asp Asp Asp
770                 775                 780

Pro Asp Pro Asn Ala Asn Ala Ala Asn Gly Ser Asp Glu Ile Asp Gln
785                 790                 795                 800

Leu Val Ser Ser Leu Pro Asp Pro Ser Thr Leu Ala Gly Phe Lys Leu
            805                 810                 815

Glu Pro Val Asp Phe Glu Lys Asp Asp Asp Thr Asn His His Ile Glu
        820                 825                 830

Phe Ile Thr Ala Cys Ser Asn Cys Arg Ala Gln Asn Tyr Phe Ile Glu
    835                 840                 845

Thr Ala Asp Arg Gln Lys Thr Lys Phe Ile Ala Gly Arg Ile Ile Pro
850                 855                 860

Ala Ile Ala Thr Thr Thr Ser Leu Val Thr Gly Leu Val Asn Leu Glu
865                 870                 875                 880

Leu Tyr Lys Leu Ile Asp Asn Lys Thr Asp Ile Glu Gln Tyr Lys Asn
            885                 890                 895

Gly Phe Val Asn Leu Ala Leu Pro Phe Phe Gly Phe Ser Glu Pro Ile
        900                 905                 910

Ala Ser Pro Lys Gly Glu Tyr Asn Asn Lys Lys Tyr Asp Lys Ile Trp
    915                 920                 925

Asp Arg Phe Asp Ile Lys Gly Asp Ile Lys Leu Ser Asp Leu Ile Glu
930                 935                 940

His Phe Glu Lys Asp Glu Gly Leu Glu Ile Thr Met Leu Ser Tyr Gly
945                 950                 955                 960

Val Ser Leu Leu Tyr Ala Ser Phe Phe Pro Pro Lys Lys Leu Lys Glu
            965                 970                 975

Arg Leu Asn Leu Pro Ile Thr Gln Leu Val Lys Leu Val Thr Lys Lys
        980                 985                 990

Asp Ile Pro Ala His Val Ser Thr Met Ile Leu Glu Ile Cys Ala Asp
    995                 1000                1005

Asp Lys Glu Gly Glu Asp Val Glu Val Pro Phe Ile Thr Ile His
    1010                1015                1020

Leu
```

<210> SEQ ID NO 21
<211> LENGTH: 1052
<212> TYPE: PRT
<213> ORGANISM: Homo sapiens

<400> SEQUENCE: 21

```
Met Glu Gly Ser Glu Pro Val Ala Ala His Gln Gly Glu Glu Ala Ser
1               5                   10                  15

Cys Ser Ser Trp Gly Thr Gly Ser Thr Asn Lys Asn Leu Pro Ile Met
            20                  25                  30

Ser Thr Ala Ser Val Glu Ile Asp Asp Ala Leu Tyr Ser Arg Gln Arg
        35                  40                  45

Tyr Val Leu Gly Asp Thr Ala Met Gln Lys Met Ala Lys Ser His Val
```

-continued

```
          50                  55                  60
Phe Leu Ser Gly Met Gly Gly Leu Gly Leu Glu Ile Ala Lys Asn Leu
 65                  70                  75                  80

Val Leu Ala Gly Ile Lys Ala Val Thr Ile His Asp Thr Glu Lys Cys
                 85                  90                  95

Gln Ala Trp Asp Leu Gly Thr Asn Phe Phe Leu Ser Glu Asp Asp Val
                100                 105                 110

Val Asn Lys Arg Asn Arg Ala Glu Ala Val Leu Lys His Ile Ala Glu
            115                 120                 125

Leu Asn Pro Tyr Val His Val Thr Ser Ser Val Pro Phe Asn Glu
130                 135                 140

Thr Thr Asp Leu Ser Phe Leu Asp Lys Tyr Gln Cys Val Val Leu Thr
145                 150                 155                 160

Glu Met Lys Leu Pro Leu Gln Lys Lys Ile Asn Asp Phe Cys Arg Ser
                165                 170                 175

Gln Cys Pro Pro Ile Lys Phe Ile Ser Ala Asp Val His Gly Ile Trp
                180                 185                 190

Ser Arg Leu Phe Cys Asp Phe Gly Asp Glu Phe Glu Val Leu Asp Thr
            195                 200                 205

Thr Gly Glu Glu Pro Lys Glu Ile Phe Ile Ser Asn Ile Thr Gln Ala
210                 215                 220

Asn Pro Gly Ile Val Thr Cys Leu Glu Asn His Pro His Lys Leu Glu
225                 230                 235                 240

Thr Gly Gln Phe Leu Thr Phe Arg Glu Ile Asn Gly Met Thr Gly Leu
                245                 250                 255

Asn Gly Ser Ile Gln Gln Ile Thr Val Ile Ser Pro Phe Ser Phe Ser
            260                 265                 270

Ile Gly Asp Thr Thr Glu Leu Glu Pro Tyr Leu His Gly Gly Ile Ala
            275                 280                 285

Val Gln Val Lys Thr Pro Lys Thr Val Phe Phe Glu Ser Leu Glu Arg
            290                 295                 300

Gln Leu Lys His Pro Lys Cys Leu Ile Val Asp Phe Ser Asn Pro Glu
305                 310                 315                 320

Ala Pro Leu Glu Ile His Thr Ala Met Leu Ala Leu Asp Gln Phe Gln
                325                 330                 335

Glu Lys Tyr Ser Arg Lys Pro Asn Val Gly Cys Gln Gln Asp Ser Glu
                340                 345                 350

Glu Leu Leu Lys Leu Ala Thr Ser Ile Ser Glu Thr Leu Glu Glu Lys
            355                 360                 365

Pro Asp Val Asn Ala Asp Ile Val His Trp Leu Ser Trp Thr Ala Gln
370                 375                 380

Gly Phe Leu Ser Pro Leu Ala Ala Ala Val Gly Gly Val Ala Ser Gln
385                 390                 395                 400

Glu Val Leu Lys Ala Val Thr Gly Lys Phe Ser Pro Leu Cys Gln Trp
                405                 410                 415

Leu Tyr Leu Glu Ala Ala Asp Ile Val Glu Ser Leu Gly Lys Pro Glu
                420                 425                 430

Cys Glu Glu Phe Leu Pro Arg Gly Asp Arg Tyr Asp Ala Leu Arg Ala
            435                 440                 445

Cys Ile Gly Asp Thr Leu Cys Gln Lys Leu Gln Asn Leu Asn Ile Phe
            450                 455                 460

Leu Val Gly Cys Gly Ala Ile Gly Cys Glu Met Leu Lys Asn Phe Ala
465                 470                 475                 480
```

```
Leu Leu Gly Val Gly Thr Ser Lys Glu Lys Gly Met Ile Thr Val Thr
                485                 490                 495

Asp Pro Asp Leu Ile Glu Lys Ser Asn Leu Asn Arg Gln Phe Leu Phe
            500                 505                 510

Arg Pro His His Ile Gln Lys Pro Lys Ser Tyr Thr Ala Ala Asp Ala
        515                 520                 525

Thr Leu Lys Ile Asn Ser Gln Ile Lys Ile Asp Ala His Leu Asn Lys
    530                 535                 540

Val Cys Pro Thr Thr Glu Thr Ile Tyr Asn Asp Glu Phe Tyr Thr Lys
545                 550                 555                 560

Gln Asp Val Ile Ile Thr Ala Leu Asp Asn Val Glu Ala Arg Arg Tyr
                565                 570                 575

Val Asp Ser Arg Cys Leu Ala Asn Leu Arg Pro Leu Leu Asp Ser Gly
            580                 585                 590

Thr Met Gly Thr Lys Gly His Thr Glu Val Ile Val Pro His Leu Thr
        595                 600                 605

Glu Ser Tyr Asn Ser His Arg Asp Pro Pro Glu Glu Ile Pro Phe
    610                 615                 620

Cys Thr Leu Lys Ser Phe Pro Ala Ala Ile Glu His Thr Ile Gln Trp
625                 630                 635                 640

Ala Arg Asp Lys Phe Glu Ser Ser Phe Ser His Lys Pro Ser Leu Phe
                645                 650                 655

Asn Lys Phe Trp Gln Thr Tyr Ser Ser Ala Glu Glu Val Leu Gln Lys
            660                 665                 670

Ile Gln Ser Gly His Ser Leu Glu Gly Cys Phe Gln Val Ile Lys Leu
        675                 680                 685

Leu Ser Arg Arg Pro Arg Asn Trp Ser Gln Cys Val Glu Leu Ala Arg
    690                 695                 700

Leu Lys Phe Glu Lys Tyr Phe Asn His Lys Ala Leu Gln Leu Leu His
705                 710                 715                 720

Cys Phe Pro Leu Asp Ile Arg Leu Lys Asp Gly Ser Leu Phe Trp Gln
                725                 730                 735

Ser Pro Lys Arg Pro Pro Ser Pro Ile Lys Phe Asp Leu Asn Glu Pro
            740                 745                 750

Leu His Leu Ser Phe Leu Gln Asn Ala Ala Lys Leu Tyr Ala Thr Val
        755                 760                 765

Tyr Cys Ile Pro Phe Ala Glu Glu Asp Leu Ser Ala Asp Ala Leu Leu
    770                 775                 780

Asn Ile Leu Ser Glu Val Lys Ile Gln Glu Phe Lys Pro Ser Asn Lys
785                 790                 795                 800

Val Val Gln Thr Asp Glu Thr Ala Arg Lys Pro Asp His Val Pro Ile
                805                 810                 815

Ser Ser Glu Asp Glu Arg Asn Ala Ile Phe Gln Leu Glu Lys Ala Ile
            820                 825                 830

Leu Ser Asn Glu Ala Thr Lys Ser Asp Leu Gln Met Ala Val Leu Ser
        835                 840                 845

Phe Glu Lys Asp Asp His Asn Gly His Ile Asp Phe Ile Thr Ala
    850                 855                 860

Ala Ser Asn Leu Arg Ala Lys Met Tyr Ser Ile Glu Pro Ala Asp Arg
865                 870                 875                 880

Phe Lys Thr Lys Arg Ile Ala Gly Lys Ile Ile Pro Ala Ile Ala Thr
                885                 890                 895

Thr Thr Ala Thr Val Ser Gly Leu Val Ala Leu Glu Met Ile Lys Val
            900                 905                 910
```

```
Thr Gly Gly Tyr Pro Phe Glu Ala Tyr Lys Asn Cys Phe Leu Asn Leu
        915                 920                 925

Ala Ile Pro Ile Val Val Phe Thr Glu Thr Thr Glu Val Arg Lys Thr
930                 935                 940

Lys Ile Arg Asn Gly Ile Ser Phe Thr Ile Trp Asp Arg Trp Thr Val
945                 950                 955                 960

His Gly Lys Glu Asp Phe Thr Leu Leu Asp Phe Ile Asn Ala Val Lys
        965                 970                 975

Glu Lys Tyr Gly Ile Glu Pro Thr Met Val Val Gln Gly Val Lys Met
            980                 985                 990

Leu Tyr Val Pro Val Met Pro Gly His Ala Lys Arg Leu Lys Leu Thr
        995                 1000                1005

Met His Lys Leu Val Lys Pro Thr Thr Glu Lys Lys Tyr Val Asp
        1010                1015                1020

Leu Thr Val Ser Phe Ala Pro Asp Ile Asp Gly Asp Glu Asp Leu
        1025                1030                1035

Pro Gly Pro Pro Val Arg Tyr Tyr Phe Ser His Asp Thr Asp
        1040                1045                1050

<210> SEQ ID NO 22
<211> LENGTH: 1053
<212> TYPE: PRT
<213> ORGANISM: Mus musculus

<400> SEQUENCE: 22

Met Glu Arg Ser Glu Pro Leu Ala Val Leu Ser Cys Glu Glu Ala Ser
1               5                   10                  15

Cys Ser Ser Trp Gly Ala Cys Gly Ala Ser Lys Asn Leu Pro Thr Met
                20                  25                  30

Thr Thr Glu Ser Leu Glu Ile Asp Asp Gly Leu Tyr Ser Arg Gln Arg
            35                  40                  45

Tyr Val Leu Gly Asp Thr Ala Met Gln Lys Met Ala Lys Ser Cys Val
    50                  55                  60

Phe Leu Ser Gly Met Gly Gly Leu Gly Val Glu Ile Ala Lys Asn Leu
65                  70                  75                  80

Val Leu Ala Gly Ile Lys Ala Leu Thr Ile His Asp Thr Lys Lys Cys
                85                  90                  95

Gln Ala Trp Asp Leu Gly Thr Asn Phe Phe Leu Cys Glu Asp Asp Val
            100                 105                 110

Val Asn Glu Arg Asn Arg Ala Glu Ala Val Leu His Arg Ile Ala Glu
        115                 120                 125

Leu Asn Pro Tyr Val Gln Val Ser Ser Ser Ala Pro Leu Asp Glu
        130                 135                 140

Thr Thr Asp Leu Ser Phe Leu Glu Lys Tyr Gln Cys Val Val Leu Thr
145                 150                 155                 160

Glu Ile Lys Leu Thr Leu Gln Lys Lys Ile Asn Asn Phe Cys His Ser
                165                 170                 175

His Cys Pro Pro Ile Lys Phe Ile Ser Ala Asp Val His Gly Ile Trp
            180                 185                 190

Ser Arg Leu Phe Cys Asp Phe Gly Asp Glu Phe Glu Val Ser Asp Thr
        195                 200                 205

Thr Gly Glu Glu Pro Lys Glu Ile Phe Ile Ser Asn Ile Thr Gln Ala
    210                 215                 220

Asn Pro Gly Ile Val Thr Cys Leu Glu Ser His Pro His Lys Leu Glu
225                 230                 235                 240
```

```
Thr Gly Gln Phe Leu Thr Phe Arg Glu Ile His Gly Met Thr Gly Leu
            245                 250                 255

Asn Gly Ser Val Gln Gln Ile Thr Val Ile Ser Pro Phe Ser Phe Ser
            260                 265                 270

Ile Gly Asp Thr Thr Lys Leu Asp Pro Tyr Leu His Gly Gly Ile Ala
            275                 280                 285

Val Gln Val Lys Thr Pro Lys Thr Phe Cys Phe Glu Pro Leu Glu Ser
            290                 295                 300

Gln Ile Lys His Pro Arg Cys Leu Ile Ala Asp Phe Ser Lys Pro Glu
305                 310                 315                 320

Ala Pro Leu Glu Ile His Leu Ala Met Leu Ala Leu Asp Gln Phe Gln
            325                 330                 335

Glu Asn Tyr Asn Arg Lys Pro Asn Ile Arg Cys Gln Gln Asp Ser Asp
            340                 345                 350

Glu Leu Leu Lys Leu Thr Val Ser Ile Asn Glu Thr Leu Glu Glu Lys
            355                 360                 365

Pro Glu Val Asn Ala Asp Ile Val His Trp Leu Ser Trp Thr Ala Gln
            370                 375                 380

Gly Phe Leu Pro Pro Leu Ala Ala Val Gly Val Ala Ser Gln
385                 390                 395                 400

Glu Val Leu Lys Ala Val Thr Gly Lys Phe Ser Pro Leu Cys Gln Trp
            405                 410                 415

Leu Tyr Leu Glu Ala Ala Asp Thr Val Glu Ser Leu Gly Asn Pro Gly
            420                 425                 430

His Glu Glu Phe Leu Pro Arg Gly Asp Arg Tyr Asp Ala Ile Arg Ala
            435                 440                 445

Cys Ile Gly Asn Thr Leu Cys Gln Lys Leu Gln Asn Leu Asn Ile Phe
            450                 455                 460

Leu Val Gly Cys Gly Ala Ile Gly Cys Glu Met Leu Lys Asn Phe Ala
465                 470                 475                 480

Leu Leu Gly Val Gly Thr Gly Arg Glu Lys Gly Met Val Thr Val Thr
            485                 490                 495

Asp Pro Asp Leu Ile Glu Lys Ser Asn Leu Asn Arg Gln Phe Leu Phe
            500                 505                 510

Arg Pro His His Ile Gln Lys Pro Lys Ser Tyr Thr Ala Ala Glu Ala
            515                 520                 525

Thr Leu Lys Ile Asn Pro Gln Leu Lys Ile Asp Ala His Leu Asn Lys
            530                 535                 540

Val Cys Pro Ala Thr Glu Ser Ile Tyr Ser Asp Glu Phe Tyr Thr Lys
545                 550                 555                 560

Gln Asp Ile Ile Ile Thr Ala Leu Asp Asn Val Glu Ala Arg Arg Tyr
            565                 570                 575

Val Asp Ser Arg Cys Leu Ala Asn Leu Arg Pro Leu Leu Asp Ser Gly
            580                 585                 590

Thr Met Gly Thr Lys Gly His Thr Glu Ile Ile Val Pro Gln Leu Thr
            595                 600                 605

Glu Ser Tyr Asn Ser His Arg Asp Pro Pro Glu Glu Ile Pro Phe
            610                 615                 620

Cys Thr Leu Lys Ser Phe Pro Ala Ala Ile Glu His Thr Ile Gln Trp
625                 630                 635                 640

Ala Arg Asp Lys Phe Glu Ser Ser Phe Ser His Lys Pro Ser Leu Phe
            645                 650                 655

Asn Lys Phe Trp Gln Ala Tyr Pro Ser Ala Glu Asp Val Leu Gln Lys
```

-continued

```
            660                 665                 670
Ile Gln Asn Gly Gln Ser Leu Glu Gly Cys Phe Gln Val Ile Lys Leu
            675                 680                 685
Leu Ser Arg Arg Pro Arg Ile Trp Ser Gln Cys Val Glu Leu Ala Arg
            690                 695                 700
Leu Lys Phe Glu Lys Tyr Phe Asn His Lys Ala Leu Gln Leu Leu His
705                 710                 715                 720
Cys Phe Pro Leu Glu Thr Arg Leu Lys Asp Gly Ser Leu Phe Trp Gln
            725                 730                 735
Ser Pro Lys Arg Pro Ser Pro Ile Lys Phe Asp Leu Asn Glu Pro
            740                 745                 750
Leu His Leu Ser Phe Leu Gln Ser Ala Ala Lys Leu Tyr Ala Thr Val
            755                 760                 765
Tyr Cys Ile Pro Phe Ser Glu Lys Asp Leu Ser Val Asn Ser Leu Met
            770                 775                 780
Asp Ile Leu Ser Glu Val Lys Ile Glu Glu Phe Lys Pro Ser Asn Lys
785                 790                 795                 800
Val Val Gln Thr Asp Glu Thr Ala Arg Lys Pro Asp His Val Pro Val
            805                 810                 815
Ser Ser Glu Asp Glu Arg Asn Ala Val Phe Gln Leu Glu Glu Ala Leu
            820                 825                 830
Ser Ser Asn Lys Ala Thr Lys Ser Asp Leu Gln Met Thr Val Leu Ser
            835                 840                 845
Phe Glu Lys Asp Asp Asp Arg Asn Gly His Ile Asp Phe Ile Thr Ala
850                 855                 860
Ala Ser Asn Leu Arg Ala Lys Met Tyr Ser Ile Glu Pro Ala Asp Arg
865                 870                 875                 880
Phe Lys Thr Lys Arg Ile Ala Gly Lys Ile Ile Pro Ala Ile Ala Thr
            885                 890                 895
Ser Thr Ala Ala Val Ser Gly Leu Val Ala Leu Glu Met Ile Lys Val
            900                 905                 910
Ala Gly Gly Tyr Pro Phe Asp Ala Tyr Lys Asn Cys Phe Leu Asn Leu
            915                 920                 925
Ala Ile Pro Ile Ile Val Phe Thr Glu Thr Ser Glu Val Arg Lys Thr
            930                 935                 940
Glu Ile Arg Asn Gly Ile Ser Phe Thr Ile Trp Asp Arg Trp Thr Val
945                 950                 955                 960
His Gly Lys Glu Asp Phe Thr Leu Ser Asp Phe Ile Asn Ala Val Lys
            965                 970                 975
Glu Asn Tyr Gly Ile Glu Pro Thr Met Val Val Gln Gly Val Lys Met
            980                 985                 990
Leu Tyr Val Pro Val Met Pro Gly His Ala Lys Arg Leu Lys Leu Thr
            995                 1000                1005
Met His Lys Leu Val Lys Pro Ser Thr Glu Lys Lys Tyr Val Asp
            1010                1015                1020
Leu Thr Val Ser Phe Ala Pro Asp Ala Asp Gly Asp Glu Asp Leu
            1025                1030                1035
Pro Gly Pro Pro Val Arg Tyr Tyr Phe Ser His Asp Thr Asn Glu
            1040                1045                1050

<210> SEQ ID NO 23
<211> LENGTH: 991
<212> TYPE: PRT
<213> ORGANISM: Danio rerio
```

<400> SEQUENCE: 23

```
Asp Ser Met Asp Ile Asp Asp Ser Leu Tyr Ser Arg Gln Arg Tyr Val
1               5                   10                  15

Leu Gly Asp Ser Ala Met His Gln Met Ala Gln Ser Thr Val Phe Val
            20                  25                  30

Ser Gly Met Gly Ala Leu Gly Val Glu Ile Ala Lys Asn Ile Val Leu
        35                  40                  45

Ala Gly Val Lys Leu His Asp Ser Lys Arg Cys Glu Val Trp Asp Leu
50                  55                  60

Gly Thr Asn Phe Phe Ile Arg Glu Glu Asp Val Asn Asn Gln Lys Lys
65                  70                  75                  80

Arg Val Glu Ala Val His Ser Arg Val Ala Glu Leu Asn Pro Tyr Val
                85                  90                  95

Gln Val Thr Met Ser Thr Asp Val Leu Asp Glu Ser Thr Asp Leu Ser
            100                 105                 110

Phe Leu Lys Arg Tyr Gln Cys Val Val Leu Thr Glu Lys Lys Leu Thr
        115                 120                 125

Leu Gln Lys Arg Ile Asn His Phe Cys His Thr Gln Gln Pro Pro Ile
130                 135                 140

Lys Phe Ile Gly Phe Gly Ile Cys Ser Arg Val Phe Cys Asp Phe Gly
145                 150                 155                 160

Glu Thr Phe Glu Val Ser Asp Pro Thr Gly Glu Glu Ser Lys Glu Ile
                165                 170                 175

Phe Ile Gln Asn Ile Ser Gln Gly Ser Pro Gly Val Val Thr Cys Met
            180                 185                 190

Asp Ser Arg Thr His Gly Leu Gln Met Gly Gln Ser Val Cys Leu Lys
        195                 200                 205

Glu Ile Asn Gly Met Thr Glu Leu Asn Gly Thr Met His Gln Ile Thr
210                 215                 220

Val Leu Ser Pro Tyr Thr Phe Ala Ile Gly Asp Thr Ser Ser Phe His
225                 230                 235                 240

Pro Tyr Thr His Phe Arg Leu Val Lys Ile Pro Lys Thr Thr Phe Ser
                245                 250                 255

Phe Glu Lys Met Glu Gln Gln Leu Ser Asp Pro Arg Leu Leu Thr Pro
            260                 265                 270

Asp Phe Ser Lys Pro Glu Val Pro Leu Gln Leu His Ala Ile Met Leu
        275                 280                 285

Ala Leu Asp Ala Phe Leu Glu Gln His Ala Arg Leu Pro Asn Ile Gly
290                 295                 300

Cys Leu Gln Asp Ser Glu Leu Leu Lys Tyr Thr Glu Glu Ile Ile
305                 310                 315                 320

Lys Thr Leu Lys Asn Lys Val Cys Ile Asn Pro Asp Leu Val Arg Cys
                325                 330                 335

Val Ala Arg Gly Cys Leu Phe Pro Leu Ala Ala Thr Val Gly Gly Ile
            340                 345                 350

Ala Ser Gln Glu Val Leu Lys Ala Leu Thr Gly Lys Phe Ser Pro Leu
        355                 360                 365

Gln Gln Trp Phe Tyr Leu Asp Ala Leu Glu Val Val Gln Pro Leu Gln
370                 375                 380

Ser Leu Pro Ala Glu Glu Phe Ser Pro Arg Gly Asp Arg Tyr Asp Ala
385                 390                 395                 400

Leu Arg Ala Cys Ile Gly Gln Ser Leu Cys Leu Lys Leu His Lys Phe
                405                 410                 415
```

-continued

```
Gln Val Phe Met Val Gly Cys Gly Ala Ile Gly Cys Glu Met Leu Lys
             420                 425                 430

Leu Leu Gly Val Gly Leu Ser Arg Phe Leu Gly Glu Ile Cys Ile Thr
             435                 440                 445

Asp Pro Asp Leu Ile Glu Lys Ser Asn Leu Asn Arg Gln Phe Leu Phe
450                 455                 460

Arg Pro His His Ile Gln Val Phe Asn Ser Leu Gln Gln Gln Ser
465                 470                 475                 480

Phe Ile Lys Asn Asn Pro Arg Leu Gln Ile His Ala His Leu His Lys
                 485                 490                 495

Val Cys Pro Ala Thr Glu Asp Ile Tyr Ser Asp Phe Phe Ser Arg
                 500                 505                 510

Leu Asn Val Val Thr Ala Leu Asp Asn Val Glu Ala Arg Arg Ser
             515                 520                 525

Arg Ser Val Ser Asn Gln Lys Ala Leu Leu Asp Ser Gly Thr Met Gly
                 530                 535                 540

Thr Lys Gly His Thr Glu Ile Ile Val Pro Asn Leu Thr Glu Ser Tyr
545                 550                 555                 560

Asn Ser His Arg Asp Pro Pro Glu Glu Ile Pro Phe Cys Thr Leu
                 565                 570                 575

Lys Ser Phe Pro Ala Val Thr Glu His Thr Ile Gln Trp Ala Arg Asp
             580                 585                 590

Lys Phe Glu Ser Ala Phe Ala His Lys Pro Ser Met Tyr Asn Met Phe
             595                 600                 605

Trp Gln Ser His Ser Ser Ala Gln Gly Val Leu Gln Arg Met Met Gly
             610                 615                 620

Met Glu Gly Ser Phe Gln Val Ile Lys Leu Leu Ser Arg Arg Pro Thr
625                 630                 635                 640

Gln Trp Asp His Cys Ile Thr Leu Ala Arg Leu Lys Phe Asp Lys Tyr
                 645                 650                 655

Phe Lys Arg Lys Ala Leu Gln Leu Leu His Ser Phe Pro Leu Asp Thr
                 660                 665                 670

Arg Leu Lys Asp Gly Ser Leu Phe Trp Gln Ser Pro Lys Arg Pro Pro
             675                 680                 685

Ser Pro Ile Asp Phe Asp Leu Ser Asp Pro Leu His Phe Gly Phe Val
690                 695                 700

Val Ser Ala Ala Arg Leu Phe Ala Gly Ile Tyr Asn Ile Pro Tyr Ser
705                 710                 715                 720

Glu Ser Tyr Glu Asp Val Ser Arg Val Leu Ala Glu Val Asp Val Pro
                 725                 730                 735

Glu Tyr Lys Pro Ala Glu Lys His Ile Glu Thr Asp Glu Thr Val Lys
                 740                 745                 750

Lys Pro Asp Gln Leu Lys Ile Thr Val Ser Ser Glu Glu Arg Glu
                 755                 760                 765

Ala Ile Ser Gln Leu Gln Glu Ala Ile Asn Ser Asn Leu Val Thr Pro
                 770                 775                 780

Glu Arg Leu Cys Met Ser Pro Leu Phe Phe Glu Lys Asp Asp Thr
785                 790                 795                 800

Asn Gly His Met Asp Phe Val Ala Ser Ala Ser Ala Leu Arg Ala Arg
                 805                 810                 815

Ile Glu Ala Ala Asp Arg Leu Gln Thr Lys Arg Ile Ala Gly Lys Ile
                 820                 825                 830

Ile Pro Ala Ile Ala Thr Ser Thr Ala Ala Val Ala Gly Leu Val Ser
                 835                 840                 845
```

Met Glu Leu Ile Lys Ile Ala Gly Gly Tyr Gly Phe Glu Leu Phe Lys
        850                 855                 860

Asn Cys Phe Phe Asn Leu Ala Ile Pro Val Val Leu Thr Glu Thr
865                 870                 875                 880

Ala Gln Val Lys Arg Thr Gln Ile Arg Asp Asp Ile Ser Phe Ser Ile
                885                 890                 895

Trp Asp Arg Trp Thr Ile Phe Gly Arg Glu Asp Phe Asp Phe Ile Ser
            900                 905                 910

Ala Val Arg Glu Lys Tyr Gly Ile Glu Pro Thr Met Val Val His Gly
        915                 920                 925

Val Lys Met Leu Tyr Val Pro Val Met Pro Gly His Asn Lys Arg Leu
    930                 935                 940

Lys Leu Thr Met His Lys Leu Ile Lys Pro Ser Ser Gly Arg Lys Tyr
945                 950                 955                 960

Val Asp Leu Thr Val Ser Phe Ala Pro Glu Val Asp Gly Asp Glu Asp
                965                 970                 975

Leu Pro Gly Pro Pro Val Arg Tyr Tyr Phe Ser Gly Glu Asn Glu
            980                 985                 990

<210> SEQ ID NO 24
<211> LENGTH: 76
<212> TYPE: PRT
<213> ORGANISM: Artificial sequence
<220> FEATURE:
<223> OTHER INFORMATION: Ubiquitin fragment of Uba6 obtained by mass
      spectrometry

<400> SEQUENCE: 24

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 25
<211> LENGTH: 111
<212> TYPE: PRT
<213> ORGANISM: Mus musculus

<400> SEQUENCE: 25

Tyr Asn Gln Glu Trp Thr Leu Trp Asp Arg Phe Glu Val Gln Gly Leu
1               5                   10                  15

Gln Pro Asn Gly Glu Glu Met Thr Leu Lys Gln Phe Leu Asp Tyr Phe
            20                  25                  30

Lys Thr Glu His Lys Leu Glu Ile Thr Met Leu Ser Gln Gly Val Ser
        35                  40                  45

Met Leu Tyr Ser Phe Phe Met Pro Ala Ala Lys Leu Lys Glu Arg Leu
    50                  55                  60

Asp Gln Pro Met Thr Glu Ile Val Ser Arg Val Ser Lys Arg Lys Leu
65                  70                  75                  80

Gly Arg His Val Arg Ala Leu Val Leu Glu Leu Cys Cys Asn Asp Glu
                85                  90                  95

-continued

Ser Gly Glu Asp Val Glu Val Pro Tyr Val Arg Tyr Thr Ile Arg
            100                 105                 110

<210> SEQ ID NO 26
<211> LENGTH: 111
<212> TYPE: PRT
<213> ORGANISM: Homo sapiens

<400> SEQUENCE: 26

Tyr Asn Gln Glu Trp Thr Leu Trp Asp Arg Phe Glu Val Gln Gly Leu
1               5                   10                  15

Gln Pro Asn Gly Glu Glu Met Thr Leu Lys Gln Phe Leu Asp Tyr Phe
            20                  25                  30

Lys Thr Glu His Lys Leu Glu Ile Thr Met Leu Ser Gln Gly Val Ser
        35                  40                  45

Met Leu Tyr Ser Phe Phe Met Pro Ala Ala Lys Leu Lys Glu Arg Leu
50                  55                  60

Asp Gln Pro Met Thr Glu Ile Val Ser Arg Val Ser Lys Arg Lys Leu
65                  70                  75                  80

Gly Arg His Val Arg Ala Leu Val Leu Glu Leu Cys Cys Asn Asp Glu
                85                  90                  95

Ser Gly Glu Asp Val Glu Val Pro Tyr Val Arg Tyr Thr Ile Arg
            100                 105                 110

<210> SEQ ID NO 27
<211> LENGTH: 111
<212> TYPE: PRT
<213> ORGANISM: Danio rerio

<400> SEQUENCE: 27

Tyr Glu Gln Glu Trp Thr Leu Trp Asp Arg Phe Lys Val Gln Gly Leu
1               5                   10                  15

Gln Pro Asn Gly Glu Glu Met Thr Leu Lys Gln Phe Leu Asp Tyr Phe
            20                  25                  30

Lys Asn Glu His Lys Leu Glu Ile Thr Met Leu Ser Gln Gly Val Ser
        35                  40                  45

Met Leu Tyr Ser Phe Phe Met Pro Ala Ala Lys Leu Lys Glu Arg Leu
50                  55                  60

Asp Gln Pro Met Thr Glu Ile Val Ser Arg Val Ser Lys Arg Lys Leu
65                  70                  75                  80

Gly Arg His Val Arg Ala Leu Val Leu Glu Leu Cys Cys Asn Asp Glu
                85                  90                  95

Ser Gly Glu Asp Val Glu Val Pro Tyr Val Arg Tyr Thr Ile Arg
            100                 105                 110

<210> SEQ ID NO 28
<211> LENGTH: 105
<212> TYPE: PRT
<213> ORGANISM: Saccharomyces cerevisiae

<400> SEQUENCE: 28

Asn Asn Lys Lys Tyr Asp Lys Ile Trp Asp Arg Phe Asp Ile Lys Gly
1               5                   10                  15

Asp Ile Lys Leu Ser Asp Leu Ile Glu His Phe Glu Lys Asp Glu Gly
            20                  25                  30

Leu Glu Ile Thr Met Leu Ser Tyr Gly Val Ser Leu Leu Tyr Ala Ser
        35                  40                  45

Phe Phe Pro Pro Lys Lys Leu Lys Glu Arg Leu Asn Leu Pro Ile Thr
50                  55                  60

Gln Leu Val Lys Leu Val Thr Lys Lys Asp Ile Pro Ala His Val Ser
65                  70                  75                  80

Thr Met Ile Leu Glu Ile Cys Ala Asp Asp Lys Glu Gly Glu Asp Val
                85                  90                  95

Glu Val Pro Phe Ile Thr Ile His Leu
            100                 105

<210> SEQ ID NO 29
<211> LENGTH: 106
<212> TYPE: PRT
<213> ORGANISM: Homo sapiens

<400> SEQUENCE: 29

Arg Asn Gly Ile Ser Phe Thr Ile Trp Asp Arg Trp Thr Val His Gly
1               5                   10                  15

Lys Glu Asp Phe Thr Leu Leu Asp Phe Ile Asn Ala Val Lys Glu Lys
                20                  25                  30

Tyr Gly Ile Glu Pro Thr Met Val Val Gln Gly Val Lys Met Leu Tyr
            35                  40                  45

Val Pro Val Met Pro Gly His Ala Lys Arg Leu Lys Leu Thr Met His
50                  55                  60

Lys Leu Val Lys Pro Ser Thr Glu Lys Lys Tyr Val Asp Leu Thr Val
65                  70                  75                  80

Ser Phe Ala Pro Asp Ile Asp Gly Asp Glu Asp Leu Pro Gly Pro Pro
                85                  90                  95

Val Arg Tyr Tyr Phe Ser His Asp Thr Asp
            100                 105

<210> SEQ ID NO 30
<211> LENGTH: 107
<212> TYPE: PRT
<213> ORGANISM: Mus musculus

<400> SEQUENCE: 30

Arg Asn Gly Ile Ser Phe Thr Ile Trp Asp Arg Trp Thr Val His Gly
1               5                   10                  15

Lys Glu Asp Phe Thr Leu Ser Asp Phe Ile Asn Ala Val Lys Glu Asn
                20                  25                  30

Tyr Gly Ile Glu Pro Thr Met Val Val Gln Gly Val Lys Met Leu Tyr
            35                  40                  45

Val Pro Val Met Pro Gly His Ala Lys Arg Leu Lys Leu Thr Met His
50                  55                  60

Lys Leu Val Lys Pro Ser Thr Glu Lys Lys Tyr Val Asp Leu Thr Val
65                  70                  75                  80

Ser Phe Ala Pro Asp Ala Asp Gly Asp Glu Asp Leu Pro Gly Pro Pro
                85                  90                  95

Val Arg Tyr Tyr Phe Ser His Asp Thr Asn Glu
            100                 105

<210> SEQ ID NO 31
<211> LENGTH: 106
<212> TYPE: PRT
<213> ORGANISM: Danio rerio

<400> SEQUENCE: 31

Arg Asp Asp Ile Ser Phe Ser Ile Trp Asp Arg Trp Thr Ile Phe Gly
1               5                   10                  15

Arg Glu Asp Phe Thr Leu Ser Asp Phe Ile Ser Ala Val Arg Glu Lys

```
                  20                  25                  30
Tyr Gly Ile Glu Pro Thr Met Val Val His Gly Val Lys Met Leu Tyr
            35                  40                  45
Val Pro Val Met Pro Gly His Asn Lys Arg Leu Lys Leu Thr Met His
        50                  55                  60
Lys Leu Ile Lys Pro Ser Ser Gly Arg Lys Tyr Val Asp Leu Thr Val
65                  70                  75                  80
Ser Phe Ala Pro Glu Val Asp Gly Asp Glu Asp Leu Pro Gly Pro Pro
                85                  90                  95
Val Arg Tyr Tyr Phe Ser Gly Glu Asn Glu
                100                 105
```

```
<210> SEQ ID NO 32
<211> LENGTH: 9
<212> TYPE: PRT
<213> ORGANISM: Artificial sequence
<220> FEATURE:
<223> OTHER INFORMATION: Uba6 fragment isolated from cell lysate

<400> SEQUENCE: 32

Glu Ser Thr Leu His Leu Val Leu Arg
1               5

<210> SEQ ID NO 33
<211> LENGTH: 9
<212> TYPE: PRT
<213> ORGANISM: Artificial sequence
<220> FEATURE:
<223> OTHER INFORMATION: Uba6 fragment isolated from cell lysate

<400> SEQUENCE: 33

Thr Leu Ser Asp Tyr Asn Ile Gln Lys
1               5

<210> SEQ ID NO 34
<211> LENGTH: 13
<212> TYPE: PRT
<213> ORGANISM: Artificial Sequence
<220> FEATURE:
<223> OTHER INFORMATION: Uba6 fragment isolated from cell lysate

<400> SEQUENCE: 34

Ile Gln Asp Lys Glu Gly Ile Pro Pro Asp Gln Gln Arg
1               5                   10

<210> SEQ ID NO 35
<211> LENGTH: 16
<212> TYPE: PRT
<213> ORGANISM: Artificial sequence
<220> FEATURE:
<223> OTHER INFORMATION: Uba6 fragment isolated from cell lysate

<400> SEQUENCE: 35

Thr Ile Thr Leu Glu Val Glu Pro Ser Asp Thr Ile Glu Asn Val Lys
1               5                   10                  15

<210> SEQ ID NO 36
<211> LENGTH: 20
<212> TYPE: PRT
<213> ORGANISM: Artificial sequence
<220> FEATURE:
<223> OTHER INFORMATION: C terminal peptide of Ub obtained from insect
      cells

<400> SEQUENCE: 36
```

-continued

Ser Asp Tyr Asn Ile Gln Lys Glu Ser Thr Leu His Leu Val Leu Arg
1               5                   10                  15

Leu Arg Gly Gly
            20

<210> SEQ ID NO 37
<211> LENGTH: 20
<212> TYPE: PRT
<213> ORGANISM: Artificial sequence
<220> FEATURE:
<223> OTHER INFORMATION: C terminal peptide of Nedd8 obtained from
      insect cells

<400> SEQUENCE: 37

Ala Asp Tyr Lys Ile Leu Gly Gly Ser Val Leu His Leu Val Leu Ala
1               5                   10                  15

Leu Arg Gly Gly
            20

<210> SEQ ID NO 38
<211> LENGTH: 20
<212> TYPE: PRT
<213> ORGANISM: Artificial sequence
<220> FEATURE:
<223> OTHER INFORMATION: C terminal peptide of SUMO obtained from
      insect cells

<400> SEQUENCE: 38

Lys Glu Leu Gly Met Glu Glu Glu Asp Val Ile Glu Val Tyr Gln Glu
1               5                   10                  15

Gln Thr Gly Gly
            20

<210> SEQ ID NO 39
<211> LENGTH: 5
<212> TYPE: PRT
<213> ORGANISM: Artificial sequence
<220> FEATURE:
<223> OTHER INFORMATION: C terminal peptide of Fub1 obtained from
      insect cells

<400> SEQUENCE: 39

Arg Met Leu Gly Gly
1               5

<210> SEQ ID NO 40
<211> LENGTH: 13
<212> TYPE: PRT
<213> ORGANISM: Artificial sequence
<220> FEATURE:
<223> OTHER INFORMATION: C terminal peptide of Urm1 obtained from
      insect cells

<400> SEQUENCE: 40

Gln Asp Ser Val Leu Phe Ile Ser Thr Leu His Gly Gly
1               5                   10

<210> SEQ ID NO 41
<211> LENGTH: 9
<212> TYPE: PRT
<213> ORGANISM: Artificial sequence
<220> FEATURE:
<223> OTHER INFORMATION: C terminal peptide of ISG15 obtained from
      insect cells

<400> SEQUENCE: 41

Phe Met Asn Leu Arg Leu Arg Gly Gly

-continued

<210> SEQ ID NO 42
<211> LENGTH: 14
<212> TYPE: PRT
<213> ORGANISM: Artificial sequence
<220> FEATURE:
<223> OTHER INFORMATION: C terminal peptide of Fat10 obtained from
      insect cells

<400> SEQUENCE: 42

Lys Gly Asn Leu Leu Phe Leu Ala Ser Tyr Cys Ile Gly Gly
1               5                   10

<210> SEQ ID NO 43
<211> LENGTH: 9
<212> TYPE: PRT
<213> ORGANISM: Artificial sequence
<220> FEATURE:
<223> OTHER INFORMATION: A ubiquitin-derived Uba6 peptide isolated
      from 293T cells

<400> SEQUENCE: 43

Thr Leu Ser Asp Tyr Asn Ile Gln Lys
1               5

<210> SEQ ID NO 44
<211> LENGTH: 356
<212> TYPE: PRT
<213> ORGANISM: Mus musculus

<400> SEQUENCE: 44

Met Ala Glu Ser Pro Thr Glu Ala Ala Thr Ala Thr Ala Gly Ala
1               5                   10                  15

Gly Ala Ala Gly Pro Gly Ser Ser Gly Val Ala Gly Val Val Gly Val
                20                  25                  30

Ser Gly Ser Gly Gly Gly Phe Gly Pro Pro Phe Leu Pro Asp Val Trp
            35                  40                  45

Ala Ala Ala Ala Ala Ala Gly Gly Ala Gly Gly Pro Gly Ser Gly Leu
        50                  55                  60

Ala Pro Leu Pro Gly Leu Pro Pro Ser Ala Ala Ala His Gly Ala Ala
65                  70                  75                  80

Leu Leu Ser His Trp Asp Pro Thr Leu Ser Ser Asp Trp Asp Gly Glu
                85                  90                  95

Arg Thr Ala Pro Gln Cys Leu Leu Arg Ile Lys Arg Asp Ile Met Ser
            100                 105                 110

Ile Tyr Lys Glu Pro Pro Pro Gly Met Phe Val Val Pro Asp Thr Val
        115                 120                 125

Asp Met Thr Lys Ile His Ala Leu Ile Thr Gly Pro Phe Asp Thr Pro
    130                 135                 140

Tyr Glu Gly Gly Phe Phe Leu Phe Val Phe Arg Cys Pro Pro Asp Tyr
145                 150                 155                 160

Pro Ile His Pro Pro Arg Val Lys Leu Met Thr Thr Gly Asn Asn Thr
                165                 170                 175

Val Arg Phe Asn Pro Asn Phe Tyr Arg Asn Gly Lys Val Cys Leu Ser
            180                 185                 190

Ile Leu Gly Thr Trp Thr Gly Pro Ala Trp Ser Pro Ala Gln Ser Ile
        195                 200                 205

Ser Ser Val Leu Ile Ser Ile Gln Ser Leu Met Thr Glu Asn Pro Tyr
    210                 215                 220

His Asn Glu Pro Gly Phe Glu Gln Glu Arg His Pro Gly Asp Ser Lys
225                 230                 235                 240

Asn Tyr Asn Glu Cys Ile Arg His Glu Thr Ile Arg Val Ala Val Cys
            245                 250                 255

Asp Met Met Glu Gly Lys Cys Pro Cys Pro Glu Pro Leu Arg Gly Val
        260                 265                 270

Met Glu Lys Ser Phe Leu Glu Tyr Tyr Asp Phe Tyr Glu Val Ala Cys
    275                 280                 285

Lys Asp Arg Leu His Leu Gln Gly Gln Thr Met Gln Asp Pro Phe Gly
290                 295                 300

Glu Lys Arg Gly His Phe Asp Tyr Gln Ser Leu Leu Met Arg Leu Gly
305                 310                 315                 320

Leu Ile Arg Gln Lys Val Leu Glu Arg Leu His Asn Glu Asn Ala Glu
                325                 330                 335

Met Asp Ser Asp Ser Ser Ser Gly Thr Glu Thr Asp Leu His Gly
            340                 345                 350

Ser Leu Arg Val
        355

<210> SEQ ID NO 45
<211> LENGTH: 356
<212> TYPE: PRT
<213> ORGANISM: R. norvegicus

<400> SEQUENCE: 45

Met Ala Glu Ser Pro Thr Glu Glu Ala Thr Ala Thr Ala Gly Ala
1               5                   10                  15

Gly Ala Ala Gly Pro Gly Ser Ser Gly Val Ala Gly Val Val Gly Val
                20                  25                  30

Ser Gly Ser Gly Gly Gly Phe Gly Pro Pro Phe Leu Pro Asp Val Trp
            35                  40                  45

Ala Ala Ala Ala Ala Ala Gly Gly Ala Gly Pro Gly Ser Gly Leu
        50                  55                  60

Ala Pro Leu Pro Gly Leu Pro Pro Ser Ala Ala His Gly Ala Ala
65                  70                  75                  80

Leu Leu Ser His Trp Asp Pro Thr Leu Ser Ser Asp Trp Asp Gly Glu
                85                  90                  95

Arg Thr Ala Pro Gln Cys Leu Leu Arg Ile Lys Arg Asp Ile Met Ser
                100                 105                 110

Ile Tyr Lys Glu Pro Pro Pro Gly Met Phe Val Val Pro Asp Thr Val
            115                 120                 125

Asp Met Thr Lys Ile His Ala Leu Ile Thr Gly Pro Phe Asp Thr Pro
        130                 135                 140

Tyr Glu Gly Gly Phe Phe Leu Phe Val Phe Arg Cys Pro Pro Asp Tyr
145                 150                 155                 160

Pro Ile His Pro Pro Arg Val Lys Leu Met Thr Thr Gly Asn Asn Thr
                165                 170                 175

Val Arg Phe Asn Pro Asn Phe Tyr Arg Asn Gly Lys Val Cys Leu Ser
            180                 185                 190

Ile Leu Gly Thr Trp Thr Gly Pro Ala Trp Ser Pro Ala Gln Ser Ile
        195                 200                 205

Ser Ser Val Leu Ile Ser Ile Gln Ser Leu Met Thr Glu Asn Pro Tyr
210                 215                 220

His Asn Glu Pro Gly Phe Glu Gln Glu Arg His Pro Gly Asp Ser Lys
225                 230                 235                 240

-continued

```
Asn Tyr Asn Glu Cys Ile Arg His Glu Thr Ile Arg Val Ala Val Cys
                245                 250                 255

Asp Met Met Glu Gly Lys Cys Pro Cys Pro Glu Pro Leu Arg Gly Val
            260                 265                 270

Met Glu Lys Ser Phe Leu Glu Tyr Tyr Asp Phe Tyr Gly Val Ala Cys
        275                 280                 285

Lys Asp Arg Leu His Leu Gln Gly Gln Thr Met Gln Asp Pro Phe Gly
    290                 295                 300

Glu Lys Arg Gly His Phe Asp Tyr Gln Ser Leu Leu Met Arg Leu Gly
305                 310                 315                 320

Leu Ile Arg Gln Lys Val Leu Glu Arg Leu His Asn Glu Asn Ala Glu
                325                 330                 335

Met Asp Ser Asp Ser Ser Ser Ser Gly Thr Glu Thr Asp Leu His Gly
            340                 345                 350

Ser Leu Arg Val
        355

<210> SEQ ID NO 46
<211> LENGTH: 354
<212> TYPE: PRT
<213> ORGANISM: Homo sapiens

<400> SEQUENCE: 46

Met Ala Glu Ser Pro Thr Glu Glu Ala Ala Thr Ala Gly Ala Gly Ala
1               5                   10                  15

Ala Gly Pro Gly Ala Ser Ser Val Ala Gly Val Val Gly Val Ser Gly
            20                  25                  30

Ser Gly Gly Gly Phe Gly Pro Pro Phe Leu Pro Asp Val Trp Ala Ala
        35                  40                  45

Ala Ala Ala Ala Gly Gly Ala Gly Gly Pro Gly Ser Gly Leu Ala Pro
    50                  55                  60

Leu Pro Gly Leu Pro Pro Ser Ala Ala His Gly Ala Ala Leu Leu Leu
65                  70                  75                  80

Ser His Trp Asp Pro Thr Leu Ser Ser Asp Trp Asp Gly Glu Arg Thr
                85                  90                  95

Ala Pro Gln Cys Leu Leu Arg Ile Lys Arg Asp Ile Met Ser Ile Tyr
            100                 105                 110

Lys Glu Pro Pro Pro Gly Met Phe Val Val Pro Asp Thr Val Asp Met
        115                 120                 125

Thr Lys Ile His Ala Leu Ile Thr Gly Pro Phe Asp Thr Pro Tyr Glu
    130                 135                 140

Gly Gly Phe Phe Leu Phe Val Phe Arg Cys Pro Pro Asp Tyr Pro Ile
145                 150                 155                 160

His Pro Pro Arg Val Lys Leu Met Thr Thr Gly Asn Asn Thr Val Arg
                165                 170                 175

Phe Asn Pro Asn Phe Tyr Arg Asn Gly Lys Val Cys Leu Ser Ile Leu
            180                 185                 190

Gly Thr Trp Thr Gly Pro Ala Trp Ser Pro Ala Gln Ser Ile Ser Ser
        195                 200                 205

Val Leu Ile Ser Ile Gln Ser Leu Met Thr Glu Asn Pro Tyr His Asn
    210                 215                 220

Glu Pro Gly Phe Glu Gln Glu Arg His Pro Gly Asp Ser Lys Asn Tyr
225                 230                 235                 240

Asn Glu Cys Ile Arg His Glu Thr Ile Arg Val Ala Val Cys Asp Met
                245                 250                 255
```

```
Met Glu Gly Lys Cys Pro Cys Pro Glu Pro Leu Arg Gly Val Met Glu
                260                 265                 270

Lys Ser Phe Leu Glu Tyr Tyr Asp Phe Tyr Glu Val Ala Cys Lys Asp
            275                 280                 285

Arg Leu His Leu Gln Gly Gln Thr Met Gln Asp Pro Phe Gly Glu Lys
        290                 295                 300

Arg Gly His Phe Asp Tyr Gln Ser Leu Leu Met Arg Leu Gly Leu Ile
305                 310                 315                 320

Arg Gln Lys Val Leu Glu Arg Leu His Asn Glu Asn Ala Glu Met Asp
                325                 330                 335

Ser Asp Ser Ser Ser Gly Thr Glu Thr Asp Leu His Gly Ser Leu
            340                 345                 350

Arg Val

<210> SEQ ID NO 47
<211> LENGTH: 380
<212> TYPE: PRT
<213> ORGANISM: Danio rerio

<400> SEQUENCE: 47

Met Ala Asp Ser Val Thr Glu Glu Ala Asn Gly Ser Val Gly Ala Ala
1               5                   10                  15

Gln Gly His Gly Ala Gln Leu Ser Ala Ser Leu Gly Asn Ser Ile Pro
            20                  25                  30

Gly His Ser Ser Ala Ser Pro Pro Ala Asp Thr Gly Leu Ala Val
        35                  40                  45

Val Glu Pro Gly Met Ala His Thr Ile Thr Pro Ala Val Glu Ser Gly
50                  55                  60

Leu Gly Val Leu Thr His Ala Val Ser Ser Thr Val Pro Val Ala Val
65                  70                  75                  80

Leu Pro Ser Leu Pro Pro Gly Ile Gly Ser Gly Val Pro Ala Gly Ala
                85                  90                  95

Gly Leu Leu Ser Gln Ile His Ala Thr Ser Trp Asp Pro Thr Leu Ser
            100                 105                 110

Thr Asp Trp Asp Asn Glu Lys Ala Ser Gln Gln Cys Ile Leu Arg Ile
        115                 120                 125

Lys Arg Asp Ile Met Ser Ile Tyr Lys Glu Pro Pro Pro Gly Met Phe
130                 135                 140

Val Val Pro Asp Pro His Asp Met Thr Lys Ile His Ala Leu Ile Thr
145                 150                 155                 160

Gly Pro Phe Asp Thr Pro Tyr Glu Gly Gly Phe Phe Leu Phe Leu Phe
                165                 170                 175

Arg Cys Pro Pro Asp Tyr Pro Ile His Pro Pro Arg Val Lys Leu Ile
            180                 185                 190

Thr Thr Gly His Asn Thr Val Arg Phe Asn Pro Asn Phe Tyr Arg Asn
        195                 200                 205

Gly Lys Val Cys Leu Ser Ile Leu Gly Thr Trp Thr Gly Pro Ala Trp
210                 215                 220

Ser Pro Ala Gln Ser Ile Ser Ser Val Leu Ile Ser Ile Gln Ser Leu
225                 230                 235                 240

Met Thr Glu Asn Pro Tyr His Asn Glu Pro Gly Phe Glu Gln Glu Arg
                245                 250                 255

His Pro Gly Asp Ser Lys Asn Tyr Asn Glu Cys Ile Arg His Glu Thr
            260                 265                 270

Met Arg Val Ala Val Cys Asp Met Leu Glu Gly Lys Val Ser Cys Pro
```

```
                      275                 280                 285
Glu Ala Leu Trp Ser Val Met Glu Lys Ser Phe Leu Glu Tyr Tyr Asp
    290                 295                 300
Phe Tyr Glu Gly Val Cys Lys Glu Arg Leu His Leu Gln Gly Gln Asn
305                 310                 315                 320
Met Gln Asp Pro Phe Gly Lys Arg Gly Arg Phe Asp Tyr Gln Gly
            325                 330                 335
Leu Leu Thr Arg Leu Arg Ala Ile Gln Arg Arg Leu Arg Glu Lys Cys
                340                 345                 350
Pro Pro Glu Asp Asn Asp Gly Asp Ser Asp Ser Asp Thr Ser Ser Ser
                355                 360                 365
Gly Thr Asp Pro Asp Ser Gln Gly Ser Ser Gln Pro
            370                 375                 380

<210> SEQ ID NO 48
<211> LENGTH: 356
<212> TYPE: PRT
<213> ORGANISM: Xenopus laevis

<400> SEQUENCE: 48

Met Ala Glu Ser Pro Thr Glu Glu Ala Ala Thr Ala Thr Ala Gly Ala
1               5                   10                  15
Gly Ala Ala Gly Pro Gly Ser Ser Gly Val Ala Gly Val Val Gly Val
                20                  25                  30
Ser Gly Ser Gly Gly Gly Phe Gly Pro Pro Phe Leu Pro Asp Val Trp
            35                  40                  45
Ala Ala Ala Ala Ala Gly Gly Ala Gly Gly Pro Gly Ser Gly Leu
        50                  55                  60
Ala Pro Leu Pro Gly Leu Pro Pro Ser Ala Ala His Gly Ala Ala
65                  70                  75                  80
Leu Leu Ser His Trp Asp Pro Thr Leu Ser Ser Asp Trp Asp Gly Glu
                85                  90                  95
Arg Thr Ala Pro Gln Cys Leu Leu Arg Ile Lys Arg Asp Ile Met Ser
                100                 105                 110
Ile Tyr Lys Glu Pro Pro Pro Gly Met Phe Val Val Pro Asp Thr Val
            115                 120                 125
Asp Met Thr Lys Ile His Ala Leu Ile Thr Gly Pro Phe Asp Thr Pro
        130                 135                 140
Tyr Glu Gly Gly Phe Phe Leu Phe Val Phe Arg Cys Pro Pro Asp Tyr
145                 150                 155                 160
Pro Ile His Pro Pro Arg Val Lys Leu Met Thr Thr Gly Asn Asn Thr
                165                 170                 175
Val Arg Phe Asn Pro Asn Phe Tyr Arg Asn Gly Lys Val Cys Leu Ser
                180                 185                 190
Ile Leu Gly Thr Trp Thr Gly Pro Ala Trp Ser Pro Ala Gln Ser Ile
            195                 200                 205
Ser Ser Val Leu Ile Ser Ile Gln Ser Leu Met Thr Glu Asn Pro Tyr
        210                 215                 220
His Asn Glu Pro Gly Phe Glu Gln Glu Arg His Pro Gly Asp Ser Lys
225                 230                 235                 240
Asn Tyr Asn Glu Cys Ile Arg His Glu Thr Ile Arg Val Ala Val Cys
                245                 250                 255
Asp Met Met Glu Gly Lys Cys Pro Cys Pro Glu Pro Leu Arg Gly Val
            260                 265                 270
Met Glu Lys Ser Phe Leu Glu Tyr Tyr Asp Phe Tyr Glu Val Ala Cys
```

```
                 275                 280                 285
Lys Asp Arg Leu His Leu Gln Gly Gln Thr Met Gln Asp Pro Phe Gly
    290                 295                 300

Glu Lys Arg Gly His Phe Asp Tyr Gln Ser Leu Leu Met Arg Leu Gly
305                 310                 315                 320

Leu Ile Arg Gln Lys Val Leu Glu Arg Leu His Asn Glu Asn Ala Glu
                325                 330                 335

Met Asp Ser Asp Ser Ser Ser Gly Thr Glu Thr Asp Leu His Gly
                340                 345                 350

Ser Leu Arg Val
        355

<210> SEQ ID NO 49
<211> LENGTH: 234
<212> TYPE: PRT
<213> ORGANISM: Strongylocentrotus purpuratus

<400> SEQUENCE: 49

Met Glu Thr Met Glu Glu Pro Asp Glu Glu His Ile Glu Ala Thr Ala
1               5                   10                  15

Thr Leu Met Ala Ser Gln Leu Val Gln Ala Gln Leu Ser Pro Trp Asp
            20                  25                  30

Pro Ile Lys Cys Lys Asp Trp Glu Asn Gln Lys Pro Ser Gln Leu Cys
        35                  40                  45

Leu Leu Arg Ile Lys Arg Asp Ile Met Asn Ile Tyr Thr Asp Pro Pro
    50                  55                  60

Leu Gly Met Cys Ile Val Pro Glu Glu Asp Ile Thr Arg Val His Ala
65                  70                  75                  80

Leu Ile Thr Gly Pro Phe Asp Thr Pro Tyr Glu Gly Gly Phe Phe His
                85                  90                  95

Phe Phe Val Lys Phe Pro Pro Asp Tyr Pro Ile Arg Pro Pro Arg Ile
            100                 105                 110

Lys Leu Met Thr Thr Gly Asp Gly Ser Val Arg Phe Asn Pro Asn Leu
        115                 120                 125

Tyr Arg Ser Gly Lys Val Cys Leu Ser Ile Leu Gly Thr Trp Arg Gly
    130                 135                 140

Pro Ala Trp Ser Pro Ala Gln Ser Leu Ser Ser Val Leu Met Ser Ile
145                 150                 155                 160

Gln Ser Leu Met Asn Glu Lys Pro Tyr His Asn Glu Pro Gly Phe Glu
                165                 170                 175

Gln Asp Pro Phe Gly Glu Lys Arg Gly Lys Phe Asp Tyr Ala Thr Leu
            180                 185                 190

Leu Lys Thr Leu Lys Ala Ile Lys Val Lys Leu Asp Glu Ala Ser Gln
        195                 200                 205

Met Glu Val Ser Ser Asp Ser Glu Ser Ser Gly Gly Ser Asp Leu Asp
    210                 215                 220

Thr Lys Leu Ser Gly Pro Asp Thr Ser Ser
225                 230

<210> SEQ ID NO 50
<211> LENGTH: 83
<212> TYPE: PRT
<213> ORGANISM: Homo sapiens

<400> SEQUENCE: 50

Thr Leu Trp Asp Arg Phe Glu Val Gln Gly Leu Gln Pro Asn Gly Glu
1               5                   10                  15
```

Glu Met Thr Leu Lys Gln Phe Leu Asp Tyr Phe Lys Thr Glu His Lys
            20                  25                  30

Leu Glu Ile Thr Met Leu Ser Gln Gly Val Ser Met Leu Tyr Ser Phe
        35                  40                  45

Phe Met Pro Ala Leu Lys Glu Arg Leu Asp Gln Pro Met Thr Glu Ile
    50                  55                  60

Val Ser Arg Val Ser Lys Arg Lys Leu Gly Arg His Val Arg Ala Leu
65                  70                  75                  80

Val Leu Glu

<210> SEQ ID NO 51
<211> LENGTH: 79
<212> TYPE: PRT
<213> ORGANISM: Homo sapiens

<400> SEQUENCE: 51

Thr Ile Trp Asp Arg Trp Thr Val His Gly Lys Glu Asp Phe Thr Leu
1               5                   10                  15

Leu Asp Phe Ile Asn Ala Val Lys Glu Lys Tyr Gly Ile Glu Pro Thr
            20                  25                  30

Met Val Val Gln Gly Val Lys Met Leu Tyr Val Pro Val Met Pro Gly
        35                  40                  45

His Ala Lys Arg Leu Lys Leu Thr Met His Lys Leu Val Lys Pro Thr
    50                  55                  60

Thr Glu Lys Lys Tyr Val Asp Leu Thr Val Ser Phe Ala Pro Asp
65                  70                  75

<210> SEQ ID NO 52
<211> LENGTH: 93
<212> TYPE: PRT
<213> ORGANISM: Homo sapiens

<400> SEQUENCE: 52

Pro Gln Asn Ile Gln Phe Ser Pro Ser Ala Lys Leu Gln Glu Val Leu
1               5                   10                  15

Asp Tyr Leu Thr Asn Ser Ala Ser Leu Gln Met Lys Ser Pro Ala Ile
            20                  25                  30

Thr Ala Thr Leu Glu Gly Lys Asn Arg Thr Leu Tyr Leu Gln Ser Val
        35                  40                  45

Thr Ser Ile Glu Glu Arg Thr Arg Pro Asn Leu Ser Lys Thr Leu Lys
    50                  55                  60

Glu Leu Gly Leu Val Asp Gly Gln Glu Leu Ala Val Ala Asp Val Thr
65                  70                  75                  80

Thr Pro Gln Thr Val Leu Phe Lys Leu His Phe Thr Ser
                85                  90

<210> SEQ ID NO 53
<211> LENGTH: 25
<212> TYPE: DNA
<213> ORGANISM: Artificial sequence
<220> FEATURE:
<223> OTHER INFORMATION: Oligonucleotide used for RNA interference

<400> SEQUENCE: 53
ggtcaaactg atgacaacgg gcaat                                          25

<210> SEQ ID NO 54
<211> LENGTH: 25
<212> TYPE: DNA

<213> ORGANISM: Artificial sequence
<220> FEATURE:
<223> OTHER INFORMATION: Oligonucleotide used for RNA interference

<400> SEQUENCE: 54
tcctttctgg agtattacga cttct        25

<210> SEQ ID NO 55
<211> LENGTH: 25
<212> TYPE: DNA
<213> ORGANISM: Artificial sequence
<220> FEATURE:
<223> OTHER INFORMATION: Oligonucleotide used for RNA interference

<400> SEQUENCE: 55
gcctgcacct tcaaggccaa actat        25

<210> SEQ ID NO 56
<211> LENGTH: 930
<212> TYPE: PRT
<213> ORGANISM: Artificial sequence
<220> FEATURE:
<223> OTHER INFORMATION: Consensus sequence

<400> SEQUENCE: 56

```
Met Ser Ser Ser Leu Ser Lys Lys Arg Arg Val Ser Gly Asp Pro Gly
1               5                   10                  15

Ser Cys Ser Ala Ser Val Pro Thr Asn Met Lys Asn Glu Asp Ile Asp
            20                  25                  30

Glu Ser Leu Tyr Ser Arg Gln Leu Tyr Val Leu Gly His Glu Ala Met
        35                  40                  45

Lys Arg Met Gln Thr Ser Ser Val Leu Val Ser Gly Leu Arg Gly Leu
    50                  55                  60

Gly Val Glu Ile Ala Lys Asn Ile Ile Leu Gly Gly Val Lys Leu His
65                  70                  75                  80

Asp Gly Gly Gln Trp Ala Asp Leu Ser Ser Gln Phe Phe Leu Arg Glu
                85                  90                  95

Glu Asp Ile Gly Lys Asn Arg Ala Glu Val Ser Gln Pro Arg Leu Ala
            100                 105                 110

Glu Leu Asn Ser Tyr Val Pro Val Thr Tyr Thr Gly Thr Leu Asp Val
        115                 120                 125

Phe Leu Ser Lys Phe Gln Val Val Leu Thr Asn Thr Leu Glu Gln
    130                 135                 140

Leu Arg Ile Glu Phe Cys His Ser Arg Gly Ile Lys Ile Val Arg Gly
145                 150                 155                 160

Leu Phe Gly Gly Leu Phe Cys Asp Phe Gly Glu Glu Ile Val Thr Gly
                165                 170                 175

Ser Gly Glu Pro Leu Ser Ala Met Val Ser Met Ile Thr Lys Asp Asn
            180                 185                 190

Pro Gly Val Val Thr Cys Leu Asp Glu Arg His Gly Glu Ser Gly Asp
        195                 200                 205

Phe Val Ser Phe Ser Glu Val Gln Gly Met Thr Glu Leu Asn Gly Thr
    210                 215                 220

Pro Met Glu Ile Lys Val Leu Gly Pro Tyr Thr Phe Ser Ile Asp Thr
225                 230                 235                 240

Ser Phe Ser Asp Tyr Ile Arg Val Ser Gln Val Lys Val Pro Lys Lys
                245                 250                 255

Ile Ser Phe Lys Ser Leu Leu Glu Pro Asp Phe Val Val Thr Asp Phe
            260                 265                 270
```

```
Ala Lys Phe Asp Arg Pro Ala Gln Leu His Ile Gly Phe Gln Ala Leu
        275                 280                 285
His Gln Phe Gln His Arg Pro Arg Pro Arg Asn Glu Glu Asp Ala Glu
        290                 295                 300
Glu Leu Val Lys Leu Ala Val Asn Ala Ser Leu Gln Glu Leu Asp Leu
305                 310                 315                 320
Ile Arg Lys Leu Ala Ala Gly Asp Leu Ala Pro Ile Asn Ala Phe Ile
                325                 330                 335
Gly Gly Leu Ala Ala Gln Glu Val Met Lys Ala Cys Ser Gly Lys Phe
                340                 345                 350
Met Pro Ile Gln Trp Leu Tyr Phe Asp Ala Leu Glu Cys Leu Pro Glu
        355                 360                 365
Leu Glu Glu Glu Cys Leu Pro Arg Gln Arg Tyr Asp Gly Gln Val Ala
        370                 375                 380
Val Phe Gly Ser Asp Leu Gln Glu Lys Leu Gly Lys Gln Lys Tyr Phe
385                 390                 395                 400
Leu Val Gly Ala Gly Ala Ile Gly Cys Glu Leu Leu Lys Met Leu Gly
                405                 410                 415
Leu Gly Ser Gly Glu Asp Gly Glu Ile Ile Val Thr Asp Met Asp Thr
                420                 425                 430
Ile Glu Lys Ser Asn Leu Asn Arg Gln Phe Leu Phe Arg Pro Trp Asp
        435                 440                 445
Val Thr Lys Leu Lys Ser Asp Thr Ala Ala Ala Val Arg Met Asn
450                 455                 460
Pro Ile Arg Ile Ala His Gln Asn Arg Val Gly Pro Asp Thr Glu Arg
465                 470                 475                 480
Ile Tyr Asp Asp Asp Phe Phe Lys Leu Asp Gly Val Ala Asn Ala Leu
                485                 490                 495
Asp Asn Val Asp Ala Arg Met Arg Arg Cys Val Tyr Tyr Arg Lys Pro
                500                 505                 510
Leu Leu Glu Ser Gly Thr Leu Gly Thr Lys Gly Asn Gln Val Val Ile
        515                 520                 525
Pro Phe Leu Thr Glu Ser Tyr Ser Ser Ser Asp Pro Pro Glu Lys Ser
        530                 535                 540
Ile Pro Ile Cys Thr Leu Lys Phe Pro Asn Ala Ile Glu His Thr Ile
545                 550                 555                 560
Gln Trp Ala Arg Asp Glu Phe Glu Gly Leu Phe Lys Gln Ala Glu Asn
                565                 570                 575
Val Asn Gln Tyr Leu Thr Asp Lys Phe Val Glu Arg Thr Leu Gln Leu
                580                 585                 590
Gly Thr Glu Val Leu Glu Val Ile Ser Leu Val Ser Arg Pro Arg Asn
        595                 600                 605
Trp Asp Cys Val Thr Trp Ala Arg Leu His Trp Glu Lys Gln Tyr Asn
        610                 615                 620
His Asn Ile Arg Gln Leu Leu His Asn Phe Pro Pro Asp Gln Leu Thr
625                 630                 635                 640
Ser Ser Gly Ala Phe Trp Ser Gly Pro Lys Arg Cys Pro His Pro Leu
                645                 650                 655
Phe Asp Val Asn Asn Pro Leu His Leu Asp Tyr Val Met Ala Ala Ala
                660                 665                 670
Asn Leu Phe Ala Thr Tyr Gly Leu Pro Ser Ala Val Leu Leu Gln Asp
        675                 680                 685
Val Val Pro Glu Phe Thr Pro Lys Ser Gly Val Lys Ile His Val Ser
```

```
                    690                 695                 700
Asp Gln Glu Leu Gln Ser Ser Ala Ser Val Asp Asp Ser Arg Leu Glu
705                 710                 715                 720

Glu Leu Lys Ala Leu Leu Pro Ser Pro Asp Thr Leu Gly Phe Lys Met
                725                 730                 735

Pro Ile Asp Phe Glu Lys Asp Asp Ser Asn Phe His Met Asp Phe
                740                 745                 750

Ile Val Ala Ala Ser Asn Leu Arg Ala Cys Ile Glu Pro Ala Asp Arg
                755                 760                 765

His Lys Ser Lys Leu Ile Ala Gly Lys Ile Ile Pro Ala Ile Ala Thr
                770                 775                 780

Thr Thr Ala Ala Val Val Gly Leu Val Cys Leu Glu Leu Tyr Lys Val
785                 790                 795                 800

Val Gln Gly His Leu Glu Ser Tyr Lys Asn Gly Phe Leu Asn Leu Ala
                805                 810                 815

Leu Pro Phe Phe Gly Phe Ser Glu Pro Leu Ala Pro Lys His Gln Tyr
                820                 825                 830

Tyr Asn Glu Trp Thr Leu Trp Asp Arg Phe Glu Val Lys Gly Leu Gln
                835                 840                 845

Pro Gly Glu Glu Met Phe Leu Asp Tyr Phe Lys Glu His Leu Glu Ile
850                 855                 860

Thr Met Leu Ser Gln Gly Val Ser Met Leu Tyr Ser Phe Met Pro Ala
865                 870                 875                 880

Lys Leu Lys Glu Arg Leu Asp Leu Pro Met Thr Glu Ile Val Lys Val
                885                 890                 895

Ser Lys Lys Lys Leu Gly Arg His Val Arg Leu Val Leu Glu Leu Cys
                900                 905                 910

Cys Asn Asp Asp Ser Gly Glu Asp Val Glu Val Pro Tyr Val Arg Tyr
                915                 920                 925

Ile Arg
    930

<210> SEQ ID NO 57
<211> LENGTH: 83
<212> TYPE: PRT
<213> ORGANISM: Artificial sequence
<220> FEATURE:
<223> OTHER INFORMATION: Consensus sequence

<400> SEQUENCE: 57

Ile Trp Thr Ile Trp Asp Arg Phe Val Lys Gly Glu Asp Met Thr Leu
1               5                   10                  15

Asp Phe Ile Asp Phe Lys Glu Gly Leu Glu Ile Thr Met Leu Ser Gln
                20                  25                  30

Gly Val Ser Met Leu Tyr Phe Met Pro Ala Lys Leu Lys Glu Arg Leu
                35                  40                  45

Leu Pro Met Thr Leu Val Lys Val Ser Lys Lys Lys Leu His Val Thr
                50                  55                  60

Leu Val Glu Leu Cys Ala Asp Asp Glu Asp Val Glu Val Pro Tyr Val
65                  70                  75                  80

Arg Tyr Ile

<210> SEQ ID NO 58
<211> LENGTH: 353
<212> TYPE: PRT
<213> ORGANISM: Artificial sequence
<220> FEATURE:
```

<223> OTHER INFORMATION: Consensus sequence

<400> SEQUENCE: 58

```
Met Ala Glu Ser Pro Thr Glu Glu Ala Ala Thr Ala Thr Gly Ala
 1               5                  10                  15
Gly Ala Ala Gly Pro Gly Ser Gly Val Ala Gly Val Val Gly Val Ser
                20                  25                  30
Gly Ser Gly Gly Gly Phe Gly Pro Pro Phe Leu Pro Asp Val Trp Ala
                35                  40                  45
Ala Ala Ala Ala Ala Gly Gly Ala Gly Gly Pro Gly Ser Gly Leu Ala
            50                  55                  60
Pro Leu Pro Gly Leu Pro Pro Ser Ala Ala Ala His Gly Ala Ala Leu
 65                 70                  75                  80
Leu Ser His Trp Asp Pro Thr Leu Ser Ser Asp Trp Asp Glu Arg Thr
                85                  90                  95
Pro Gln Cys Leu Leu Arg Ile Lys Arg Asp Ile Met Ser Ile Tyr Lys
            100                 105                 110
Glu Pro Pro Pro Gly Met Phe Val Val Pro Asp Thr Val Asp Met Thr
            115                 120                 125
Lys Ile His Ala Leu Ile Thr Gly Pro Phe Asp Thr Pro Tyr Glu Gly
130                 135                 140
Gly Phe Phe Leu Phe Val Phe Arg Cys Pro Pro Asp Tyr Pro Ile His
145                 150                 155                 160
Pro Pro Arg Val Lys Leu Met Thr Thr Gly Asn Asn Thr Val Arg Phe
                165                 170                 175
Asn Pro Asn Phe Tyr Arg Asn Gly Lys Val Cys Leu Ser Ile Leu Gly
            180                 185                 190
Thr Trp Thr Gly Pro Ala Trp Ser Pro Ala Gln Ser Ile Ser Ser Val
            195                 200                 205
Leu Ile Ser Ile Gln Ser Leu Met Thr Glu Asn Pro Tyr His Asn Glu
210                 215                 220
Pro Gly Phe Glu Gln Glu Arg His Pro Gly Asp Ser Lys Asn Tyr Asn
225                 230                 235                 240
Glu Cys Ile Arg His Glu Thr Ile Arg Val Ala Val Cys Asp Met Met
                245                 250                 255
Glu Gly Lys Cys Pro Cys Pro Glu Pro Leu Arg Gly Val Met Glu Lys
            260                 265                 270
Ser Phe Leu Glu Tyr Tyr Asp Phe Tyr Glu Val Ala Cys Lys Asp Arg
            275                 280                 285
Leu His Leu Gln Gly Gln Thr Met Gln Asp Pro Phe Gly Glu Lys Arg
        290                 295                 300
Gly His Phe Asp Tyr Gln Ser Leu Leu Met Arg Leu Gly Leu Ile Arg
305                 310                 315                 320
Gln Lys Val Leu Glu Arg Leu His Asn Glu Asn Ala Glu Met Asp Ser
                325                 330                 335
Asp Ser Ser Ser Ser Gly Thr Glu Thr Asp Leu His Gly Ser Leu Arg
            340                 345                 350
Val
```

<210> SEQ ID NO 59
<211> LENGTH: 14
<212> TYPE: PRT
<213> ORGANISM: Homo sapiens

<400> SEQUENCE: 59

-continued

```
Ser Ser Gln Lys Ala Leu Leu Leu Glu Leu Lys Gly Leu Gln
1               5                   10

<210> SEQ ID NO 60
<211> LENGTH: 14
<212> TYPE: PRT
<213> ORGANISM: Homo sapiens

<400> SEQUENCE: 60

Gln Cys Leu Leu Arg Ile Lys Arg Asp Ile Met Ser Ile Tyr
1               5                   10

<210> SEQ ID NO 61
<211> LENGTH: 14
<212> TYPE: PRT
<213> ORGANISM: Homo sapiens

<400> SEQUENCE: 61

Ala Ala Gln Leu Arg Ile Gln Lys Asp Ile Asn Glu Leu Asn
1               5                   10
```

ACTIVATION AND TRANSFER CASCADE FOR UBIQUITIN

RELATED APPLICATIONS

This application claims priority from International Application number PCT/US2008/051312, filed Jan. 17, 2008; U.S. provisional patent application No. 60/946,757, filed Jun. 28, 2007; and U.S. provisional patent application No. 60/885,431, filed Jan. 18, 2007; each of which is hereby incorporated herein by reference in its entirety for all purposes.

STATEMENT OF GOVERNMENT INTERESTS

This invention was made with government support under National Institutes of Health grant numbers AG011085 and GM54137. The Government has certain rights in the invention.

BACKGROUND

Protein turnover through the ubiquitin-proteasome pathway (UPP) constitutes a major system used by cells to control signaling networks. In this process, proteins are marked with a chain of ubiquitin molecules, which are linked to the target and to each other through isopeptide linkages with lysine residues (Pickart et al. (2004) *Biochim. Biophys. Acta.* 1695: 55; Pickart (2004) *Cell* 116:181). Ubiquitin is a 76 amino acid protein which becomes linked to lysine residues through its C-terminal glycine residue. Addition of four or more ubiquitin molecules is generally thought to be sufficient for recognition by the proteasome, where poly-ubiquitinated proteins are degraded (Lam et al. (2002) *Nature* 416:763). Protein turnover through the UPP is known to regulate many diverse cellular functions and to be intimately linked to human disease (Petroski and Deshaies (2005) *Nat. Rev. Mol. Cell. Biol.* 6:9). Several components of the ubiquitin system have been found to be mutated in cancer. Most frequently, alterations in the UPP system can lead to inappropriate degradation of tumor suppressor and over-expression of oncogenes, thereby promoting uncontrolled proliferation (Cardozo and Pagano (2004) *Nat. Rev. Mol Cell Biol.* 5:739). Defects in the UPP can also contribute to neurodegenerative diseases, such as Parkinson's Disease and the like. While ubiquitination plays a critical role in targeted protein degradation, it also plays important roles in controlling protein localization, the function of membrane proteins, endocytosis and other processes.

Protein ubiquitination is known to involve three major protein activities (Hershko et al. (1983) *J. Biol. Chem.* 258: 8206; Ganoth et al. (1988) *J. Biol. Chem.* 263:12412). First, ubiquitin is activated to form a high-energy thiol ester bond with an E1 ubiquitin activating enzyme. This process initially involves formation of an ubiquitin adenylate with the C-terminal glycine of ubiquitin (G76), consuming one molecule of ATP, followed by transfer of the G76 carboxylate to the active site cysteine to form a thiol ester (Haas et al. (1982) *J. Biol. Chem.* 257:10329); Haas et al. (1982) *J. Biol. Chem.* 257: 2543). In the second step, the E1~Ub thiol ester complex binds an E2 ubiquitin conjugating enzyme through the E1s C-terminal E2-binding domain. Ubiquitin is then transferred from the active site cysteine in E1 to the active site cysteine in the E2 (Pickart et al. (1985) *J. Biol. Chem.* 260:1573. The E2~Ub complex then dissociates from the E1 where it can interact with E3 ubiquitin ligases to promote transfer of ubiquitin to lysine residues either in the substrate or on growing poly-ubiquitin chains (Eletr et al. (2005) *Nat. Struct. Mol. Biol.* 12:933). Thus, the E1 enzyme plays a critical role in the ubiquitination process by allowing ubiquitin activation and facilitating ubiquitin transfer.

There is widespread interest in the use of UPP components as drug targets for disease. Indeed, the first drug targeting the UPP, VELCADE® (Millennium Pharmaceuticals, Inc., Cambridge, Mass.), was approved by the FDA in 2003 (Popat et al. (2006) *Expert Opin. Pharmacother.* 7:1337). VELCADE® targets the 26S proteasome, thereby blocking degradation of all proteins whose turnover requires the proteasome. VELCADE® has proven useful for the treatment of multiple myeloma. Id. Its mode of action appears to rely on the enhanced sensitivity of certain types of cancer cells for proteasome activity, possibly reflecting an increased requirement for the NFκB pathway, which relies on the proteasome. However, proteasome inhibition is also potentially toxic to normal cells and therefore, obtaining new drug targets with increased specificity would be useful.

SUMMARY

The present invention is based in part on the surprising discovery of a novel ubiquitin activating enzyme, Uba6. This discovery is particularly unexpected given the long-standing dogma in the field that a single activating enzyme exists for ubiquitin. The enzymatic properties of Uba6 differ substantially from the classical ubiquitin activating enzyme Ube1, indicating that Uba6 plays biological roles that are distinct from Ube1. Because Uba6 employs ATP in its catalytic mechanism, small molecule inhibitors that selectively inhibit the activity of Uba6 could be useful in controlling signaling pathways that depend specifically upon the activity of Uba6 in organisms such as humans.

In certain embodiments, methods for inhibiting a Uba6 activity are provided. In certain aspects, inhibition is achieved by contacting Uba6 with a compound that inhibits formation of a ubiquitin-adenylate intermediate (e.g., the compound binds an adenylation domain of Uba6), contacting Uba6 with a compound that inhibits thiol esterification of Uba6, or contacting Uba6 with a compound that inhibits transfer of ubiquitin to a ubiquitin conjugating enzyme (e.g., the compound binds a Ubl domain of Uba6). In certain aspects, inhibition is performed in vitro (e.g., using cell extracts) or in vivo (e.g., in a tissue culture cell or in an organism). In other aspects, the ubiquitin conjugating enzyme is one or more of E2C, E2D1, E2D2, E2D3, E2D4, E2E1, E2G, E2S, E2T and E2Z (also referred to herein as Use1).

In another embodiment, a method for inhibiting ubiquitin activation including contacting Uba6 with a compound that inhibits a catalytic cysteine domain of Uba6 is provided. In certain aspects, inhibition is performed in vitro (e.g., cell extracts) or in vivo (e.g., in a tissue culture cell or in an organism).

In another embodiment, a method of reducing a Uba6 activity in an organism in need thereof including administering to the organism one or more siRNAs complementary to a portion of a Uba6 mRNA is provided. In certain aspects, the siRNA is an RNA sequence including one or more of SEQ ID NO:1, SEQ ID NO:2 and SEQ ID NO:3. In other aspects, the portion of the Uba6 mRNA encodes a ThiF domain, a catalytic cysteine domain, an adenylate domain or a ubiquitin-like domain. In still other aspects, the organism is a human.

In another embodiment, a method of reducing ubiquitination in an organism in need thereof including administering to the organism one or more compounds that inhibits one or more Uba6 activities in the organism is provided. In certain aspects, the compound is an antibody or an siRNA. In other aspects, the organism is a human.

In yet another embodiment, a method of identifying a compound that inhibits charging of E2Z including providing a sample including E2Z and ubiquitin, contacting the sample with the compound, contacting the sample with Uba6 or a biologically active portion thereof, and determining whether the ubiquitin is bound to the E2Z in the presence of the compound, wherein the ubiquitin is not bound to the E2Z if the compound inhibits charging of E2Z is provided. In certain aspects, the method further includes visualizing E2Z on an SDS-PAGE gel.

In still another embodiment, a method of identifying a compound that inhibits a Uba6 activity including providing a sample including a ubiquitin conjugating enzyme and ubiquitin, contacting the sample with the compound, contacting the sample with Uba6 or a biologically active portion thereof, and determining whether the ubiquitin is bound to the ubiquitin conjugating enzyme in the presence of the compound, wherein the ubiquitin is not bound to the ubiquitin conjugating enzyme if the compound inhibits the Uba6 activity is provided. In certain aspects, the ubiquitin conjugating enzyme is selected from the group consisting of: E2C, E2D1, E2D2, E2D3, E2D4, E2E1, E2G, E2S, E2T and E2Z.

In yet another embodiment, a method of identifying a compound that inhibits a Uba6 activity including providing a sample including ubiquitin, contacting the sample with the compound, contacting the sample with Uba6 or a biologically active portion thereof, and determining whether the ubiquitin is bound to the Uba6 or the biologically active portion thereof in the presence of the compound, wherein the ubiquitin is not bound to the Uba6 if the compound inhibits the Uba6 activity is provided. In certain aspects, the ubiquitin is bound to the Uba6 or the biologically active portion thereof via thiol conjugation. In other aspects, the ubiquitin is immobilized.

In another embodiment, an RNA sequence having at least about 70% identity to a nucleic acid sequence selected from the group consisting of SEQ ID NO:1, SEQ ID NO:2 and SEQ ID NO:3, wherein the RNA sequence can inhibit a Uba6 activity is provided. In certain aspects, the Uba6 activity is selected from one or more of ubiquitin activation, ubiquitin-adenylate intermediate formation, ubiquitin thiol esterification, ubiquitin transfer to a ubiquitin-conjugating enzyme and/or ubiquitination of a target polypeptide. In other aspects, the RNA is siRNA.

In another embodiment, an RNA sequence selected from the group consisting of SEQ ID NO:1, SEQ ID NO:2 and SEQ ID NO:3 is provided. In certain aspects, the RNA sequence can inhibit a Uba6 activity such as ubiquitin activation, ubiquitin-adenylate intermediate formation, ubiquitin thiol esterification, ubiquitin transfer to a ubiquitin-conjugating enzyme and/or ubiquitination of a target polypeptide. In other aspects, the RNA is siRNA.

BRIEF DESCRIPTION OF THE DRAWINGS

FIGS. 3A-3C depict data showing that Uba6 and Ube1 display distinct preferences for charging of E2 ubiquitin conjugating enzymes. (A) The indicated E2s were produced using a bacterial in vitro translation system and metabolically labeled with $^{35}$S-methionine. E2s were mixed with Flag-HA-Uba6 or Flag-HA-Ube1 (expressed and purified from insect cells) and incubated at 30° C. for 30 minutes. Reaction mixtures were subjected to non-reducing SDS-PAGE and proteins visualized by autoradiography. An aliquot of E2 was included as a control for charging. (B) Summary of E2 charging data. (C) The ability of Uba6 to promote charging of E2D1 requires its active site cysteine (C625).

FIGS. 4A-4C depict data showing that E2 specificity of Uba6 resides in its C-terminal Ubl domain. (A) Domain structures of Ube1 and Uba6 showing the percent conservation over the catalytic domains and the C-terminal Ubiquitin-like (Ubl) domain. (B) Conservation of the C-terminal Ubl domains from Ube1 and Uba6. Sequence identifiers are set forth as follows: Ube1MmUb1 (SEQ ID NO:25); Ube1HsUb1 (SEQ ID NO:26); Ube1DrUb1 (SEQ ID NO:27); Ube1ScUb1 (SEQ ID NO:28); Uba6HsUb1 (SEQ ID NO:29); Uba6MmUb1 (SEQ ID NO:30); Uba6DrUb1 (SEQ ID NO:31); Consensus (SEQ ID NO:57). Alignment was generated using ClustalW. (C) Chimeric proteins in which the Ubl domains of Uba6 and Ube1 were swapped with each other were created. These proteins, along with wild-type and Ubl-deletion mutants, were expressed in insect cells as Flag-HA fusion proteins, purified, and assayed for their ability to promote charging of Cdc34. Cdc34 is charged by Ube1 but not Uba6 (lanes 2 and 3). Both E1s lacking the Ubl domain were inactive, while Uba6 containing the Ubl domain of Ube1 was active for Cdc34 charging.

FIG. 5 depicts the cDNA sequence encoding *Homo sapiens* Uba6 (SEQ ID NO:4) (GenBank Accession Number NM_018227).

FIG. 6 depicts the amino acid sequence of *Homo sapiens* Uba6 (SEQ ID NO:5) (GenPept Accession Number NP_060697).

FIG. 7 depicts the cDNA sequence encoding *Mus musculus* Uba6 (SEQ ID NO:6) (Gen Bank Accession Number NM_172712).

FIG. 8 depicts the amino acid sequence of *Mus musculus* Uba6 (SEQ ID NO:7) (GenPept Accession Number NP_766300).

FIG. 9 depicts the cDNA sequence encoding E2Z from *Homo sapiens* (SEQ ID NO:8) (Gen Bank Accession Number NM_023079.2).

FIG. 10 depicts the amino acid sequence encoding E2Z from *Homo sapiens* (SEQ ID NO:9) (GenPept Accession Number NP_075567.1 has the partial sequence).

FIGS. 11A-11D depict data showing that the C-terminal domains of Ube1 and Uba6 control E2 specificity. (A) Domain structures of Uba6 and Ube1 and a schematic showing how the C-terminal Ubl domains were interchanged to form the chimeric proteins. (B) Model of the domain structure of an E1 enzyme based on the crystal structure of the Nedd8 activating enzyme. (C) E2 charging assays were performed using the indicated E1 proteins and E2 conjugating enzymes. (D) Predicted structures of the Ubl domains of Ube1 and Uba6.

FIGS. 14A-14D depict the systematic analysis of E2 conjugating enzymes for targets of Uba6. (A) E2 charging activity of ubiquitin E1s depicted on a phylogenetic tree of active E2s. (B) Uba6 and Ube1 display distinct E2 charging activities in vitro. Assays employed $^{35}$S-methionine labeled E2s made in *E. coli* S30 extracts, KO ubiquitin, and the indicated E1, as described in METHODS. *, non-specific translation products. (C) Sequence conservation of human Ube1 and Uba6. (D) Charging of Cdc34B, UbCH5D, and Use1 (also referred to herein as E2Z) in vitro by chimeric E1 proteins was examined using $^{35}$S-methionine labeled E2s.

FIGS. 16A-16C depict structural information of E1s. (A) Structural organization of E1s. Ube1, UbeL1 and Uba6 are single chain E1s while Uba3/APP-BP1 and Uba2/Sae1 are heterodimeric E1s. (B) Predicted structure of Ufd domains from Uba6 and Ube1, and a comparison with the Ufd domain from Uba3. Predicted structures were generated using "Modeller" software (release 8v2) with the SUMO E1 Sae2 as template (PDB code 1Y8Q) and displayed using Pymol. $Ufd^{Ube1}$: residues 948-1058. $Ufd^{Uba6}$: residues 949-1052. $Ufd^{Uba3}$: residues 349-440. (C) Domain specific sequence identities among human Uba6, Ube1 and Ube1L. Percent identities and percent similarities are shown.

FIGS. 18A-18F depict the analysis of GST-UBL proteins. (A) Ube1L activates ISG15 but not ubiquitin. GST-Ube1L, GST-Ube1, or GST-MP1 as a negative control (300 nM) were tested for their ability to activate GST-ISG15 or GST-Ub (6 µM) in the presence of 2 mM ATP (30 min, 30° C.). Reaction mixtures were subjected to 4-12% Tris-glycine and proteins visualized with Coomassie Blue. GST-Ube1L, GST-Ube1, and GST-MP1 were expressed in insect cells and purified as described previously (Zhao et al. (2004) *Proc. Natl. Acad. Sci. U.S.A.* 101:7578). (B) GST-Nedd8 is activated by Uba3/APPBP1 in vitro. Uba3/APPBP1 (300 nM) was incubated with 6 µM GST-Nedd8 or GST as a control (as described in panel a) and analyzed for thioester formation by non-reducing 4-12% Tris-glycine. (C) Uba6 does not activate Nedd8 in vitro. Flag-Uba6 (8 nM) was incubated with varying concentrations of GST-Ub or GST-Nedd8 (0, 5, 10, 20, 40, 80 ng) in the presence of 2 mM ATP and reaction mixtures subjected to 4-12% Tris-glycine and immunoblotting using anti-Flag antibodies. Uba6 activated GST-Ub but not GST-Nedd8. (D) GST-ubiquitin titration. Eight nM Uba6 or Ube1 was incubated with the indicated concentration of GST-ubiquitin for 10 min at 30° C. Samples were subjected to electrophoresis on a 4-12% Tris-glycine non-reducing gel prior to immunoblotting with the indicated antibody. (E) Time course for GST-ubiquitin activation. Reactions contained 500 nM GST-ubiquitin and 8 nM Uba6 or Ube1 and were incubated for the indicated time at 30° C. (F) Summary of mass spectral data identifying C-terminal peptides from GST-UBL proteins used in UBL activation assays. Sequence identifiers are set forth as follows: Ub (SEQ ID NO:36); Nedd8 (SEQ ID NO:37); SUMO (SEQ ID NO:38); Fub1 (SEQ ID NO:39); Urm1 (SEQ ID NO:40); ISG15 (SEQ ID NO:41); Fat10 (SEQ ID NO:42).

FIGS. 20A-20H depict sequence alignments of Use1 proteins from vertebrates and analysis of E2 charging. (A) Phylogenetic tree of the human E2 ubiquitin conjugating enzyme family, including the non-catalytic sub-class typified by Uev. The accession numbers for individual E2 family members used to generate the tree are provided. E2 sequences were aligned in ClustalW and the tree displayed in Treeview. (B) Alignments were generated in Clustal W. Sequences for frog (*Xenopus*) and zebrafish (*Danio rerio*) Use1 were obtained by blast analysis of the EST database using human Use1 as the query. Mm gene ID: 268470 (SEQ ID NO:44); Rn gene ID: 303478 (SEQ ID NO:45); Hs gene ID: 65264 (SEQ ID NO:46); *Danio* accession number: XP_001337511 (SEQ ID NO:47); *Xenopus* accession number: Q6PCF7 (SEQ ID NO:48); Spur (*S. purpuratus*) accession number: XP_785296 (SEQ ID NO:49); Consensus: (SEQ ID NO:58). (C) The catalytic cysteine of Uba6 is required for charging of Ubc5 and Use1. Assays were performed as described further herein using wild-type or mutant (C625A) Uba6. (D) Charging of purified Use1 by Uba6. Use1 was purified from bacteria as described under METHODS. Use1 (2.5 µM) was used in charging assays with increasing concentrations of Flag-Uba6 (0, 0.025, 0.05, 0.1, 0.2, 0.4 µM, purified from insect cells) in the presence of 25 µM ubiquitin and 2 mM ATP. (E) Amino acid sequences of the Ufd domains from Ube1 and Uba6 proteins. Black and grey, conserved in Ube1 and Uba6; purple, conserved in Ube1; yellow, conserved in Uba6. Sequence identifiers are set forth as follows: Ube1 Mm Ufd (SEQ ID NO:25); Ube1 Hs Ufd (SEQ ID NO:26); Ube1 Dr Ufd (SEQ ID NO:27); Ube1 Sc Ufd (SEQ ID NO:28); Uba6 Mm Ufd (SEQ ID NO:30); Uba6 Hs Ufd (SEQ ID NO:29); Uba6 Dr Ufd (SEQ ID NO:31); consensus (SEQ ID NO:57). (F) An assay that measures the extent of charging for ubiquitin E2s. Cells were lysed in buffers from pH 3 to pH 5 as described further herein, subjected to non-reducing 4-12% Bis-Tris gel, and immunoblots probed with anti-Cdc34, which reacts with both Cdc34A and Cdc34B proteins. In lanes 5-8, lysates were boiled in the presence of 200 mM DTT for 5 min prior to electrophoresis. (G) Specificity of Use1 antibodies. 293T cell extracts for cells transfected with the indicated siRNAs (72 hours post-transfection) were subjected to 4-12% Tris-glycine under reducing conditions and immunoblotted with affinity purified Use1 antibody. (H) 293T cells were lysed in pH 4.5 MES Lysis buffer and 10 µg subjected to electrophoresis on a 4-12% Bis-Tris gel in the presence of absence of DTT. Gels were probed against the indicated antibodies.

FIGS. 21A-21E depict structural modeling of Uba6$^{Ufd}$-Use1 and Ube1$^{Ufd}$-Cdc34 interfaces. (A) Model-based sequence alignments of human Uba6, Ube1, and Uba3 as well as alignments for the H1 helices of Cdc34A, Use1, and Ubc12. Sequence identifiers are as follows: Ube1 (SEQ ID NO:50); Uba6 (SEQ ID NO:51); Ubc12 (SEQ ID NO:52); Cdc34A (SEQ ID NO:59); Use1 (SEQ ID NO:60); Ubc12 (SEQ ID NO:61). Residues located at the interface are shown in red. Identical residues are shaded in black. Similar residues are shaded in grey. (B) Structure of the Ubc12-Uba3$^{Ufd}$ (Huang et al. (2005) *Mol. Cell* 17:341). Ubc12 is in marine. Uba3$^{Ufd}$ is in green. Residues at the interface are indicated. (C) Model of Use1-Uba6$^{Ufd}$. Use1 is in marine. Uba6$^{Ufd}$ is in green. Residues at the interface are indicated. (D) Model of Cdc34AUbe1$^{Ufd}$. Cdc34A is in marine. Ube1$^{Ufd}$ is in green. Residues at the interface are indicated. (E) Surface depiction of charged residues in Uba3$^{Ufd}$ (structure), Uba6$^{Ufd}$ (model), and Ube1$^{Ufd}$ (model). The corresponding ribbon images are shown for orientation purposes.

FIG. 22 depicts the sequences of genes examined as described further herein. Sequence identifiers are as follows: Ube1-1 (SEQ ID NO:13); Ube1-2 (SEQ ID NO:14); Ube1-3 (SEQ ID NO:15); Ub21L2-1 (SEQ ID NO:10); Ub21L2-2 (SEQ ID NO:11); Ub21L2-3 (SEQ ID NO:12); Ube2z-1 (SEQ ID NO:53); Ube2z-2 (SEQ ID NO:54); Ube2z-3 (SEQ ID NO:55).

DETAILED DESCRIPTION

Figure 1A:
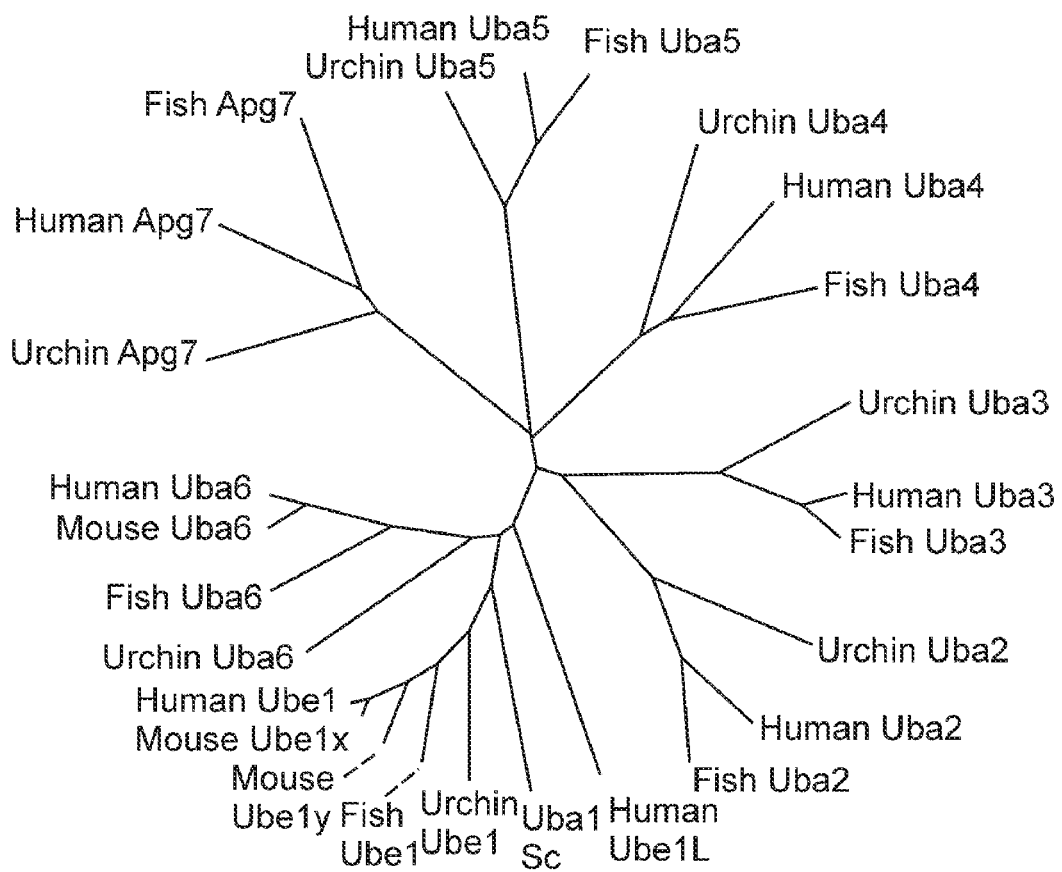
FIGS. 1A-1H depict physical and functional characteristics of Uba6. (A) Phylogenetic tree for ThiF-domain containing proteins in humans, zebrafish (*D. rerio*) and sea urchin (*S. purpuratus*). Also included are mouse Ube1x and Ube1y proteins as well as *S. cerevisiae* Uba1p. The sequences and tree were generated using ClustalW. (B) SDS-PAGE analysis of Flag-tagged Uba6 (Uba6$^F$) expressed and purified from insect cells (Coomassie staining) (C, D) Uba6 functions as an activating enzyme for ubiquitin but not for several ubiquitin-like proteins (Ulps). The indicated GST-Ulps were purified after expression in bacteria and mixed with purified Uba6$^F$ in the presence of ATP. After 10 minutes at 30° C., reaction mixtures were subjected to SDS-PAGE under non-reducing conditions prior to visualization using Coomassie blue. In lane 4, Uba6$^F$ is converted to a Uba6$^F$~GST-Ub conjugate. In panel D, various components were omitted to demonstrate a requirement for GST-Ub and ATP and to demonstrate that the conjugate is sensitive to the reducing agent DTT. *, GST breakdown products. (E) The related E1 enzyme Ube1L promotes activation of ISG15 but not ubiquitin. As an indication of specificity, GST-Ube1L (purified from insect cells) was assayed for activation of GST-ISG15 and GST-Ub. While it was active toward ISG15, as expected, it failed to activate GST-Ub, even though it is more closely related to Ube1 phylogenetically than is Uba6. GST-MP1 was used as a negative control. (F) Kinetics of ubiquitin activation by Ube1 and Uba6 were performed as described further herein. Error bars indicate standard deviation of duplicate assays. (G) Association of Uba6 with ubiquitin-agarose. E1 capture on ubiquitin-Agarose using 293T/Flag-HA-Uba6 extracts (pH 7.5). Extracts from 293T cells stably expressing HA-Flag-Uba6 were subjected to the classical ubiquitin affinity chromatography experiments of Hershko (infra). Extracts were incubated with ubiquitin-agarose in the presence of ATP to allow for ubiquitin charging. Beads were then washed with buffer containing Triton X-100 followed by elution with DTT. Load, flow-thru, washes, eluate and proteins remaining bound to ubiquitin-agarose were then subjected to immunoblotting with anti-Ube1 and anti-HA antibodies to detect HA-Flag-Uba6. (H) Conservation of Uba6 in vertebrates. Alignment of Uba6 and Ube1 from human (Hs), mouse (Mm), *S. cerevisiae* (Sc) and zebrafish (*Danio rerio*, Dr). Zebrafish sequences were provided under accession number XP_1695755.2. Sequence identifiers are set forth as follows: NP_695012 Ube1 Hs is set forth as SEQ ID NO:16; NP_033483 Ube1x Mm is set forth as SEQ ID NO:17; NP_035797 Ube1y Mm is set forth as SEQ ID NO:18; NP_998227 Ube1 Dr is set forth as SEQ ID NO:19; YKL210w Ube1 Sc is set forth as SEQ ID NO:20; NP_060697 Uba6 Hs is set forth as SEQ ID NO:21; NP_766300 Uba6 Mm is set forth as SEQ ID NO:22; Uba6 Dr is set forth as SEQ ID NO:23; Consensus is set forth as SEQ ID NO:56. Unlike humans, the mouse contains two closely related (90% identical) Ube1 proteins, Ube1x located on the X-chromosome and Ube1y located on the Y-chromosome. The Ube1y protein is thought to be involved in spermatogenesis (Levy et al. (2000) *Mamm. Genome* 11:164; Mitchell et al. (1992) *Nature* 359:528). Dark green, adenylate domain; light green, ThiF motifs; red, catalytic cysteine domain (CCD); blue, ubiquitin-fold domain (Ufd).

It is generally thought that Ube1 is the sole activating enzyme for ubiquitin encoded by the genomes of all eukaryotes. This conclusion is based on the presence of a single essential ubiquitin E1 in budding yeast and the finding that rodent tissue culture cells containing temperature sensitive mutations in Ube1 display cell cycle arrest phenotypes consistent with there being only a single gene (Finley et al. (1984) Cell 37:43; Ciechanover et al. (1984) J. Cell. Biochem. 24:27). As described further herein, it has surprisingly been discovered that this dogma is incorrect, and vertebrate organisms contain two distinct activating enzymes for ubiquitin. Without intending to be bound by theory, this novel enzyme, Uba6, promotes the conjugation of ubiquitin to ubiquitin conjugating enzymes (e.g., E2s) in a manner that appears to be distinct from Ube1. Accordingly, Uba6 can have specific functions in the ubiquitin pathway and, therefore, is an important drug target.

The ubiquitin-proteasome pathway (UPP) plays a central role in the turnover of many key regulatory proteins involved in transcription, cell cycle progression and apoptosis, all of which are important in disease states. See, e.g., King et al. (1996) Science 274:1652; Vorhees et al. (2003) Clin. Cancer Res. 9:6316; Adams et al. (2004) Nat. Rev. Cancer 4:349. Accordingly, targeting ubiquitin-activating enzymes provides a unique opportunity to interfere with a variety of biochemical pathways important for maintaining the integrity of cell division and cell signaling. Ubiquitin-activating enzymes, such as Uba6, function at the first step of ubiquitin conjugation pathways. Thus, inhibition of a Uba6 enzyme should specifically modulate the downstream biological consequences of a ubiquitin modification. As such, inhibition of these activating enzymes, and the resultant inhibition of downstream effects of ubiquitin-conjugation, represents a method of interfering with the integrity of cell division, cell signaling, and several aspects of cellular physiology which are important for disease mechanisms. Thus, ubiquitin-activating enzymes such as Uba6, as regulators of diverse cellular functions, are potentially important therapeutic targets for the identification of novel approaches to treatment of a variety of diseases and disorders (i.e., "ubiquitin-related disorders").

In at least certain embodiments, the Uba6 and/or E2Z (also referred to herein as Use1) modulating agents described herein can be used in the treatment of cellular proliferative disorders, e.g., cancer. The role of the UPP pathway in oncogenesis has led to the investigation of proteasome inhibition as a potential anticancer therapy. For example, modulation of the UPP pathway by inhibition of the 26S proteasome by VELCADE™ has proven to be an effective treatment in certain cancers and is approved for the treatment of relapsed and refractory multiple myeloma.

Examples of proteins whose levels are controlled by the UPP pathway include the CDK inhibitor p27$^{Kip1}$ and the inhibitor of NFκB, IκB. See, Podust et al. (2000) Proc. Natl. Acad. Sci. USA 97:4579; Read et al. (2000) Mol. Cell. Biol. 20:2326. Inhibition of the degradation of p27 can block the progression of cells through the G1 and S phases of the cell cycle. Interfering with the degradation of IκB can prevent the nuclear localization of NF-κB, transcription of various NF-κB-dependent genes associated with the malignant phenotype, and resistance to standard cytotoxic therapies. NF-κB plays a key role in the expression of a number of pro-inflammatory mediators, implicating a role for such inhibitors in inflammatory disorders. Accordingly, inhibition of UPP is useful for the treatment of inflammatory disorders, including, e.g., rheumatoid arthritis, asthma, multiple sclerosis, psoriasis, reperfusion injury and the like.

Inhibition of UPP is also useful for treatment of disorders such as neurodegenerative disorders, including e.g., Parkinson's disease, Alzheimer's disease, triplet repeat disorders; neuropathic pain; ischemic disorders, e.g., stroke, infarction, kidney disorders; and cachexia. See, e.g., Elliott and Ross (2001) Am. J. Clin. Pathol. 116:637; Elliott et al. (2003) J. Mol. Med. 81:235; Tarlac and Storey (2003) J. Neurosci. Res. 74:406; Mori et al. (2005) Neuropath. Appl. Neurobiol. 31:53; Manning (2004) Curr. Pain Headache Rep. 8:192; Dawson and Dawson (2003) Science 302:819; Kukan (2004) Physiol. Pharmacol. 55:3; Wojcik and DiNapoli (2004) Stroke 35:1506; Lazarus et al. (1999) Am. J. Physiol. 27:E332.

Treatment of cellular proliferative disorders is intended to include inhibition of proliferation including rapid proliferation. As used herein, the term "cellular proliferative disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995)). The terms "neoplasm" and "tumor" refer to an abnormal tissue that grows by cellular proliferation more rapidly than normal and continues to grow after the stimuli that initiated proliferation is removed (see, for example, PDR Medical Dictionary 1st edition (1995)). Such abnormal tissue shows partial or complete lack of structural organization and functional coordination with the normal tissue which may be either benign (i.e., benign tumor) or malignant (i.e., malignant tumor).

The language "treatment of cellular proliferative disorders" is intended to include the prevention of the growth of neoplasms in a subject or a reduction in the growth of pre-existing cancers in a subject. The inhibition also can be the inhibition of the metastasis of a cancer from one site to another.

In certain embodiments, the cancer is a solid tumor. Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma and the like.

In certain other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sidroblasts (RARS), (refractory anemia with excess blasts (RAEB), and RAEB in transformation (RAEB-T); myeloproliferative syndromes and the like.

Cellular proliferative disorders can further include disorders associated with hyperproliferation of vascular smooth muscle cells such as proliferative cardiovascular disorders, e.g., atherosclerosis and restinosis. Cellular proliferation disorders can also include disorders such as proliferative skin disorders, e.g., X-linked ichthyosis, psoriasis, atopic dermatitis, allergic contact dermatitis, epidermolytic hyperkeratosis, and seborrheic dermatitis. Cellular proliferative disorders can further include disorders such as autosomal dominant polycystic kidney disease (ADPKD), mastocystosis, and cellular proliferation disorders caused by infectious agents such as viruses.

Pharmaceutical Compounds

Compounds of the present invention include inhibitors of one or more ubiquitin-activating enzyme activities. In particular, the compounds are designed to be inhibitors of one or more Uba6 activities (e.g., ubiquitin activation; ubiquitin-adenylate intermediate formation; ubiquitin thiol esterification; ubiquitin transfer to one or more ubiquitin-conjugating enzymes (e.g., E2s); and/or ubiquitination of one or more target polypeptides (e.g., ubiquitin, an E2, a target polypeptide and/or protein or the like)) and/or one or more E2Z activities (e.g., ubiquitin activation; ubiquitin-adenylate intermediate formation; ubiquitin thiol esterification; ubiquitin transfer to one or more ubiquitin-protein ligases (e.g., E3s); and/or ubiquitination of one or more target polypeptides (e.g., ubiquitin, an E3, a target polypeptide and/or protein or the like)).

Inhibitors include, but are not limited to, compounds which modulate (e.g., reduce) the promoting effects of E1 enzymes in ubiquitin conjugation to target proteins (e.g., reduction of ubiquitin activation and/or facilitating ubiquitin transfer to E2). Inhibitors also include, but are not limited to, compounds which modulate (e.g., reduce) the promoting effects of E2Z enzymes in ubiquitin conjugation to target proteins (e.g., reduction of ubiquitin activation and/or facilitating ubiquitin transfer to E3). Thus, the compounds of this invention may be assayed for their ability to inhibit a Uba6 enzyme and/or an E2Z enzyme in vitro or in vivo (e.g., in cells or animal models) according to methods provided in further detail herein, or methods known in the art. The compounds may be assessed for their ability to bind or mediate a Uba6 enzyme and/or an E2Z enzyme activity directly. Alternatively, the activity of compounds may be assessed through indirect cellular assays, or assays of downstream effects of Uba6 and/or E2Z activation to assess inhibition of downstream effects of Uba6 inhibition. For example, activity may be assessed by detection of ubiquitin-conjugated substrates (e.g., ubiquitin-conjugated E2s, ubiquitin-conjugated E3s, ubiquitinated substrates and the like); detection of downstream protein substrate stabilization; detection of inhibition of UPP activity; and the like. Assays for assessing activities are described further herein and/or are known in the art.

One embodiment of this invention relates to a composition comprising a compound described herein or a pharmaceutically acceptable salt thereof, and a pharmaceutically acceptable carrier. It will be appreciated that the compounds of this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the present compounds, similar to the metabolically labile esters or carbamates, which are capable of producing the parent compounds described herein in vivo, are within the scope of this invention.

If pharmaceutically acceptable salts of the compounds of the invention are utilized in these compositions, the salts may be derived from inorganic or organic acids and bases. For reviews of suitable salts, see, e.g., Berge et al (1977) *J. Pharm. Sci.* 66:1; and Remington: *The Science and Practice of Pharmacy,* 20th Ed., ed. A. Gennaro, Lippincott Williams & Wilkins, 2000.

As used herein, the term "pharmaceutically acceptable carrier" is intended to include, but is not limited to, a material that is compatible with a recipient subject, such as a mammal (e.g., a human), and is suitable for delivering an active agent to the target site without terminating the activity of the agent. The toxicity or adverse effects, if any, associated with the carrier preferably are commensurate with a reasonable risk/benefit ratio for the intended use of the active agent.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, solubilizing agents, bioavailability modifiers and combinations of these.

Pharmaceutical formulations may be prepared as liquid suspensions or solutions using a liquid, such as, but not limited to, an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, e.g., peanut oil, sesame oil, cottonseed oil, corn oil, olive oil and the like. Suspension preparations may also contain esters of fatty acids such as ethyl oleate, isopropyl myristate, fatty acid glycerides and acetylated fatty acid glycerides. Suspension formulations may include alcohols including, but not limited to, ethanol, isopropyl alcohol, hexadecyl alcohol, glycerol and propylene glycol. Ethers, including, but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates and carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to certain embodiments, the compositions of this invention are formulated for pharmaceutical administration to a mammal, such as a human. Such pharmaceutical compositions may be administered orally, parenterally, by inhalation spray, topically, rectally, nasally, buccally, vaginally or via an implanted reservoir. The term "parenteral," as used herein includes, but is not limited to, subcutaneous, intravenous, intraperitoneal, intramuscular, intra-articular, intra-synovial, intrasternal, intrathecal, intrahepatic, intralesional and intracranial injection or infusion techniques. In certain aspects, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Sterile, injectable forms of the compositions described herein may be aqueous or oleaginous suspensions. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

Pharmaceutical compositions may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutical compositions may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

Pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of compounds described herein include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

Pharmaceutical compositions may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Pharmaceutical compositions described herein are particularly useful in therapeutic applications relating to disorders as described herein (e.g., proliferation disorders, e.g., cancers, inflammatory disorders, neurodegenerative disorders). In certain embodiments, the composition is formulated for administration to a patient having or at risk of developing or experiencing a recurrence of the relevant disorder being treated. The term "patient," as used herein, is intended to refer to an animal, e.g., a mammal such as a human. In certain embodiments, a pharmaceutical composition described herein may further comprise another therapeutic agent. The therapeutic agent can be one normally administered to patients with the disorder, disease or condition being treated.

By "therapeutically effective amount" is meant an amount of compound or composition sufficient, upon single or multiple dose administration, to cause a detectable decrease in one or more Uba6 enzyme activities and/or the severity of one or more disorders or disease states being treated. "Therapeutically effective amount" is also intended to include an amount sufficient to treat a cell, prolong or prevent advancement of the disorder or disease state being treated (e.g., prevent additional tumor growth of a cancer, prevent additional inflammatory response), ameliorate, alleviate, relieve, or improve a subject's symptoms of the a disorder beyond that expected in the absence of such treatment.

The amount of a Uba6 enzyme modulator (e.g., inhibitor) required will depend on the particular compound of the composition given, the type of disorder being treated, the route of administration, and the length of time required to treat the disorder. A therapeutically effective amount of compound (i.e., an effective dosage) can range from about 0.001 to 30 mg/kg body weight, about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. It should also be understood that a specific dosage and treatment regimen for any particular patient will depend upon a variety of factors, including the activity of the specific compound employed, the age, body weight, general health, sex, and diet of the patient, time of administration, rate of excretion, drug combinations, the judgment of the treating physician, and the severity of the particular disease being treated. In certain aspects where the inhibitor is administered in combination with another agent, the amount of additional therapeutic agent present in a composition typically will be no more than the amount that would normally be administered in a composition comprising that therapeutic agent as the only active agent. In certain aspects, the amount of additional therapeutic agent will range from about 50% to about 100% of the amount normally present in a composition comprising that agent as the only therapeutically active agent.

One embodiment of the invention relates to a method of modulating (e.g., inhibiting) or decreasing one or more Uba6 enzyme activities in a sample comprising contacting the sample with one or more compounds and/or compositions described herein. The sample can include, without limitation, a purified or partially purified Uba6 enzyme, cultured cells or extracts of cell cultures, biopsied cells or fluid obtained from a mammal or extracts thereof, and one or more bodily fluids (e.g., blood, serum, saliva, urine, feces, semen, tears, breast milk and the like) or extracts thereof. Inhibition of one or more Uba6 enzyme activities in a sample may be carried out in vitro, in vivo or in situ.

In another embodiment, method for treating a patient having one or more ubiquitin-related disorders described herein, one or more symptoms of one or more ubiquitin-related disorders described herein, and/or at risk of developing or experiencing a recurrence of one or more ubiquitin-related disorders described herein. Such methods comprise administering to the patient one or more compounds and/or pharmaceutical composition described herein. As used herein, the term "treating" is intended to include, but is not limited to, curing, healing, alleviating, relieving, altering, remedying, ameliorating, palliating, improving or affecting the disorder, one or more symptoms of the disorder or the predisposition toward the disorder.

Depending on the particular disorder or condition to be treated, one or more Uba6 enzyme inhibitors are administered in conjunction with additional therapeutic agent or agents. In certain embodiments, the additional therapeutic agent is one that is normally administered to patients with the disorder or condition being treated. The one or more Uba6 inhibitors may be administered with the other therapeutic agent in a single dosage form or as a separate dosage form. When administered as a separate dosage form, the other therapeutic agent may be administered prior to, at the same time as, or following administration of the one or more Uba6 inhibitors.

In certain embodiments, the one or more Uba6 inhibitors are administered in conjunction with one or more therapeutic agents including, but not limited to, cytotoxic agents, radiotherapy, and immunotherapy appropriate for treatment of proliferative disorders and cancer. Non-limiting examples of cytotoxic agents suitable for use in combination with the one or more Uba6 inhibitors include antimetabolites (e.g., capecitibine, gemcitabine, 5-fluorouracil or 5-fluorouracil/ leucovorin, fludarabine, cytarabine, mercaptopurine, thioguanine, pentostatin, and methotrexate); topoisomerase inhibitors (e.g., etoposide, teniposide, camptothecin, topotecan, irinotecan, doxorubicin, and daunorubicin); vinca alkaloids (e.g., vincristine and vinblastin; taxanes, including, e.g., paclitaxel and docetaxel); platinum agents (e.g., cisplatin, carboplatin, and oxaliplatin); antibiotics (e.g., actinomycin D, bleomycin, mitomycin C, adriamycin, daunorubicin, idarubicin, doxorubicin and pegylated liposomal doxorubicin); alkylating agents (e.g., melphalan, chlorambucil, busulfan, thiotepa, ifosfamide, carmustine, lomustine, semustine, streptozocin, decarbazine, and cyclophosphamide); protein tyrosine kinase inhibitors (e.g., imatinib mesylate and gefitinib); proteasome inhibitors (e.g., bortezomib, thalidomide and related analogs); antibodies (e.g., trastuzumab, rituximab, cetuximab, and bevacizumab); mitoxantrone; dexamethasone; prednisone; temozolomide and the like.

Other examples of agents the one or more Uba6 inhibitors may be combined with include anti-inflammatory agents (e.g., corticosteroids, TNF blockers, Il-1 RA, azathioprine, cyclophosphamide, and sulfasalazine); immunomodulatory and/or immunosuppressive agents (e.g., cyclosporine, tacrolimus, rapamycin, mycophenolate mofetil, interferons, corticosteroids, cyclophosphamide, azathioprine, methotrexate, and sulfasalazine); antibacterial and antiviral agents; and agents for Alzheimer's treatment (e.g., donepezil, galantamine, memantine and rivastigmine).

Screening Assays

The invention provides methods (also referred to herein as a "screening assays") for identifying modulators, i.e., candidate or test compounds or agents (e.g., peptides, cyclic peptides, peptidomimetics, small molecules, small organic molecules, or other drugs) which bind to one or more Uba6 enzymes, or have a stimulatory or inhibitory effect on Uba6 expression or on one or more Uba6 activities.

As used herein, the term "small organic molecule" refers to an organic molecule, either naturally occurring or synthetic, that has a molecular weight of more than about 25 daltons and less than about 3000 daltons, preferably less than about 2500 daltons, more preferably less than about 2000 daltons, preferably between about 100 to about 1000 daltons, more preferably between about 200 to about 500 daltons.

In one embodiment, assays for screening candidate or test compounds which bind to or modulate the activity of Uba6, a Uba6 polypeptide or biologically active portion thereof, E2Z, or an E2Z polypeptide or biologically active portion thereof are provided. The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412), or on beads (Lam (1991) *Nature* 354:82), chips (Fodor (1993) *Nature* 364:555), bacteria (Ladner U.S. Pat. No. 5,223,409), spores (Ladner U.S. Pat. No. 5,223,409), plasmids (Cull et al. (1992) *Proc. Natl. Acad. Sci. USA* 89:1865) or on phage (Scott and Smith (1990) *Science* 249:386; Devlin (1990) *Science* 249:404; Cwirla et al. (1990) *Proc. Natl. Acad. Sci. USA* 87:6378; Felici (1991) *J. Mol. Biol.* 222:301; Ladner supra).

Examples of methods for introducing a molecular library of randomized nucleic acids into a population of cells can be found in the art, for example in U.S. Pat. No. 6,365,344. A molecular library of randomized nucleic acids can provide for the direct selection of candidate or test compounds with desired phenotypic effects. The general method can involve, for instance, expressing a molecular library of randomized nucleic acids in a plurality of cells, each of the nucleic acids comprising a different nucleotide sequence, screening for a cell of exhibiting a changed physiology in response to the presence in the cell of a candidate or test compound, and detecting and isolating the cell and/or candidate or test compound.

In one embodiment, the introduced nucleic acids are randomized and expressed in the cells as a library of isolated randomized expression products, which may be nucleic acids, such as mRNA, RNAi reagents, antisense RNA, siRNA, ribozyme components, etc., or peptides (e.g., cyclic peptides). For example, RNAi reagents include, but are not limited to, double-stranded or hairpin sequences corresponding to the coding sequence of Uba6 (e.g., a nucleic acid sequence corresponding to the cysteine 625 region of human Uba6 (SEQ ID NO:5) (e.g., the catalytic cysteine domain); a nucleic acid sequence corresponding to amino acids 947 to 1052 of human Uba6 (SEQ ID NO:5) (e.g., the C-terminal ubiquitin-like (Ubl) domain); an adenylate domain; and/or one or two ThiF domains). The library should provide a sufficiently structurally diverse population of randomized expression products to effect a probabilistically sufficient range of cellular responses to provide one or more cells exhibiting a desired response.

The introduced nucleic acids and resultant expression products are randomized, meaning that each nucleic acid and peptide consists of essentially random nucleotides and amino acids, respectively. The library may be fully random or biased, e.g. in nucleotide/residue frequency generally or per position. In other embodiments, the nucleotides or residues are randomized within a defined class, e.g. of hydrophobic amino acids, of purines, etc.

Functional and structural isolation of the randomized expression products may be accomplished by providing free (i.e., not covalently coupled) expression product, though in some situations, the expression product may be coupled to a functional group or fusion partner, preferably a heterologous (to the host cell) or synthetic (not native to any cell) functional group or fusion partner. Exemplary groups or partners include, but are not limited to, signal sequences capable of constitutively localizing the expression product to a predetermined subcellular locale such as the Golgi, endoplasmic reticulum, nucleoli, nucleus, nuclear membrane, mitochondria, chloroplast, secretory vesicles, lysosome, and the like; binding sequences capable of binding the expression product to a predetermined protein while retaining bioactivity of the expression product; sequences signaling selective degradation, of itself or co-bound proteins; and secretory and membrane-anchoring signals.

It may also be desirable to provide a partner which conformationally restricts the randomized expression product to more specifically define the number of structural conformations available to the cell. For example, such a partner may be a synthetic presentation structure: an artificial polypeptide capable of intracellularly presenting a randomized peptide as a conformation-restricted domain. Generally such presentation structures comprise a first portion joined to the N-terminal end of the randomized peptide, and a second portion joined to the C-terminal end of the peptide. Exemplary presentation structures maximize accessibility to the peptide by presenting it on an exterior loop, for example of coiled-coils (Myszka and Chaiken (1994) *Biochemistry* 33:2362). To increase the functional isolation of the randomized expression product, the presentation structures are selected or designed to have minimal biologically active as expressed in the target cell. In addition, the presentation structures may be modified, randomized, and/or matured to alter the presentation orientation of the randomized expression product. For example, determinants at the base of the loop may be modified to slightly modify the internal loop peptide tertiary structure, while maintaining the absolute amino acid identity. Other presentation structures include zinc-finger domains, loops on beta-sheet turns and coiled-coil stem structures in which non-critical residues are randomized; loop structures held together by cysteine bridges, cyclic peptides, etc.

In one embodiment, an assay is a cell-based assay in which a cell which expresses a Uba6 protein or biologically active portion thereof is contacted with a test compound and the ability of the test compound to modulate one or more Uba6 activities, e.g., ubiquitin activation; ubiquitin-adenylate intermediate formation; ubiquitin thiol esterification; ubiquitin transfer to one or more ubiquitin-conjugating enzymes (e.g., E2s); and/or ubiquitination of one or more target polypeptides is determined. In another embodiment, an assay is a cell-based assay in which a cell which expresses a E2Z protein or biologically active portion thereof is contacted with a test compound and the ability of the test compound to modulate one or more E2Z activities, e.g., ubiquitin activation; ubiquitin-adenylate intermediate formation; ubiquitin thiol esterification; ubiquitin transfer to one or more ubiquitin-protein ligases (e.g., E3s); and/or ubiquitination of one or more target polypeptides is determined.

Determining the ability of the test compound to modulate one or more Uba6 activities and/or one or more E2Z activities can be accomplished by monitoring, for example, ubiquitin activation, formation of a ubiquitin-adenylate intermediate, ubiquitin thiol esterification, ubiquitin transfer to one or more ubiquitin-conjugating enzymes, ubiquitin transfer to one or more ubiquitin-protein ligases and/or ubiquitination of one or more target proteins or polypeptides using, for example, one or more of the assays described herein.

Determining the ability of the test compound to modulate one or more Uba6 and/or E2Z activities can be accomplished, for example, by coupling Uba6 or a Uba6 substrate (e.g., ubiquitin, an E2 and/or a target polypeptide or protein) and/or E2Z or an E2Z substrate (e.g., ubiquitin, an E3 and/or a target polypeptide or protein) with a radioisotope or enzymatic label such that alteration of Uba6, Uba6 substrate, E2Z and/or a E2Z substrate (e.g., by ubiquitination, thiol esterification, ubiquitin adenylation or the like) can be determined by detecting an alteration of the Uba6, Uba6 substrate, E2Z and/or a E2Z substrate (e.g., altered mobility on an SDS-PAGE gel). For example, compounds can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with Uba6 and/or E2Z without the labeling of any of the interactants. For example, a microphysiometer can be used to detect the interaction of a compound with Uba6 and/or E2Z without the labeling of either the compound or Uba6 and/or E2Z (McConnell, H. M. et al. (1992) *Science* 257:1906). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and Uba6 and/or E2Z.

In another embodiment, an assay is a cell-based assay comprising contacting a cell expressing Uba6 and/or E2Z (e.g., ubiquitin, an E2, an E3 a target polypeptide or protein) with a test compound and determining the ability of the test compound to modulate (e.g., stimulate or inhibit) the activity of Uba6, a Uba6 target molecule, E2Z and/or an E2Z target molecule. Determining the ability of the test compound to modulate the activity of Uba6, a Uba6 target molecule, E2Z and/or an E2Z target molecule can be accomplished, for example, by determining the ability of the Uba6 and/or the E2Z to bind to modulate ubiquitin activation.

Determining the ability of Uba6 and/or E2Z to modulate ubiquitin activation can be accomplished by one of the methods described above for determining direct binding. In an exemplary embodiment, determining the ability of Uba6 and/or E2Z to modulate ubiquitin activation can be accomplished by detecting one or more Uba6 and/or E2Z activities, e.g., ubiquitin activation; ubiquitin-adenylate intermediate formation; ubiquitin thiol esterification; ubiquitin transfer to one or more ubiquitin-conjugating enzymes (e.g., E2s); ubiquitin transfer to one or more ubiquitin-protein ligases (e.g., E3s); and/or ubiquitination of one or more target polypeptides (e.g., ubiquitin, an E2, an E3, a target polypeptide and/or protein or the like).

In yet another embodiment, an assay of the present invention is a cell-free assay in which Uba6 and/or E2Z is contacted with a test compound and the ability of the test compound to bind to Uba6 and/or E2Z or a biologically active portion of Uba6 and/or E2Z is determined. Biologically active portions of Uba6 to be used in assays of the present invention include, but are not limited to, ThiF domains (e.g., amino acids 50-200 and 460-600 of SEQ ID NO:5, for ThiF domain 1 and ThiF domain 2, respectively), catalytic cysteine domains (e.g., amino acid sequences including cysteine 625 of SEQ ID NO:5), adenylate domains (e.g., amino acids 1-610 of SEQ ID NO:5), C-terminal ubiquitin-like (Ubl) domains (e.g., amino acids 947-1052 of SEQ ID NO:5), and the like. Binding of the test compound to Uba6 and/or E2Z can be determined either directly or indirectly as described above. In an exemplary embodiment, the assay includes contacting Uba6 and/or E2Z or biologically active portion of Uba6 and/or E2Z with a known compound which binds Uba6 and/or E2Z to form an assay mixture, contacting the assay mixture with a test compound, and determining the ability of the test compound to interact with Uba6 and/or E2Z, wherein determining the ability of the test compound to interact with Uba6 and/or E2Z comprises determining the ability of the test compound to preferentially bind to Uba6 and/or E2Z or a biologically active portion of Uba6 and/or E2Z as compared to the known compound.

In another embodiment, the assay is a cell-free assay in which Uba6 and/or E2Z or a biologically active portion of Uba6 and/or E2Z is contacted with a test compound and the ability of the test compound to modulate (e.g., stimulate or inhibit) the activity of Uba6 and/or E2Z or a biologically active portion of Uba6 and/or E2Z is determined. Determining the ability of the test compound to modulate the activity of Uba6 and/or E2Z can be accomplished, for example, by determining the ability of Uba6 and/or E2Z to bind to a Uba6 and/or an E2Z target molecule by one of the methods described above for determining direct binding. Determining the ability of Uba6 and/or E2Z to bind to a Uba6 and/or E2Z target molecule, respectively, can also be accomplished using a technology such as real-time Biomolecular Interaction Analysis (BIA) (Sjolander, S, and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting Uba6 and/or E2Z or a biologically active portion of Uba6 and/or E2Z with a known compound which binds Uba6 and/or E2Z, respectively, to form an assay mixture, contacting the assay mixture with a test compound, and determining the ability of the test compound to interact with Uba6 and/or E2Z, wherein determining the ability of the test compound to interact with Uba6 and/or E2Z comprises determining the ability of Uba6 and/or E2Z to preferentially bind to or modulate the activity of a Uba6 and/or E2Z target molecule (e.g., ubiquitin activation; ubiquitin-adenylate intermediate formation; ubiquitin thiol esterification; ubiquitin transfer to one or more ubiquitin-conjugating enzymes (e.g., E2s); ubiquitin transfer to one or more ubiquitin-protein ligases (e.g., E3s); and/or ubiquitination of one or more target polypeptides (e.g., ubiquitin, an E2, an E3, a target polypeptide and/or protein or the like) and the like).

In more than one embodiment of the above assay methods of the present invention, it may be desirable to immobilize either Uba6, a Uba6 target molecule, E2Z and/or an E2Z target molecule to facilitate separation of complexed from uncomplexed forms of one or both of the proteins, as well as to accommodate automation of the assay. Binding of a test compound to Uba6 and/or E2Z, or interaction of Uba6 and/or E2Z with one or more target molecules in the presence and absence of a candidate compound, can be accomplished in any vessel suitable for containing the reactants. Examples of such vessels include microtitre plates, test tubes, and microfuge tubes. In one embodiment, a fusion protein can be provided which adds a domain that allows one or both of the proteins to be bound to a matrix. For example, glutathione-S-transferase/Uba6 fusion proteins or glutathione-S-transferase/target fusion proteins can be adsorbed onto glutathione sepharose beads (Sigma, St. Louis, Mo.) or glulathione-derivatized microtitre plates, which are then combined with the test compound or the test compound and either the non-adsorbed target protein or Uba6, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of Uba6 binding or activity determined using standard techniques.

Other techniques for immobilizing proteins on matrices can also be used in the screening assays of the invention. For example, Uba6, a Uba6 target molecule, E2Z and/or an E2Z target molecule can be immobilized utilizing conjugation of biotin and avidin or streptavidin. Biotinylated Uba6 and/or E2Z or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce). Alternatively, antibodies reactive with Uba6 and/or E2Z or target molecules that do not interfere with binding of Uba6 and/or E2Z to its target molecule can be derivatized to the wells of the plate, and unbound target or Uba6 and/or E2Z trapped in the wells by antibody conjugation. Methods for detecting such complexes, in addition to those described above for the GST-immobilized complexes, include immunodetection of complexes using antibodies reactive with Uba6 and/or E2Z or one or more Uba6 and/or E2Z target molecules, as well as enzyme-linked assays which rely on detecting an enzymatic activity associated with Uba6 and/or E2Z.

In another embodiment, modulators of Uba6 and/or E2Z expression are identified in a method wherein a cell is contacted with a candidate compound and the expression of Uba6 protein, Uba6 mRNA, E2Z protein, and/or E2Z mRNA in the cell is determined. The level of Uba6 protein, Uba6 mRNA, E2Z protein, and/or E2Z mRNA in the presence of the candidate compound is compared to the level of Uba6 protein, Uba6 mRNA, E2Z protein, and/or E2Z mRNA in the absence of the candidate compound. The candidate compound can then be identified as a modulator of Uba6 and/or E2Z protein expression and/or Uba6 and/or E2Z mRNA expression based on this comparison. For example, when expression of Uba6 and/or E2Z protein and/or Uba6 and/or E2Z mRNA is greater (statistically significantly greater) in the presence of the candidate compound than in its absence, the candidate compound is identified as a stimulator of Uba6 and/or E2Z protein expression and/or Uba6 and/or E2Z mRNA expression, respectively. Alternatively, when expression of Uba6 and/or E2Z protein and/or Uba6 and/or E2Z mRNA is less (statistically significantly less) in the presence of the candidate compound than in its absence, the candidate compound is identified as an inhibitor of Uba6 and/or E2Z protein expression and/or Uba6 and/or E2Z mRNA expression, respectively. The level of Uba6 and/or E2Z mRNA or protein expression in the cells can be determined by methods described herein for detecting Uba6 and/or E2Z mRNA or protein.

In yet another aspect of the invention, Uba6 and/or E2Z can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Twabuchi et al. (1993) *Oncogene* 8:1693-1696; and Brent WO 94/10300), to identify other proteins, which bind to or interact with Uba6 ("Uba6-binding proteins") and are involved in one or more Uba6 activities (e.g., ubiquitin activation; ubiquitin-adenylate intermediate formation; ubiquitin thiol esterification; ubiquitin transfer to one or more ubiquitin-conjugating enzymes (e.g., E2s); and/or ubiquitination of one or more target polypeptides (e.g., ubiquitin, an E2, a target polypeptide and/or protein or the like)). Alternatively, such Uba6-binding proteins are likely to be Uba6 inhibitors.

In another embodiment, an assay is an animal model based assay comprising contacting a an animal with a test compound and determining the ability of the test compound to alter Uba6 and/or E2Z expression and/or Uba6 and/or E2Z activity. Animals include, but are not limited to, mammals such as non-human primates, rabbits, rats, mice, and the like.

This invention further pertains to novel agents identified by the above-described screening assays. Accordingly, it is within the scope of this invention to further use an agent identified as described herein in an appropriate animal model as described herein. For example, an agent identified as described herein (e.g., a Uba6 and/or E2Z modulating agent) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments of ubiquitin-related disorders (e.g., cellular proliferative disorders and/or neurodegenerative disorders) described herein.

Uba6 Nucleic Acid and Amino Acid Sequences

One aspect of the invention pertains to isolated nucleic acid molecules that encode Uba6 and/or E2Z proteins or biologically active portions thereof, as well as nucleic acid fragments sufficient for use as hybridization probes to identify Uba6- and/or E2Z-encoding nucleic acid molecules (e.g., Uba6 and/or E2Z mRNA, respectively) and fragments for use as PCR primers for the amplification or mutation of Uba6 nucleic acid molecules. As used herein, the term "nucleic acid molecule" is intended to include, but is not limited to, DNA molecules (e.g., cDNA or genomic DNA) and RNA molecules (e.g., mRNA) and analogs of the DNA or RNA generated using nucleotide analogs. The nucleic acid molecule can be single-stranded or double-stranded DNA.

An "isolated" nucleic acid molecule is one which is separated from other nucleic acid molecules which are present in the natural source of the nucleic acid. In an exemplary embodiment, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Uba6 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:4 or SEQ ID NO:6, or a portion thereof, can be isolated using standard molecular biology techniques and the sequence information provided herein. Using all or portion of the nucleic acid sequence of SEQ ID NO:4 or SEQ ID NO:6 as a hybridization probe, Uba6 nucleic acid molecules can be isolated using standard hybridization and cloning techniques (e.g., as described in Sambrook, J., Fritsh, E. F., and Maniatis, T., *Molecular Cloning: A Laboratory Manual*, 2nd, ed., Cold Spring Harbor Laboratory, Cold Spring Harbor Laboratory Press, Cold Spring Harbor, N.Y., 1989). Moreover, a nucleic acid molecule encompassing all or a portion of SEQ ID NO:4 or SEQ ID NO:6 can be isolated by the polymerase chain reaction (PCR) using synthetic oligonucleotide primers designed based upon the sequence of SEQ ID NO:4 or SEQ ID NO:6.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to Uba6 and/or E2Z nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:4 or SEQ ID NO:6, or a portion of either of these nucleotide sequences. In another embodiment, an isolated nucleic acid molecule of the invention comprises a nucleic acid molecule which is a complement of the nucleotide sequence shown in SEQ ID NO:4 or SEQ ID NO:6, or a portion of any of these nucleotide sequences. A nucleic acid molecule which is complementary to the nucleotide sequence shown in SEQ ID NO:4 or SEQ ID NO:6, is one which is sufficiently complementary to the nucleotide sequence shown in SEQ ID NO:4 or SEQ ID NO:6, such that it can hybridize to the nucleotide sequence shown in SEQ ID NO:4 or SEQ ID NO:6, thereby forming a stable duplex.

In still another embodiment, an isolated nucleic acid molecule of the present invention comprises a nucleotide sequence which is at least about 50%, 55%, 60%, 65%, 70%, 75%, 80%, 85%, 90%, 95% or more identical to the entire length of the nucleotide sequence shown in SEQ ID NO:4 or SEQ ID NO:6, or a portion of either of these nucleotide sequences.

Moreover, the nucleic acid molecule of the invention can comprise only a portion of the nucleic acid sequence of SEQ ID NO:4 or SEQ ID NO:6, for example a fragment which can be used as a probe or primer or a fragment encoding a biologically active portion of a Uba6 protein. The nucleic acid sequence of SEQ ID NO:4 or SEQ ID NO:6 allows for the generation of probes and primers designed for use in identifying and/or cloning other Uba6 family members, as well as Uba6 homologues from other species.

The probe/primer typically comprises substantially purified oligonucleotide. The oligonucleotide typically comprises a region of nucleotide sequence that hybridizes under stringent conditions to at least about 12 or 15, about 20 or 25, about 30, 35, 40, 45, 50, 55, 60, 65, or 75 consecutive nucleotides of a sense sequence of SEQ ID NO:4 or SEQ ID NO:6, of an anti-sense sequence of SEQ ID NO:4 or SEQ ID NO:6, or of a naturally occurring allelic variant or mutant of SEQ ID NO:4 or SEQ ID NO:6. In an exemplary embodiment, a nucleic acid molecule of the present invention comprises a nucleotide sequence which is 350-400, 400-450, 450-500, 500-550, 550-600, 600-650, 650-700, 700-750, 750-800, 800-850, 850-900, 900-950, 950-1000, 1000-1500, 1500-2000, 2000-2500, 2500-3000, 3000-3500, 3500-4000, 4000-4500, 4500-5000, 5101, 5386, 5000-5500 or more nucleotides in length and hybridizes under stringent hybridization conditions to a nucleic acid molecule of SEQ ID NO:4 or SEQ ID NO:6.

Probes based on the Uba6 nucleotide sequences can be used to detect transcripts or genomic sequences encoding the same or homologous proteins. In certain embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which mis-express Uba6, such as by measuring a level of a Uba6-encoding nucleic acid in a sample of cells from a subject e.g., detecting Uba6 mRNA levels or determining whether a genomic Uba6 gene has been mutated or deleted.

A nucleic acid fragment encoding a "biologically active portion of a Uba6 protein" can be prepared by isolating a portion of the nucleotide sequence of SEQ ID NO:4 or SEQ ID NO:6 which encodes a polypeptide having a Uba6 biological activity (the biological activities of the Uba6 proteins are described herein), expressing the encoded portion of the Uba6 protein (e.g., by recombinant expression in vitro) and assessing the activity of the encoded portion of Uba6.

The invention further encompasses nucleic acid molecules that differ from the nucleotide sequence shown in SEQ ID NO:4 or SEQ ID NO:6 due to degeneracy of the genetic code and thus encode the same Uba6 proteins as those encoded by the nucleotide sequence shown in SEQ ID NO:4 or SEQ ID NO:6. In another embodiment, an isolated nucleic acid molecule of the invention has a nucleotide sequence encoding a protein having an amino acid sequence shown in SEQ ID NO:5 or SEQ ID NO:7.

In addition to the Uba6 nucleotide sequences of SEQ ID NO:4 or SEQ ID NO:6, it will be appreciated by those skilled in the art that DNA sequence polymorphisms that lead to changes in the amino acid sequences of the Uba6 proteins may exist within a population (e.g., the human population). Such genetic polymorphism in the Uba6 genes may exist among individuals within a population due to natural allelic variation. As used herein, the terms "gene" and "recombinant gene" refer to nucleic acid molecules which include an open reading frame encoding Uba6, such as a mammalian or mouse or zebrafish Uba6, and can further include non-coding regulatory sequences, and introns.

Allelic variants of Uba6 include both functional and non-functional Uba6 proteins. Functional allelic variants are naturally occurring amino acid sequence variants of the Uba6 that maintain the ability to bind a Uba6 ligand and/or modulate any of the Uba6 activities described herein. Functional allelic variants will typically contain only conservative substitution of one or more amino acids of SEQ ID NO:5 or SEQ ID NO:7 or substitution, deletion or insertion of non-critical residues in non-critical regions of the protein.

Non-functional allelic variants are naturally occurring amino acid sequence variants of the Uba6 that do not have the ability to either bind a Uba6 ligand and/or modulate any of the Uba6 activities described herein. Non-functional allelic variants will typically contain a non-conservative substitution, a deletion, or insertion or premature truncation of the amino acid sequence of SEQ ID NO:5 or SEQ ID NO:7 or a substitution, insertion or deletion in critical residues or critical regions.

The present invention further provides non-human orthologs of a Uba6 protein. Orthologs of a Uba6 protein are proteins that are isolated from various organisms that possess the same Uba6 ligand binding and/or modulation of any of the Uba6 activities described herein. Orthologs of Uba6 can readily be identified as comprising an amino acid sequence that is substantially identical to SEQ ID NO:5 or SEQ ID NO:7.

Moreover, nucleic acid molecules encoding other Uba6 family members and, thus, which have a nucleotide sequence which differs from the Uba6 sequences of SEQ ID NO:4 or SEQ ID NO:6 are intended to be within the scope of the invention. For example, another Uba6 cDNA can be identified based on the nucleotide sequence of human or mouse Uba6. Moreover, nucleic acid molecules encoding Uba6 proteins from different species, and thus which have a nucleotide sequence which differs from the Uba6 sequences of SEQ ID NO:4 or SEQ ID NO:6 are intended to be within the scope of the invention. For example, a monkey Uba6 cDNA can be identified based on the nucleotide sequence of a human or mouse Uba6.

Nucleic acid molecules corresponding to natural allelic variants and homologues of the Uba6 cDNAs of the invention can be isolated based on their homology to the Uba6 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:4 or SEQ ID NO:6. In other embodiment, the nucleic acid is at least 30, 50, 100, 150, 200, 250, 300, 307, 350, 400, 450, 500, 550, 600, 650, 700, 750, 800, 850, 900, 950, 1000, 1500, 2000, 2500, 3000, 3500, 4000, 4500, 5000, 5101, 5386, or 5500 nucleotides in length. As used herein, the term "hybridizes under stringent conditions" is intended to describe conditions for hybridization and washing under which nucleotide sequences at least 60% identical to each other typically remain hybridized to each other. In exemplary embodiments, the conditions are such that sequences at least about 70%, at least about 80%, at least about 85%, at least about 90% or 95% identical to each other typically remain hybridized to each other. Such stringent conditions are known to those skilled in the art and can be found in *Current Protocols in Molecular Biology*, John Wiley & Sons, N.Y. (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., in certain aspects at 55° C., and in other aspects at 60° C. or 65° C. In certain aspects, an isolated nucleic acid molecule of the invention that hybridizes under stringent conditions to the sequence of SEQ ID NO:4 or SEQ ID NO:6 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the Uba6 sequences that may exist in the population, the skilled artisan will further appreciate that changes can be introduced by mutation into the nucleotide sequences of SEQ ID NO:4 or SEQ ID NO:6, thereby leading to changes in the amino acid sequence of the encoded Uba6 proteins, without altering the functional ability of the Uba6 proteins. For example, nucleotide substitutions leading to amino acid substitutions at "non-essential" amino acid residues can be made in the sequence of SEQ ID NO:4 or SEQ ID NO:6. A "non-essential" amino acid residue is a residue that can be altered from the wild-type sequence of Uba6 (e.g., the sequence of SEQ ID NO:5 or SEQ ID NO:7) without altering the biological activity, whereas an "essential" amino acid residue is required for biological activity. For example, amino acid residues that are conserved among the Uba6 proteins of the present invention, are predicted to be particularly unamenable to alteration. Furthermore, additional amino acid residues that are conserved between the Uba6 proteins of the present invention and other members of the Uba6 family of proteins are not likely to be amenable to alteration.

Accordingly, another aspect of the invention pertains to nucleic acid molecules encoding Uba6 proteins that contain changes in amino acid residues that are not essential for activity. Such Uba6 proteins differ in amino acid sequence from SEQ ID NO:5 or SEQ ID NO:7, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95% or more identical to SEQ ID NO:5 or SEQ ID NO:7.

An isolated nucleic acid molecule encoding a Uba6 protein homologous to the protein of SEQ ID NO:5 or SEQ ID NO:7 can be created by introducing one or more nucleotide substitutions, additions or deletions into the nucleotide sequence of SEQ ID NO:4 or SEQ ID NO:6, such that one or more amino acid substitutions, additions or deletions are introduced into the encoded protein. Mutations can be introduced into SEQ ID NO:4 or SEQ ID NO:6 by standard techniques, such as site-directed mutagenesis and PCR-mediated mutagenesis. In certain embodiments, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In certain aspects, a predicted nonessential amino acid residue in a Uba6 protein is replaced with another amino acid residue from the same side chain family. Alternatively, in another embodiment, mutations can be introduced randomly along all or part of a Uba6 coding sequence, such as by saturation mutagenesis, and the resultant mutants can be screened for Uba6 biological activity to identify mutants that retain activity. Following mutagenesis of SEQ ID NO:4 or SEQ ID NO:6, the encoded protein can be expressed recombinantly and the activity of the protein can be determined.

In an exemplary embodiment, a mutant Uba6 protein can be assayed for the ability to (1) activate ubiquitin; (2) mediate ubiquitin-adenylate intermediate formation; (3) mediate ubiquitin thiol esterification; (4) transfer ubiquitin to one or more ubiquitin-conjugating enzymes (e.g., E2s); and/or (5) ubiquitinate one or more target polypeptides (e.g., ubiquitin, an E2, a target polypeptide and/or protein or the like). In another exemplary embodiment, a mutant E2Z protein can be assayed for the ability to (1) activate ubiquitin; (2) mediate ubiquitin-adenylate intermediate formation; (3) mediate ubiquitin thiol esterification; (4) transfer ubiquitin to one or more ubiquitin-protein ligases (e.g., E3s); and/or (5) ubiquitinate one or more target polypeptides (e.g., ubiquitin, an E3, a target polypeptide and/or protein or the like).

In addition to the nucleic acid molecules encoding Uba6 and/or E2Z proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Uba6 and/or E2Z coding strand, or to only a portion thereof. In one embodiment, an antisense nucleic acid molecule is antisense to a "coding region" of the coding strand of a nucleotide sequence encoding Uba6 and/or E2Z. The term "coding region" refers to the region of the nucleotide sequence comprising codons which are translated into amino acid residues. In another embodiment, the antisense nucleic acid molecule is antisense to a "non-coding region" of the coding strand of a nucleotide sequence encoding Uba6 and/or E2Z. The term "non-coding region" refers to 5' and 3' sequences which flank the coding region that are not translated into amino acids (i.e., also referred to as 5' and 3' untranslated regions).

Embodiments of the present invention provide amino acid sequences having one or more biologically active portions of a Uba6 and/or E2Z protein. As used herein, a "biologically active portion of a Uba6 protein" includes a fragment of a Uba6 protein which participates in an interaction between a Uba6 molecule and a non-Uba6 molecule. As used herein, a "biologically active portion of an E2Z protein" includes a fragment of a E2Z protein which participates in an interaction between an E2Z molecule and a non-E2Z molecule. Biologically active portions of a Uba6 protein include peptides comprising amino acid sequences sufficiently identical to or derived from the amino acid sequence of the Uba6 protein, e.g., the amino acid sequence shown in SEQ ID NO:5 or SEQ ID NO:7, which include less amino acids than a full length Uba6 protein, and exhibit at least one activity of a Uba6 protein. Typically, biologically active portions comprise a domain or motif (e.g., one, two or more ThiF domains, one or more catalytic cysteine domains, one or more adenylate domains and/or one or more C-terminal ubiquitin-like (Ubl) domains) with at least one activity of the Uba6 protein (e.g., ubiquitin activation; ubiquitin-adenylate intermediate formation; ubiquitin thiol esterification; ubiquitin transfer to one or more ubiquitin-conjugating enzymes (e.g., E2s); and/or ubiquitination of one or more target polypeptides (e.g., ubiquitin, an E2, a target polypeptide and/or protein or the like). A biologically active portion of a Uba6 protein can be a polypeptide which is, for example, 10, 25, 50, 100, 200, 300, 400, 500, 600, 700, 800, 900, 1000, 1050, 1052, 1053 or more amino acids in length. Biologically active portions of a Uba6 protein can be used as targets for developing agents which modulate a UPP activity. In one embodiment, a biologically active portion of a Uba6 protein comprises at least one ThiF domain, catalytic cysteine domain, adenylate domain and/or a C-terminal ubiquitin-like domain.

It is to be understood that in certain embodiments, a biologically active portion of a Uba6 protein of the present invention may contain at least one of the above-identified structural domains. In other embodiments, a biologically active portion of a Uba6 protein may contain at least two, at least three or at least four of the above-identified structural domains. Moreover, other biologically active portions, in which other regions of the protein are deleted, can be prepared by recombinant techniques and evaluated for one or more of the functional activities of a native Uba6 protein.

In an exemplary embodiment, the Uba6 protein has an amino acid sequence shown in SEQ ID NO:5 or SEQ ID NO:7. In other embodiments, the Uba6 protein is substantially homologous to SEQ ID NO:5 or SEQ ID NO:7, and retains the functional activity of the protein of SEQ ID NO:5 or SEQ ID NO:7, yet differs in amino acid sequence due to natural allelic variation or mutagenesis, as described in detail above. Accordingly, in another embodiment, the Uba6 protein is a protein which comprises an amino acid sequence at least about 50%, 55%, 60%, 65%, 70%, 75%, 80%, 85%, 90%, 95% or more identical to SEQ ID NO:5 or SEQ ID NO:7.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In an exemplary embodiment, the length of a reference sequence aligned for comparison purposes is at least 30%, at least 40%, at least 50%, at least 60%, and even at least 70%, 80%, or 90% of the length of the reference sequence (e.g., when aligning a second sequence to the Uba6 amino acid sequence having 1052 and 1053 amino acid residues, respectively, at least 315, at least 420, at least 526, at least 631, and even at least 736, 841 or 946 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In an exemplary embodiment, the percent identity between two amino acid sequences is determined using the Needleman and Wunsch (*J. Mol. Biol.* (48): 444-453 (1970)) algorithm which has been incorporated into the GAP program in the GCG software package (available at world wide website gcg.com), using either a Blosum 62 matrix or a PAM250 matrix, and a gap weight of 16, 14, 12, 10, 8, 6, or 4 and a length weight of 1, 2, 3, 4, 5, or 6. In yet another exemplary embodiment, the percent identity between two nucleotide sequences is determined using the GAP program in the GCG software package (available at the website gcg.com), using a NWSgapdnaCMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS* (1989) 4:11) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403. BLAST nucleotide searches can be performed with the NBLAST program, score=100, wordlength=12 to obtain nucleotide sequences homologous to Uba6 nucleic acid molecules of the invention. BLAST protein searches can be performed with the XBLAST program, score=50, wordlength=3 to obtain amino acid sequences homologous to Uba6 protein molecules of the invention. To obtain gapped alignments for comparison purposes, Gapped BLAST can be utilized as described in Altschul et al., (1997) *Nucleic Acids Res.* 25(17): 3389. When utilizing BLAST and Gapped BLAST programs, the default parameters of the respective programs (e.g., XBLAST and NBLAST) can be used (ncbi.nlm.nih.gov website).

Recombinant Expression Vectors and Host Cells

Another aspect of the invention pertains to vectors, such as expression vectors, containing a nucleic acid encoding a Uba6 and/or an E2Z protein (or a portion thereof). As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., Uba6 and/or E2Z proteins, mutant forms of Uba6 and/or E2Z proteins, fusion proteins, and the like).

The recombinant expression vectors of the invention can be designed for expression of Uba6 in prokaryotic or eukaryotic cells. For example, Uba6, Uba6 fragments, E2Z and/or E2Z fragments can be expressed in bacterial cells such as *E. coli*, insect cells (using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of polypeptides in prokaryotes is most often carried out in *E. coli* with vectors containing constitutive or inducible promoters directing the expression of either fusion or non-fusion proteins. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111). Such alteration of nucleic acid sequences of the invention can be carried out by standard DNA synthesis techniques.

In another embodiment, the Uba6 expression vector is a yeast expression vector. Examples of vectors for expression in yeast *S. cerevisiae* include pYepSec1 (Baldari et al., (1987) *Embo J.* 6:229), pMFa (Kurjan and Herskowitz, (1982) *Cell* 30:933), pJRY88 (Schultz et al., (1987) *Gene* 54:113), pYES2 (Invitrogen, San Diego, Calif.), and picZ (Invitrogen, San Diego, Calif.).

Alternatively, Uba6 and/or E2Z polypeptides can be expressed in insect cells using baculovirus expression vectors. Baculovirus vectors available for expression of proteins in cultured insect cells (e.g., Sf 9 cells) include the pAc series (Smith et al. (1983) *Mol. Cell. Biol.* 3:2156) and the pVL series (Lucklow and Summers (1989) *Virology* 170:31).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187). When used in mammalian cells, the expression vector's control functions are often provided by viral regulatory elements. For example, commonly used promoters are derived from polyoma, adenovirus 2, cytomegalovirus and Simian virus 40. For other suitable expression systems for both prokaryotic and eukaryotic cells see chapters 16 and 17 of Sambrook, J., Fritsh, E. F., and Maniatis, T., *Molecular Cloning: A Laboratory Manual*, 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268), lymphoid-specific promoters (Calame and Eaton (1988) *Adv. Immunol.* 43:235), in particular promoters of T cell receptors (Winoto and Baltimore (1989) *EMBO J.* 8:729) and immunoglobulins (Banerji et al. (1983) *Cell* 33:729; Queen and Baltimore (1983) *Cell* 33:741), neuron-specific promoters (e.g., the neurofilament promoter; Byrne and Ruddle (1989) *Proc. Natl. Acad. Sci. U.S.A.* 86:5473), pancreas-specific promoters (Edlund et al. (1985) *Science* 230:912), and mammary gland-specific promoters (e.g., milk whey promoter; U.S. Pat. No. 4,873,316 and European Application Publication No. 264,166). Developmentally regulated promoters are also encompassed, for example the murine hox promoters (Kessel and Gruss (1990) *Science* 249:374) and the α-fetoprotein promoter (Campes and Tilghman (1989) *Genes Dev.* 3:537).

In one embodiment, the present invention provides a nucleic acid molecule which is antisense to a Uba6 nucleic acid molecule. As used herein, the term "antisense" refers to a nucleic acid that interferes with the function of DNA and/or RNA and may result in suppression of expression of the RNA and/or DNA. The antisense nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire Uba6 coding strand, or to only a portion thereof.

An antisense nucleic acid molecule can be delivered to a cell to express an exogenous nucleotide sequence, to inhibit, eliminate, augment, or alter expression of an endogenous nucleotide sequence, or to express a specific physiological characteristic not naturally associated with the cell. In certain embodiments, the antisense nucleic acid is an antisense RNA, an interfering double stranded RNA ("dsRNA"), a short interfering RNA ("siRNA") or a ribozyme.

As used herein, the term "siRNA" refers to double-stranded RNA that is less than 30 bases, such as 21-25 bases in length. siRNA may be prepared by any method known in the art. For a review of siRNA and RNA interference, see Macrae et al. (2006) *Science* 311:195; Vermeulen et al. (2005) *RNA* 11:674; Nishikura (2001) *Cell* 16:415; Fire et al. (1998) *Nature* 391:806. In one embodiment, single-stranded, gene-specific sense and antisense RNA oligomers with overhanging 3' deoxynucleotides are prepared and purified. For example, two oligomers, can be annealed by heating to 94° C. for 2 minutes, cooling to 90° C. for 1 minute, and then cooling to 20° C. at a rate of 1° C. per minute. The siRNA can then be injected into an animal or delivered into a desired cell type using methods of nucleic acid delivery described herein.

Another aspect of the invention pertains to host cells into which a recombinant expression vector of the invention has been introduced, containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, host cells can be bacterial cells such as *E. coli*, insect cells (e.g., *Drosophila* cells), yeast, *Xenopus* cells, zebrafish cells, or mammalian cells (such as Chinese hamster ovary cells (CHO), African green monkey kidney cells (COS), or fetal human cells (293T)). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*, 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Exemplary selectable markers include those which confer resistance to drugs, such as G418, hygromycin and methotrexate. Nucleic acid encoding a selectable marker can be introduced into a host cell on the same vector as that encoding a detectable translation product or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a Uba6 and/or an E2Z protein or portion thereof. Accordingly, the invention further provides methods for producing a Uba6 and/or an E2Z protein or portion thereof using the host cells of the invention. In one embodiment, the method comprises culturing the host cell of invention (into which a recombinant expression vector encoding a detectable translation product has been introduced) in a suitable medium such that a detectable translation product is produced. In another embodiment, the method further comprises isolating a Uba6 and/or an E2Z protein or portion thereof from the medium or the host cell.

The host cells of the invention can also be used to produce nonhuman transgenic animals. For example, in one embodiment, a host cell of the invention is a fertilized oocyte or an embryonic stem cell into which Uba6-coding sequences have been introduced. Such host cells can then be used to create non-human transgenic animals in which exogenous Uba6 sequences have been introduced into their genome. As used herein, a "transgenic animal" is a non-human animal, such as a mammal (e.g., a rodent such as a rat or mouse), in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal such as a mamma (e.g., a mouse), in which an endogenous gene has been altered by homologous recombination between the endogenous gene and an exogenous DNA molecule introduced into a cell of the animal, e.g., an embryonic cell of the animal, prior to development of the animal.

Methods for generating transgenic animals via embryo manipulation and microinjection, particularly animals such as mice, have become conventional in the art and are described, for example, in U.S. Pat. Nos. 4,736,866 and 4,870,009, in U.S. Pat. No. 4,873,191 by Wagner et al., in Hogan, B., *Manipulating the Mouse Embryo*, (Cold Spring Harbor Laboratory Press, Cold Spring Harbor, N.Y., 1986), and in Wilmut et al. (1997) *Nature* 385:810. Similar methods are used for production of other transgenic animals. Methods for producing transgenic non-humans animals that contain selected systems which allow for regulated expression of the transgene are described in Lakso et al. (1992) *Proc. Natl. Acad. Sci. U.S.A.* 89:6232; and O'Gorman et al. (1991) *Science* 251:1351).

Diagnostic Assays

An exemplary method for detecting Uba6 and/or E2Z expression or Uba6 and/or E2Z activity in a biological sample involves obtaining a biological sample from a test subject and contacting the biological sample with a compound or an agent capable of detecting Uba6 and/or E2Z expression or Uba6 and/or E2Z activity (e.g., ubiquitin activation; ubiquitin-adenylate intermediate formation; ubiquitin thiol esterification; ubiquitin transfer to one or more ubiquitin-conjugating enzymes (e.g., E2s); ubiquitin transfer to one or more ubiquitin-protein ligases (e.g., E3s); and/or ubiquitination of one or more target polypeptides).

In certain aspects, an agent for detecting Uba6 and/or E2Z expression or Uba6 and/or E2Z activity (e.g., ubiquitin activation; ubiquitin-adenylate intermediate formation; ubiquitin thiol esterification; ubiquitin transfer to one or more ubiquitin-conjugating enzymes (e.g., E2s); ubiquitin transfer to one or more ubiquitin-protein ligases (e.g., E3s); and/or ubiquitination of one or more target polypeptides) is an antibody capable of binding to Uba6, ubiquitin and/or a target polypeptide or protein, such as an antibody. Antibodies can be polyclonal or monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells and biological fluids isolated from a subject, as well as tissues, cells and fluids present within a subject. That is, the detection method of the invention can be used to detect Uba6 and/or E2Z expression or Uba6 and/or E2Z activity in a biological sample in vitro as well as in vivo. For example, in vitro techniques for detection of Uba6 and/or E2Z include enzyme linked immunosorbent assays (ELISAs), Western blots, immunoprecipitations and immunofluorescence. Furthermore, in vivo techniques for detection of Uba6 and/or E2Z expression or Uba6 and/or E2Z activity include introducing into a subject a labeled anti-Uba6 and/or an anti-E2Z antibody, a labeled anti-ubiquitin antibody, a labeled anti-E2 antibody, a labeled anti-E3 antibody, a labeled anti-target protein or the like. For example, the antibody can be labeled with a radioactive marker whose presence and location in a subject can be detected by standard imaging techniques.

In one embodiment, the biological sample contains protein molecules from the test subject. In certain aspects, a biological sample is a serum sample isolated by conventional means from a subject.

In another embodiment, the methods further involve obtaining a control biological sample from a control subject, contacting the control sample with a compound or agent capable of detecting Uba6 and/or E2Z expression or Uba6 and/or E2Z activity, such that the presence of Uba6 and/or E2Z expression or Uba6 and/or E2Z activity is detected in the biological sample, and comparing the presence of Uba6 and/or E2Z expression or Uba6 activity in the control sample with the presence of Uba6 and/or E2Z expression or Uba6 and/or E2Z activity in the test sample.

The invention also encompasses kits for detecting the presence of Uba6 and/or E2Z expression or Uba6 and/or E2Z activity in a biological sample. For example, the kit can comprise a labeled compound or agent capable of detecting Uba6 and/or E2Z expression or Uba6 and/or E2Z activity in a biological sample; means for determining the amount of Uba6 and/or E2Z expression or Uba6 and/or E2Z activity in the sample; and means for comparing the amount of Uba6 and/or E2Z expression or Uba6 and/or E2Z activity in the sample with a standard. The compound or agent can be packaged in a suitable container. The kit can further comprise instructions for using the kit to detect Uba6 and/or E2Z expression or Uba6 and/or E2Z activity.

Prognostic Assays

The diagnostic methods described herein can furthermore be utilized to identify subjects having or at risk of developing a disease or disorder associated with aberrant Uba6 expression or activity (e.g., cancer). For example, the assays described herein, such as the preceding diagnostic assays or the following assays, can be utilized to identify a subject having or at risk of developing a disorder associated with a misregulation in Uba6 expression and/or activity, such as ubiquitin-related disorders such as cancer, inflammatory disorders, neurodegenerative disorders and the like.

Thus, the present invention provides a method for identifying a disease or disorder associated with aberrant Uba6 and/or E2Z expression or activity in which a test sample is obtained from a subject and Uba6 and/or E2Z expression and/or Uba6 and/or E2Z activity is detected, wherein the presence of Uba6 and/or E2Z expression and/or Uba6 and/or E2Z activity is diagnostic for a subject having or at risk of developing a disease or disorder associated with aberrant Uba6 and/or E2Z expression and/or Uba6 and/or E2Z activity expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant Uba6 and/or E2Z expression or activity. For example, such methods can be used to determine whether a subject can be effectively treated with an agent for cancer. Thus, the present invention provides methods for determining whether a subject can be effectively treated with an agent for a disorder associated with aberrant Uba6 and/or E2Z expression or activity in which a test sample is obtained and Uba6 and/or E2Z expression and/or Uba6 and/or E2Z activity is detected.

The methods of the invention can also be used to detect genetic alterations in a Uba6 and/or an E2Z gene, thereby determining if a subject with the altered gene is at risk for a disorder characterized by misregulation in Uba6 and/or E2Z activity, such as cancer. In certain embodiments, the methods include detecting, in a sample of cells from the subject, the presence or absence of a genetic alteration characterized by at least one of: an alteration affecting the integrity of a gene encoding a Uba6 and/or E2Z protein; the misexpression of the Uba6 and/or E2Z gene; or aberrant activity of the Uba6 and/or E2Z protein. For example, such genetic alterations can be detected by ascertaining the existence of at least one of: 1) a deletion of one or more nucleotides from a Uba6 and/or an E2Z gene; 2) an addition of one or more nucleotides to a Uba6 and/or an E2Z gene; 3) a substitution of one or more nucleotides of a Uba6 and/or an E2Z gene, 4) a chromosomal rearrangement of a Uba6 and/or an E2Z gene; 5) an alteration in the level of a messenger RNA transcript of a Uba6 and/or an E2Z gene; 6) aberrant modification of a Uba6 and/or an E2Z gene, such as of the methylation pattern of the genomic DNA; 7) the presence of a non-wild type splicing pattern of a messenger RNA transcript of a Uba6 and/or an E2Z gene; 8) a non-wild type level of a Uba6 and/or an E2Z protein; 9) allelic loss of a Uba6 and/or an E2Z gene; and 10) inappropriate Uba6 and/or E2Z activity. As described herein, there are a large number of assays known in the art which can be used for detecting alterations in a Uba6 and/or an E2Z gene.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077; and Nakazawa et al. (1994) *Proc. Natl. Acad. Sci. USA* 91:360), the latter of which can be particularly useful for detecting point mutations in the Uba6 gene (see Abravaya et al. (1995) *Nucleic Acids Res.* 23:675). This method can include the steps of collecting a sample of cells from a subject, isolating nucleic acid (e.g., genomic, mRNA or both) from the cells of the sample, contacting the nucleic acid sample with one or more primers which specifically hybridize to a Uba6 gene under conditions such that hybridization and amplification of the Uba6 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874), transcriptional amplification system (Kwoh et al. (1989) *Proc. Natl. Acad. Sci. USA* 86:1173), Q-Beta Replicase (Lizardi, P. M. et al. (1988) *Biotechnology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Uba6 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Uba6 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244; Kozal, M. J. et al. (1996) *Nature Medicine* 2:753). For example, genetic mutations in Uba6 can be identified in two dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Uba6 and/or E2Z gene and detect mutations by comparing the sequence of the sample Uba6 and/or E2Z with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147).

Other methods for detecting mutations in the Uba6 and/or E2Z gene include methods in which protection from cleavage agents is used to detect mismatched bases in RNA/RNA or RNA/DNA heteroduplexes (Myers et al. (1985) *Science* 230: 1242). In general, the art technique of "mismatch cleavage" starts by providing heteroduplexes formed by hybridizing (labeled) RNA or DNA containing the wild-type Uba6 and/or E2Z sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397; Saleeba et al. (1992) *Methods Enzymol.* 217:286. In an exemplary embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Uba6 and/or E2Z cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657). According to an exemplary embodiment, a probe based on a Uba6 and/or an E2Z sequence, e.g., a wild-type Uba6 and/or E2Z sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Uba6 and/or E2Z genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766, see also Cotton (1993) *Mutat. Res.* 285:125; and Hayashi (1992) *Genet. Anal Tech. Appl.* 9:73). Single-stranded DNA fragments of sample and control Uba6 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an exemplary embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucl. Acids Res.* 17:2437) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell. Probes* 6: 1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Uba6 gene. Furthermore, any cell type or tissue in which Uba6 is expressed may be utilized in the prognostic assays described herein.

Monitoring of Effects During Clinical Trials

Monitoring the influence of agents (e.g., drugs) on the expression or one or more activities of Uba6 and/or E2Z (e.g., ubiquitin activation; ubiquitin-adenylate intermediate formation; ubiquitin thiol esterification; ubiquitin transfer to one or more ubiquitin-conjugating enzymes (e.g., E2s); ubiquitin transfer to one or more ubiquitin-protein ligases (e.g., E3s); and/or ubiquitination of one or more target polypeptides (e.g., ubiquitin, an E2, an E3, a target polypeptide and/or protein or the like) can be applied not only in basic drug screening, but also in clinical trials. For example, the effectiveness of an agent determined by a screening assay as described herein to increase Uba6 and/or E2Z gene expression or protein levels, or upregulate Uba6 and/or E2Z activity, can be monitored in clinical trials of subjects exhibiting decreased Uba6 and/or E2Z gene expression, protein levels, or downregulated Uba6 and/or E2Z activity. Alternatively, the effectiveness of an agent determined by a screening assay to decrease Uba6 and/or E2Z gene expression, or protein levels, or downregulate or Uba6 and/or E2Z activity, can be monitored in clinical trials of subjects exhibiting increased Uba6 and/or E2Z gene expression, protein levels, or upregulated Uba6 and/or E2Z activity.

In an exemplary embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a Uba6 and/or an E2Z protein, mRNA, or genomic DNA or of the level of Uba6 and/or E2Z activity in the preadministration sample; (iii) obtaining one or more post-administration samples from the subject; (iv) detecting the level of expression or activity of the Uba6 and/or E2Z protein, mRNA, or genomic DNA or of the level of Uba6 and/or E2Z activity in the post-administration samples; (v) comparing the level of expression or activity of the Uba6 and/or E2Z protein, mRNA, or genomic DNA or of the level of Uba6 and/or E2Z activity in the pre-administration sample with the Uba6 and/or E2Z protein, mRNA, or genomic DNA or Uba6 and/or E2Z activity in the post administration sample or samples; and (vi) altering the administration of the agent to the subject accordingly. For example, increased administration of the agent may be desirable to increase the expression or activity of Uba6 and/or E2Z to higher levels than detected, i.e., to increase the effectiveness of the agent. Alternatively, decreased administration of the agent may be desirable to decrease expression or activity of Uba6 to lower levels than detected, i.e. to decrease the effectiveness of the agent. According to such an embodiment, Uba6 and/or E2Z expression or activity may be used as an indicator of the effectiveness of an agent, even in the absence of an observable phenotypic response.

This invention is further illustrated by the following examples, which should not be construed as limiting. The contents of all references, patents and published patent applications cited throughout this application are hereby incorporated by reference in their entirety for all purposes.

Example I

A Novel Vertebrate E1 Protein, Uba6, Promotes Activation of Ubiquitin In Vitro

Figure 1B:
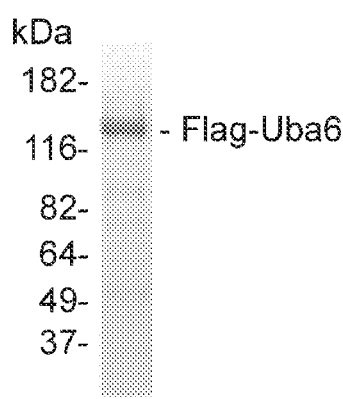
Figure 1C:
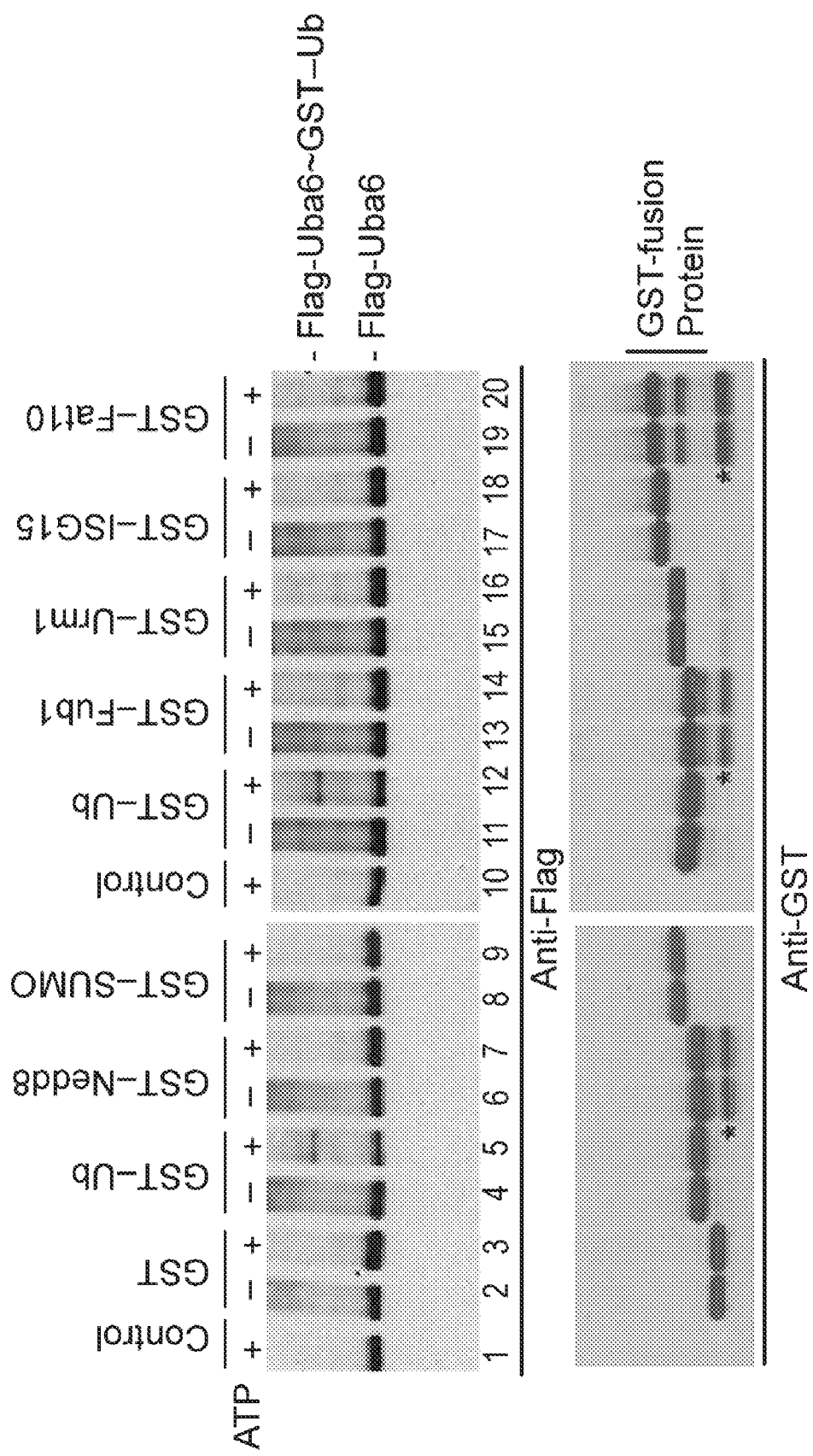
Figure 1D:
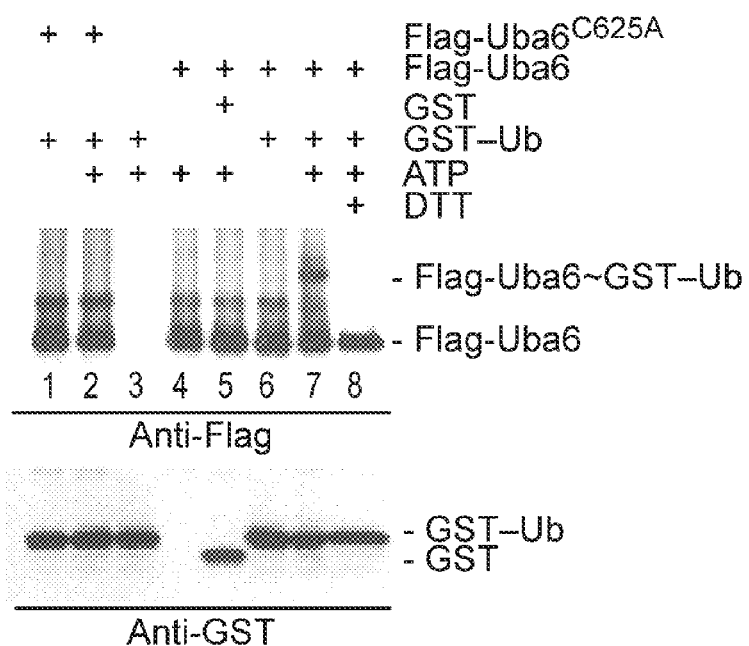
Figure 1E:
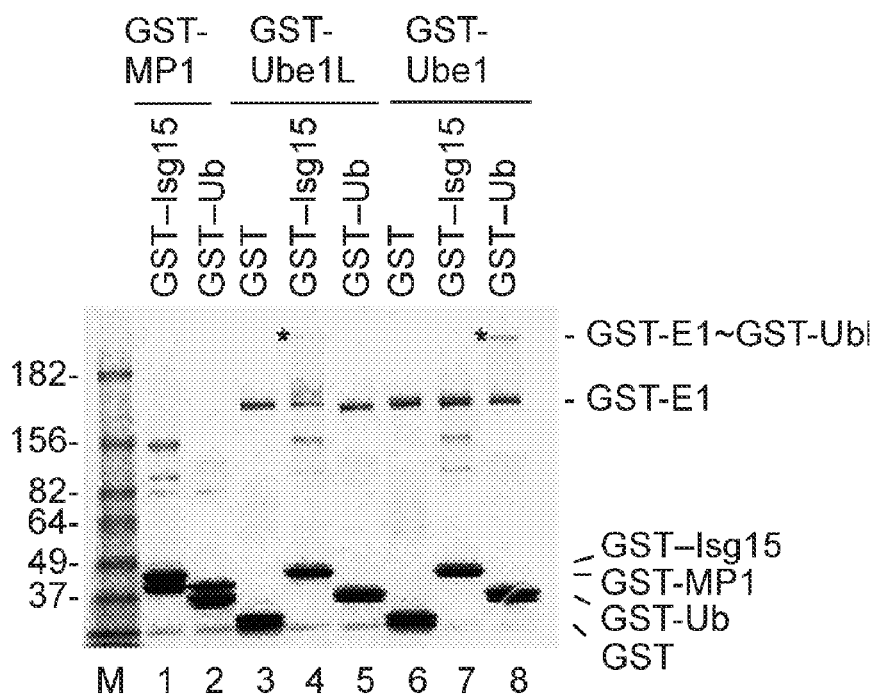
Figure 1F:
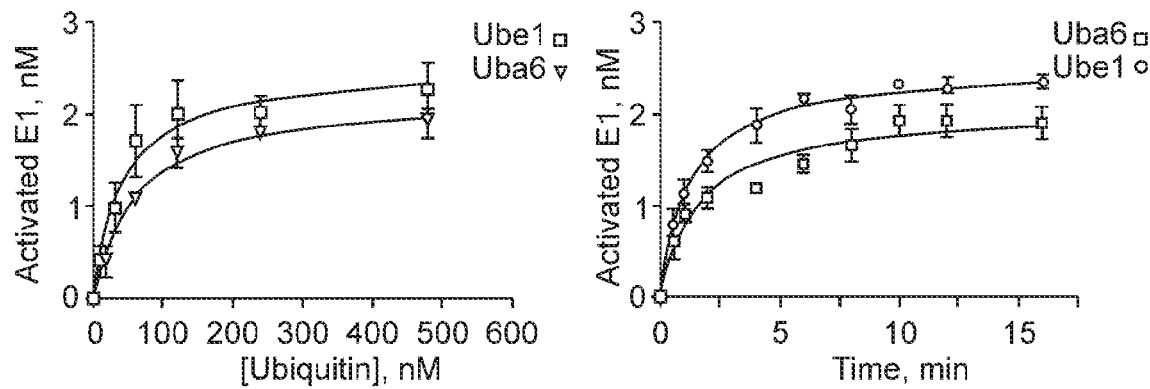
Figure 1G:
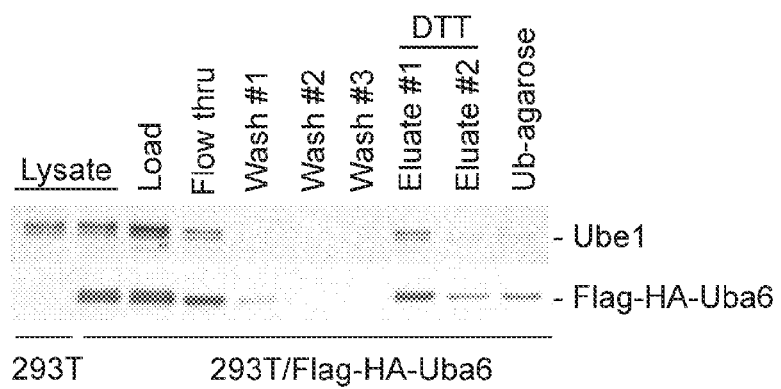
Figure 1H:
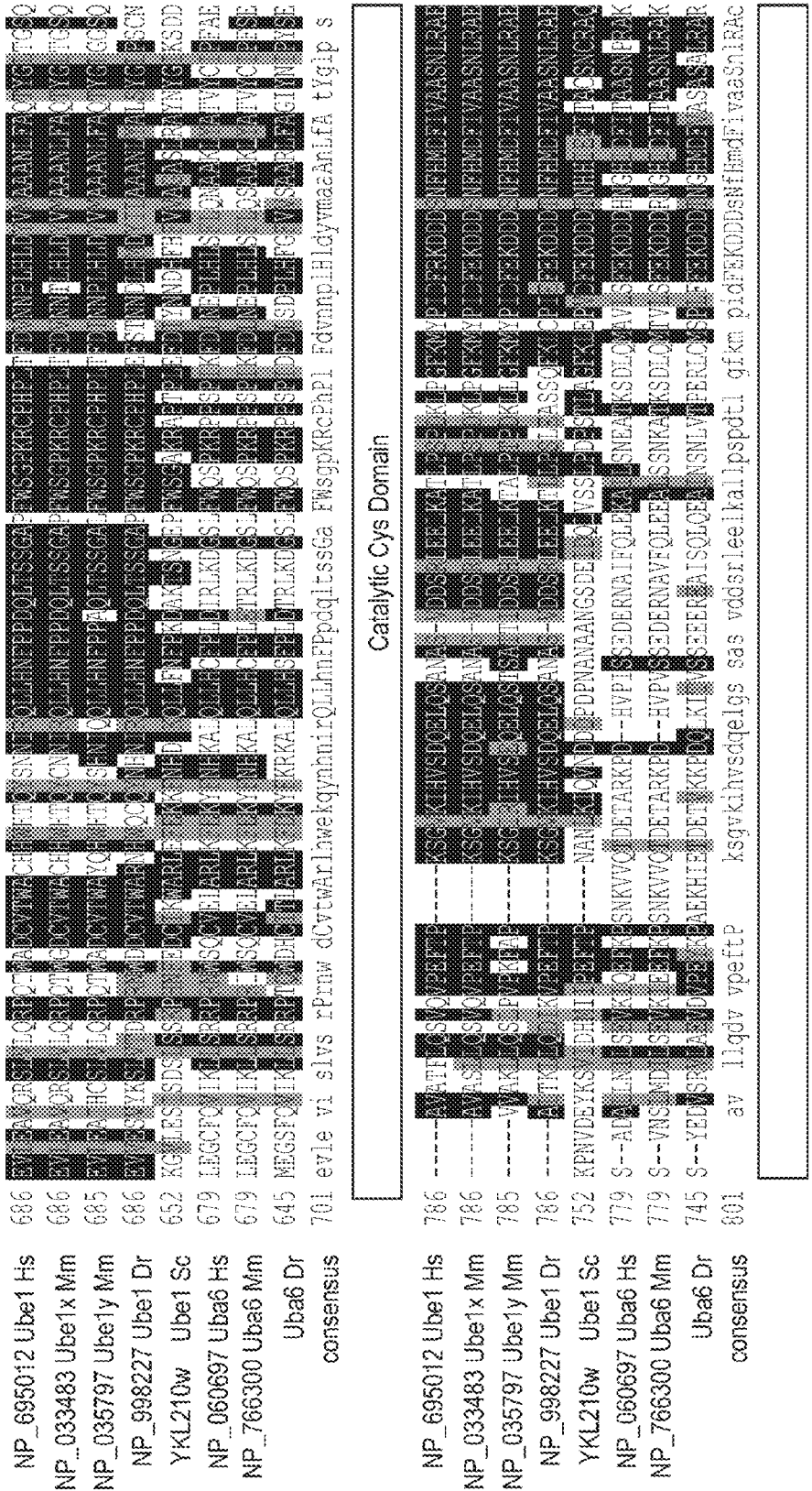

The E1 for ubiquitin is a member of a family of proteins that contains a protein fold, the ThiF domain, found in ancient metabolic enzymes in bacteria (Lake et al. (2001) *Nature* 414:325). Using this domain to identify related proteins bioinformatically, a previously uncharacterized protein was identified with similarity to Ube1, the canonical E1 activating enzyme for ubiquitin (GenBank Accession FLJ10808), Uba6. Uba6 orthologs exist in mouse, rat, and zebrafish (Dr), but are not found in non-vertebrate metazoans or in yeast (FIG. 1A). Phylogenetically, Uba6 is more distantly related to Ube1 than is Ube1L (FIG. 1G).

The ability of recombinant Uba6 (expressed in and purified from insect cells, FIG. 1B) to activate several ubiquitin like proteins as well as ubiquitin itself was examined. Surprisingly, it was determined that Uba6 could activate ubiquitin, but not any of the other ubiquitin like proteins tested, as determined by the appearance of an Uba6~Ub thiol ester upon non-reducing SDS-PAGE analysis (FIG. 1C, lane 4). As expected, the formation of Uba6~Ub could be reversed by the addition of DTT, indicative of the presence of a thiol ester (FIG. 1D, lanes 5 and 6). The ability of Uba6 to promote ubiquitin activation appeared to be specific, as Ube1L, which is more closely related to Ube1 than is Uba6 (FIG. 1A) was not capable of activating ubiquitin but was able to activate its known target, ISG15 (FIG. 1E). Taken together, these data indicate that Uba6 can promote the charging of ubiquitin but not a number of other ubiquitin-like proteins.

The identification of Uba6 as an activating enzyme for ubiquitin was unexpected and therefore several experiments described below were performed to validate this conclusion. Initially, the classical approaches of Hershko (Hershko et al. (1983) *J. Biol. Chem.* 258:8206) were used to purify Ube1 to examine whether Uba6 could be similarly purified. Extracts were made from 293T cells stably expressing Flag-HA-Uba6 and were incubated with ubiquitin-agarose in the presence of ATP. Beads were subsequently washed with buffer lacking DTT and proteins then eluted with buffer containing DTT, which reverses thiol esters between E1s and ubiquitin or ubiquitin-like proteins. Load, flow-through, washes and eluates, as well as proteins remaining associated with the ubiquitin-agarose beads, were then subjected to immunoblotting with anti-Ube1 to detect Ube1 and anti-HA to detect Flag-HA-Uba6. The elution pattern of Uba6 closely paralleled that of Ube1 (FIG. 1F). In particular, Uba6 was eluted specifically upon treatment with DTT. These data indicate that, like Ube1, Uba6 can be chemically crosslinked to ubiquitin in a thiol-dependent manner.

Example II

Identification of Uba6 Conjugated to Ubiquitin In Vivo

In order to validate the association between Uba6 and ubiquitin in vivo, cell lines were developed that stably expressed three forms of Uba6: 1) the wild-type protein containing an N-terminal Flag-HA tag; 2) the C625A mutant in which the catalytic cysteine was mutated to alanine, also as an N-terminal Flag-HA fusion; and 3) the C625S mutant in which the catalytic cysteine was mutated to serine, also as an N-terminal Flag-HA fusion. Replacement of the active site cysteine with alanine was expected to inactivate the ability of the protein to promote ubiquitin activation. In contrast, the cysteine to serine mutant was expected to support formation of an ester linked ubiquitin or ubiquitin like protein which is more stable that the thiol ester formed with cysteine. Indeed, previous studies (Komatsu et al. (2004) *Embo J.* 23:1977) have demonstrated that in certain cases, more stable conjugates can be formed with ester linkages than with thiol ester linkages.

Figure 2A:
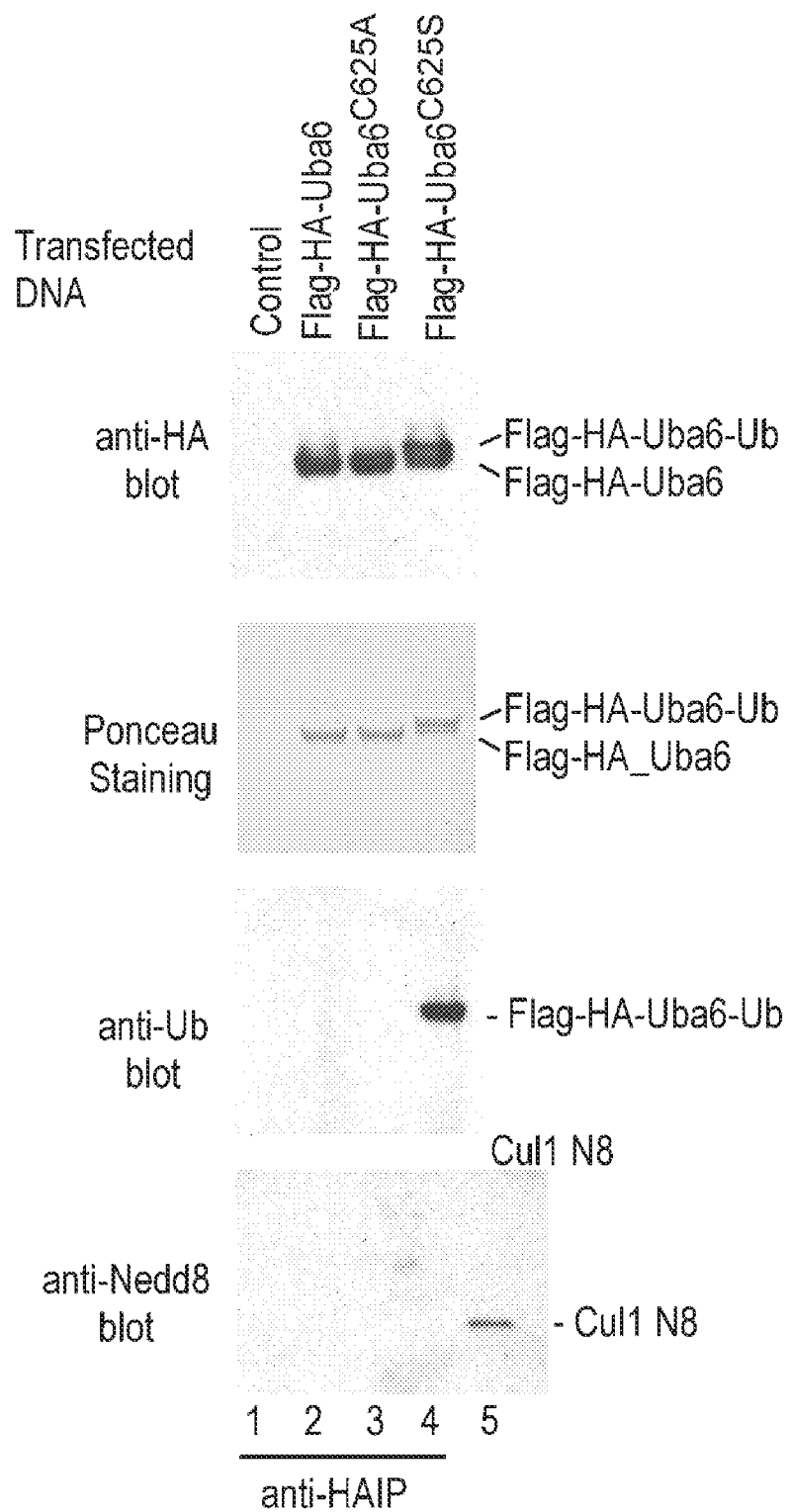
FIGS. 2A-2D depict data showing that Uba6 is charged with ubiquitin in vivo. (A) 293T cells stably expressing Flag-HA-Uba6, Flag-HA-Uba6$^{C625A}$, or Flag-HA-Uba6$^{C625S}$ using a lentiviral vector under control of the CMV promoter were lysed in extraction buffer and subjected to immunoprecipitation with anti-HA antibodies. Immune complexes were separated by SDS-PAGE under non-reducing conditions and either immunoblotted with anti-HA, anti-Nedd8, or anti-ubiquitin, or alternatively, the blot was stained with Ponceau S to reveal proteins. (B) 293T cells expressing Flag-HA-Uba6, Flag-HA-Uba6$^{C625A}$, or Flag-HA-Uba6$^{C625S}$ at near endogenous levels were lysed and extracts subjected to immunoblotting with anti-HA to detect the Flag-HA-Uba6 fusion or with anti-Uba6 to detect both the transgene and the endogenous Uba6 protein. The Flag-HA-Uba6$^{C625S}$ protein migrates as a doublet with the slower mobility band corresponding to the position of ubiquitin-charged Flag-HA-Uba6$^{C625S}$. (C) Identification of ubiquitin in association with Flag-HA-Uba6$^{C625S}$. Extracts from cells expressing Flag- HA-Uba6C625S were subjected to purification using anti-Flag and anti-HA resins and the proteins separated by SDS-PAGE. Individual bands were subjected to mass spectrometry. The slower mobility band contained three peptides from ubiquitin set forth in SEQ ID NO:24), while the faster mobility form lacked associated ubiquitin-derived peptides. (D) Depletion of Uba6 using RNAi. siRNAs targeting GFP (as a control) or Uba6 were transfected into 293T cells using OLIGOFECTAMINE™ (Invitrogen, Carlsbad, Calif.). After 72 hours, cells were lysed and extracts subjected to immunoblotting using anti-Uba6 antibodies. The siRNA sequences used for Uba6 were: #1: CCUUGGAA-GAGAAGCCUGAUGUAAA (SEQ ID NO:1); #2: ACACUGAAGUUAUUGUACCGCAUUU (SEQ ID NO:2); #3: GGGAUCGAUGGACCGUACAUGGAAA (SEQ ID NO:3). Purified Flag-Ha-Uba6 was used as a positive control for the immunoblot.

All three proteins were expressed at comparable levels upon analysis in SDS-PAGE in the absence of reducing agents (FIG. 2A). While the wild-type protein and the C625A mutant migrated at identical positions, a large fraction of the C625S mutant protein displayed reduced mobility by SDS-PAGE, as observed by both immunoblotting with anti-HA antibodies and by staining the membrane with Ponceau stain (FIG. 2A). These data indicate that Uba6 forms a stable ester with ubiquitin or a ubiquitin-like protein via S625 in this mutant protein. To examine whether the slow mobility form of Uba6 might be carrying ubiquitin or the ubiquitin-like protein Nedd8, an immunoblot was performed using anti-ubiquitin or anti-Nedd8 antibodies (FIG. 2A). While ubiquitin was detected in the slower mobility form of Uba6 when C625 was replaced by serine, no ubiquitin was found with either the wild-type protein or the C625A mutant protein, indicating that the more slowly migrating form of the $Uba6^{C625S}$ protein contained ubiquitin. In contrast, Nedd8 was not detected, although Nedd8 was clearly detected in an SCF complex used as a positive control (FIG. 2A).

Next, additional confirmation that $Uba6^{C625S}$ was conjugated to ubiquitin was sought. Preparative samples of Flag-HA-$Uba6^{C625S}$ were purified from 293T cells stably expressing Flag-HA-$Uba6^{C625S}$ under control of the CMV promoter. Approximately 30% of the isolated protein was determined to migrate at a position consistent with its modification by a ubiquitin-like protein (FIG. 3C). Mass spectral analysis of the more slowly migrating protein identified three peptides from ubiquitin (FIG. 3C), consistent with $Uba6^{C625S}$ forming conjugates with ubiquitin. In contrast, the more rapidly migrating form of the protein lacked peptides for ubiquitin. Neither form of $Uba6^{C625S}$ contained peptides for any other ubiquitin-like protein, indicating that other ubiquitin-like proteins were not able to be activated by Uba6 under these conditions.

Figure 2B:
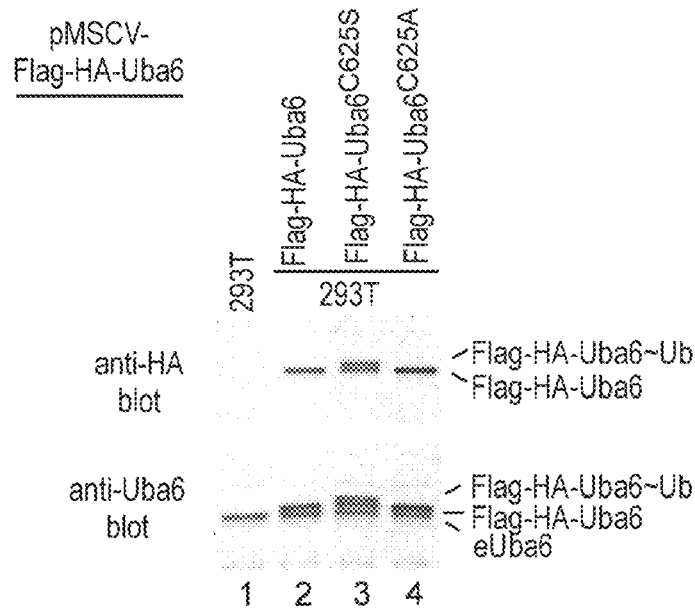
Figure 2C:
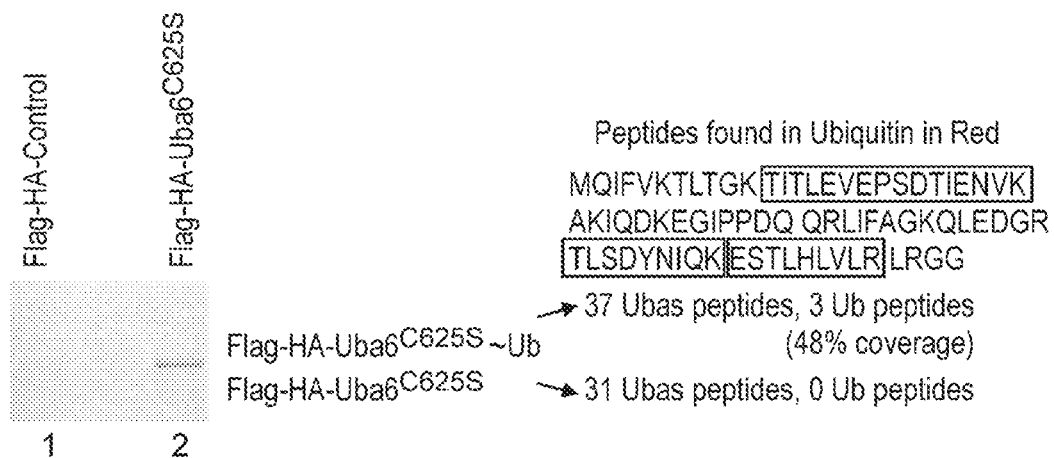

To rule out any effects of overexpression on these results, Flag-HA-Uba6, Flag-HA-$Uba6^{C625A}$ and Flag-HA-$Uba6^{C625S}$ were expressed at near endogenous levels from a lentiviral vector driven by the PGK promoter. Again, the C625S mutant, but not WT or C625A proteins, expressed a more slowly migrating protein consistent with ubiquitination (FIG. 2B). Taken together, these data indicate that Uba6 functions to activate ubiquitin in tissue culture cells.

Example III

Uba6 Promotes Transfer of Ubiquitin to E2s with Specificity Distinct from Ube1

Figure 3A:
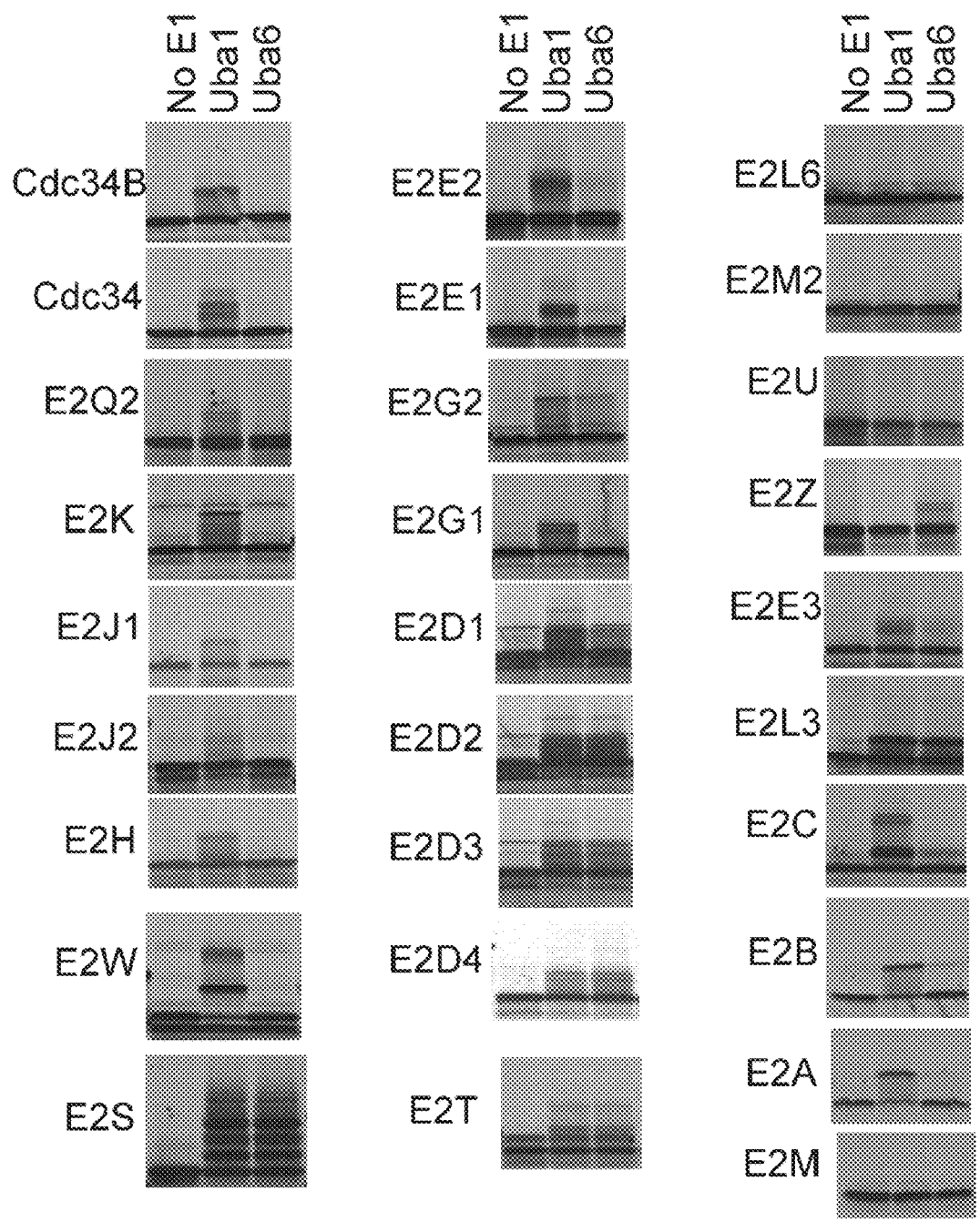

Ube1 promotes the transfer of ubiquitin from its active site cysteine residue to the active site cysteine of an E2 ubiquitin conjugating enzyme. A subset of E2s are known to be activated by Ube1, although a small number of E2s are specific for transfer to ubiquitin-like proteins (E2M/Ubc12 is charged by Nedd8, E21/Ubc9 is charged by SUMO, and E2L/Ubc8 is charged by ISG15). To determine whether Uba6 was capable of transferring ubiquitin to one or more E2s, more than two dozen E2s found in the human genome were cloned and in vitro charging assays were performed using non-reducing SDS-PAGE. In this assay, charged E2s migrated more slowly than the uncharged E2s. Examples of charging assays are shown in FIG. 3A and the data for all of the E2s studies is collected in FIG. 3B. It was discovered that the specificity of Ube1 and Uba6 for these E2s was distinct. Neither Ube1 or Uba6 promoted charging of E2M, E2M3, HSPC, E2L6, E2U or E21, as expected. Ube1 selectively promoted charging of E2J1, E2J2, E2K, E2Q2, E2R1/Cdc34, E2R2/Cdc34B and E2W, while both Ube1 and Uba6 promoted charging of E2C, E2D1, E2D2, E2D3, E2D4, E2E1, E2G, E2S and E2T, to varying degrees. Interestingly, Uba6 but not Ube1 promoted charging of E2Z, a previously uncharacterized E2 of unknown function. Without intending to be bound by theory, these data indicate that Ube1 and Uba6 have distinct substrate specificities with respect to the E2s they charge and, therefore, may function in distinct pathways. Without intending to be bound by theory, Uba6 may function with non-canonical E2s (i.e., E2s that cannot be identified through sequence relationships with the known E2s). Methods known in the art will be used to easily identify such proteins.

Example IV

The Ubl Domain of Ube1 and Uba6 Control their Substrate Specificities

Figure 4B:
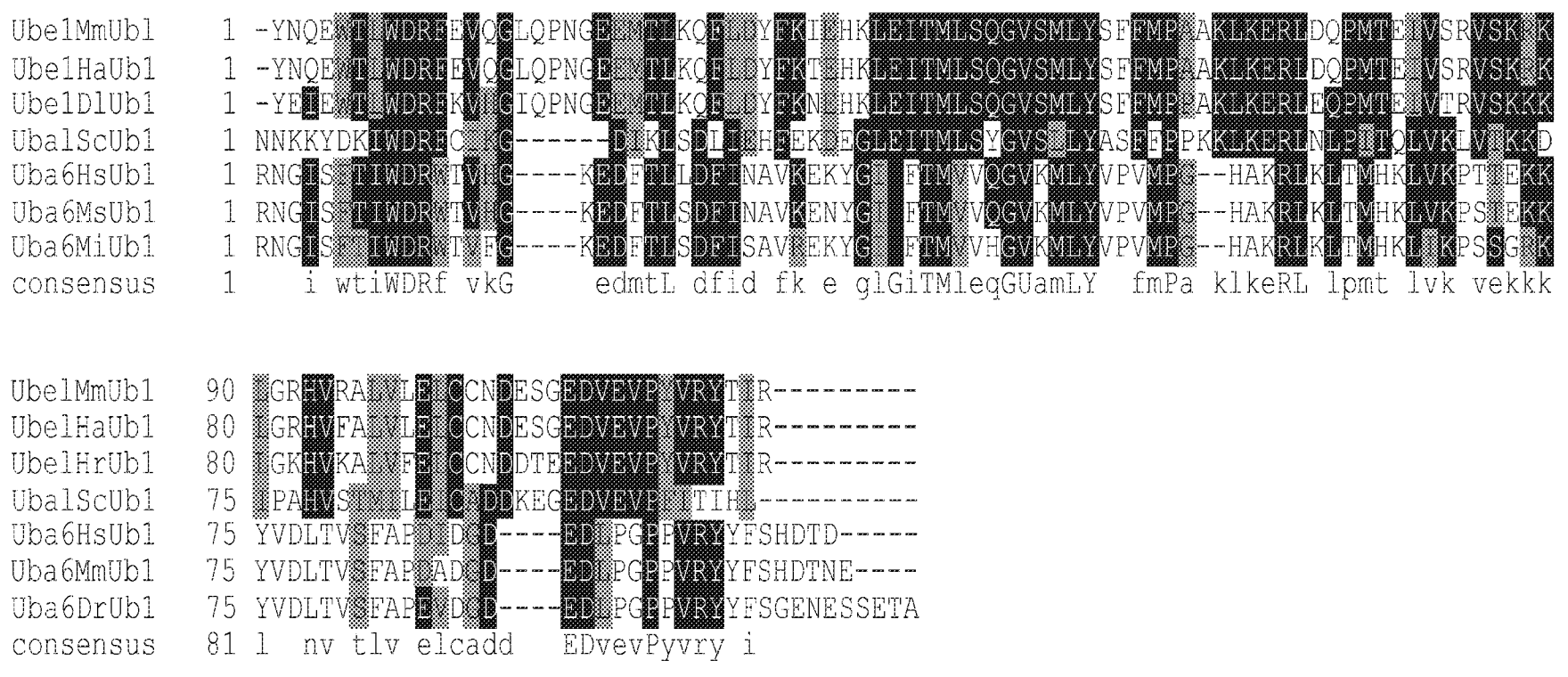
Figure 4C:
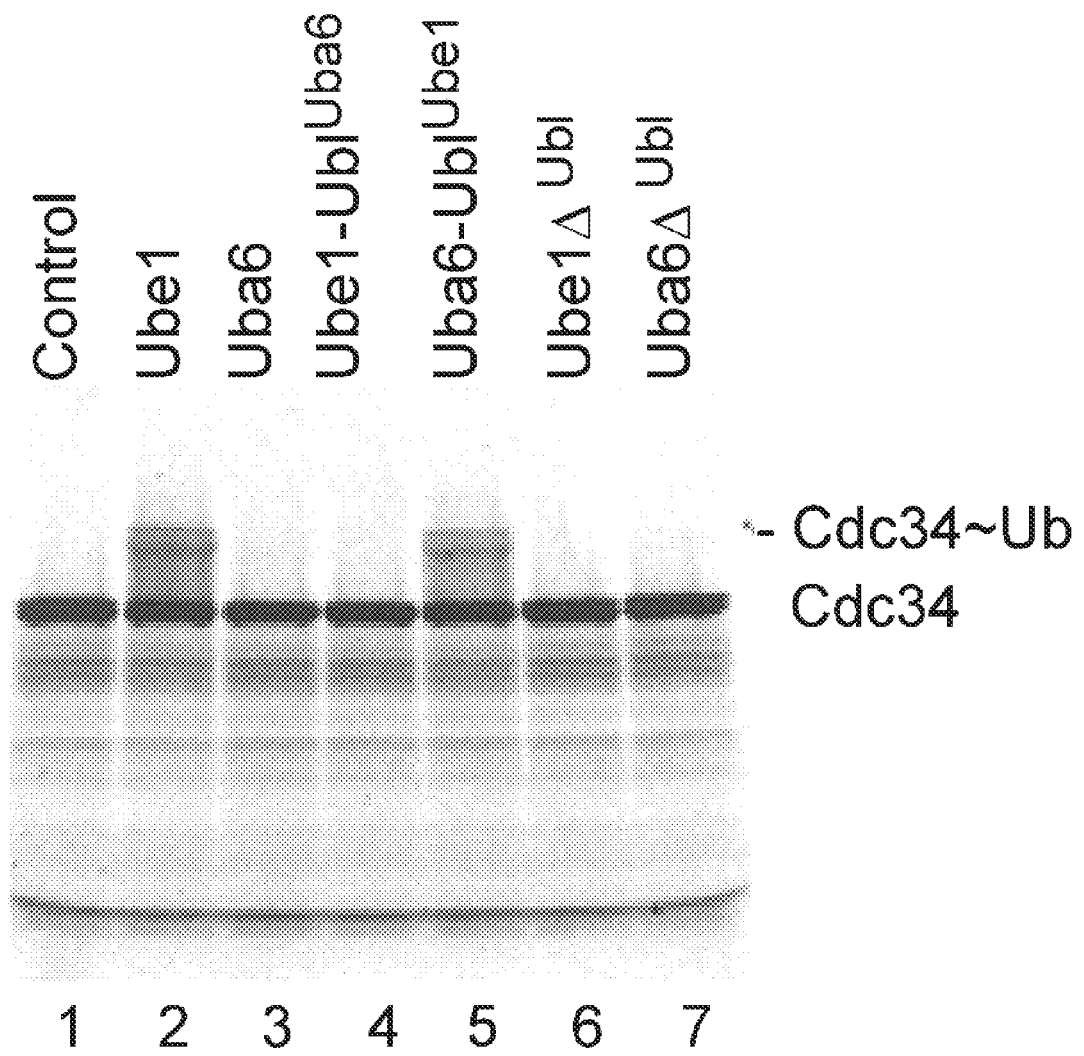

Previous studies with Uba3, a subunit of the E1 for Nedd8, have revealed that its C-terminal ubiquitin fold is involved in recognizing its specific E2, Ubc12 (Huang et al. (2004) *Nat. Struct. Mol. Biol.* 11:927). While the ThiF and catalytic domains of Ube1 and Uba6 are 43% identical, their C-terminal ubiquitin-like domains are more distantly related (~33% identical) (FIG. 4A, B). In contrast, the Ubl domains in Uba6 are very highly conserved in Uba6 proteins from zebrafish to human (~75%) (FIG. 1G), indicating selective pressure to maintain sequences in the C-terminal Ubl domain of Uba6. To examine whether substrate selectivity of Uba6 relative to Uba1 may reflect its Ubl domain, a Ubl-domain swap experiment was performed (FIG. 4C). The Ubl domain of Ube1 was replaced with the Ubl domain from Uba6 and vice versa. While Ube1 could activate Cdc34/E2R1, Uba6 was defective in this activity. However, Uba6 carrying the Ubl domain of Ube1 was active in Cdc34 charging. Consistent with this, Ube1 containing the Ubl domain from Uba6 was defective in Cdc34 charging. Both Ube1 and Uba6 lacking their Ubl domains were defective for Cdc34 charging. These data indicate that the C-terminal Ubl domains in Ube1 and Uba6 are important for the specificity of ubiquitin charging, and that the Ubl domain of Uba6 is more discriminating than is the Ubl domain of Ube1.

Example V

A Method for Reducing the Abundance of Uba6 in Animal Cells

Figure 2D:
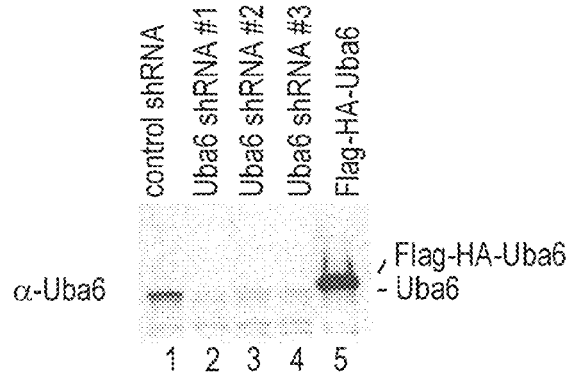

In order to detect Uba6 in animal cells, an antibody was developed against the C-terminal Ubl domain. This antibody recognized a doublet of proteins at approximately 125 Kd, the expected size of Uba6, in extracts from several cell lines including 293T cells (FIG. 2D). This antibody also reacted with purified Flag-HA-Uba6, which migrates slightly slower on SDS-PAGE than does the endogenous protein due to the presence of an epitope tag. It was determined that three different siRNAs targeting Uba6 could greatly reduce its steady-state levels (FIG. 2D). These data indicates that the activity/function of Uba6 can be inhibited using RNAi.

Example VI

Ubc5 Charging

Figure 11C:
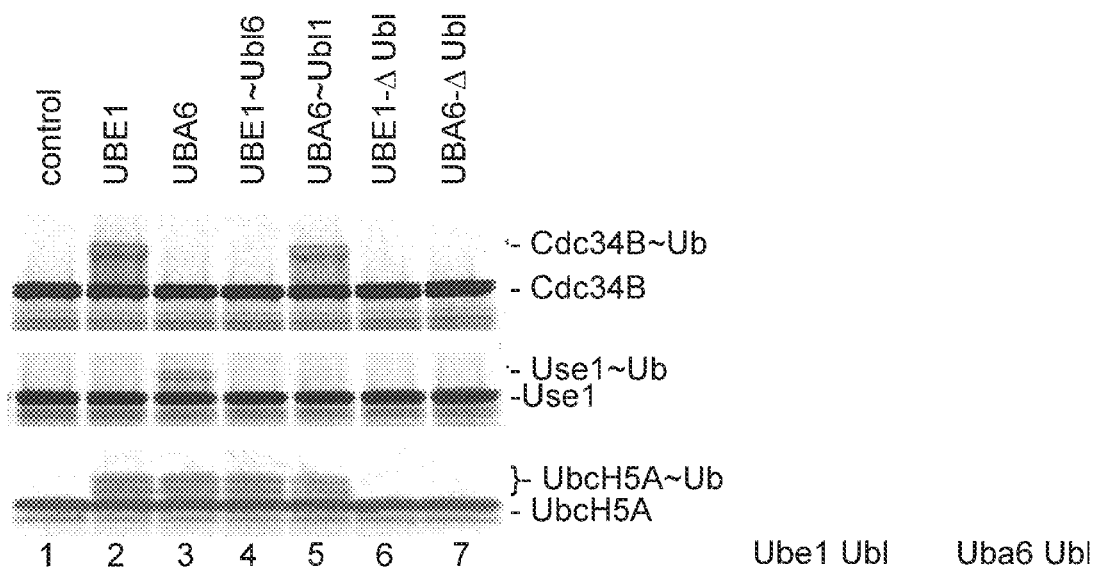
Figure 11D:
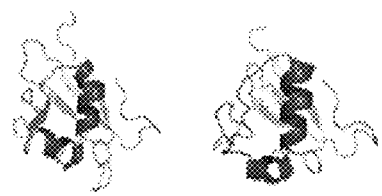

An analysis of the activity of chimeric proteins (replacement of the Ubl domain of Uba1 with the Ubl domain of Ube1; replacement of the Ubl domain from Ube1 with the Ubl domain of Uba6 (FIGS. 11A and 11B)) toward Ubc5, which is charged by both Ube1 and Uba6, was performed. It was determined that, while Uba6 and Ube1 lacking the Ubl domains were devoid of activity toward Ubc5, each of the chimeric proteins was active (FIG. 11C). These data indicate that the Ubl domains are interchangeable with respect to this shared E2. It also indicates that the absence of activity of the chimeras towards Cdc34 or E2Z was not because the protein is generally non-functional. Importantly, the Ube1 protein containing the Uba6 Ubl domain was still inactive toward E2Z, indicating that additional structural features outside the Ubl domain may be required for specificity. Molecular modeling studies were also performed that indicated that the Ubl domains from both Uba6 and Ube1 fold into ubiquitin-like folds (FIG. 11D).

Example VII

Uba6 is Required to Charge E2Z In Vivo

Figure 12:
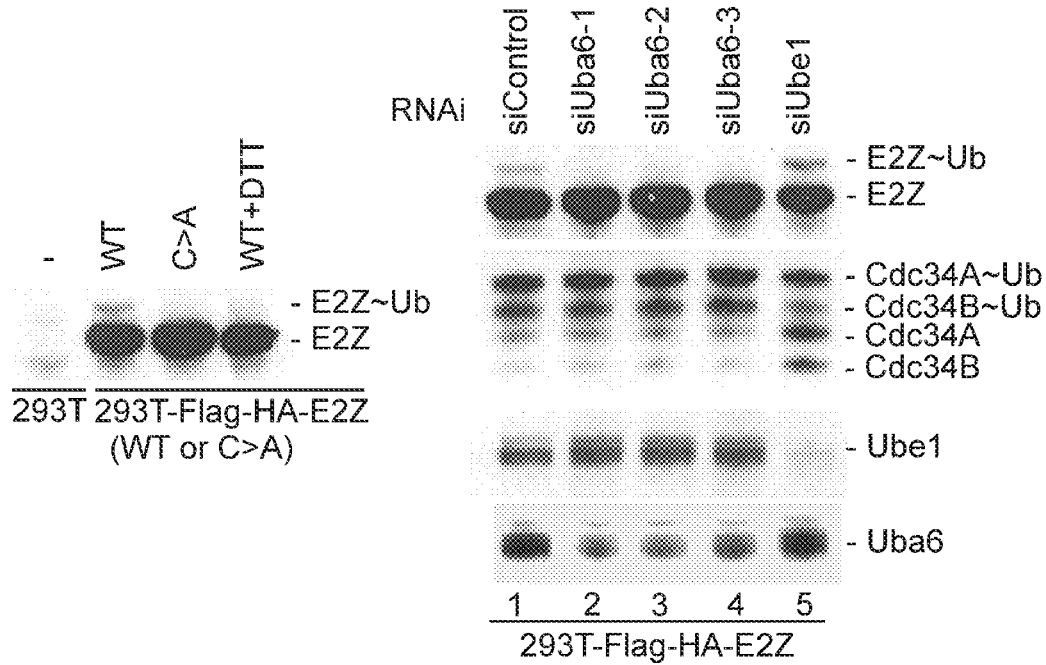
FIG. 12 depicts data showing that Uba6 is required to charge E2Z in vivo. Left panel: formation of the E2Z~ubiquitin thiolester required the active site cysteine of E2Z (C>A mutant) and was reduced by addition of DTT. Right panel: Depletion of Uba6, but not Ube1, by RNAi blocked charging of E2Z in vivo. The indicated siRNAs were transfected into 293T cells stably expressing Flag-HA-E2Z. Extracts were generated in MES buffer (pH 4.5) and proteins immediately separated by SDS-PAGE. After transfer to nitrocellulose, blots were probed with the indicated antibodies.
Figures 13A, 13E:
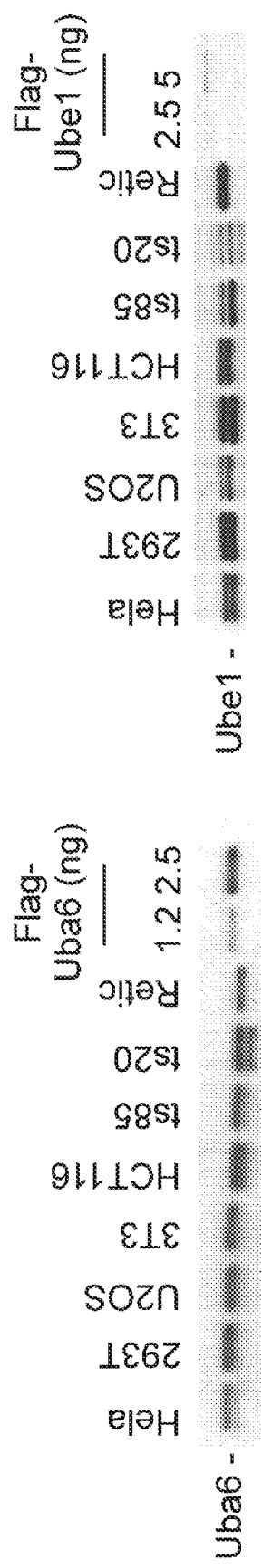
FIGS. 13A-E depict Uba6 activation of ubiquitin in vivo. (A) E1 expression in cultured cells. Anti-Uba6 and anti-Ube1 were used to probe blots of extracts from the indicated cell lines, with recombinant Flag-E1a as controls. (B) Lysates (pH 7.5) from 293T/Flag-HA-Uba6 cells (wild-type, C625S or C625A; 20 µg) or anti-HA immune complexes from 0.2 mg of extract were separated on 4-12% Tris-glycine reducing gels and immunoblotted with anti-Uba6, anti-HA or anti-ubiquitin. (C) Lysates (pH 4.5) from 293T/Flag-HA-Uba6 cells (wild-type or C625A; 20 µg) or anti-HA immune complexes from 0.2 mg of extract were separated on 4-12% Bis-Tris non-reducing gels prior to immunoblotting with anti-HA or anti-ubiquitin. (D) Flag-HA-Uba6 was immunoprecipitated from 293T/Flag-HA-Uba6 cell lysates (pH 4.5, 2 mg) and separated on a 4-12% Bis-Tris non-reducing gel. (E) Mass spectral analysis of ubiquitin-activated Uba6. Sequence identifiers are set forth as follows: position 64-72 (SEQ ID NO:32); position 55-63 (SEQ ID NO:33); position 30-42 (SEQ ID NO:34); position 12-27 (SEQ ID NO:35). The Flag-HA-Uba6$^{C625S}$ protein used is described further herein.
Figure 13B:
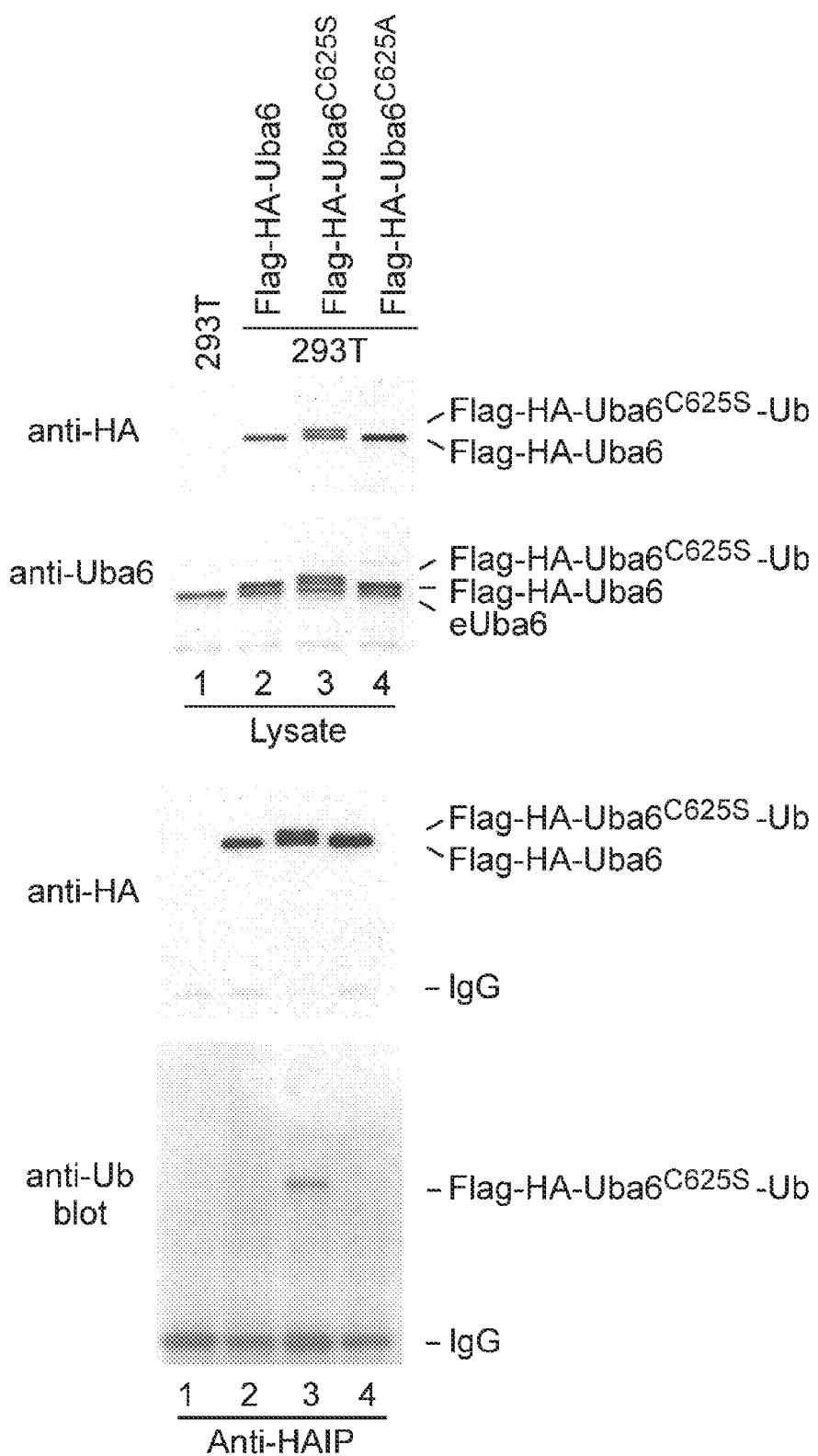
Figure 13C:
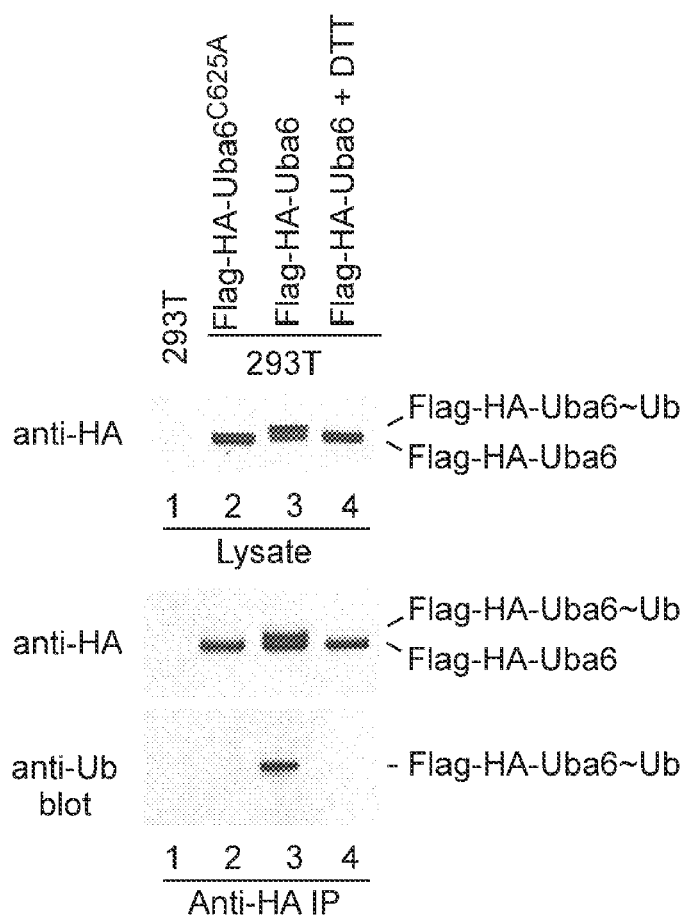
Figure 13D:
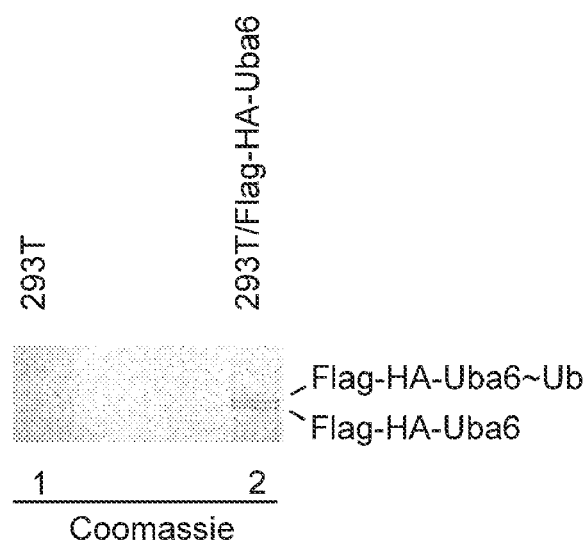

An in vivo charging assay coupled with RNAi was used to deplete either Uba6 or Ube1. In the in vivo charging assay, cell lysates were generated using buffers at pH ~4.5 [50 mM MES, pH 4.5, 0.5% NP40, 100 mM NaCl] and immediately subjected to non-reducing SDS-PAGE. Under these conditions, the E2 thiol esters remained relatively stable, allowing their separation by SDS-PAGE. Charged and uncharged E2s were then detected by immunoblot. Because antibodies against E2Z were not available, a cell line that stably expresses a Flag-HA-tagged version of E2Z was generated. As shown in FIG. 12A, a fraction of E2Z migrated slightly more slowly than the majority of the protein. This band was absent when a mutant form of E2Z was employed in which the active site cysteine was mutated to alanine and could not be ubiquitinated, or when DTT was added to wild-type E2Z (which will reduce the thiol-ester). As shown in FIG. 12B, using three different siRNAs to deplete Uba6, it was determined that in vivo charging of E2Z was completely dependent on Uba6. In contrast, depletion of Ube1 had no effect on the extent of charging of E2Z. Ube1 depletion did, however, reduce the extent of charging of the Ube1-specific E2 Cdc34.

Example VIII

Structural and Functional Diversity of Ubiquitin E1s

Figure 20A:
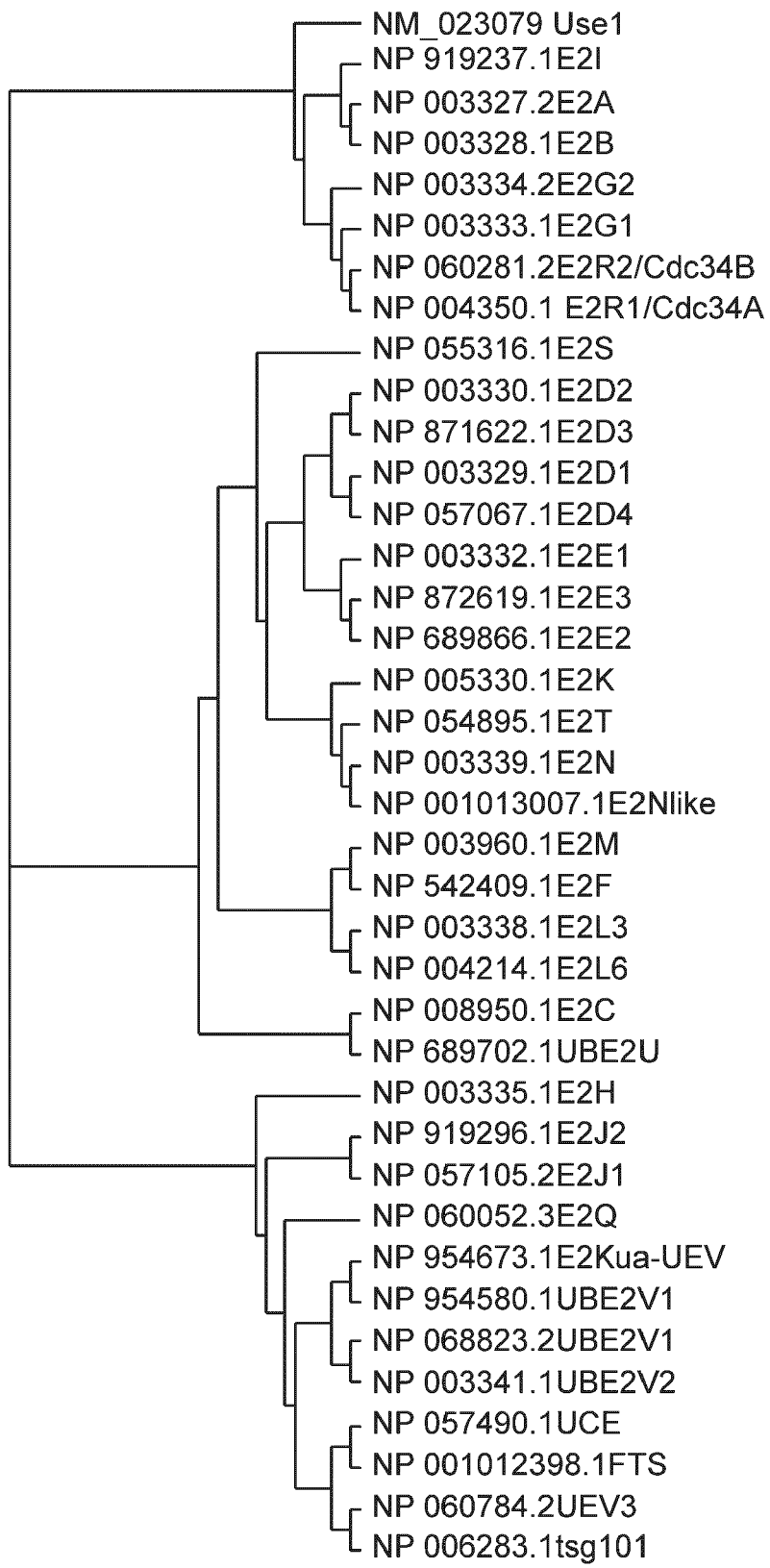
Figure 20C:
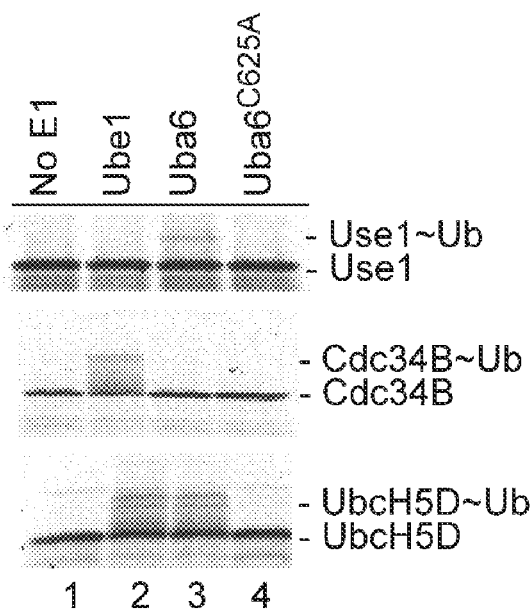
Figure 20D:
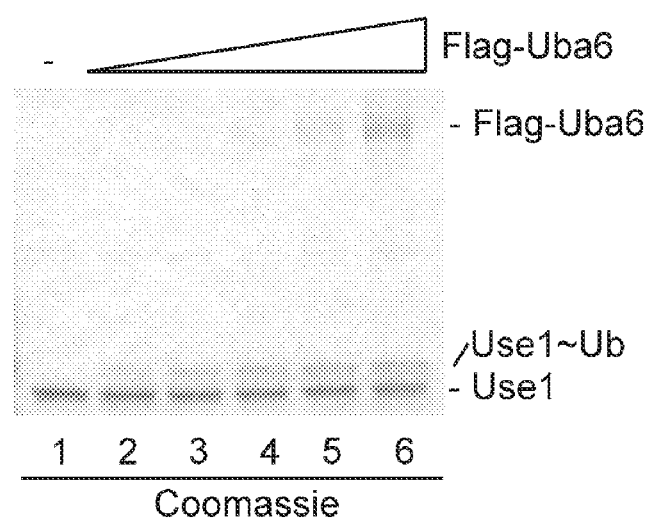

Humans, chimps, old-world monkeys, and zebrafish contain only a single UBE1 gene, which, in humans, is located on the X-chromosome. However, in the mouse, there appears to have been a duplication of the X-linked UBE1 gene, as there is a second gene located on the Y-chromosome (Levy et al. (2000) *Mamm. Genome* 11: 164; Mitchell et al. (1992) *Nature* 359:528; Odorisio et al. (1996) *Dev. Biol.* 180:336). The mouse Ube1y protein is ~90% identical to mouse Ube1x and these proteins are located on the same clad of the E1 dendogram (FIG. 20). In fact, mouse Ube1y is more closely related to mouse Ube1x and the corresponding human Ube1 protein than is the zebrafish Ube1 protein (FIG. 20). There are also UBE1 related sequences on rat chromosome-Y but these sequences do not appear to constitute a complete UBE1 gene (see GenBank ID 25225). Multiple Ube1 orthologs exist in plants (for example, 2 genes in *Arabidopsis* (Hatfield et al. (1997) *Plant J.* 11:213) and three genes in wheat, FIG. 20). Again, the encoded E1 proteins within each species are closely related to each other (~90% identical) and form a single clad on the E1 dendogram (FIG. 20). Previous studies have failed to identify differences in the functional properties of Ube1-related E1s, indicating that these genes likely provide the same biochemical functions but in different cell types or in different developmental settings. *Arabidopsis* Ube1 proteins have identical activities towards all E2s tested (Hatfield et al. (1997) *Plant J.* 11:213). In addition, it was previously concluded that mouse Ube1y is expressed exclusively in the testes and its induction during spermatogenesis is thought to reflect a requirement for increased levels of conventional ubiquitin-activating enzyme activity during this stage of development where the Ube1x protein is also expressed (Odorisio et al. (1996) *Dev. Biol.* 180:336). In contrast, human, mouse and zebrafish Uba6 genes are more closely related to each other and distantly related to the Ube1 clad (FIG. 20). Indeed, the Uba6 proteins form their own clad, consistent with the finding that human Uba6 and Ube1 play distinct roles in E2 charging in vivo (FIG. 15).

In contrast to *C. elegans, D. melanogaster, S. pombe*, and *S. cerevisiae*, which appear to lack Uba6 orthologs, both Ube1 and Uba6 orthologs were identified in sea urchin (*S. purpuratus*) (XP_795302, 65% identity and XP_780782, 56% identity over 709 residues, respectively).

Example IX

Specificity Elements in the E1$^{Ufd}$-E2 Interface

Figure 14B:
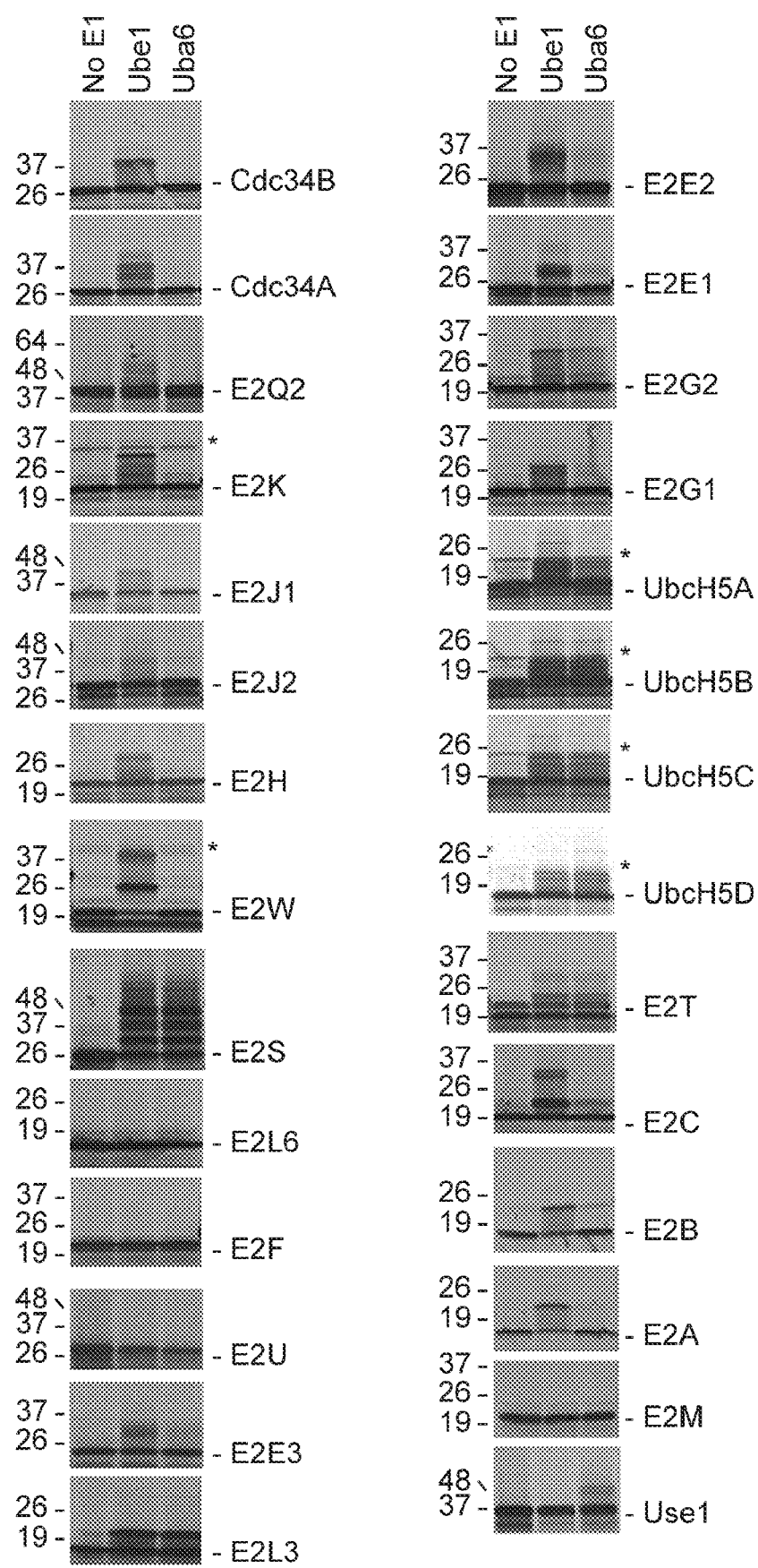
Figure 15A:
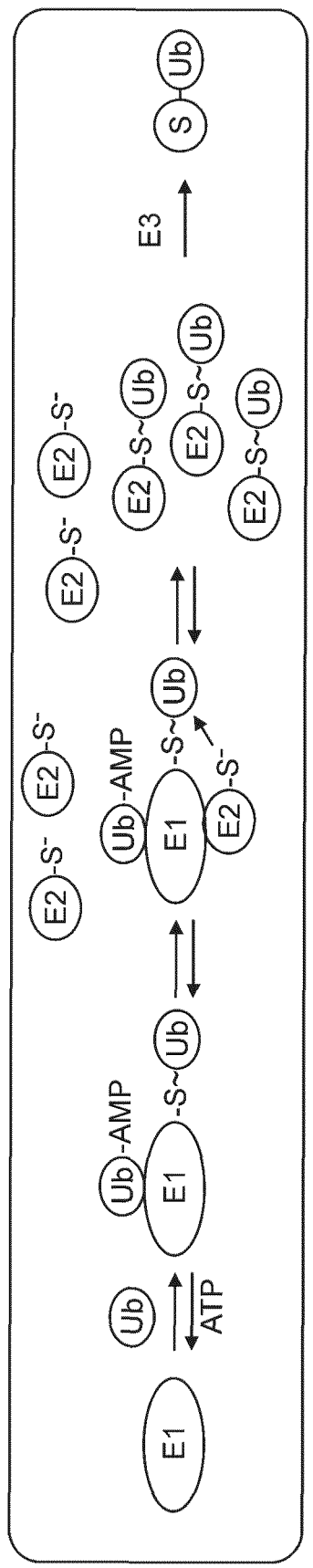
FIGS. 15A-15D depict the distinct requirements for charging of the ubiquitin conjugating enzymes Use1 and Cdc34 in vivo. (A) Scheme depicting the mechanism of E2 charging in cells. E2s exist as a mixture of charged and uncharged forms, depending upon how rapidly the charged form is generated and used. (B) HeLa cells were transfected with the indicated siRNAs. After 72 hours, cells were lysed at pH 4.5, proteins separated on a non-reducing 4-12% Bis-Tris gradient gel and immunoblotted. (C) Use1 is charged in mammalian cells through its catalytic cysteine. 293T or 293T/Flag-HA-Use1 (wild-type or C190A) cells were lysed (pH 4.5) prior to separation on a non-reducing 4-12% Bis-Tris gradient gel and immunoblotted. In lane 4, the sample was pre-treated with DTT (200 mM, 5 minutes). (D) A model depicting two independent systems for activating and charging ubiquitin.
Figure 15B:
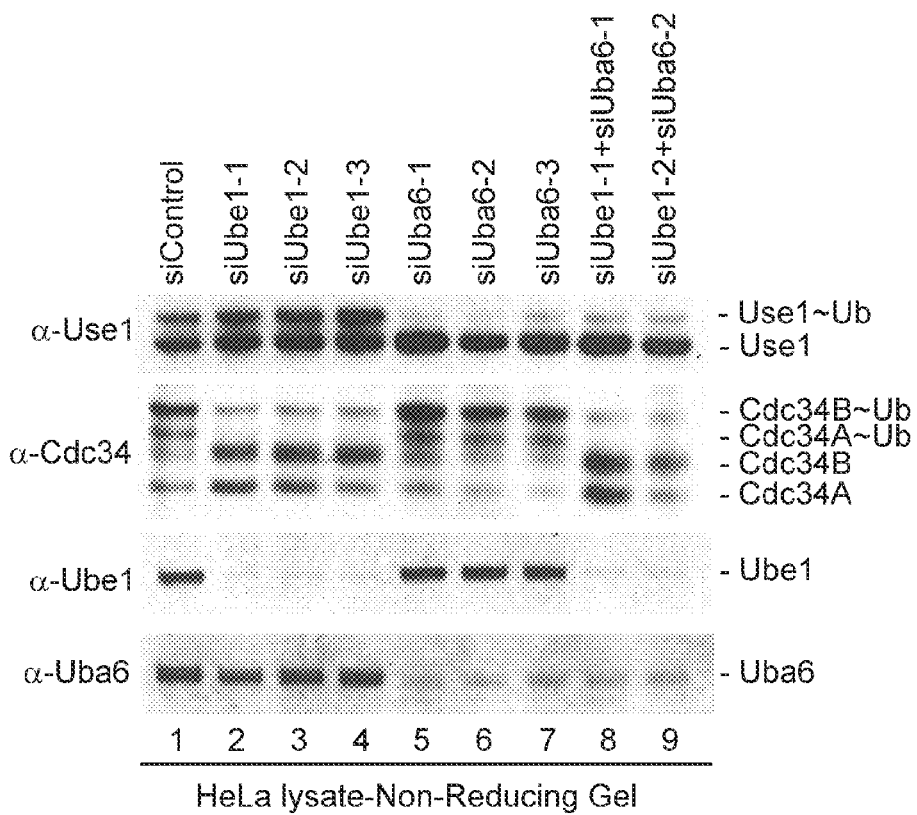
Figure 15C:
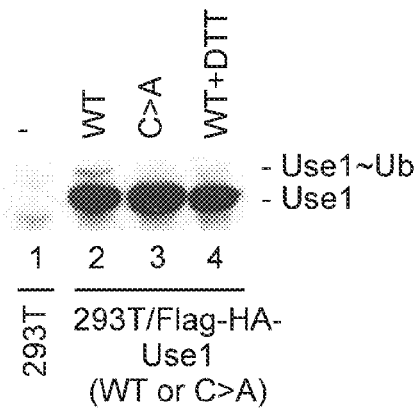
Figure 15D:
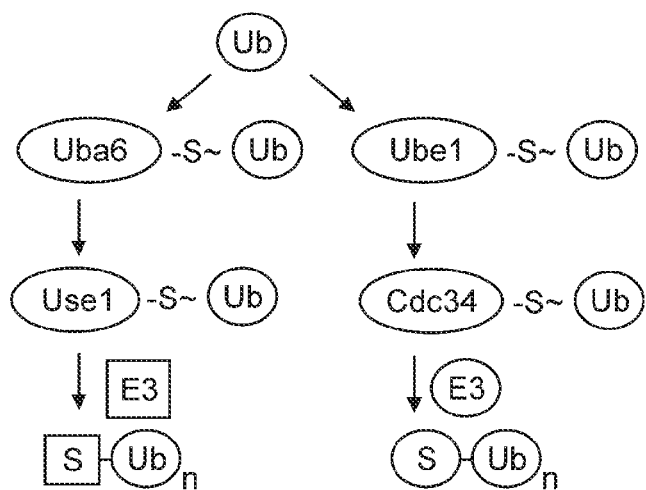
Figures 16A, 16C:
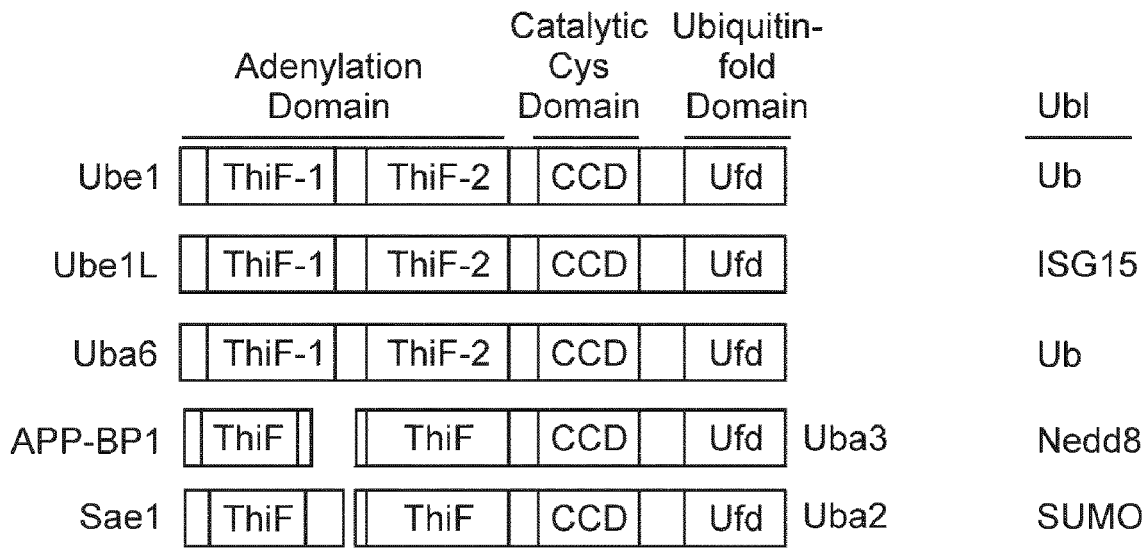
Figure 17:
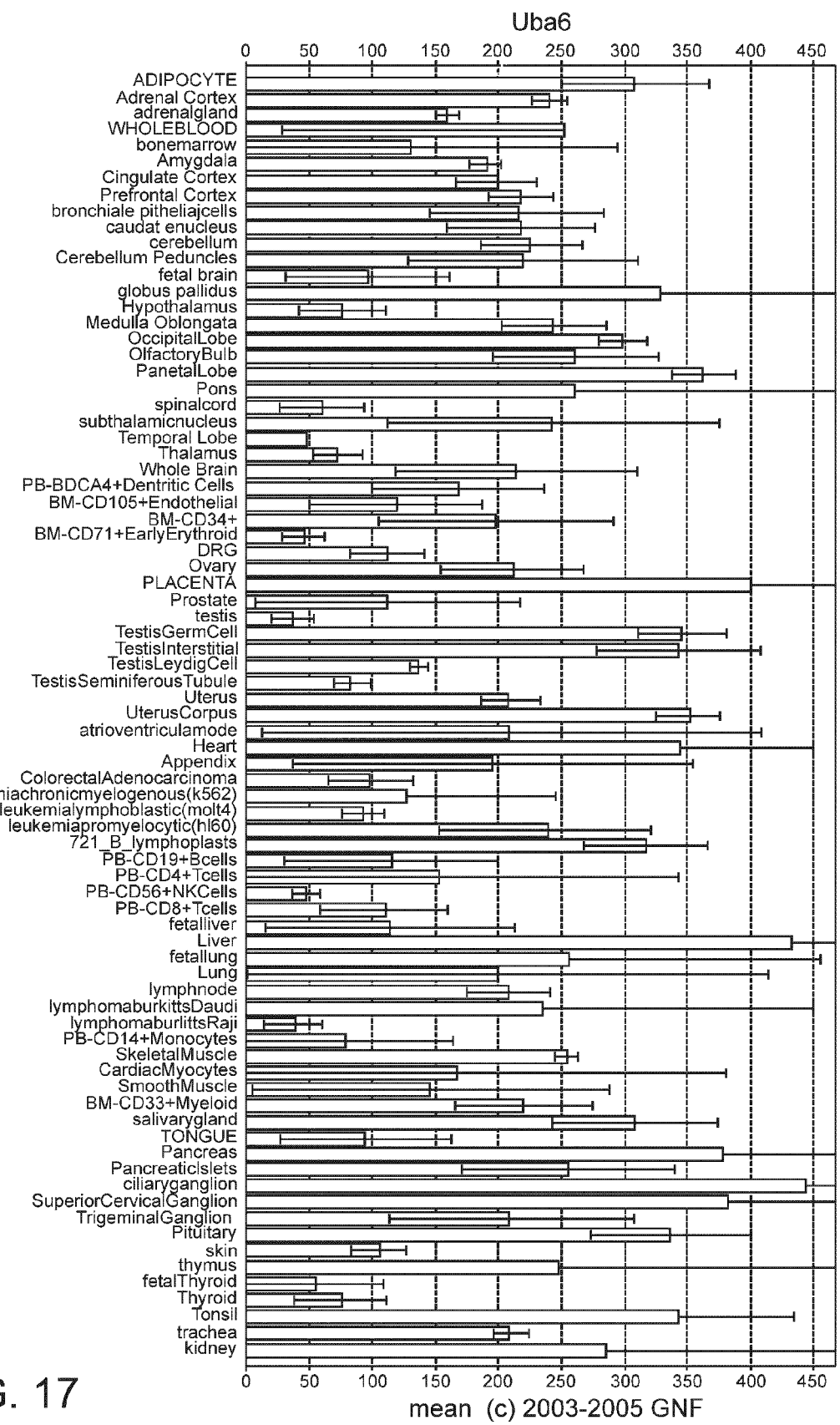
FIG. 17 depicts that Uba6 and Use1 are widely expressed in human cell lines and tissues. Expression of Ube1 is shown for comparison. Expression patterns were obtained using the Genomics Institute of the Novartis Research Foundation transcriptional profiling resource (Su et al. (2002) *Proc. Natl. Acad. Sci. U.S.A.* 99:4465; Su et al. (2004) *Proc. Natl. Acad. Sci. U.S.A.* 101:6062).
Figure 17:
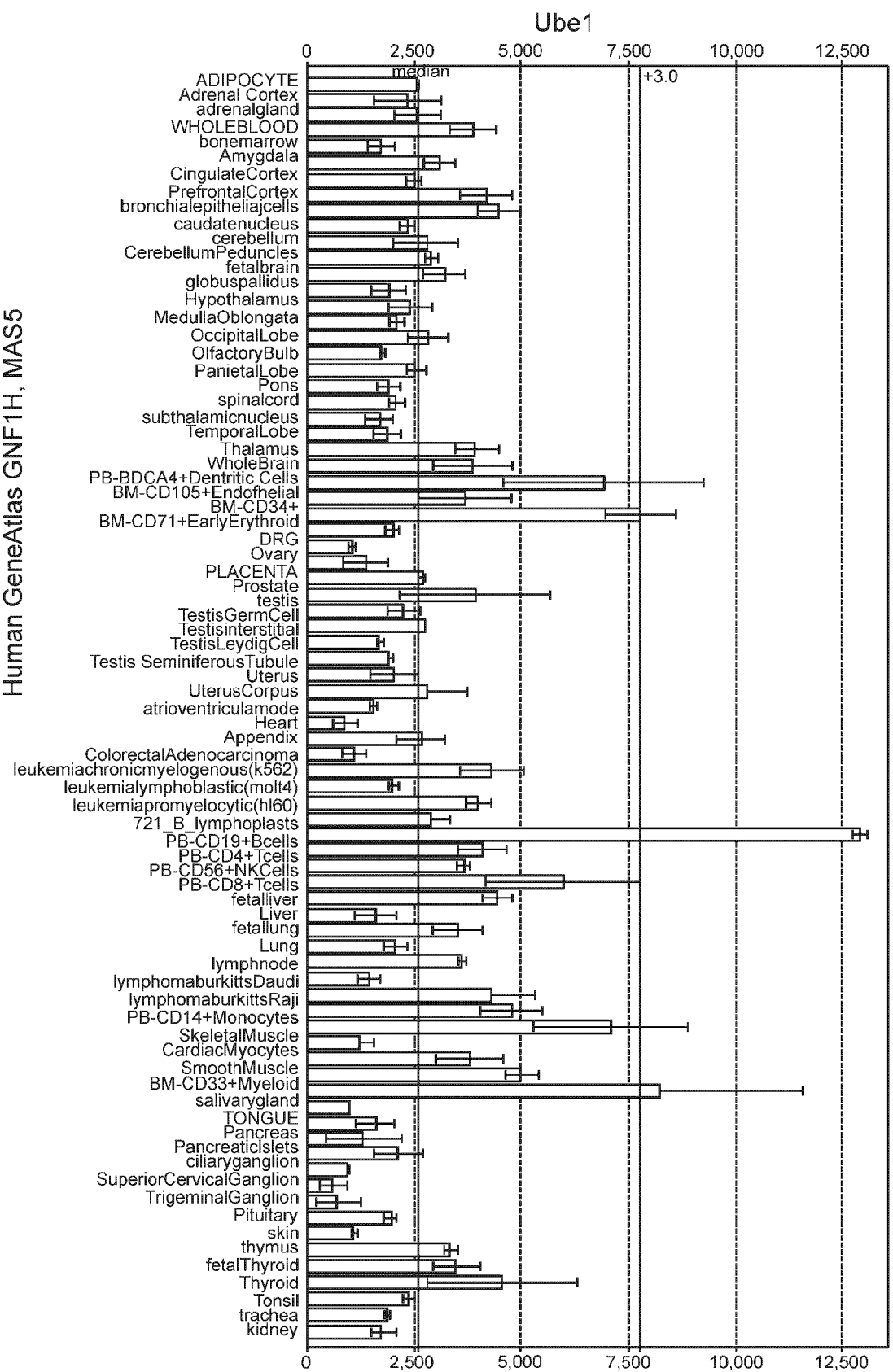
Figure 17:
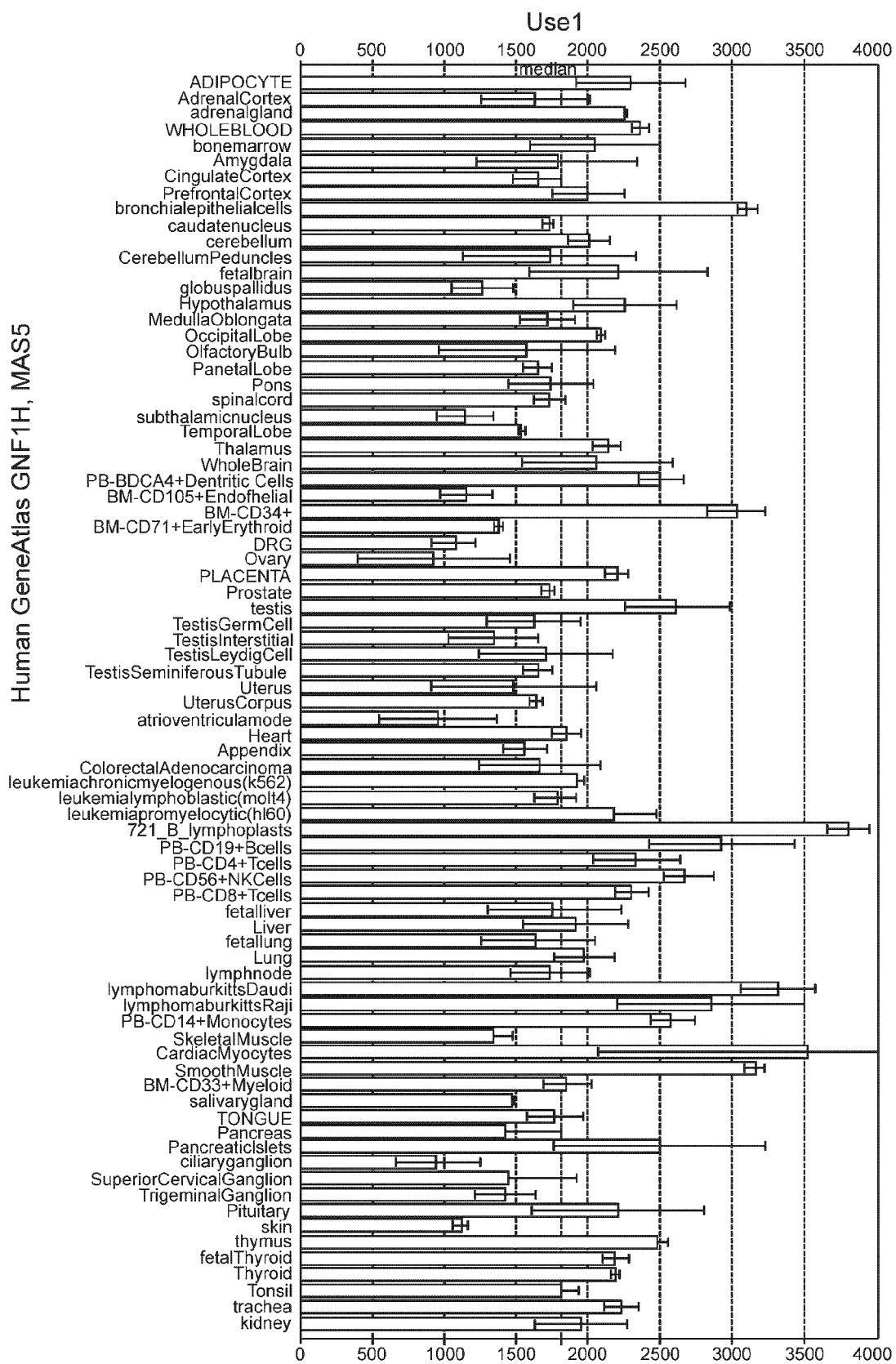
Figure 17:
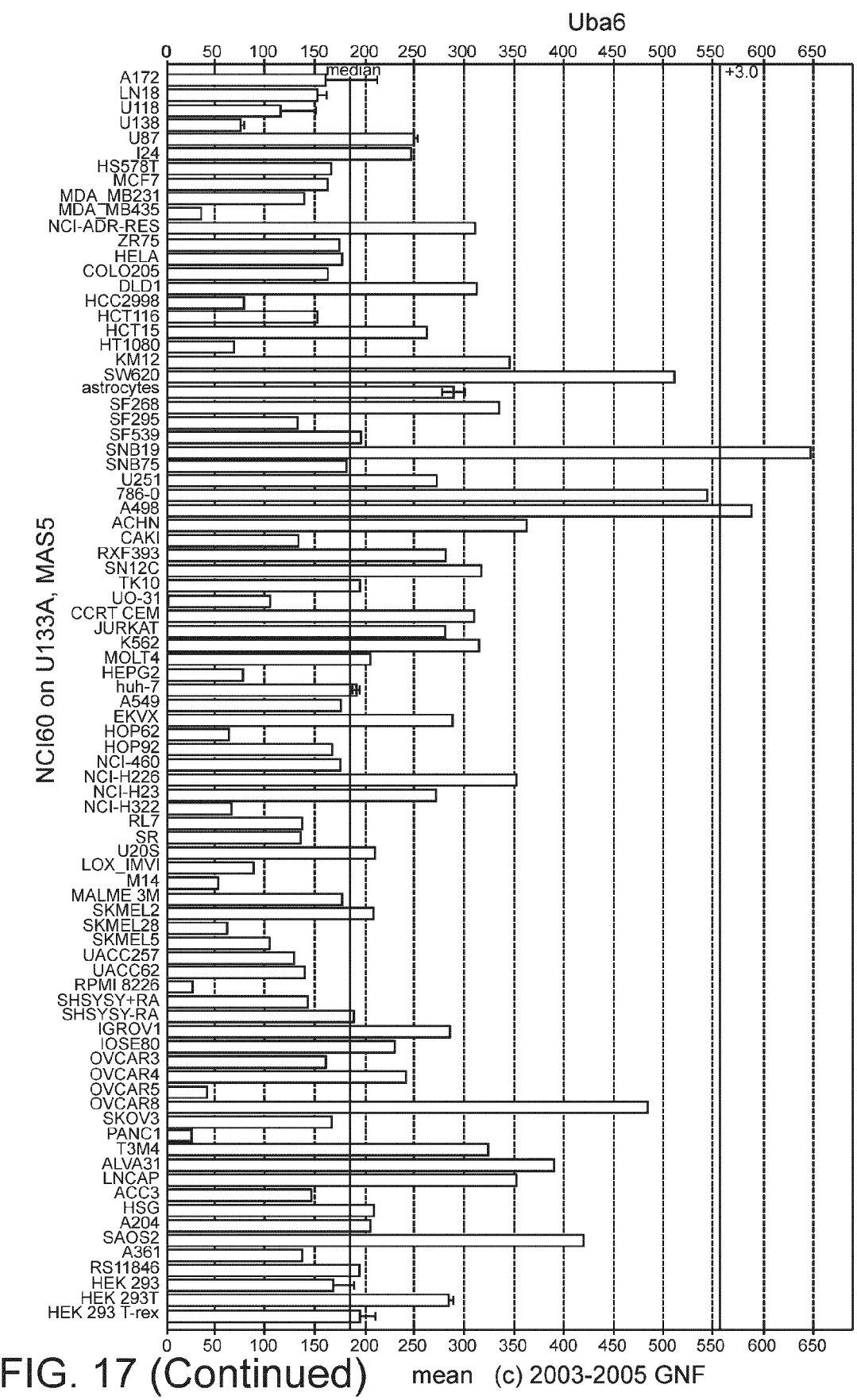
Figure 17:
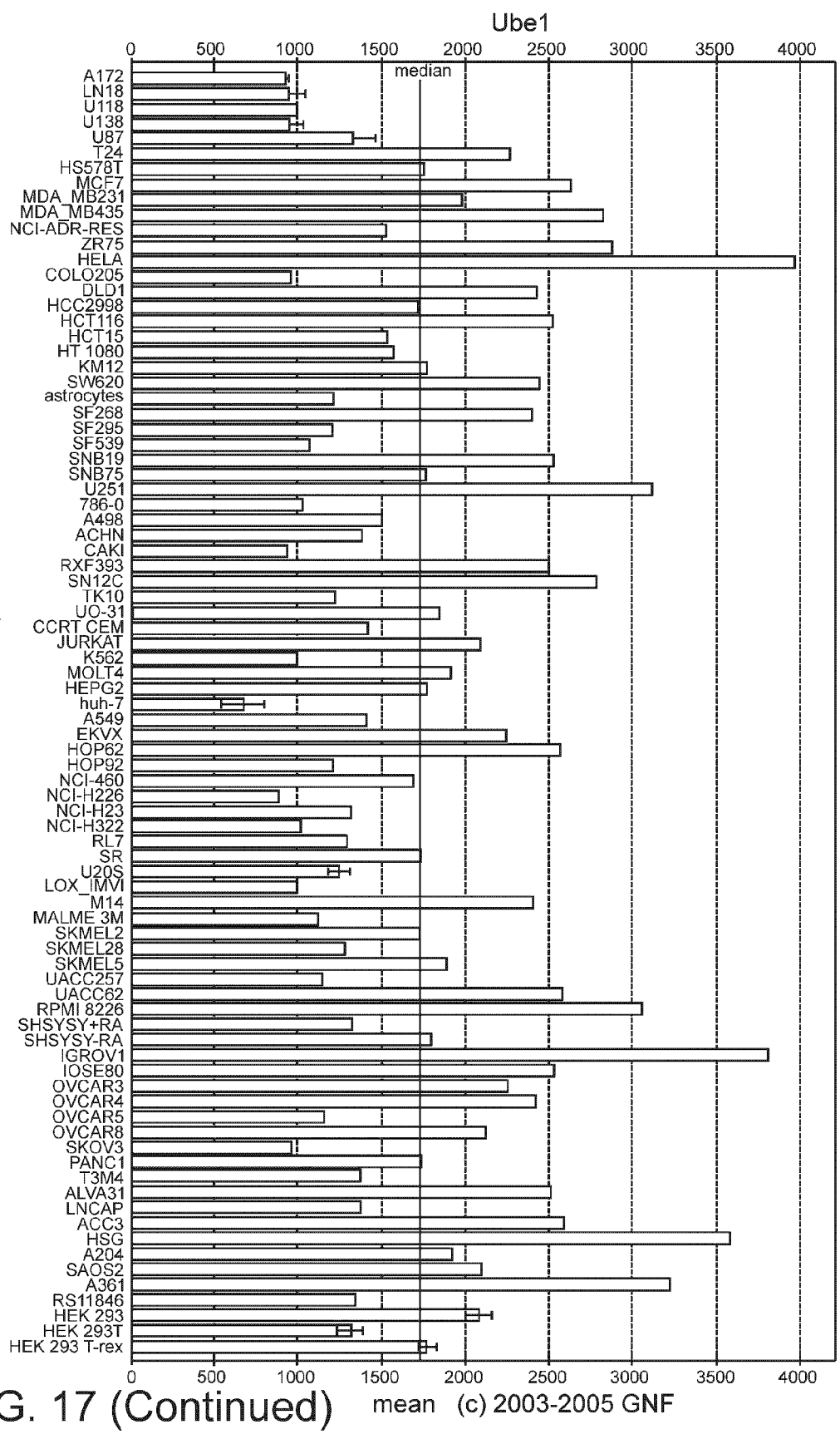
Figure 17:
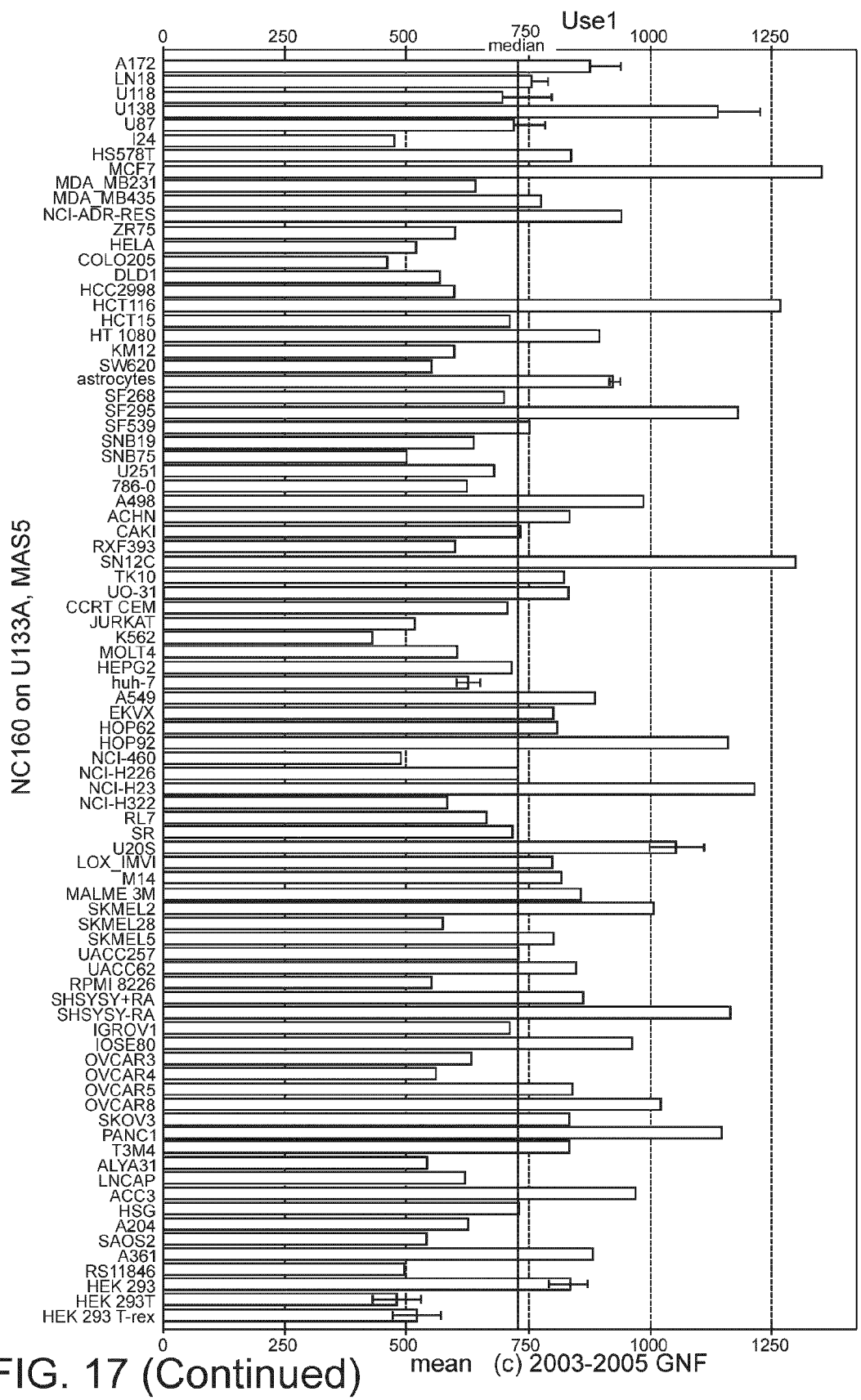
Figure 18A:
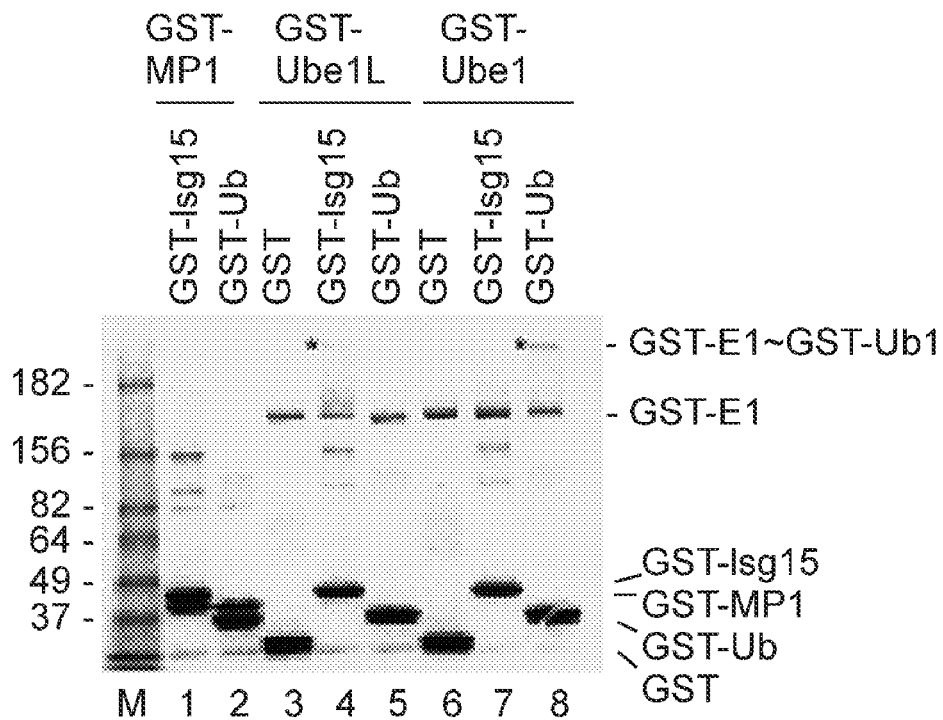
Figure 18B:
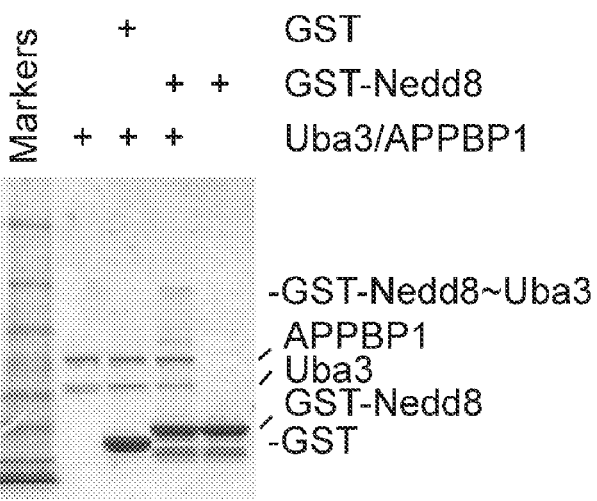
Figure 18C:
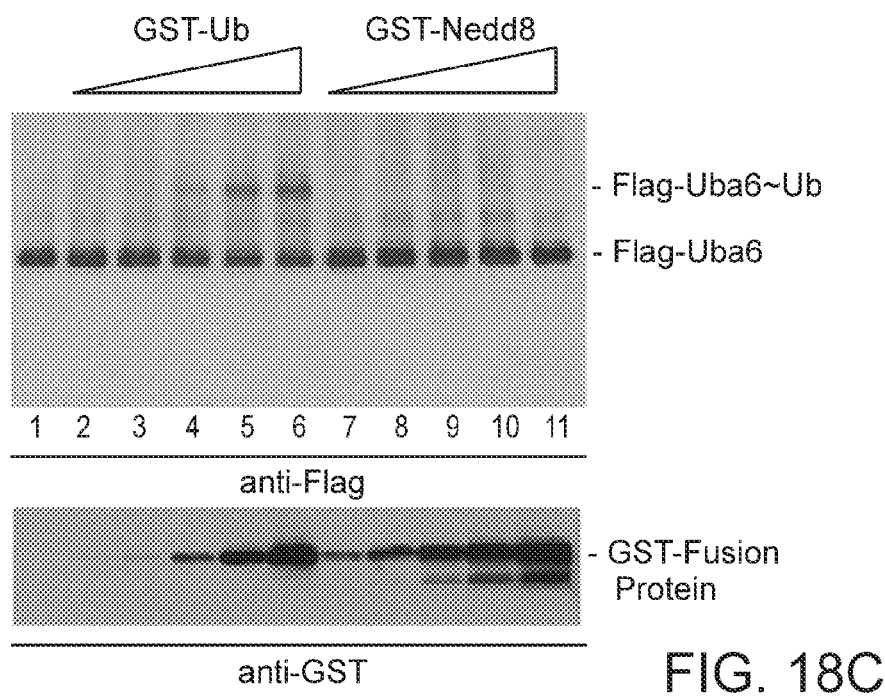
Figure 18D:
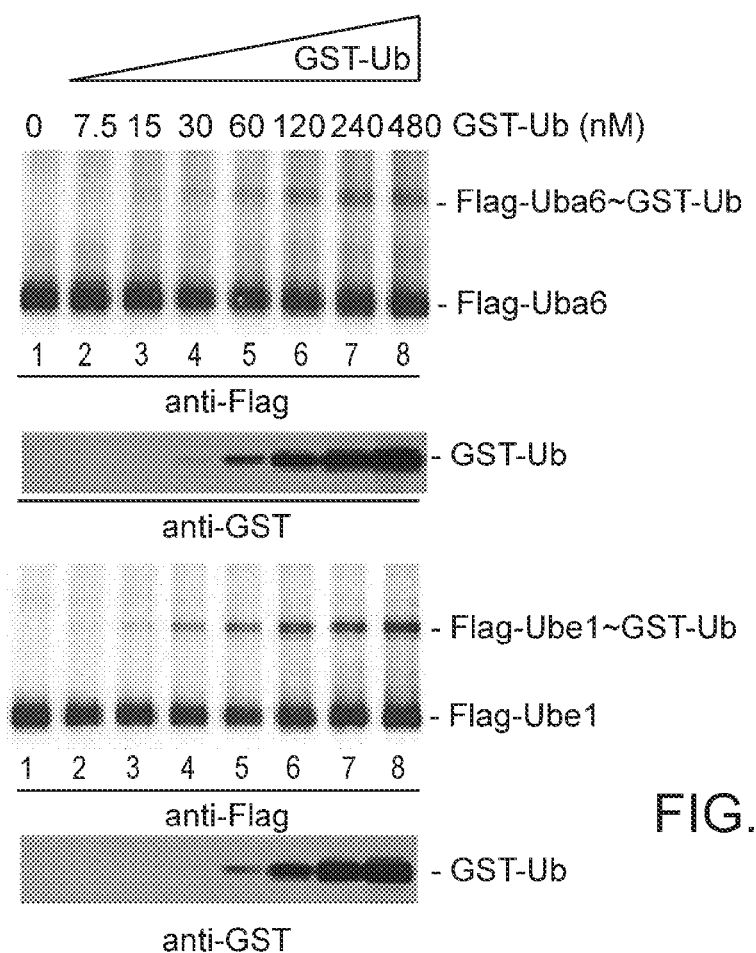
Figure 18E:
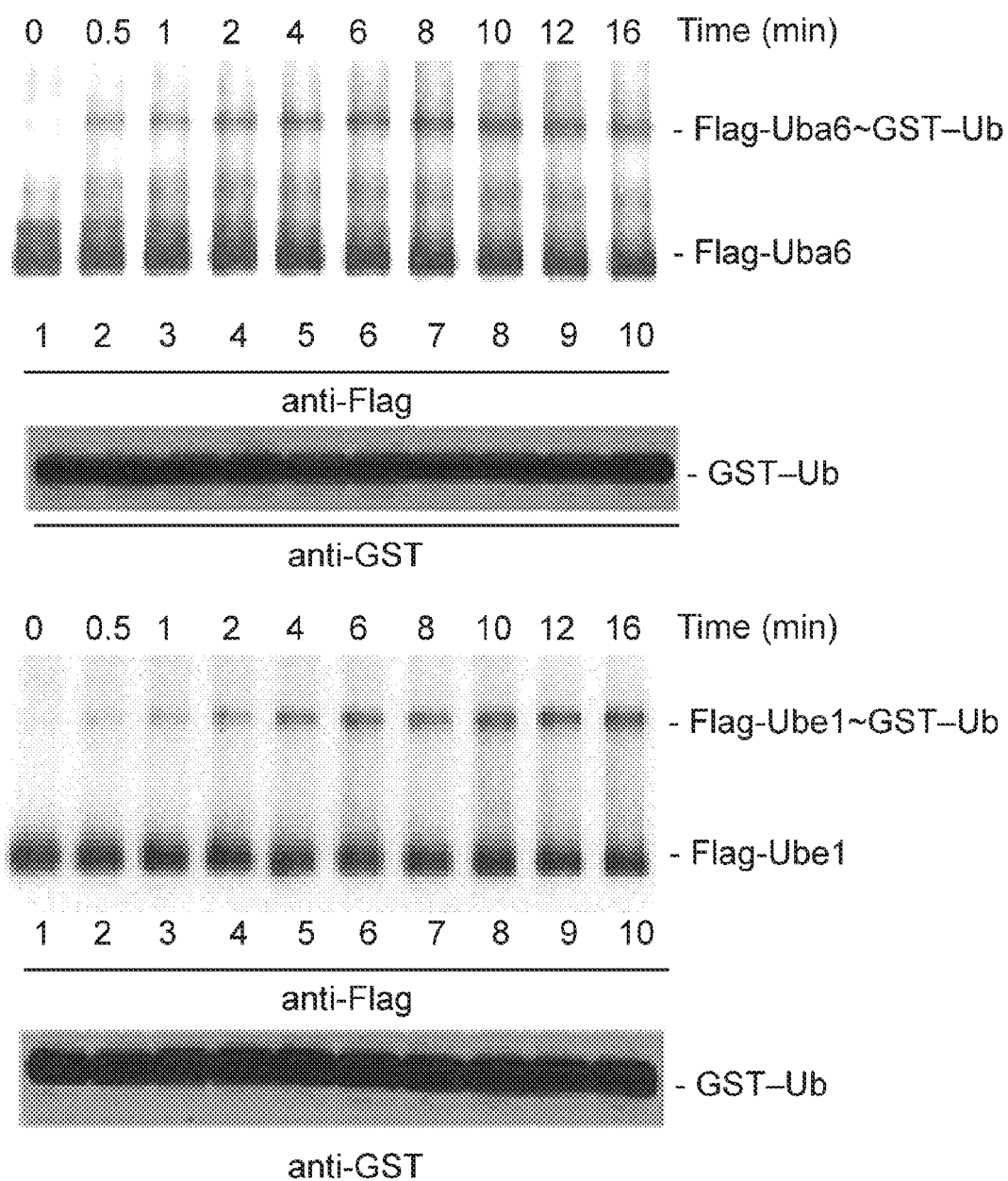
Figure 19A:
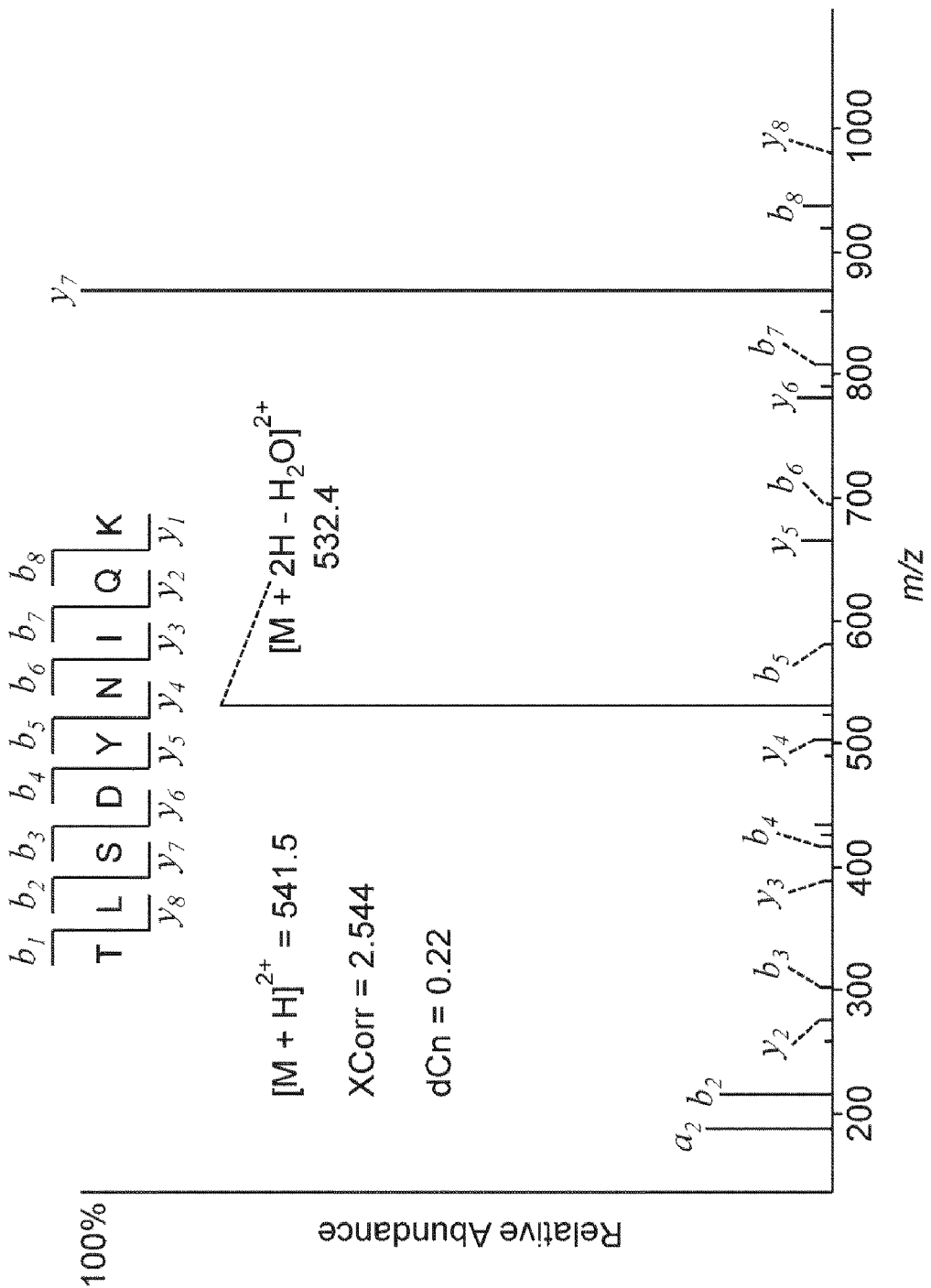
FIGS. 19A-19B depict that Uba6 activates ubiquitin but not Nedd8 in vivo and in vitro. (A) Tandem mass spectra for a ubiquitin-derived peptide co-migrating with the slow-mobility form of Flag-HA-Uba6$^{C625S}$ isolated from 293T cells. The spectra of the TLSDYNIQK peptide (SEQ ID NO:43) from ubiquitin is shown. (B) Flag-HA-Uba6 was isolated from extracts (10 mg) derived from the indicated cell lines lysed in pH 7.5 buffer and proteins separated by non-reducing 4-12% Tris-glycine followed by staining with Coomassie Blue. Upper and lower bands were subjected to mass spectrometer. The ubiquitin peptides identified (SEQ ID NO:24) are shown and the relevant statistics for these peptides were collected as described further herein.
Figure 19B:
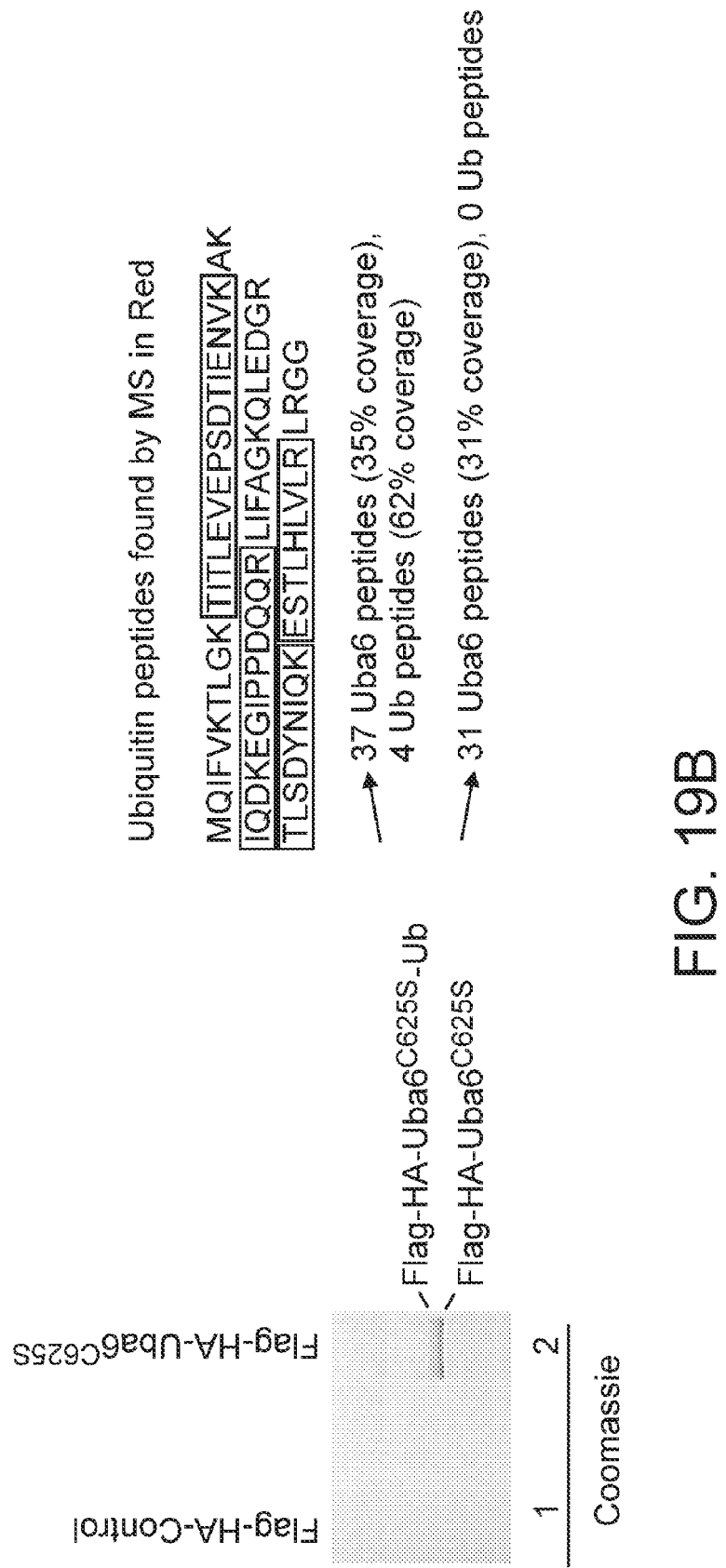

The results presented herein indicate that Ube1 and Uba6 have the capability of interacting and charging different sets of E2 conjugating enzymes and based on deletion analysis and the analysis of chimeric proteins. The results presented herein also indicate that the C-terminal Ubiquitin-fold domain (Ufd) of Uba6 and Ube1 contribute to recruitment and/or transthiolation of E2s (FIG. 14). Currently, there are no structures available for Ube1, Uba6, Use1 or Cdc34. Models of these proteins were built based on the structures of related proteins: the Ufd from SUMO1 (pdb code: 1Y8Q) for Uba6 and Ube1, UbcH1 (1TTE) in the case of Cdc34A, and UbCH5B (2ESQ) in the case of Use1. Models for Ufds and Cdc34 were generated using Modeller while models for Use1 were generated using Swissmodel. These models were then compared with the structure of the Uba3$^{Ufd}$-Ucb12 complex (1Y8X) (Huang et al. (2005) *Mol. Cell.* 17:341) in Pymol.

Figures 21A, 21B:

In the Ubc12/Uba3$^{Ufd}$ structure (FIG. 21B), the N-terminal helix (Helix 1) of Ubc12 makes several contacts with the surface of a β-sheet in the Ufd composed primarily of S2, S3, and S4 (FIG. 21B). The surface of the Ufd β-sheet facing the Ubc12 helix is composed primarily of residues with small and/or hydrophilic side chains (A380, T382, T384, T391, A424, A426) (FIGS. 21A and 21B). This facilitates interaction with Q31, L32, Q35, and N39 in the Ubc12 helix. R390 in the Uba3$^{Ufd}$ protrudes from the opposite side of the β-sheet and makes contacts with D427 in the L2 loop of Ubc12 (FIG. 21B). Structure-based alignment of Uba6 and Ube1 with the SUMO1 Ufd fold, and Use1 and Cdc34A with the UBC fold provides models of Uba6$^{Ufd}$-Use1 and Ube1$^{Ufd}$ Cdc34 complex (FIGS. 21C and 21D). Although it is not possible to directly discern the structural basis for specificity from these models, it is possible to identify differences between Ufd and UBC sequences within the presumptive interface which may participate in specificity. First, the β-sheet surfaces of the three Ufds have distinct charge distributions (FIG. 21D). The Uba3$^{Ufd}$ is the most basic (blue), followed by the Ube1$^{Ufd}$ and the Uba6$^{Ufd}$. Moreover, the Uba3$^{Ufd}$ has an acidic patch (red) not seen in the Ufds from Uba6 or Ube1. In contrast to the H1 helix of Ubc12, the H1 helix of Use1 is much more hydrophobic in character, consistent with the more hydrophobic character of the predicted S2 and S3 β-sheets in the Uba6$^{Ufd}$ compared with the Uba3$^{Ufd}$ (FIGS. 21A and 21C). The L2 loop of Use1 likely makes interactions with the S3 and H2 in the Uba6$^{Ufd}$ but uncertainties in the structural prediction make it impossible to assess these potential interactions. The predicted structure of the Ube1$^{Ufd}$ contains a poorly modeled segment which clashes with H1 of Cdc34 when superimposed on the Uba3$^{Ufd}$-Ubc12 structure (FIG. 21D). Nevertheless, it is possible to identify both similarities and differences in the interface residues that may make contacts in the respective interfaces. For example, R1029 at the end of S4 in Ube1 corresponds to D1023 in Uba6 and A426 in Uba3 (FIG. 21A). In addition, L997 in S2 of Ube1 corresponding to V986 in Uba6 and T384 in Uba3 (FIG. 21A). Likewise, significant differences exist in the residues in H1 of the respective specific E2s (FIG. 21A).

Although differences in residues predicted to be at the interface of the E2 and the Ufd for the complexes analyzed here are evident, without intending to be bound by theory, it is believed, based on the data presented herein, that specificity in this system is unlikely to reflect one or a small number of changes in amino acids at the interface between E2 and Ufd. First, an in-depth analysis of E2 sequences (especially the N-terminal helix which binds Ufds) failed to identify classes of residues that might segregate E2s into distinct classes related to the E1s that they function with (Winn et al. (2004) *Structure* 12:1563). Second, extensive alanine scanning mutagenesis of the Ubc12/Uba3-Ufd interaction indicates that many residues will contribute to the interaction. For example, mutation of 8 of 9 interface residues in Ubc12 reduced or abolished its charging by Nedd8 (Huang et al. (2005) *Mol. Cell.* 17:341; Huang et al. (2007) *Nature* 445: 394). Likewise, mutation of 4 of 5 residues on the interaction surface of Uba3's Ufd reduced charging of Ubc12 (Huang et al. (2005) *Mol. Cell.* 17:341). Thus, structural analysis will likely be required to address this important and interesting question.

Example X

Materials and Methods

Plasmids

Open reading frames for Ube1, Uba6, E2 ubiquitin conjugating enzymes, and ubiquitin-like proteins were amplified by PCR from either cDNA templates or cDNA libraries and cloned into pENTR/D-Topo (Invitrogen, Carlsbad, Calif.). These open reading frames were then transferred to the indicated destination plasmids using recombination-mediated cloning with CLONASE™ (Invitrogen, Carlsbad, Calif.). Mutations were created using PCR-based mutagenesis. All open reading frames were sequenced in their entirety. Baculoviruses expressing GST-Ube1L and GST-MP1 were provided by Brenda Schulman (St. Jude Children's Research Hospital, Memphis, Tenn.).

Figure 20E:
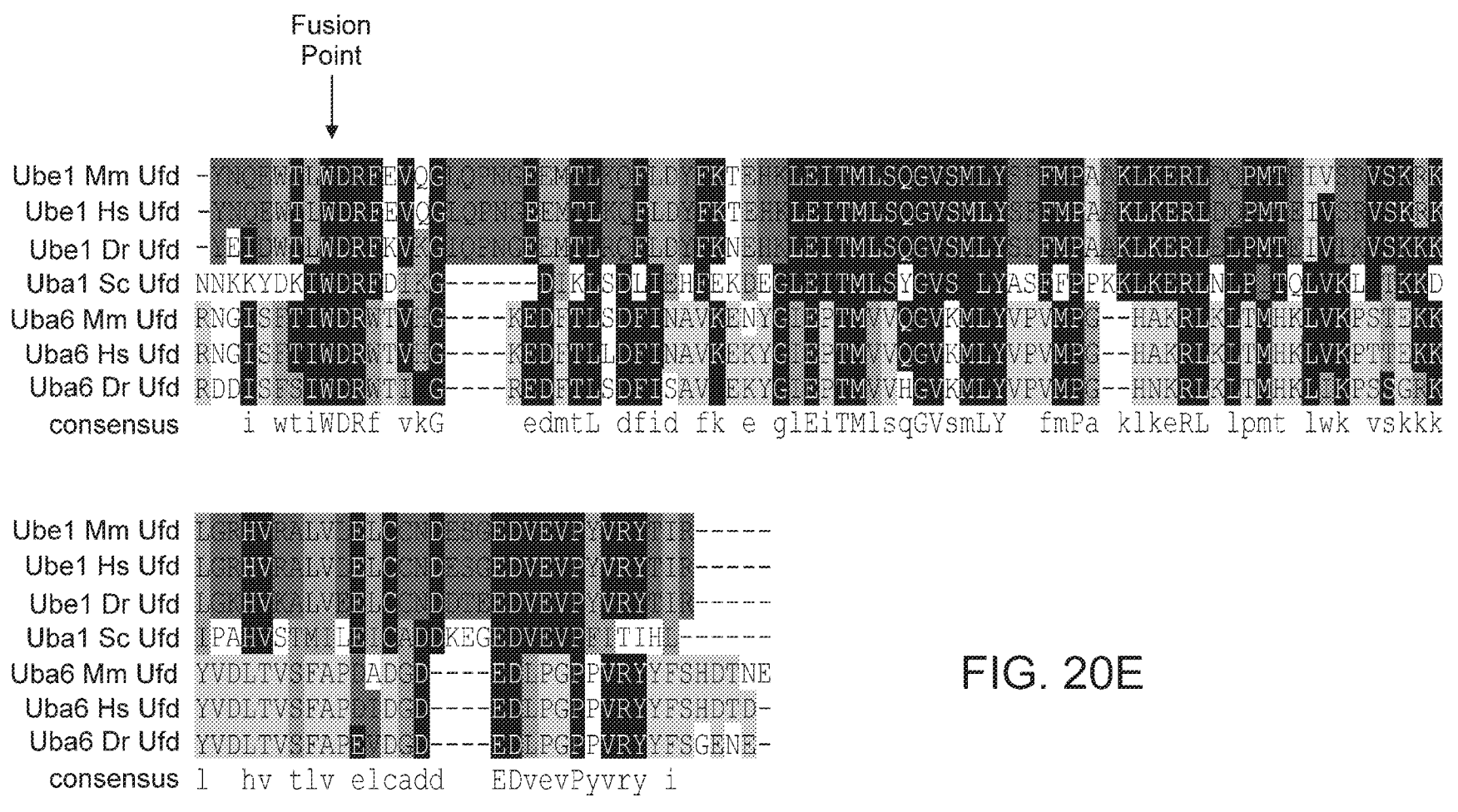
Figures 21E, 22:
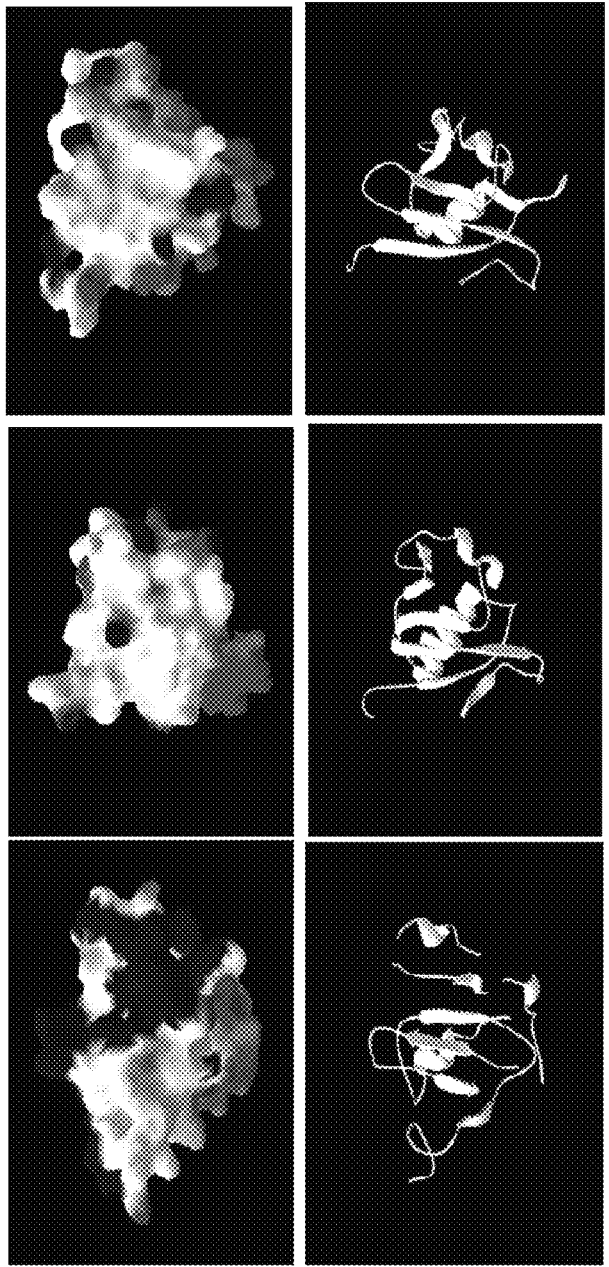

Unless otherwise noted, open reading frames were cloned into pENTR/TOPO (Invitrogen, Carlsbad, Calif.) and transferred into the appropriate expression plasmid using in vitro recombination with Clonase (Invitrogen). The pHAGE-Flag-HA vector (puromycin resistant) places the open reading frame under control of the PGK promoter. Open reading frames for E2s were placed into vectors containing T7 promoters and an N-terminal His-6 tag. For expression of Use1 in bacteria, the Use1 open reading frame (NM_023079) was cloned into pENTR-2 containing a TEV protease cleavage site upstream of the open reading frame and transferred into pDEST-15 (N-terminal GST tag from Invitrogen). The annotated open reading frame for Use1 (referred to as UBE2Z) (Gu, X. et al. Cloning and characterization of a gene encoding the human putative ubiquitin conjugating enzyme E2Z (UBE2Z). Mol Biol Rep (2006)) is incorrect, as determined by the size of the endogenous protein detected using anti-Use1 antibodies and by DNA sequence analysis. The actual open reading frame initiates 109 amino acids prior to the annotated start site (FIG. 20B). The sequences of all the genes examined are collected in FIG. 22.

mRNA Expression

Analysis of mRNA expression for Uba6, Ube1, and Use1 was performed using the Genomics Institute of the Novartis Research Foundation transcriptional profiling resource (Su et al. (2002) *Proc. Natl. Acad. Sci. U.S.A.* 99:4465; Su et al. (2004) *Proc. Natl. Acad. Sci. U.S.A.* 101:6062). This analysis employed GNF1H chips in combination with the MAS5 transcriptional profiling algorithm (Su et al. (2004) *Proc. Natl. Acad. Sci. U.S.A.* 101:6062).

Phylogenetic Trees

Trees and alignments were generated using ClustalW in conjunction with Treeview.

Antibodies

Uba6 and Use1 antibodies were generated in rabbits using a GST-Uba6 fusion protein (residues 869-1052) and GST-Use1, respectively, made in bacteria. Antibodies were affinity purified prior to use. The specificity of antibodies was determined by RNAi against Uba6 Use1.

Protein Expression and Purification

For production of proteins in insect cells, recombinant baculoviruses were used to infect Sf9 cells (40 h) and cleared cell extracts in lysis buffer (50 mM Tris-HCl, pH 7.5, 0.5 mM DTT, 150 mM NaCl, 0.5% Nonidet-P40, protease inhibitors (Roche)) were bound to anti-Flag or GSH-Sepharose beads. Washed beads were eluted with Flag peptide (500 µg/ml) or with glutathione (40 mM) and the protein dialyzed against 50 mM Tris-HCl, pH 7.5, 0.5 mM DTT, 150 mM NaCl, 50% glycerol. Bacterial expression was performed in Rosetta/DE3 cells using 0.4 mM IPTG induction for 3 h at 37° C. Cells were disrupted in lysis buffer prior to purification using GSH-Sepharose. All GST-UBL proteins were found to contain the appropriate C-termini by mass spectrometry.

Unless otherwise noted, expression of proteins in mammalian cells was accomplished by viral transduction using Gateway-compatible pHAGE (lentiviral) based vectors. Vectors were packaged in 293T cells and used to transduce the indicated cell line prior to selection with puromycin. For immunoprecipitation, extracts were generated in lysis buffer prior to incubation with the indicated antibodies. Proteins were separated on 4-12% Tris-glycine gradient gels (Invitrogen). To examine E2 charging, cells were lysed in 50 mM MES, 150 mM NaCl, 0.2% Nonidet-P40, protease inhibitors (Roche, Indianapolis, Ind.) (pH 3-5 as indicated) buffer and cleared by centrifugation. Ten µg of extract was subjected to non-reducing Novex 4-12% Bis-Tris gel prior to immunoblotting. In cases where RNAi was employed, cells were transfected with the indicated siRNAs (33 nM) using Oligofectamine (Invitrogen). After 72 hours, cells were lysed as described above to examine E2 charging. The sequences of siRNAs are provided herein. In order to examine thioesters between ubiquitin and Flag-HA-Uba6, cells expressing Flag-HA-Uba6 (wild-type or the C625A mutant) were lysed in 50 mM MES, pH 4.5, 150 mM NaCl, 0.2% Nonidet-P40, protease inhibitors and extracts subjected to immunoprecipitation with anti-HA-agarose. Immune complexes were washed with lysis buffer (pH 4.5), eluted with HA peptide, and then subjected to electrophoresis on a 412% Bis-Tris gel in the absence of reducing agent. In some cases, samples were treated with 200 mM DTT prior to electrophoresis in order to reduce thioester bonds. Gels were transferred to PVDF and probed with the indicated antibodies or, in some cases, bands were excised and subjected to mass spectrometry as described below.

In Vitro Ubiquitin Activation and E2 Charging Assays

For ubiquitin activation, the indicated E1 (8 nM) was incubated with 100 nM GSTUBL and 2 mM ATP in reaction buffer (50 mM Tris-HCl, 5 mM KCl, 5 mM $MgCl_2$) for 15 minutes at 30° C. (total volume 10 µl), the reaction quenched by addition of 2× Laemli sample buffer lacking reducing agent, and immediately subjected to non-reducing 4-12% Tris-glycine gel and immunoblotting. To measure the kinetics of ubiquitin activation, reactions were performed with 8 nM E1 and 0.5 µM ubiquitin for the indicated time at 30° C. and immunoblots quantified using CCD detection of chemiluminescence. This was accomplished using an Alpha Innotech FlourChem 8900 instrument. In experiments where the dependent on GST-ubiquitin concentration was determined, the GST-ubiquitin concentrations were 0, 7.5, 15, 30, 60, 120, 240, and 480 nM and the reaction time was 10 minutes. The average reaction rates for 2 independent experiments are shown together with the standard deviation. To examine E2 charging, the indicated E2 was in vitro translated using a bacterial S30 extract (Promega) in the presence of $^{35}$S-methionine. Bacterial S30 extracts lack ubiquitin activating and conjugating enzymes which could interfere with the assays. Radiolabeled E2 (1 µl) was incubated with 40 nM of the indicated E1, 25 µM lysine-free ubiquitin (Boston Biochem, Waltham Mass.), 2 mM ATP in reaction buffer (15 min, 30° C.) (10 µl total volume). Reactions were analyzed as described for ubiquitin activation. In some experiments, Use1 purified from bacteria was employed. Ube1 was released from GST-TEV-Use1 using TEV protease and the eluted Use1 dialyzed against 50 mM Tris-HCl, pH 7.5, 0.5 mM DTT, 150 mM NaCl, 50% glycerol. Capture of Uba6 and Ube1 using ubiquitin-Sepharose was performed as described previously (Pickart et al. (1985) *J. Biol. Chem.* 260:1573;

Ciechanover et al. (1982) *J. Biol. Chem.* 257:2537) using extracts from cells stably expressing Flag-HA-Uba6.

Mass Spectroscopy

Unless otherwise stated, mass spectrometry was performed on peptides produced by in-gel trypsinization using a Thermo-Electron LTQ mass spectrometer. Searches were performed using Sequest. For determination of C-termini in GST-UBL fusion proteins, 2 µg of protein was excised from SDS-PAGE gels and digested with the protease indicated. Digested peptides were then subjected to LC/MS/MS under conditions where >3250 MS/MS scans were obtained for each LC/MS/MS run. The predicted C-terminal peptides as well as XCorr and dCn scores for the match with the predicted spectra. For analysis of peptides from Flag-HA-Uba6~Ub purified from mammalian cells, trypsinized samples were subjected to LC/MS/MS using an LTQ-Orbitrap instrument to identify peptides with high mass accuracy. Tandem mass spectra were first searched using Sequest against the human genome, identifying peptides against ubiquitin and Uba6 but not other ubiquitin like proteins. In order to more effectively rule out the presence of additional UBLs, a focused database containing protein sequences for human ubiquitin, Nedd8, SUMO-1, SUMO-2, SUMO-3, Fub1, Fat10, Urm1, Ufm1, Gdx, Isg15, and Apg12 was searched using a 100 mass unit filter (facilitated by the high mass accuracy afforded by orbitrap detection). Peptides corresponding to only ubiquitin were obtained (see FIG. 2), making it extremely unlikely that Uba6 efficiently charges UBLs in addition to ubiquitin.

For production of proteins in insect cells, recombinant baculoviruses were used to infect Sf9 cells (40 hours) and cleared cell extracts in lysis buffer (50 mM Tris-HCl, pH 7.5, 0.5 mM DTT, 150 mM NaCl, 0.5% Nonidet-P40, protease inhibitors (Roche)) were bound to anti-Flag or GSH-Sepharose beads. Washed beads were eluted with Flag peptide (500 µg/ml) or with glutathione (40 mM) and the protein dialyzed against 50 mM Tris-HCl, pH 7.5, 0.5 mM DTT, 150 mM NaCl, 50% glycerol. Bacterial expression was performed in Rosetta/DE3 cells using 0.4 mM IPTG induction for 3 h at 37° C. Cells were disrupted in lysis buffer prior to purification using GSH-Sepharose. All GST-UBL proteins were found to contain the appropriate C-termini by mass spectrometry.

Unless otherwise noted, expression of proteins in mammalian cells was accomplished by viral transduction using Gateway-compatible pHAGE (lentiviral) based vectors. Vectors were packaged in 293T cells and used to transduce the indicated cell line prior to selection with puromycin. For immunoprecipitation, extracts were generated in lysis buffer prior to incubation with the indicated antibodies. Proteins were separated on 4-12% Tris-glycine gradient gels (Invitrogen). To examine E2 charging, cells were lysed in 50 mM MES, 150 mM NaCl, 0.2% Nonidet-P40, protease inhibitors (Roche, Indianapolis, Ind.) (pH 3-5 as indicated) buffer and cleared by centrifugation. Ten µg of extract was subjected to non-reducing Novex 4-12% Bis-Tris gel prior to immunoblotting. In cases where RNAi was employed, cells were transfected with the indicated siRNAs (33 nM) using Oligofectamine (Invitrogen). After 72 hours, cells were lysed as described above to examine E2 charging. The sequences of siRNAs are provided herein. In order to examine thioesters between ubiquitin and Flag-HA-Uba6, cells expressing Flag-HA-Uba6 (wild-type or the C625A mutant) were lysed in 50 mM MES, pH 4.5, 150 mM NaCl, 0.2% Nonidet-P40, protease inhibitors and extracts subjected to immunoprecipitation with anti-HA-agarose. Immune complexes were washed with lysis buffer (pH 4.5), eluted with HA peptide, and then subjected to electrophoresis on a 412% Bis-Tris gel in the absence of reducing agent. In some cases, samples were treated with 200 mM DTT prior to electrophoresis in order to reduce thioester bonds. Gels were transferred to PVDF and probed with the indicated antibodies or, in some cases, bands were excised and subjected to mass spectrometry as described below.

Tissue Culture

Tissue culture cells were grown in Dulbecco's Modified Eagle Medium at 37° C. in 5% $CO_2$. To generate cell lines stably expressing Flag-HA-Uba6 or relevant mutants, the Uba6 ORFs were recombined into either pHAGE-CMV-Flag-HA-GAW or pHAGE-PGK-Flag-HA-GAW and viruses were packaged using standard lentivirus packaging procedures. Viral supernatants were used to infect 293T cells at a multiplicity of infection of approximately 0.5. Cells were selected for integration using puromycin.

Expression of Proteins in *E. coli*

For expression of GST-ubiquitin and ubiquitin-like proteins in *E. coli*, BL21/DE3 cells (Novagen, Madison, Wis.) were transformed with the appropriate expression plasmid (pDEST-27, Invitrogen) and plasmids selected using carbocyclin. Cells were grown to 0.8 OD and induced with 0.4 mM IPTG. After three hours, cells were harvested, lysed in 50 mM Tris-HCl (pH 7.5), 150 mM NaCl, 1 mM EDTA, 0.5% NP40, and subjected to centrifugation at 12,000 g. Extracts were subjected to purification using GSH-Sepharose (Pharmacia, Piscataway, N.J.). After washing the beads with lysis buffer, proteins were eluted using 0.1 M Tris-HCl, pH 8, and 40 mM glutathione. To translate E2s in vitro, coding sequences in vectors containing a T7 promoter were transcribed and translated using an *E. coli* in vitro translation system (Promega) in the presence of $^{35}$S-methionine. Proteins were then employed in thiolester assays as described below.

Expression of Proteins in Insect Cells

For expression in insect cells, ORF clones were recombined with baculoviral sequences using Bac-N-Blue (Invitrogen) via co-transfection of Sf9 cells and viral supernatants isolated three days after transfection. Viral stocks were amplified in Sf9 cells. For protein production, Sf9 cells were infected with viral stocks and cells were lysed after 40 hours using 50 mM Tris-HCl (pH 7.5), 150 mM NaCl, 1 mM EDTA, and 0.5% NP40 in the presence of proteasome inhibitors (Roche, Basel, Switzerland). Extracts were cleared by centrifugation and lysates were incubated with either anti-Flag (Sigma, St. Louis, Mo.) or GSH-Sepharose (Pharmacia, Piscataway, N.J.) resins. Resins were washed with lysis buffer prior to elution with either Flag peptide (Sigma) or glutathione as described above. Proteins were dialyzed against 50 mM Tris-HCl, 50 mM NaCl, and 50% glycerol at 4° C. for 2 hours and stored at −80° C.

Ubiquitin Activation and Transfer Reactions

To examine ubiquitin activation, Ube1 or Uba6 (100 ng) was incubated in 50 mM Tris-HCl, pH 7.5, 50 mM NaCl, and 4 mM ATP for the time indicated above in the presence of 10 µg ubiquitin or ubiquitin-like protein (final volume of 10 µl). Reaction mixtures were subjected to non-reducing SDS-PAGE at the indicated times. Gels were either stained with Coomassie or subjected to immunoblotting with the antibodies indicated above.

To examine transfer of ubiquitin from Uba6 to an E2, a thiol ester assay was performed. Reactions were performed as described above except that 2 µl of in vitro translated and $^{35}$S-methionine labeled E2 was added. After the indicated time, reaction mixtures were subjected to non-reducing SDS-PAGE and dried gels subjected to autoradiography to visualize the E2 protein and their thiol ubiquitin forms. In some experiments, ubiquitin lacking lysine residues (UbKO) was employed.

Expression of Proteins in Mammalian Cells

In order to examine ubiquitin conjugates for Uba6 in mammalian cells, the indicated cell lines stably or transiently expressing Uba6 or mutants were lysed. Cleared lysates were subjected to immunoprecipitation using anti-HA resin. After washing the resin with lysis buffer, proteins were subjected to non-reducing SDS-PAGE and immunoblotting with the indicated antibodies. In certain cases, gels were stained with Coomassie and proteins excised prior to mass spectrometry at the Taplin Mass Spectrometry Core Facility (Harvard Medical School).

General Methods

Ubiquitin activation assays contained 8 nM E1, 100 nM GST-UBL and 2 mM ATP in 50 mM Tris-HCl, 5 mM KCl, 5 mM $MgCl_2$ for 15 min at 30° C. (total volume 10 µl). Reactions were quenched with 2× Laemli sample buffer lacking reducing agent, and subjected to non-reducing 4-12% Trisglycine gel and immunoblotting. To examine E2 charging, the indicated E2 was in vitro translated using a bacterial S30 extract (Promega, Madison, Wis.) in the presence of $^{35}$S-methionine. E2 (1 µl) was incubated with 40 nM E1, 25 µM KO ubiquitin (Boston Biochem, Waltham, Mass.), 2 mM ATP (15 min, 30° C.) (10 µl total volume) before 4-12% Trisglycine gel/autoradiography.

For immunoprecipitation, cell extracts were generated in pH 7.5 lysis buffer [50 mM Tris-HCl, pH 7.5, 150 mM NaCl, 0.5% Nonidet-P40, protease inhibitors (Roche, Indianapolis, Ind.)] or pH 4.5 lysis buffer (50 mM MES, pH 4.5, 150 mM NaCl, 0.2% Nonidet-P40, protease inhibitors). Proteins were separated on non-reducing 4-12% Tris-glycine or 4-12% Bis-Tris gradient gels prior to blotting or mass spectrometry. To examine E2 charging in vivo, cells were lysed in 50 mM MES (pH 3 to 5 as indicated), 150 mM NaCl, 0.2% Nonidet-P40, protease inhibitors and cleared by centrifugation. Extracts (10 µg) were subjected to non-reducing 4-12% Bis-Tris gel prior to immunoblotting. Where indicated, extracts were boiled (5 minutes) with 200 mM dithiothreitol (DTT). For RNAi, cells were transfected using Oligofectamine (Invitrogen, Carlsbad, Calif.). After 72 hours, cells were lysed as described herein. siRNA sequences: siUba6-1, CCTTG-GAAGAGAAGCCTGATGTAAA (SEQ ID NO:10); siUba6-2, ACACTGAAGTTATTGTACCGCATTT (SEQ ID NO:11); siUba6-3, GGGATCGATGGACCGTACATG-GAAA (SEQ ID NO:12); siUbe1-1, GAGAAGCTGGGCAAGCAGAAGTATT (SEQ ID NO:13); siUbe1-2, CCGACAGCTTGACTCC TACAA-GAAT (SEQ ID NO:14); siUbe1-3, TCCTCAACTTGGC-CCTGCCTTTCTT (SEQ ID NO:15).

Example XI

References

Gu, X. et al., "Cloning and characterization of a gene encoding the human putative ubiquitin conjugating enzyme E2Z (UBE2Z)," *Mol. Biol. Rep.*, 34:183-188 (2006).

Pickart, C. M. & Eddins, M. J., "Ubiquitin: structures, functions, mechanisms," *Biochim. Biophys. Acta*, 1695:55-72 (2004).

Huang, D. T., Walden, H., Duda, D. & Schulman, B. A., "Ubiquitin-like protein activation," *Oncogene* 23:1958-1971 (2004).

Kerscher, O., Felberbaum, R. & Hochstrasser, M., "Modification of proteins by ubiquitin and ubiquitin-like proteins," *Annu. Rev. Cell Dev. Biol.*, 22:159-180 (2006).

Ciechanover, A., Elias, S., Heller, H. & Hershko, A. "'Covalent affinity' purification of ubiquitin-activating enzyme," *J. Biol. Chem.*, 257:2537-2542 (1982).

Haas, A. L., Warms, J. V., Hershko, A. & Rose, I. A., "Ubiquitin-activating enzyme. Mechanism and role in protein-ubiquitin conjugation," *J. Biol. Chem.*, 257:2543-2548 (1982).

Hershko, A., Heller, H., Elias, S. & Ciechanover, A., "Components of ubiquitin-protein ligase system. Resolution, affinity purification, and role in protein breakdown," *J. Biol. Chem.*, 258:8206-8214 (1983).

Pickart, C. M. & Rose, I. A., "Functional heterogeneity of ubiquitin carrier proteins," *J. Biol. Chem.*, 260:1573-1581 (1985).

Pickart, C. M., "Back to the future with ubiquitin," *Cell*, 116:181-190 (2004).

Lake, M. W., Wuebbens, M. M., Rajagopalan, K. V. & Schindelin, H., "Mechanism of ubiquitin activation revealed by the structure of a bacterial MoeB-MoaD complex," *Nature*, 414:325-329 (2001).

Duda, D. M., Walden, H., Sfondouris, J. & Schulman, B. A., "Structural analysis of *Escherichia coli* ThiF," *J. Mol. Biol.*, 349:774-786 (2005).

Lehmann, C., Begley, T. P. & Ealick, S. E., "Structure of the *Escherichia coli* ThiS-ThiF complex, a key component of the sulfur transfer system in thiamin biosynthesis," *Biochemistry*, 45:11-19 (2006).

Walden, H., Podgorski, M. S. & Schulman, B. A., "Insights into the ubiquitin transfer cascade from the structure of the activating enzyme for NEDD8," *Nature*, 422:330-334 (2003).

Lois, L. M. & Lima, C. D., "Structures of the SUMO E1 provide mechanistic insights into SUMO activation and E2 recruitment to E1," *Embo. J.*, 24:439-451 (2005).

Bencsath, K. P., Podgorski, M. S., Pagala, V. R., Slaughter, C. A. & Schulman, B. A. Identification of a multifunctional binding site on Ubc9p required for Smt3p conjugation," *J. Biol. Chem.*, 277:47938-47945 (2002).

Huang, D. T. et al., "Structural basis for recruitment of Ubc12 by an E2 binding domain in NEDD8's E1," *Mol. Cell.*, 17:341-350 (2005).

Huang, D. T. et al., "Basis for a ubiquitin-like protein thioester switch toggling E1E2 affinity," *Nature*, 445:394-398 (2007).

Finley, D., Ciechanover, A. & Varshavsky, A., "Thermolability of ubiquitin activating enzyme from the mammalian cell cycle mutant ts85," *Cell*, 37:43-55 (1984).

Ciechanover, A., Finley, D. & Varshavsky, A., "Ubiquitin dependence of selective protein degradation demonstrated in the mammalian cell cycle mutant ts85," *Cell*, 37:57-66 (1984).

McGrath, J. P., Jentsch, S. & Varshavsky, A., "UBA 1: an essential yeast gene encoding ubiquitin-activating enzyme," *Embo. J.*, 10:227-236 (1991).

Odorisio, T., Mahadevaiah, S. K., McCarrey, J. R. & Burgoyne, P. S., "Transcriptional analysis of the candidate spermatogenesis gene Ube1y and of the closely related Ube1x shows that they are coexpressed in spermatogonia and spermatids but are repressed in pachytene spermatocytes," *Dev. Biol.*, 180:336-343 (1996).

Haas, A. L. & Bright, P. M., "The resolution and characterization of putative ubiquitin carrier protein isozymes from rabbit reticulocytes," *J. Biol. Chem.*, 263:13258-13267 (1988).

Komatsu, M. et al., "A novel protein-conjugating system for Ufm1, a ubiquitin-fold modifier," *Embo. J.,* 23:1977-1986 (2004).

Walden, H. et al., "The structure of the APPBP1-UBA3-NEDD8-ATP complex reveals the basis for selective ubiquitin-like protein activation by an E1," *Mol. Cell,* 12:1427-1437 (2003).

Eletr, Z. M., Huang, D. T., Duda, D. M., Schulman, B. A. & Kuhlman, B., "E2 conjugating enzymes must disengage from their E1 enzymes before E3-dependent ubiquitin and ubiquitin-like transfer," *Nat. Struct. Mol. Biol.,* 12:933-934 (2005).

Booth, J. W., Kim, M. K., Jankowski, A., Schreiber, A. D. & Grinstein, S., "Contrasting requirements for ubiquitylation during Fc receptor-mediated endocytosis and phagocytosis," *Embo. J.,* 21:251-258 (2002).

Shringarpure, R., Grune, T., Mehlhase, J. & Davies, K. J., "Ubiquitin conjugation is not required for the degradation of oxidized proteins by proteasome," *J. Biol. Chem.,* 278, 311-8 (2003).

Chen, X. et al., "N-acetylation and ubiquitin-independent proteasomal degradation of p21(Cip1)," *Mol. Cell,* 16:839-847 (2004).

What is claimed:

1. A method of identifying a compound that inhibits charging of E2Z comprising:
providing a sample including E2Z and ubiquitin;
contacting the sample with the compound;
contacting the sample with SEQ ID NO:5 or SEQ ID NO:7; and
determining whether the ubiquitin is bound to the E2Z in the presence of the compound, wherein the ubiquitin is not bound to the E2Z if the compound inhibits charging of E2Z.

2. A method of identifying a compound that inhibits a ubiquitin activating enzyme a 6 (Uba6) activity comprising:
providing a sample including E2Z and ubiquitin;
contacting the sample with the compound;
contacting the sample with SEQ ID NO:5 or SEQ ID NO:7 or an enzymatically active fragment of SEQ ID NO:5 or SEQ ID NO:7; and
determining whether the ubiquitin is bound to the E2Z in the presence of the compound, wherein the ubiquitin is not bound to the E2Z if the compound inhibits the Uba6 activity.

3. A method of identifying a compound that inhibits a ubiquitin activating enzyme a 6 (Uba6) activity comprising:
providing a sample including ubiquitin;
contacting the sample with the compound;
contacting the sample with SEQ ID NO:5 or SEQ ID NO:7 or an enzymatically active fragment of SEQ ID NO:5 or SEQ ID NO:7; and
determining whether the ubiquitin is bound to the protein in the presence of the compound, wherein the ubiquitin is not bound to the protein if the compound inhibits the Uba6 activity.

4. A method of identifying a compound that inhibits charging of E2Z comprising:
providing a sample including E2Z and ubiquitin;
contacting the sample with the compound;
contacting the sample with an amino acid sequence consisting of amino acids 947 to 1052 of SEQ ID NO:5; and
determining whether the ubiquitin is bound to the E2Z in the presence of the compound, wherein the ubiquitin is not bound to the E2Z if the compound inhibits charging of E2Z.

5. A method of identifying a compound that inhibits a ubiquitin activating enzyme a 6 (Uba6) activity comprising:
providing a sample including E2Z and ubiquitin;
contacting the sample with the compound;
contacting the sample with an amino acid sequence consisting of amino acids 947 to 1052 of SEQ ID NO:5; and
determining whether the ubiquitin is bound to the E2Z in the presence of the compound, wherein the ubiquitin is not bound to the E2Z if the compound inhibits the Uba6 activity.

6. A method of identifying a compound that inhibits a ubiquitin activating enzyme a 6 (Uba6) activity comprising:
providing a sample including ubiquitin;
contacting the sample with the compound;
contacting the sample with an amino acid sequence consisting of amino acids 947 to 1052 of SEQ ID NO:5; and
determining whether the ubiquitin is bound to the protein in the presence of the compound, wherein the ubiquitin is not bound to the protein if the compound inhibits the Uba6 activity.

* * * * *